United States Patent
Sebhat et al.

(10) Patent No.: US 10,335,399 B2
(45) Date of Patent: Jul. 2, 2019

(54) CHROMANE, ISOCHROMANE AND DIHYDROISOBENZOFURAN DERIVATIVES AS MGLUR2—NEGATIVE ALLOSTERIC MODULATORS, COMPOSITIONS, AND THEIR USE

(71) Applicant: Merck Sharp & Dohme Corp., Rahway, NJ (US)

(72) Inventors: Iyassu K. Sebhat, Jersey City, NJ (US); Ashok Arasappan, Bridgewater, NJ (US); Scott B. Hoyt, Arlington, VA (US); Robert R. Wilkening, Maplewood, NJ (US); Duane DeMong, Hanover, MA (US)

(73) Assignee: Merck Sharp & Dohme Corp.

( * ) Notice: Subject to any disclaimer, the term of this patent is extended or adjusted under 35 U.S.C. 154(b) by 0 days.

(21) Appl. No.: 15/713,769

(22) Filed: Sep. 25, 2017

(65) Prior Publication Data

US 2018/0085358 A1   Mar. 29, 2018

Related U.S. Application Data

(60) Provisional application No. 62/400,150, filed on Sep. 27, 2016.

(51) Int. Cl.
*A61K 31/439* (2006.01)
*A61K 31/166* (2006.01)
(Continued)

(52) U.S. Cl.
CPC .......... *A61K 31/439* (2013.01); *A61K 31/166* (2013.01); *C07D 221/24* (2013.01);
(Continued)

(58) Field of Classification Search
CPC .. A61K 31/439; C07D 221/24; C07D 491/04; C07D 491/18
USPC ...................................................... 514/302
See application file for complete search history.

(56) References Cited

U.S. PATENT DOCUMENTS 9,278,960 B2   3/2016   Bungard et al.
9,382,208 B1   7/2016   Conn et al.
(Continued)

FOREIGN PATENT DOCUMENTS

WO   2005014543 A1   2/2005
WO   2010021693 A2   2/2010
(Continued)

OTHER PUBLICATIONS

Christain Wood et al , Investigating the role of mGluR2 versus mGluR3 in antipysychotic-like effects . . . (Year: 2018).*
(Continued)

*Primary Examiner* — Rita J Desai

(74) *Attorney, Agent, or Firm* — Keith D. MacMillan; Catherine D. Fitch

(57) ABSTRACT

The present invention provides certain substituted chromane, isochromane, and dihydroisobenzofuran compounds of formula (I):

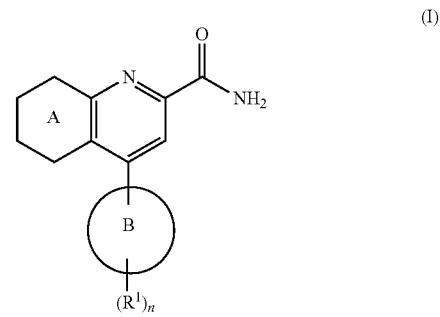

or a pharmaceutically acceptable salt thereof, wherein ring A is a moiety selected from:

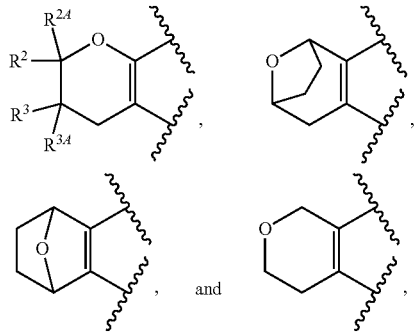

and ring B, n, $R^1$, $R^2$, $R^{2,4}$, $R^3$, and $R^{3,4}$ are as defined herein. The compounds of the invention are useful as mGluR2 inhibitors, or mGluR2 negative allosteric modulators (NAMs), and may be useful in methods of treating a patient for diseases or disorders in which the mGluR2-NAM receptor is involved, such as Alzheimer's disease, cognitive impairment, mild cognitive impairment, schizophrenia and other mood disorders, pain disorders and sleep disorders, by administering to the patient a therapeutically effective amount of a compound of the invention, or a pharmaceutically acceptable salt thereof. The invention is also directed to pharmaceutical compositions comprising a compound of the invention, or a pharmaceutically acceptable salt thereof, (optionally in combination with one or more additional active ingredients), and a pharmaceutically acceptable carrier, and the use of the compounds and pharmaceutical compositions of the invention in the treatment of such diseases.

28 Claims, No Drawings

(51) Int. Cl.
    *C07D 221/24*   (2006.01)
    *C07D 491/04*   (2006.01)
    *C07D 491/18*   (2006.01)
    *A61K 31/015*   (2006.01)
    *A61K 31/03*    (2006.01)

(52) U.S. Cl.
    CPC ......... *C07D 491/04* (2013.01); *C07D 491/18* (2013.01); *A61K 31/015* (2013.01); *A61K 31/03* (2013.01)

(56) References Cited

U.S. PATENT DOCUMENTS

| | | |
|---|---|---|
| 9,636,337 B2 | 5/2017 | Bungard et al. |
| 9,663,506 B2 | 5/2017 | Bungard et al. |

FOREIGN PATENT DOCUMENTS

| | | | |
|---|---|---|---|
| WO | 2011075699 A2 | 6/2011 | |
| WO | 2013066736 | 5/2013 | |
| WO | 2014195311 A1 | 12/2014 | |
| WO | 2016029454 A1 | 3/2016 | |
| WO | 2016032921 A1 | 3/2016 | |
| WO | 2016194324 A1 | 3/2016 | |
| WO | 2017018475 A1 | 2/2017 | |
| WO | WO-2018063955 A1 * | 4/2018 | ........... A61K 31/166 |

OTHER PUBLICATIONS

Felts, As et al., Design of 4-Oxo-1-aryl-1,4-dihydroquinoline-3-carboxamides as selective negative allosteric modulators of metabotropic glutamate receptor subtype 2, Journal of Medicinal Chemistry, 2015, 9027-9040, 58.

* cited by examiner

CHROMANE, ISOCHROMANE AND DIHYDROISOBENZOFURAN DERIVATIVES AS MGLUR2—NEGATIVE ALLOSTERIC MODULATORS, COMPOSITIONS, AND THEIR USE

FIELD OF THE INVENTION

The invention is directed to certain chromane, isochromane, and dihydroisobenzofuran derivatives, their salts, pharmaceutical compositions comprising them and their use in therapy of the human body. The compounds of the invention have been found to modulate the metabotropic glutamate receptor 2 (mGluR2), and hence are expected to be useful in the treatment of Alzheimer's Disease and other diseases mediated by the mGluR2 receptor.

BACKGROUND OF THE INVENTION

The metabotropic glutamate receptors are known to contain one or more allosteric sites, which may alter the affinity with which glutamate and other metabotropic glutamate (mGluR) ligands bind to the primary binding or orthosteric sites. As the orthosteric binding site is highly conserved between all of the known metabotropic glutamate receptors, functional selectivity may best be achieved through allosteric interaction with the receptor.

Modulation of metabotropic glutamate receptor 2 (mGluR2), which is prevalent on presynaptic nerve terminals in the cortex and hippocampus and regulates the release of the brain's major excitatory neurotransmitter glutamate at key neural synapses, has been demonstrated to have a major role in cognitive processing. Neurodegenerative diseases and disorders affecting cognition are thought to be influenced by glutamate signaling. Such neurodegenerative diseases and disorders affecting cognition include (but are not limited to) various forms of dementia, including dementia of the Alzheimer's type (Alzheimer's disease), including mild, moderate, and severe Alzheimer's disease, mild cognitive impairment, and others. Such diseases and disorders may result in, or be identified by manifestations such as progressive memory impairment, loss of language and visuospatial skills, behavioral deficits and others. The potential for inhibition of mGluR2 to improve cognitive performance has been demonstrated genetically and pharmacologically in preclinical species (Higgins et al. [2004], *Neuropharmacology* 46, 907-917). Further, inhibition of mGluR2/3 with a negative allosteric modulator shows precognitive effects in non-human primates (Goeldner et al., [2013], *Neuropharmacology* 64, 337-346). Similarly, mGluR2 inhibition with negative allosteric modulators is expected to improve cognition and reverse dementia associated with other disorders, such as schizophrenia (Marek [2010], *Eur J Pharmacol* 639, 81-90) and general mild cognitive impairment, since enhancement of downstream glutamatergic signaling has been shown to improve cognition clinically (Lynch et al. [1997], *Exp Neurol* 145, 89-92). For these reasons, inhibitors of mGluR2 are believed to be useful in improvement of cognitive performance associated with various forms of dementia, including Alzheimer's disease, cognitive impairment associated with schizophrenia, and other diseases and disorders. Patents have been filed disclosing mGluR2/3 inhibitors for these (and other) indications (Celanire et al. [2015], *Expert Opin Ther Patents* 25, 69-90).

Given the capacity of presynaptic mGluR2 to modulate glutamate release, pharmacologic inhibition of mGluR2 with negative allosteric modulators has the capacity to enhance glutamate signaling to alleviate other disorders involving glutamate signaling. Among these are mood disorders including major depressive disorder (MDD), depression associated with bipolar disorder and anxiety. Inhibition of mGluR2 and mGluR3 by orthosteric antagonists have demonstrated efficacy in rodent models of depression (Chaki et al. [2004], *Neuropharmacology* 46, 457-67) as have negative allosteric modulators (Campo et al. [2011], *J Neurogenet* 25, 152-66). Antagonists of mGluR2 and mGluR3 have also demonstrated efficacy in rodent models of anxiety (Shimazaki et al. [2004], *Eur J Pharmacol* 501, 121-5; Iijima et al. [2007], *Psychopharmacology (Berl)* 190, 233-9) which has resulted in the filing of patents for mGluR2/3 inhibitors for these (and other) indications (Celanire et al. [2015], *Expert Opin Ther Patents* 25, 69-90).

Inhibition of mGluR2 receptors with negative allosteric modulators is also expected to modulate sleep and arousal and circadian timing of sleep wake cycles. Activation of mGluR2 with a positive allosteric modulator results in deep sleep in rats and clinically in healthy human volunteers (Ahnaou et al. [2016], *Neuropharmacology* 103, 290-305) such that inhibition with a negative allosteric modulator is expected to promote arousal coincident with improved cognition. Glutamate signaling modulated by group II mGluRs (mGluR2, mGluR3) is also involved in the circadian timing of sleep/wake cycles such that inhibition of mGluR2 may be expected to improve coordination of activity to environmental light/dark cycles. Genetic loss of mGluR2 and mGluR3 as well as pharmacological inhibition with negative allosteric modulators to these receptors results in enhanced responses to light entrainment cues (Pritchett et al. [2015], *PLoS One* 10, e0125523).

Inhibition of mGluR2 with negative allosteric modulator compounds is also expected to modulate pain sensation and responses to pain. Glutamate signaling mediates both the transmission of pain information as well as peripheral and central mechanisms of pain hypersensitivity such that modulation of this signaling via mGluR2 inhibition has the potential to impact nociception as well as the central perception of pain memory (Chiechio [2016], *Adv Pharmacol* 75, 63-89).

Certain substituted quinoline carboxamides, quinoline carbonitriles, tetrahydronaphthyridines, and others, are known in the art as mGluR2 inhibitors or for other uses. See, for example, WO2016/032921, WO2013/066736, US Patent Application No. 2008/0188521, WO2007/038865, WO 1996/13500, each disclosing compounds as leukotriene inhibitors, and Canadian Patent Application No. 2169231, disclosing compounds as leukotriene and SRS-A inhibitors. There remains a need in the art for novel compounds that are effective as non-competitive mGluR2 modulators, and/or mGluR2 negative allosteric modulators (NAMs).

SUMMARY OF THE INVENTION

In one embodiment, the present invention is directed to certain novel substituted chromane, isochromane, and dihydroisobenzofuran derivatives, which are collectively or individually referred to herein as "compound(s) of the invention." The compounds of the invention, described below, are non-competitive negative allosteric modulators of the metabotropic glutamate 2 receptor (mGluR2 NAMs), and may be useful in treating diseases or disorders in which inhibition of the mGluR2 receptor is useful. Such diseases or disorders include, but may not be limited to, Alzheimer's disease, cognitive impairment, schizophrenia and other mood disorders, pain disorders, and sleep disorders. In another embodiment, the present invention is also directed to pharmaceutical compositions comprising an effective amount of a compound of the invention, or a pharmaceutically acceptable salt thereof, and a pharmaceutically acceptable carrier, and, in yet another embodiment, to the use of the compounds and pharmaceutical compositions of the invention in the treatment of such diseases or disorders. In other embodiments, the present invention is also directed to a combination comprising a compound of the invention and one, two, three or more other therapeutic agents, and for the use of said combination in the treatment of the diseases or disorders described herein. These and other embodiments are described in detail hereinbelow.

DETAILED DESCRIPTION OF THE INVENTION

In one embodiment, the compounds of the invention have the structural Formula (I):

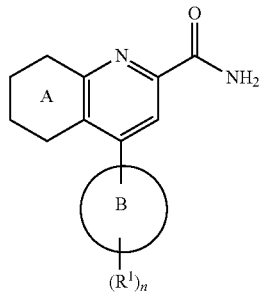

(I)

or a stereoisomer thereof, or a pharmaceutically acceptable salt of said compound or said stereoisomer, wherein:
ring A is a moiety selected from:

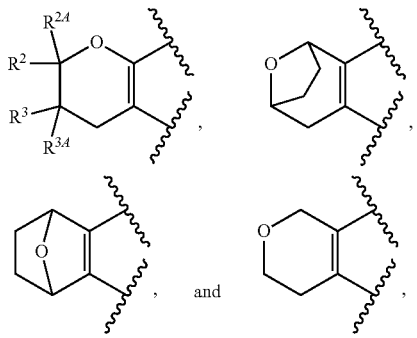

wherein:
$R^2$ is selected from H, cyclopropyl, —($C_1$-$C_4$)alkyl, —($C_1$-$C_4$)alkyl-OH, —($C_1$-$C_4$)alkyl-O$CH_3$, —($C_1$-$C_4$)haloalkyl, —($C_1$-$C_4$)alkyl-O—($C_1$-$C_4$)haloalkyl, —$CH_2$—O—($C_1$-$C_4$)haloalkyl, —CH($CH_3$)—O—($C_1$-$C_4$)haloalkyl, —$CH_2$—NH—($C_1$-$C_4$)haloalkyl, and —$CH_2$—N($CH_3$)—($C_1$-$C_4$)haloalkyl,
$R^{2A}$ is selected from H and methyl;
$R^3$ is selected from H and methyl;
$R^{3A}$ is selected from H and methyl;
ring B is a moiety selected from the group consisting of phenyl, heteroaryl, —($C_5$-$C_6$) cycloalkyl, and —($C_5$-$C_6$) cycloalkenyl;

n is 0, 1, 2, or 3, provided that the value of n does not exceed the maximum number of substitutable hydrogen atoms on ring B; and
each $R^1$ (when present) is independently selected from the group consisting of halogen, —CN, —OH, —($C_1$-$C_6$) alkyl, —O—($C_1$-$C_6$) alkyl, —($C_1$-$C_6$) haloalkyl, —O—($C_1$-$C_6$) haloalkyl, cyclopropyl, cyclobutyl, —$NH_2$, —NH($C_1$-$C_6$) alkyl, —N($C_1$-$C_6$alkyl)$_2$, —C(O)O($C_1$-$C_6$) alkyl, and phenyl.
In embodiments wherein ring A is the moiety:

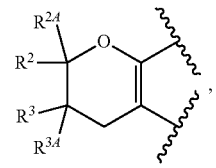

Formula (I) takes the form of Formula (IA):

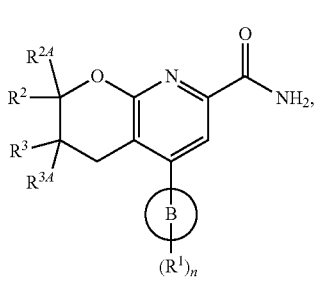

(IA)

wherein ring B, n, and each $R^1$ are as defined in Formula (I).
In one embodiment, in Formula (IA):
$R^2$ is selected from H, cyclopropyl, —$CH_3$, —CH($CH_3$)$_2$, —$CH_2$—OH, —$CH_2$—O$CH_3$, —$CH_2$F, —$CHF_2$, —$CF_3$, —$CH_2$$CH_2$F, —$CH_2$$CHF_2$, —$CH_2$$CF_3$, —$CH_2$—O—$CH_2$F, —$CH_2$—O—$CHF_2$, —CH($CH_3$)—O—$CH_2$F, —CH($CH_3$)—O—$CHF_2$, —$CH_2$—NH—$CH_2$$CF_3$, and —$CH_2$—N($CH_3$)—$CH_2$$CF_3$;
$R^{2A}$ is selected from H and methyl;
$R^3$ is selected from H and methyl;
$R^{3A}$ is selected from H and methyl;
and ring B, n, and each $R^1$ is as defined in Formula I.
In another embodiment, in Formula (IA):
$R^2$ is selected from H, cyclopropyl, —$CH_3$, —CH($CH_3$)$_2$, —$CH_2$—OH, —$CH_2$—O$CH_3$, —$CH_2$F, —$CHF_2$, —$CF_3$, —$CH_2$$CH_2$F, —$CH_2$$CHF_2$, —$CH_2$$CF_3$, —$CH_2$—O—$CH_2$F, —$CH_2$—O—$CHF_2$, —CH($CH_3$)—O—$CH_2$F, —CH($CH_3$)—O—$CHF_2$, —$CH_2$—NH—$CH_2$$CF_3$, and —$CH_2$—N($CH_3$)—$CH_2$$CF_3$;
$R^{2A}$ is selected from H and methyl;
$R^3$ is selected from H and methyl;
$R^{3A}$ is H;
and ring B, n, and each $R^1$ is as defined in Formula I.
In another embodiment, in Formula (IA):
$R^2$ and $R^{2A}$ are both methyl;
$R^3$ and $R^{3A}$ are both H;
and ring B, n, and each $R^1$ is as defined in Formula I.

In another alternative of the immediately preceding embodiment,

In embodiments wherein ring A is the moiety:

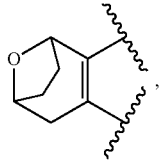

Formula (I) takes the form of Formula (IB):

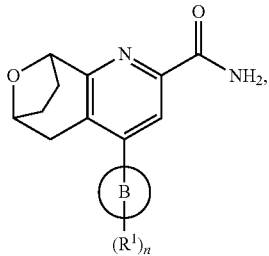

(IB)

wherein ring B, n and each $R^1$ are as defined in Formula (I).

In embodiments wherein ring A is the moiety:

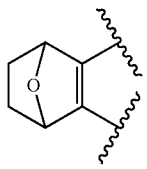 [SMILES: *C1=C(*)C2CCC1O2]

Formula (I) takes the form of Formula (IC):

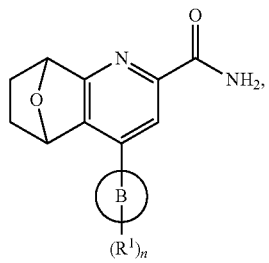

(IC)

wherein ring B, n and each $R^1$ are as defined in Formula (I).

In embodiments wherein ring A is the moiety:

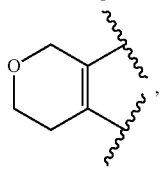

Formula (I) takes the form of Formula (ID):

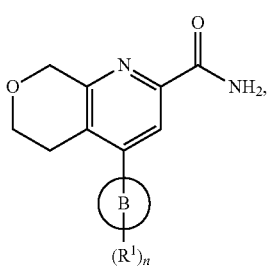

(ID)

wherein ring B, n and each $R^1$ are as defined in Formula (I).

The following alternative embodiments of ring B, n, and $R^1$ apply to each of the embodiments described above.

In one embodiment, in each of Formulas (I), (IA), (IB), (IC), and (ID):

ring B is a moiety selected from the group consisting of phenyl, cyclopentyl, cyclohexyl, pyridinyl, pyrimidinyl, pyrazolyl, thienyl, thiazolyl, thiadiazolyl, isoxazolyl, oxadiazolyl and oxazolyl;

n is 0, 1, 2, or 3, provided that the value of n does not exceed the maximum number of substitutable hydrogen atoms on ring B; and each $R^1$ (when present) is independently selected from the group consisting of halogen, —CN, —OH, —($C_1$-$C_6$) alkyl, —O—($C_1$-$C_6$) alkyl, —($C_1$-$C_6$) haloalkyl, —O—($C_1$-$C_6$) haloalkyl, cyclopropyl, cyclobutyl, —$NH_2$, —NH($C_1$-$C_6$) alkyl, —N($C_1$-$C_6$alkyl)$_2$, —C(O)O($C_1$-$C_6$) alkyl, and phenyl.

In an alternative of the immediately preceding embodiment, n is 0, 1, or 2; and each $R^1$ (when present) is independently selected from the group consisting of fluoro, chloro, —CN, —OH, —($C_1$-$C_6$) alkyl, —O—($C_1$-$C_6$) alkyl, —($C_1$-$C_6$) haloalkyl, —O—($C_1$-$C_6$) haloalkyl, cyclopropyl, cyclobutyl, —$NH_2$, —NH($C_1$-$C_6$)alkyl, —N($C_1$-$C_6$alkyl)$_2$, —C(O)O($C_1$-$C_6$) alkyl, and phenyl.

In another embodiment, in each of Formulas (I), (IA), (IB), (IC), and (ID):

ring B is a moiety selected from the group consisting of: phenyl, pyrazolyl, pyridinyl, thienyl, isoxazolyl, oxadiazolyl and oxazolyl;

n is 0, 1, 2, or 3; and each $R^1$ (when present) is independently selected from the group consisting of fluoro, chloro, —CN, —OH, —($C_1$-$C_6$) alkyl, —O—($C_1$-$C_6$) alkyl, —($C_1$-$C_6$) haloalkyl, —O—($C_1$-$C_6$) haloalkyl, cyclopropyl, cyclobutyl, —$NH_2$, —NH($C_1$-$C_6$)alkyl, —N($C_1$-$C_6$alkyl)$_2$, —C(O)O($C_1$-$C_6$) alkyl, and phenyl.

In an alternative of the immediately preceding embodiment, n is 0, 1, or 2.

In another embodiment, in each of Formulas (I), (IA), (IB), (IC), and (ID):

ring B is a moiety selected from the group consisting of: phenyl, pyrazolyl, pyridinyl, thienyl, isoxazolyl, oxadiazolyl and oxazolyl;

n is 0, 1, 2, or 3; and each $R^1$ (when present) is independently selected from the group consisting of fluoro, chloro, —$CH_3$, and —$CHCF_2$.

In an alternative of the immediately preceding embodiment, n is 0, 1, or 2.

Non-limiting examples of ring B, n, and $R^1$ are shown in the corresponding position of each of the example compounds of the invention as shown in the preparative examples and appended claims.

As described in Formulas (I), (IA), (IB), (IC), and (ID), and in each of the alternative embodiments of ring B, n and $R^1$ recited herein, ring B can be substituted with 0, 1, 2, or 3 independently selected $R^1$ groups, provided that the value of n does not exceed the maximum number of substitutable hydrogen atoms on ring B. Thus, in embodiments wherein ring B is phenyl, —($C_5$-$C_6$) cycloalkyl, —($C_5$-$C_6$) cycloalkenyl, pyridinyl, pyrimidinyl, or thienyl, n is 0, 1, 2, or 3. In an alternative of each such embodiment, n is 0, 1, or 2. In another alternative of each such embodiment, n is 0 or 1. When ring B is pyrazolyl, thiazolyl, isoxazolyl, oxadiazolyl, or oxazolyl, n is 0, 1, or 2. In an alternative of each such embodiment, n is 0 or 1. And when ring B is thiadiazolyl, n is 0 or 1.

Another embodiment is a compound of Formula (IA-1):

(IA-1)

or a stereoisomer thereof or a pharmaceutically acceptable salt of said compound or said stereoisomer, wherein:
$R^2$ is selected from H, cyclopropyl, —$CH_3$, —$CH(CH_3)_2$, —$CH_2$—OH, —$CH_2$—$OCH_3$, —$CH_2F$, —$CHF_2$, —$CF_3$, —$CH_2CH_2F$, —$CH_2CHF_2$, —$CH_2CF_3$, —$CH_2$—O—$CH_2F$, —$CH_2$—O—$CHF_2$, —$CH(CH_3)$—O—$CH_2F$, —$CH(CH_3)$—O—$CHF_2$, —$CH_2$—NH—$CH_2CF_3$, and —$CH_2$—$N(CH_3)$—$CH_2CF_3$;
$R^{2A}$ is selected from H and $CH_3$;
$R^3$ is selected from H and $CH_3$; and
$R^{3A}$ is selected from H and $CH_3$.

Another embodiment is a compound of Formula (IA-1), or a stereoisomer thereof, or a pharmaceutically acceptable salt of said compound or said stereoisomer, wherein:
$R^2$ is selected from H, cyclopropyl, —$CH_3$, —$CH(CH_3)_2$, —$CH_2$—OH, —$CH_2$—$OCH_3$, —$CH_2F$, —$CHF_2$, —$CF_3$, —$CH_2CH_2F$, —$CH_2CHF_2$, —$CH_2CF_3$, —$CH_2$—O—$CH_2F$, —$CH_2$—O—$CHF_2$, —$CH(CH_3)$—O—$CH_2F$, —$CH(CH_3)$—O—$CHF_2$, —$CH_2$—NH—$CH_2CF_3$, and —$CH_2$—$N(CH_3)$—$CH_2CF_3$;
$R^{2A}$ is selected from H and $CH_3$;
$R^3$ is selected from H and $CH_3$; and
$R^{3A}$ is H.

Another embodiment is a compound of Formula (IA-1), or a stereoisomer thereof, or a pharmaceutically acceptable salt of said compound or said stereoisomer, wherein:
$R^2$ is selected from H, cyclopropyl, —$CH_3$, —$CH(CH_3)_2$, —$CH_2$—OH, —$CH_2$—$OCH_3$, —$CH_2F$, —$CHF_2$, —$CF_3$, —$CH_2CH_2F$, —$CH_2CHF_2$, —$CH_2CF_3$, —$CH_2$—O—$CH_2F$, —$CH_2$—O—$CHF_2$, —$CH(CH_3)$—O—$CH_2F$, —$CH(CH_3)$—O—$CHF_2$, —$CH_2$—NH—$CH_2CF_3$, and —$CH_2$—$N(CH_3)$—$CH_2CF_3$;
$R^{2A}$ is H;
$R^3$ is selected from H and $CH_3$; and
$R^{3A}$ is H.

Another embodiment is a compound of Formula (IA-1), or a stereoisomer thereof, or a pharmaceutically acceptable salt of said compound or said stereoisomer, wherein:
$R^2$ is selected from H, cyclopropyl, —$CH_3$, —$CH(CH_3)_2$, —$CH_2$—OH, —$CH_2$—$OCH_3$, —$CH_2F$, —$CHF_2$, —$CF_3$, —$CH_2CH_2F$, —$CH_2CHF_2$, —$CH_2CF_3$, —$CH_2$—O—$CH_2F$, —$CH_2$—O—$CHF_2$, —$CH(CH_3)$—O—$CH_2F$, —$CH(CH_3)$—O—$CHF_2$, —$CH_2$—NH—$CH_2CF_3$, and —$CH_2$—$N(CH_3)$—$CH_2CF_3$;
$R^{2A}$ is H;
$R^3$ is H; and
$R^{3A}$ is H.

Another embodiment is a compound of Formula (IA-1a):

(IA-1a)

or a pharmaceutically acceptable salt thereof, wherein:
$R^2$ is selected from H, cyclopropyl, —$CH_3$, —$CH(CH_3)_2$, —$CH_2$—OH, —$CH_2$—$OCH_3$, —$CH_2F$, —$CHF_2$, —$CF_3$, —$CH_2CH_2F$, —$CH_2CHF_2$, —$CH_2CF_3$, —$CH_2$—O—$CH_2F$, —$CH_2$—O—$CHF_2$, —$CH(CH_3)$—O—$CH_2F$, —$CH(CH_3)$—O—$CHF_2$, —$CH_2$—NH—$CH_2CF_3$, and —$CH_2$—$N(CH_3)$—$CH_2CF_3$;
$R^3$ is H; and
$R^{3A}$ is $CH_3$.

Another embodiment is a compound of Formula (IA-1a), or a stereoisomer thereof, or a pharmaceutically acceptable salt of said compound or said stereoisomer, wherein:
$R^2$ is selected from H, cyclopropyl, —$CH_3$, —$CH(CH_3)_2$, —$CH_2$—OH, —$CH_2$—$OCH_3$, —$CH_2F$, —$CHF_2$, —$CF_3$, —$CH_2CH_2F$, —$CH_2CHF_2$, —$CH_2CF_3$, —$CH_2$—O—$CH_2F$, —$CH_2$—O—$CHF_2$, —$CH(CH_3)$—O—$CH_2F$, —$CH(CH_3)$—O—$CHF_2$, —$CH_2$—NH—$CH_2CF_3$, and —$CH_2$—$N(CH_3)$—$CH_2CF_3$;
$R^3$ is $CH_3$; and
$R^{3A}$ is H.

Another embodiment is a compound of Formula (IA-1a), or a stereoisomer thereof, or a pharmaceutically acceptable salt of said compound or said stereoisomer, wherein:
$R^2$ is selected from H, cyclopropyl, —$CH_3$, —$CH(CH_3)_2$, —$CH_2$—OH, —$CH_2$—$OCH_3$, —$CH_2F$, —$CHF_2$, —$CF_3$, —$CH_2CH_2F$, —$CH_2CHF_2$, —$CH_2CF_3$, —$CH_2$—O—$CH_2F$, —$CH_2$—O—$CHF_2$, —$CH(CH_3)$—O—$CH_2F$, —$CH(CH_3)$—O—$CHF_2$, —$CH_2$—NH—$CH_2CF_3$, and —$CH_2$—$N(CH_3)$—$CH_2CF_3$;
$R^3$ is H; and
$R^{3A}$ is H.

Another embodiment is a compound of Formula (IA-1b):

(IA-1b)

or a pharmaceutically acceptable salt thereof, wherein:
$R^2$ is selected from H, cyclopropyl, —$CH_3$, —$CH(CH_3)_2$, —$CH_2$—OH, —$CH_2$—$OCH_3$, —$CH_2F$, —$CHF_2$, —$CF_3$, —$CH_2CH_2F$, —$CH_2CHF_2$, —$CH_2CF_3$, —$CH_2$—O—$CH_2F$, —CH$_2$—O—CHF$_2$, —CH(CH$_3$)—O—CH$_2$F, —CH(CH$_3$)—O—CHF$_2$, —CH$_2$—NH—CH$_2$CF$_3$, and —CH$_2$—N(CH$_3$)—CH$_2$CF$_3$;
R$^3$ is H; and
R$^{3,4}$ is CH$_3$.

Another embodiment is a compound of Formula (IA-1b), or a stereoisomer thereof, or a pharmaceutically acceptable salt of said compound or said stereoisomer, wherein:
R$^2$ is selected from H, cyclopropyl, —CH$_3$, —CH(CH$_3$)$_2$, —CH$_2$—OH, —CH$_2$—OCH$_3$, —CH$_2$F, —CHF$_2$, —CF$_3$, —CH$_2$CH$_2$F, —CH$_2$CHF$_2$, —CH$_2$CF$_3$, —CH$_2$—O—CH$_2$F, —CH$_2$—O—CHF$_2$, —CH(CH$_3$)—O—CH$_2$F, —CH(CH$_3$)—O—CHF$_2$, —CH$_2$—NH—CH$_2$CF$_3$, and —CH$_2$—N(CH$_3$)—CH$_2$CF$_3$;
R$^3$ is CH$_3$; and
R$^{3,4}$ is H.

Another embodiment is a compound of Formula (IA-1b), or a stereoisomer thereof, or a pharmaceutically acceptable salt of said compound or said stereoisomer, wherein:
R$^2$ is selected from H, cyclopropyl, —CH$_3$, —CH(CH$_3$)$_2$, —CH$_2$—OH, —CH$_2$—OCH$_3$, —CH$_2$F, —CHF$_2$, —CF$_3$, —CH$_2$CH$_2$F, —CH$_2$CHF$_2$, —CH$_2$CF$_3$, —CH$_2$—O—CH$_2$F, —CH$_2$—O—CHF$_2$, —CH(CH$_3$)—O—CH$_2$F, —CH(CH$_3$)—O—CHF$_2$, —CH$_2$—NH—CH$_2$CF$_3$, and —CH$_2$—N(CH$_3$)—CH$_2$CF$_3$;
R$^3$ is H; and
R$^{3,4}$ is H.

In one embodiment, the compounds of the invention comprise, collectively and individually, each of the example compounds shown in the tables below, and pharmaceutically acceptable salts thereof. Suitable pharmaceutically acceptable salts of each of these compounds include those discussed hereinbelow.

Definitions

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen.

"Patient" means a human in need of a treatment described herein, as determined by an attending physician or other health care professional or by any other suitable method known to those of skill in the art. While the subject or patient to whom the compounds and compositions of the present invention are administered is generally a human being, such subjects may also include non-human mammals, including dogs, cats, mice, rats, cattle, horses, sheep, rabbits, monkeys, chimpanzees or other apes or primates, for which treatment the above noted diseases and disorders, or the study of the biological activity of the subject compounds, is desired.

"Pharmaceutical composition" (or "pharmaceutically acceptable composition") means a composition suitable for administration to a patient. Such compositions may contain the compound (or compounds) of the invention or mixtures thereof, or salts, solvates, prodrugs, isomers, or tautomers thereof, alone or optionally together with one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" (or "halo") means fluorine (F), chlorine (Cl), bromine (Br), or iodine (I). Preferred are fluorine, chlorine and bromine. More preferred are fluorine and chlorine.

"Alkyl" means an aliphatic hydrocarbon group, which may be straight or branched, comprising 1 to 6 carbon atoms. "Lower alkyl" means a straight or branched alkyl group comprising 1 to 4 carbon atoms. Branched means that one or more lower alkyl groups such as methyl, ethyl or propyl, are attached to a linear alkyl chain. Non-limiting examples of suitable alkyl groups include methyl (Me or CH$_3$), ethyl (Et), n-propyl, isopropyl, n-butyl, i-butyl, and t-butyl.

"Alkenyl" means an aliphatic hydrocarbon group containing at least one carbon-carbon double bond and which may be straight or branched and comprising 2 to 10 carbon atoms in the straight or branched chain. Branched means that one or more lower alkyl groups such as methyl, ethyl propyl, ethenyl or propenyl are attached to a linear or branched alkenyl chain. "Lower alkenyl" means 2 to 4 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide without falling outside of the definition of heteroaryl. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from N, O, and S, and oxides thereof. The point of attachment to the parent moiety is to any available ring carbon or ring heteroatom. Non-limiting examples of monocyclic heteroaryl moieties include pyridyl (or pyridinyl), pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic monocyclic or multicyclic ring system comprising 3 to 10 carbon atoms, preferably 3 to 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclopentane, 1-decalinyl, norbornyl, adamantyl and the like.

"Cycloalkenyl" means a non-aromatic mono or multicyclic ring system comprising 3 to 10 carbon atoms, preferably 4 to 6 carbon atoms which contain at least one carbon-carbon double bond. Preferred cycloalkenyl rings contain 5 to 6 ring atoms. The term "monocyclic cycloalkenyl" refers to monocyclic versions of cycloalkenyl groups described herein and includes non-aromatic 3- to 7-membered monocyclic cycloalkyl groups which contains one or more carbon-carbon double bonds. Non-limiting examples include cyclopropenyl, cyclobutenyl, cyclopentenyl, cyclohexenyl, cyclohetpenyl, cyclohepta-1,3-dienyl, and the like. Non-limiting example of a suitable multicyclic cycloalkenyl is norbornylenyl.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

When a variable appears more than once in a group, e.g., $R^6$ in —$N(R^6)_2$, or a variable appears more than once in a structure presented herein, the variables can be the same or different.

The line —, as a bond generally indicates a mixture of, or either of, the possible isomers, e.g., containing (R)- and (S)-stereochemistry. For example:

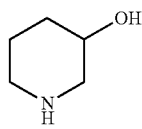

means containing both

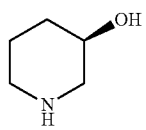

and/or

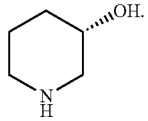

The wavy line ～, as used herein, indicates a point of attachment to the rest of the compound. Lines drawn into the ring systems, such as, for example:

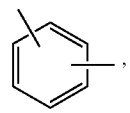

indicate that the indicated line (bond) may be attached to any of the substitutable ring carbon atoms.

"Oxo" means an oxygen atom that is double bonded to a ring carbon in a cycloalkyl, cycloalkenyl, heterocyclyl, heterocyclenyl, or such other rings as are described herein, e.g.,

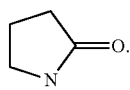

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

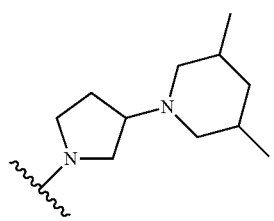 [SMILES: *N1CCC(N2CC(C)CC(C)C2)C1]

represents

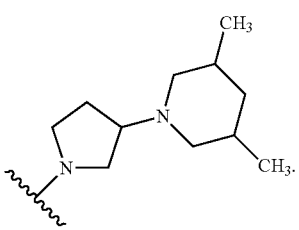 [SMILES: *N1CCC(N2CC(C)CC(C)C2)C1]

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer thereof, or pharmaceutically acceptable salt of said compound or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Those skilled in the art will recognize those instances in which the compounds of the invention may be converted to prodrugs and/or solvates, another embodiment of the present invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms where they exist. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" means an amount of compound or a composition of the present invention that will elicit the biological or medical response of a tissue, system, animal or human that is being sought by the researcher, vererinarian, medical doctor or other clinician or practitioner. In the combination therapies of the present invention, an effective amount can refer to each individual agent or to the combination as a whole, wherein the amounts of all agents administered are together effective. In some embodiments, one or more component agents of the combination may be present individually in an amount less than the amount needed to be effective when administered alone, as described further below. A "therapeutically effective amount" can vary depending on, inter alia, the compound, the disease and its severity, and the age, weight, etc., of the subject to be treated.

The term "treatment" or "treating" means any administration of a compound or composition of the present invention to a subject in need thereof, alone or in combination with one or more additional therapeutic agents, and includes (1) inhibiting or ameliorating a pathology and/or symptamotology of the disease or disorder in said subject, e.g., animal, person or patient or other subject that is experiencing or displaying the pathology or symptomatology of the disease or disorder. The term "prevention" or "prophylaxis," means any administration of a compound or composition of the present invention to a subject in need thereof, alone or in combination with one or more additional therapeutic agents, and includes (1) inhibiting or ameliorating a pathology and/or symptamotology of the disease or disorder in said subject, e.g., animal, person or patient or other subject prior to the onset or manifestation of the pathology or symptomatology of the disease or disorder. The term "controlling" includes preventing, treating, eradicating, ameliorating or otherwise reducing the severity of the disease or disorder or symptom or symptoms thereof.

The compounds and compositions of the present invention, alone or in combination with one or more additional therapeutic agents, may also be useful in the treatment or prevention of the diseases or disorders mentioned, or one or more symptoms thereof, which treatments and prevention are also contemplated as additional embodiments of the present invention.

Those skilled in the art will recognize those instances in which the compounds of the invention may form salts. In such instances, another embodiment provides pharmaceutically acceptable salts of the compounds of the invention. The term "salt(s)", as employed herein, denotes any of the following: acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also potentially useful. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002)

Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered as potentially useful alternatives to the free forms of the corresponding compounds for purposes of the invention.

Another embodiment which may be useful includes pharmaceutically acceptable esters of the compounds of the invention. Such esters may include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

The compounds of the invention may have one or more chiral (asymmetric) centers. The present invention encompasses all stereoisomeric forms of the compounds of formula I. Centers of asymmetry that are present in the compounds of Formula I can all independently of one another have an (R) or (S) configuration. As noted above, when bonds to a chiral carbon are depicted as straight lines in the structural Formulas of the invention, or when a compound name is recited without an (R) or (S) chiral designation for a chiral carbon, it is understood that both the (R) and (S) configurations of each such chiral carbon, and hence each enantiomer or diastereomer and mixtures thereof, are embraced within the Formula or by the name.

Where various stereoisomers of the compounds of the invention are possible, another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention. (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, racemates or prodrugs of the inventive compounds.

Another embodiment which may be useful include isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{11}$C, $^{13}$C, $^{14}$C, $^{15}$N, $^{18}$O, $^{17}$O, $^{31}$P, $^{32}$P, $^{35}$S, $^{18}$F, and $^{36}$Cl, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Compositions and Administration

Another embodiment provides pharmaceutical compositions which comprise a therapeutically effective amount of a compound of the invention, or a stereoisomer thereof, or a pharmaceutically acceptable salt of said compound or said stereoisomer, and a pharmaceutically acceptable carrier.

A representative dosage is about 0.001 to 100 mg/kg of body weight/day of the compound of the invention. A preferred dosage is about 0.01 to 10 mg/kg of body weight/day of a compound of the invention, or a pharmaceutically acceptable salt of said compound.

The term "pharmaceutical composition" is also intended to encompass both the bulk composition and individual dosage units comprised of more than one (e.g., two) pharmaceutically active agents such as, for example, a compound of the present invention and an additional therapeutic agent selected from the lists of the additional agents described herein below, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18th Edition, (1990), Mack Publishing Co., Easton, Pa.

Liquid form preparations include, for example, solutions, suspensions and emulsions. Examples of materials useful for forming such liquid form preparations include water or water-propylene glycol solutions for parenteral injection, or sweeteners and opacifiers for oral solutions, suspensions and emulsions. Liquid form preparations may also include solutions or suspensions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention can also be deliverable transdermally. The transdermal compositions can take the form of liquid solutions, creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 0.001 mg to about 100 mg per kg body weight of a mammal, preferably from about 0.01 mg to about 10 mg per kg. The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The compositions of the invention can further comprise one or more additional therapeutic agents, as discussed in further detail below. Accordingly, in one embodiment, the present invention provides compositions comprising: (i) a compound of the invention, or a stereoisomer thereof, or a pharmaceutically acceptable salt of said compound or said stereoisomer; (ii) one or more additional therapeutic agents, that are not compounds of the invention; and (iii) a pharmaceutically acceptable carrier, wherein the amounts in the composition are together effective to treat one of the disease or conditions discussed herein.

Uses of the Compounds of the Invention

Another embodiment provides a method of treating a patient (e.g., a human patient or a research animal) for diseases or disorders in which the mGluR2 receptor is involved. These methods comprise administering an effective amount of a compound of the invention, or composition comprising a compound of the invention (or a stereoisomer thereof, or a pharmaceutically acceptable salt of said compound or said stereoisomer), to a patient in need thereof, to treat a disease or disorder in which the mGluR2 receptor is involved.

Another embodiment provides for the use of a compound of the invention for treating a disease or disorder in which the mGluR2 receptor is involved, by administering an effective amount of a compound of the invention, or a pharmaceutically acceptable salt thereof, to a patient in need thereof. Another embodiment provides for the use of a compound of the invention for the manufacture of a medicament treating a disease or disorder in which the mGluR2 receptor is involved, by administering an effective amount of a compound of the invention, or a pharmaceutically acceptable salt thereof, to a patient in need thereof. Examples of such diseases and disorders are described herein.

In one embodiment, the compounds of the invention useful in said methods or said uses comprise a compound according to any one of Formulas (I), (IA), (IA-1), (IA-1a), (IA-1b), (IB), (IC), and (ID) as described above, or according to any of the various embodiments described herein, or a stereoisomer thereof, or a pharmaceutically acceptable salt of said compound or said stereoisomer, or a pharmaceutically acceptable composition thereof. In another embodiment, the compounds of the invention useful in said methods or said uses comprise the compound of example 2-5, or a pharmaceutically acceptable salt of said compound, or a pharmaceutically acceptable composition thereof. In another embodiment, the compound of the invention useful in said methods or said uses comprises the compound of example 2-3A or a pharmaceutically acceptable salt of said compound, or a pharmaceutically acceptable composition thereof. In another embodiment, the compound of the invention useful in said methods or said uses comprises the compound of example 2-3B or a pharmaceutically acceptable salt of said compound, or a pharmaceutically acceptable composition thereof. In another embodiment, the compound of the invention useful in said methods or said uses comprises the compound of example 3-1A or a pharmaceutically acceptable salt of said compound, or a pharmaceutically acceptable composition thereof. In another embodiment, the compound of the invention useful in said methods or said uses comprises the compound of example 3-1B or a pharmaceutically acceptable salt of said compound, or a pharmaceutically acceptable composition thereof. In another embodiment, the compound of the invention useful in said methods or said uses comprises the compound of example 3-7A or a pharmaceutically acceptable salt of said compound, or a pharmaceutically acceptable composition thereof. In another embodiment, the compound of the invention useful in said methods or said uses comprises the compound of example 3-7B or a pharmaceutically acceptable salt of said compound, or a pharmaceutically acceptable composition thereof.

In one embodiment, the present invention is directed to a method of treating a neurodegenerative disease or disorders affecting cognition, said method comprising administering a compound of the invention, or a stereoisomer thereof, or a pharmaceutically acceptable salt thereof, to a subject in need thereof. Such diseases or disorders affecting cognition include, but are not limited to, Alzheimer's disease, cognitive impairment, cognition associated with Parkinson's disease, schizophrenia, mood disorders, including depression and anxiety, gastrointestinal disorders, pain disorders and sleep disorders, and others as described herein.

Additional examples of pain disorders include acute pain, inflammatory pain and neuropathic pain. Neuropathic pain includes, but is not limited to, postherpetic neuralgia, nerve injury, the "dynias", e.g., vulvodynia, phantom limb pain, root avulsions, painful diabetic neuropathy, painful traumatic mononeuropathy, painful polyneuropathy. Additional examples of pain disorders include central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

Additional examples of cognitive disorders include mild cognitive impairment. Other conditions that may be treated by the compounds and compositions of the invention include Parkinson's Disease, pulmonary hypertension, chronic obstructive pulmonary disease (COPD), asthma, urinary incontinence, glaucoma, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism and atherosclerosis.

In preferred embodiments, the compounds of the invention may be useful in treating Alzheimer's Disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketanine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline.

In another embodiment, the present invention provides a method for treating schizophrenia or psychosis comprising administering to a patient in need thereof an effective amount of a compound (or composition providing a compound) of the invention, or a stereoisomer thereof.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Compounds of the invention may also be used to treat or prevent dyskinesias. Furthermore, compounds of the invention may be used to decrease tolerance and/or dependence to opioid treatment of pain, and for treatment of withdrawal syndrome of e.g., alcohol, opioids, and cocaine.

The subject or patient to whom the compounds of the present invention is administered is generally a human being, male or female, in whom mGluR2 receptor inhibition is desired, but may also encompass other mammals such as those listed above, including dogs, cats, mice, rats, cattle, horses, sheep, rabbits, monkeys, chimpanzees or other apes or primates, for which treatment the above noted disorders, or the study of mGluR2, is desired.

Another embodiment provides a medicament or pharmaceutical composition for the negative allosteric modulation of an mGluR2 receptor, and/or for the treatment of any of the diseases or disorders listed above to a patient (preferably a human) in need of such treatment, which comprise a compound (or composition comprising a compound) of the invention, or a stereoisomer thereof, or a pharmaceutically acceptable salt of said compound or said stereoisomer, and a pharmaceutically acceptable carrier.

Another embodiment provides a method for the manufacture of a medicament or a pharmaceutical composition for the negative allosteric modulation of an mGluR2 receptor, and/or for treating one or more diseases or conditions listed above, comprising combining a compound (or composition comprising a compound) of the invention, or a stereoisomer thereof, or a pharmaceutically acceptable salt of said compound or said stereoisomer, with a pharmaceutically acceptable carrier.

Combination Therapy

The compounds and compositions of the invention may be used in combination with one or more other drugs in the treatment of diseases or conditions for which the compounds of the invention have utility, where the combination of the drugs is desired, e.g., where the combination is safer or more effective than either drug alone. The compounds of the invention may be used in combination with one or more other drugs that treat, prevent, control, ameliorate, or reduce the risk of side effects or toxicity of the compounds of the invention. Such other drugs may be administered by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may optionally be administered as part of a unit dosage form combination product, or as a kit or treatment protocol wherein one or more additional drugs are administered in separate dosage forms as part of a treatment regimen. In one embodiment, the compounds of the invention useful in said combinations comprise a compound according to any one of Formulas (I), (IA), (IA-1), (IA-1a), (IA-1b), (IB), (IC), and (ID) as described herein, or according to any of the various embodiments described herein, or a stereoisomer thereof, or a pharmaceutically acceptable salt of said compound or said stereoisomer, or a pharmaceutically acceptable composition thereof. In another embodiment, the compounds of the invention useful in said combinations comprise the compounds of the examples, e.g., as set forth as example compounds of the invention. In another embodiment, the compounds of the invention useful in said combinations comprise the compound of example 2-5 or a pharmaceutically acceptable salt of said compound, or a pharmaceutically acceptable composition thereof. In another embodiment, the compound of the invention useful in said combinations comprises the compound of example 2-3A or a pharmaceutically acceptable salt of said compound, or a pharmaceutically acceptable composition thereof. In another embodiment, the compound of the invention useful in said combinations comprises the compound of example 2-3B or a pharmaceutically acceptable salt of said compound, or a pharmaceutically acceptable composition thereof. In another embodiment, the compound of the invention useful in said combinations comprises the compound of example 3-1A or a pharmaceutically acceptable salt of said compound, or a pharmaceutically acceptable composition thereof. In another embodiment, the compound of the invention useful in said combinations comprises the compound of example 3-1B or a pharmaceutically acceptable salt of said compound, or a pharmaceutically acceptable composition thereof. In another embodiment, the compound of the invention useful in said combinations comprises the compound of example 3-7A or a pharmaceutically acceptable salt of said compound, or a pharmaceutically acceptable composition thereof. In another embodiment, the compound of the invention useful in said combinations comprises the compound of example 3-7B or a pharmaceutically acceptable salt of said compound, or a pharmaceutically acceptable composition thereof.

In another embodiment, a compound or composition of the invention may be employed in combination with acetylcholinesterase inhibitors such as donepezil and rivastigmine, NMDA antagonists such as memantine, muscarinic receptor modulators, AMPA receptor modulators, mGluR3 receptor modulators, nicotinic alpha-7 and alpha-4-beta 2 receptor modulators, 5-HT6 and 5-HT4 receptor modulators, modulators of phosphodiesterases (PDEs), alpha 2c receptor anagonists, histone deacetylases, and antioxidant therapies.

In another embodiment, a compound or composition of the invention may be employed in combination with therapies that may alter or modify the course of disease progression, including beta-amyloid modulating therapies such as BACE inhibitors, BACE antibodies, gamma-secretase modulators, tau and/or phosphor-tau modulators, and biologic therapies which modulate placques associated with neurological disorders including antibodies, RNAi, miRNA, and cell-therapies. Suitable BACE inhibitors include but are not limited to verubecestat (Merck & Co., Inc.), AZD2392 (Eli Lilly & Co./Astra Zeneca), CTS-21166 (CoMentis), E2609 (Biogen Idec, Inc./Esai Co., Ltd.), and BAN2401 (Biogen Idec, Inc./Esai Co., Ltd.).

In another embodiment, a compound or composition of the invention may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide or pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

Additional examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib, valdecoxib, 406381 and 644784; CB-2 agonists, such as 842166 and SAB378; VR-1 antagonists, such as AMG517, 705498, 782443, PAC20030, V114380 and A425619; bradykinin B1 receptor antagonists, such as SSR240612 and NVPSAA164; sodium channel blockers and antagonists, such as VX409 and SPI860; nitric oxide synthase (NOS) inhibitors (including iNOS and nNOS inhibitors), such as SD6010 and 274150; glycine site antagonists, including lacosamide; neuronal nicotinic agonists, such as ABT 894; NMDA antagonists, such as AZD4282; potassium channel openers; AMPA/kainate receptor antagonists; calcium channel blockers, such as ziconotide and NMED160; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists, such as AZD9272; alpha agonists, such as AGNXX/YY; neuronal nicotinic agonists, such as ABT894; NMDA receptor agonists or antagonists, such as AZD4282; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

In another embodiment, the compounds and compositions of the invention may be administered in combination with compounds useful for the treatment of schizophrenia or enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists (such as suvorexant), orexin agonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, prokineticin agonists and antagonists, pyrazolopyrimidines, T-type calcium channel antagonists, triazolopyridines, and the like, or the compound of the present invention may be administered in conjunction with the use of physical methods such as with light therapy or electrical stimulation.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like.

In one embodiment, the compound of the invention is administered during a time when the additional therapeutic agent(s) exert their prophylactic or therapeutic effect, or vice versa.

In another embodiment, the compound of the invention and the additional therapeutic agent(s) are administered in doses commonly employed when such agents are used as monotherapy for treating the disorder.

In another embodiment, the compound of the invention and the additional therapeutic agent(s) are administered in doses lower than the doses commonly employed when such agents are used as monotherapy for treating the disorder.

In one embodiment, the compound of the invention and the additional therapeutic agent(s) are present in the same composition, which is suitable for oral administration.

In some embodiments, the compound of the invention and the additional therapeutic agent(s) can act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

The doses and dosage regimen of the additional therapeutic agent(s) used in the combination therapies of the present invention for the treatment or prevention of a disease or disorder can be determined by the attending clinician, taking into consideration the approved doses and dosage regimen in the package insert; the age, sex and general health of the patient; and the type and severity of the viral infection or related disease or disorder.

Another embodiment provides a kit comprising a therapeutically effective amount of the compound (or a composition comprising a compound) of the invention, or a stereoisomer thereof, or a pharmaceutically acceptable salt of said compound or said stereoisomer, optionally together with at least one additional therapeutic agent listed above, and a pharmaceutically acceptable carrier, vehicle or diluent.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like.

In one embodiment, the compound of the invention is administered during a time when the additional therapeutic agent(s) exert their prophylactic or therapeutic effect, or vice versa.

In one embodiment, the compound of the invention and the additional therapeutic agent(s) are present in the same composition, which is suitable for oral administration.

PREPARATIVE EXAMPLES

In general, the compounds in the invention may be produced by a variety of processes known to those skilled in the art and by known processes analogous thereto. The invention disclosed herein is exemplified by the following preparations and examples which should not be construed to limit the scope of the disclosure. Alternative mechanistic pathways and analogous structures will be apparent to those skilled in the art. The practitioner is not limited to these methods.

One skilled in the art will recognize that one route will be optimized depending on the choice of appendage substituents. Additionally, one skilled in the art will recognize that in some cases the order of steps has to be controlled to avoid functional group incompatability.

The prepared compounds may be analyzed for their composition and purity as well as characterized by standard analytical techniques such as, for example, elemental analysis, NMR, mass spectroscopy and IR spectra.

One skilled in the art will recognize that reagents and solvents actually used may be selected from several reagents and solvents well known in the art to be effective equivalents. Hence, when a specific solvent or reagent is mentioned, it is meant to be an illustrative example of the conditions desirable for that particular reaction scheme or for the preparation described below.

Where NMR data are presented, $^1$H spectra were obtained on either a Varian 400, AVANCE III 400 or Varian AS500, and chemical shifts are reported as ppm with number of protons and multiplicities indicated parenthetically. Where LC/MS data are presented, analyses was performed using a Waters Acquity UPLC (BEH C18 column, 1.0×50 mm, 1.7 um, UV 254 nm, 2 min 10-99% MeCN/water+0.05% TFA gradient, ESI positive) or an Agilent 1200 or Shimadzu 20AB series (with a Xtimate C18 column, 2.1×30 mm, 3 um, UV 220 or 254 nm, 1.5 mL/4 L TFA in water (solvent A) and 0.75 mL/4 L TFA in acetonitrile (solvent B), using the elution gradient 10%-80% (solvent B) over 0.9 minutes and holding at 80% for 0.6 minutes at a flow rate of 1.2 mL/min, ESI positive).

Preparative chiral HPLC separations were generally carried out using supercritical fluid chromatography by eluting a chiral column such as OJ-H, (4.6×250 mm, Chiral Technologies, Inc., West Chester, Pa.) with a mobile phase of isopropanol and supercritical CO2.

The following abbreviations may be used throughout the text:

Ac=acetyl; aq=aqueous; CO=carbon monoxide; Me=methyl; Et=ethyl; t-Bu:=tert-butyl; Ar:=aryl; Ph=phenyl; Bn=benzyl; EtOH=ethyl alcohol; IPA=isopropyl alcohol; AIBN=Azobisisobutyronitrile; ACN=acetonitrile; AcOK=potassium acetate; Boc=tert-butyloxycarbonyl; BOP:=benzotriazolyloxytris (dimethylamino) phosphonium hexafluorophosphate; calcd (or calc'd)=calculated; chiral SFC=supercritical fluid chromatography on a chiral column; ClZn=Chlorozinc; DAST=diethylaminosulfur trifluoride; DCE=dichloroethane; DCM=dichloromethane; DCM/i-PrOH=dichloromethane/iso-propanol; DEA=diethylamine; DIBAL-H=diisobutylaluminium hydride; DIPEA=N,N-diisopropylethylamine; DMA=dimethylacetamide; DMEM=Dulbecco's Modified Eagle Medium (High Glucose); DMF:=dimethylformamide; DMFDMA=N,N-dimethylformamide dimethylacetal; DMP=dess-martin periodinane; DMSO=dimethylsulfoxide; dppf=diphenylphosphorousferrocenyl; FBS=fetal bovine serum; HATU=N,N,N',N'-tetramethyl-O-(7-azabenzotriazol-1-yl)uronium hexafluorophosphate; (HCHO)$_n$= paraformaldehyde; HMDS=hexamethyldisilazane; HPLC=high performance liquid chromatography; m-CPBA=meta-chloroperoxybenzoic acid; M=molar; m-CPBA (or mCPBA)=meta-chloroperoxybenzoic acid; MS=mass spectrometry; MS (ESI) calcd=mass spec (Electrospray ionization); Ms=mesyl; NMO=N-methyl morpholine N-oxide; Pd(dtbpf)Cl2=1,1'-Bis(di-tert-butylphosphino)ferrocene]dichloropalladium(II); PMB=p-methoxybenzyl; Prep-TLC=preparative thin layer chromatography; rt=room temperature; SFC=supercritical fluid chromatography; TEA=triethylamine; TFA=trifluoroacetic acid; THF=tetrahydrofuran; TPAP=tetra-n-propyl ammonium perruthenate.

The following intermediate compounds were prepared as described below for use in the preparation of compounds of the invention.

Intermediate 2-1

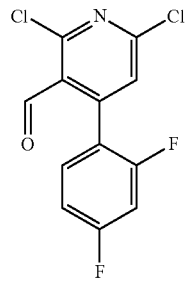 [SMILES: O=Cc1c(-c2ccc(F)cc2F)cc(Cl)nc1Cl]

2,6-dichloro-4-(2,4-difluorophenyl)nicotinaldehyde

Step 1: 4-bromo-2,6-dichloronicotinic acid

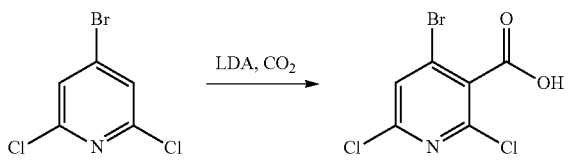 [SMILES: Clc1cc(Br)cc(Cl)n1 ; O=C(O)c1c(Br)cc(Cl)nc1Cl]

n-Butyllithium (38.8 mL, 97 mmol) was added dropwise to diisopropylamine (14.91 mL, 106 mmol) in THF (50 mL) at −78° C. The solution was stirred at −78° C. for 0.5 h and at 0° C. for 0.5 h. The crude pale yellow solution of lithium diisopropylamide was used in the next step without further purification.

To a stirred and cooled (−78° C.) solution of 4-bromo-2,6-dichloropyridine (20 g, 88 mmol) in THF (550 mL) was added dropwise the pre-formed solution of lithium diisopropylamide under N$_2$ atmosphere. The mixture was stirred at −78° C. for 1 h, (dry ice) carbon dioxide (50 g, 1136 mmol) was added to the reaction mixture at −78° C. and stirred for 1 h. 1 M aqueous Na$_2$CO$_3$ (1 L) was added to quench the reaction. The mixture was extracted with ethyl acetate (1 L), the aqueous solution was acidified with 1M aqueous HCl to pH~4. The mixture was extracted with ethyl acetate (2×1 L). The combined organic phases were dried over Na$_2$SO$_4$, filtered and concentrated under reduced pressure to give the product which was used in subsequent steps without further purification. MS (ESI) calcd for (C$_6$H$_3$BrCl$_2$NO$_2$) [M+H]$^+$, [271.86], found, [271.7].

$^1$H NMR (400 MHz, DMSO-d$_6$) δ 8.48-7.66 (m, 1H)

Step 2: (trimethylsilyl)methyl 4-bromo-2,6-dichloronicotinate and methyl 4-bromo-2,6-dichloronicotinate

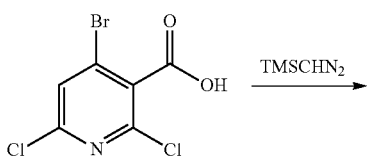

-continued

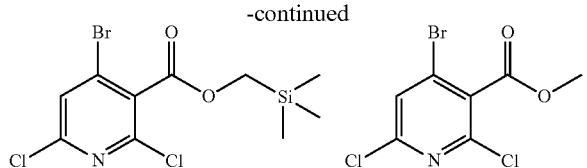

To a solution of 4-bromo-2,6-dichloronicotinic acid (19.5 g, 72.0 mmol) in THF (500 mL) was added dropwise (trimethylsilyl)diazomethane (54.0 mL, 108 mmol) at 15° C. The mixture was stirred at 15° C. for 8 h. The mixture was quenched with HCl (2M) (20 mL), dried over Na$_2$SO$_4$, filtered and concentrated under reduced pressure. The crude product was purified by silica gel chromatography (ISCO®; 120 g SepaFlash® Column, eluting with 0 to 5% ethyl acetate/petroleum ether) to give a mixture of the products. MS (ESI) calcd for (C$_{10}$H$_{13}$BrCl$_2$NO$_2$Si) [M+H]$^+$, 357.9, found, 357.8. MS (ESI) calcd for (C$_7$H$_5$BrCl$_2$NO$_2$) [M+H]$^+$, 285.9, found, 285.8.

Step 3: 4-bromo-2,6-dichloronicotinaldehyde

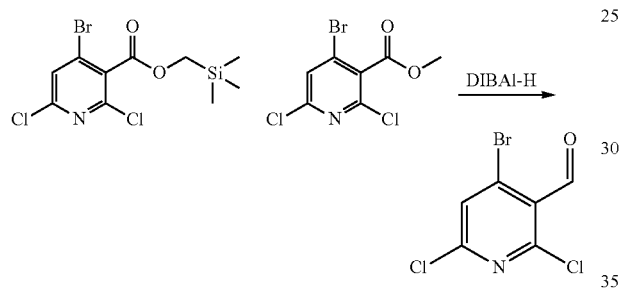

To a solution of (trimethylsilyl)methyl 4-bromo-2,6-dichloronicotinate and methyl 4-bromo-2,6-dichloronicotinate (17 g, ~60 mmol) in toluene (400 mL) was added dropwise DIBAL-H (65.6 mL, 65.6 mmol) at −78° C. The mixture was stirred at −78° C. for 2 h. The mixture was quenched with saturated aqueous NH$_4$Cl (300 mL). Aqueous HCl (2M, 150 mL) was added and the mixture was extracted with ethyl acetate (2×500 mL), the combined organics were dried over Na$_2$SO$_4$, filtered and concentrated under reduced pressure. The residue was purified by silica gel chromatography (ISCO®; 120 g SepaFlash® Column, eluting with 0 to 3% ethyl acetate/petroleum ether) to give the product. $^1$H NMR (400 MHz, CDCl$_3$) δ 10.36 (s, 1H), 7.77-7.63 (m, 1H)

Step 4:
2,6-dichloro-4-(2,4-difluorophenyl)nicotinaldehyde

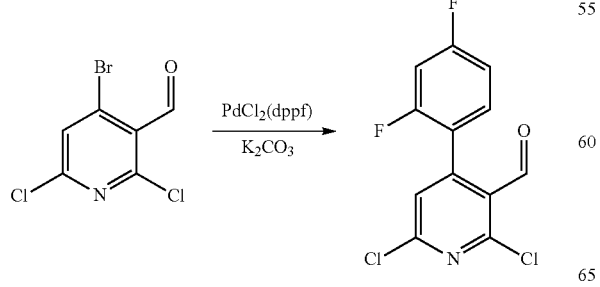

A mixture of (2,4-difluorophenyl)boronic acid (4.52 g, 28.6 mmol), 4-bromo-2,6-dichloronicotinaldehyde (7.3 g, 28.6 mmol) and Na$_2$CO$_3$ (6.07 g, 57.3 mmol) in 1,4-dioxane (120 mL) and water (12 mL) was added PdCl$_2$(dppf) (1.0 g, 1.4 mmol) under N$_2$. The mixture was heated to 100° C. for 2 h. After cooling to 20° C., the mixture was poured into water (500 mL) and extracted with ethyl acetate (2×500 mL), the combined organic layers were dried over Na$_2$SO$_4$, filtered and concentrated under reduced pressure. The residue was purified by silica gel chromatography (ISCO®; 80 g SepaFlash® Column, eluting with 0 to 3% ethyl acetate/petroleum ether) to give the title compound. $^1$H NMR (400 MHz, CDCl$_3$) δ 10.34 (s, 1H), 7.29-7.19 (m, 2H), 7.01 (dt, J=1.5, 8.3 Hz, 1H), 6.95-6.86 (m, 1H)

Intermediate 2-2

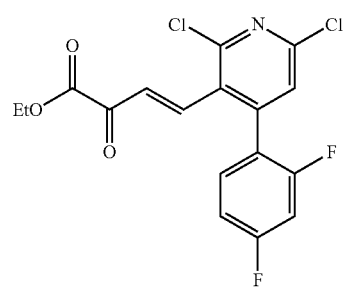 [SMILES: CCOC(=O)C(=O)/C=C/c1c(-c2ccc(F)cc2F)cc(Cl)nc1Cl]

ethyl (E)-4-(2,6-dichloro-4-(2,4-difluorophenyl)
pyridin-3-yl)-2-oxobut-3-enoate See procedure for Example 2-1A and 2-1B, Step 1
Intermediate 2-3

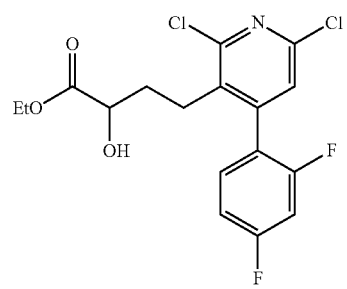 [SMILES: CCOC(=O)C(O)CCc1c(-c2ccc(F)cc2F)cc(Cl)nc1Cl]

ethyl 4-(2,6-dichloro-4-(2,4-difluorophenyl)pyridin-
3-yl)-2-hydroxybutanoate

See procedure for Example 2-1A and 2-1B, Step 2
Intermediate 2-4

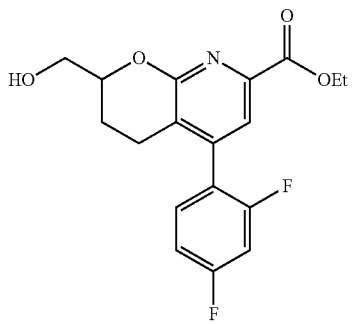 [SMILES: CCOC(=O)c1cc(-c2ccc(F)cc2F)c2c(n1)OC(CO)CC2]

ethyl 5-(2,4-difluorophenyl)-2-(hydroxymethyl)-3,4-
dihydro-2H-pyrano[2,3-b]pyridine-7-carboxylate See procedure for Example 2-1A and 2-1B, Step 5
Intermediates 2-5A, 2-5B, 2-5C and 2-5D

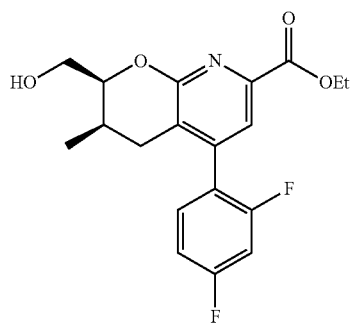

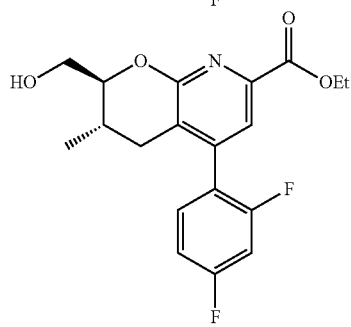

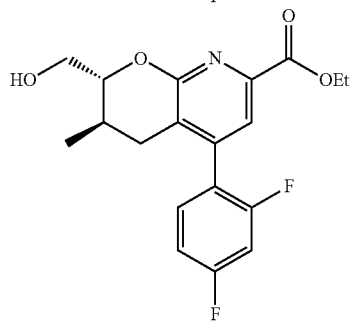

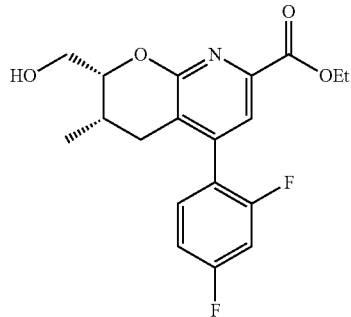

ethyl (2S,3R)-5-(2,4-difluoropheny)-2-(hydroxmethyl)-3-methyl-3,4-dihydro-2H-pyrano[2,3-b]pyridine-7-carboxylate, ethyl (2S,3S)-5-(2,4-difluorophenyl)-2-(hydroxymethyl)-3-methyl-3,4-dihydro-2H-pyrano[2,3-b]pyridine-7-carboxylate, ethyl (2R,3R)-5-(2,4-difluorophenyl)-2-(hydroxymethyl)-3-methyl-3,4-dihydro-2H-pyrano[2,3-b]pyridine-7-carboxylate and ethyl (2R,3S)-5-(2,4-difluoromethyl)-2-(hydroxymethyl)-3-methyl-3,4-dihydro-2H-pyrano[2,3-b]pyridine-7-carboxylate See procedure for Example 2-2A, 2-2B, 2-2C and 2-2D, Step 8

Intermediate 2-6

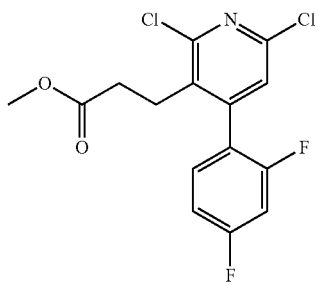 [SMILES: COC(=O)CCc1c(-c2ccc(F)cc2F)cc(Cl)nc1Cl]

methyl 3-(2,6-dichloro-4-(2,4-difluorophenyl)pyridin-3-yl)propanoate

See procedure for Example 2-3A and 2-3B, Step 3
Intermediate 2-7

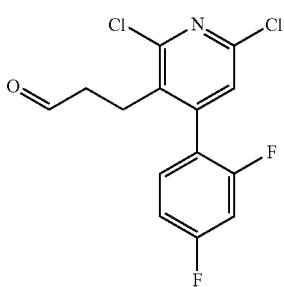 [SMILES: O=CCCc1c(-c2ccc(F)cc2F)cc(Cl)nc1Cl]

3-(2,6-dichloro-4-(2,4-difluorophenyl)pyridin-3-yl)propanal

See procedure for Example 2-3A and 2-3B, Step 5
Intermediate 3-1

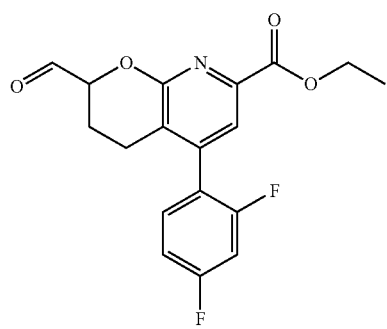 [SMILES: CCOC(=O)c1cc(-c2ccc(F)cc2F)c2c(n1)OC(C=O)CC2]

ethyl 5-(2,4-difluorophenyl)-2-formyl-3,4-dihydro-2H-pyrano[2,3-b]pyridine-7-carboxylate See procedure for Example 3-7A and 3-7B, Step 1

Intermediate 3-2

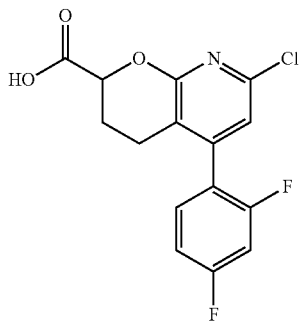 [SMILES: O=C(O)C1CCc2c(-c3ccc(F)cc3F)cc(Cl)nc2O1]

7-chloro-5-(2,4-difluorophenyl)-3,4-dihydro-2H-pyrano[2,3-b]pyridine-2-carboxylic acid See procedure for Example 2-9A, 2-9B, 2-9C and 2-9D, Step 1

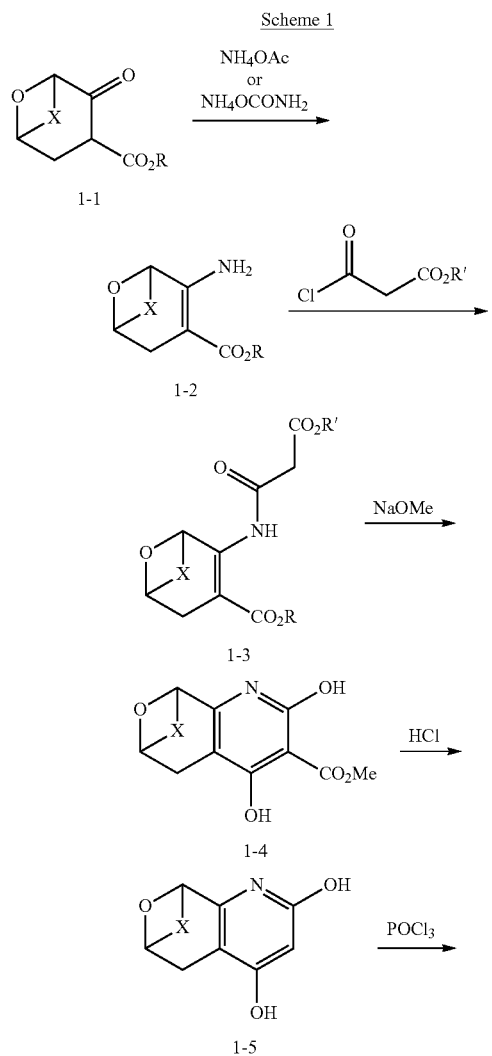

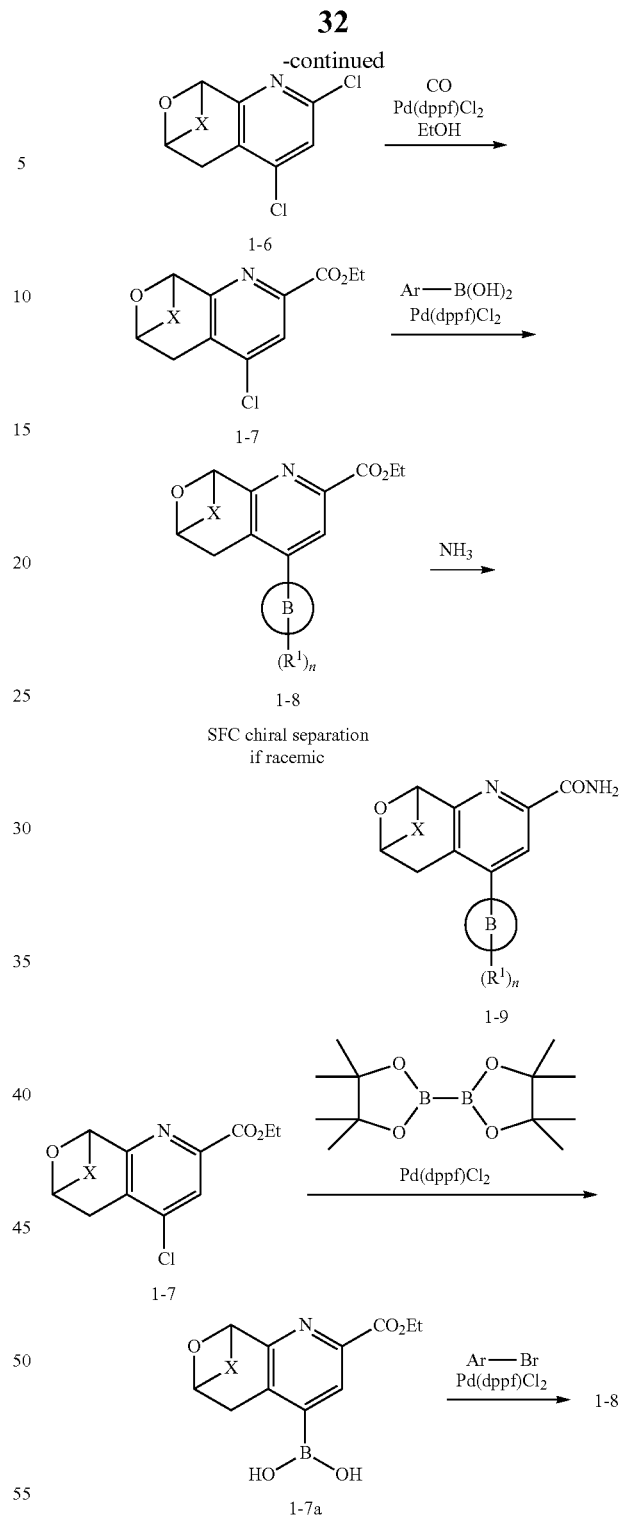

Compounds of Formula I (where in Scheme 1 X is a bridge of two methylenes or is not present, ring B, n, and each $R^1$ are as defined in Formula I, and R and R' are H or methyl) may be prepared according to Scheme 1 by the amination of aldehyde 1-1 followed by acylation and cyclization of 1-3 to form pyridine 1-4. Pyridine 1-4 is sequentially deacylated, chlorinated and carbonylated to generate chloropyridine 1-7. Chloropyridine 1-7 can either be coupled directly with an aromatic boronic acid, or itself be converted to a boronic acid 1-7a and coupled to an aromatic bromide, to form 1-8 which is treated with ammonia to furnish 1-9.

Example 1-1

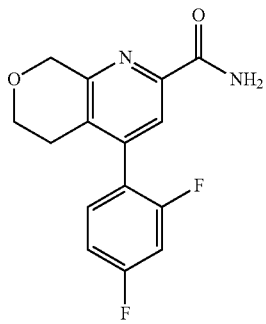 [SMILES: NC(=O)c1cc(-c2ccc(F)cc2F)c2c(n1)COCC2]

4-(2,4-difluorophenyl)-5,8-dihydro-6H-pyrano[3,4-b]pyridine-2-carboxamide

Step 1: Ethyl 5-amino-3,6-dihydro-2H-pyran-4-carboxylate

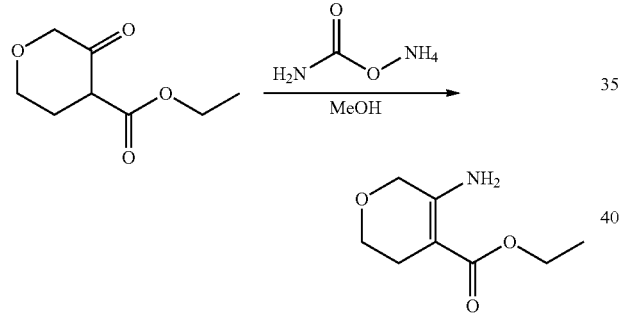

A mixture of methyl 5-(3-methoxy-3-oxopropyl)tetrahydrofuran-2-carboxylate (3 g, 17.4 mmol) and NH$_4$OCONH$_2$ (2.65 g, 34.9 mmol) in MeOH (20 mL) was stirred at 25° C. for 2 h. The mixture was concentrated under reduced pressure. The residue was purified by silica gel chromatography (eluting with 5:1 petroleum ether/ethyl acetate) to give the product. $^1$H NMR (400 MHz, CD$_3$OD) δ 4.17-4.03 (m, 4H), 3.73 (t, J=5.5 Hz, 2H), 2.37-2.19 (m, 2H), 1.24 (t, J=7.0 Hz, 3H).

Step 2: ethyl 5-(3-methoxy-3-oxopropanamido)-3,6-dihydro-2H-pyran-4-carboxylate

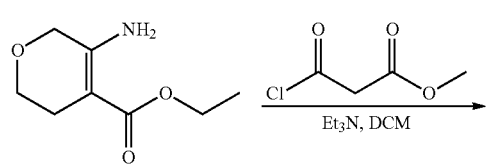

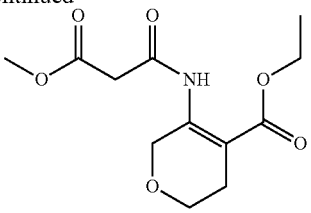

Ethyl 5-amino-3,6-dihydro-2H-pyran-4-carboxylate (2.6 g, 15 mmol) and Et$_3$N (6 mL, 45 mmol) were dissolved in DCM (50 mL), methyl 3-chloro-3-oxopropanoate (2.26 g, 16 mmol) was added and the resulting solution was stirred for 2 h at 0° C. The mixture was quenched with water (30 mL) and extracted with DCM (3×40 mL). The combined organic layers were washed with brine (30 mL), dried over Na$_2$SO$_4$, filtered and concentrated. The residue was purified by silica gel chromatography (eluting with 10:1 petroleum ether/ethyl acetate) to give the product. MS (ESI) calcd. for (C$_{12}$H$_{18}$NO$_6$) [M+H]$^+$, 272.1, found, 271.9. $^1$H NMR (400 MHz, CDCl$_3$) δ 4.77 (s, 1H), 4.17 (q, J=7.0 Hz, 1H), 3.79-3.63 (m, 3H), 3.35 (s, 1H), 2.38 (t, J=5.3 Hz, 1H), 1.24 (t, J=7.0 Hz, 3H).

Step 3: Methyl 2,4-dihydroxy-6,8-dihydro-5H-pyrano[3,4-b]pyridine-3-carboxylate

Ethyl 5-(3-methoxy-3-oxopropanamido)-3,6-dihydro-2H-pyran-4-carboxylate (1.15 g, 4 mmol) was dissolved in MeOH (15 mL), sodium methanolate (0.25 g, 4.6 mmol) was added and the resulting solution was stirred for 1 h at 80° C. The mixture was concentrated under reduced pressure to afford the product which was used in the next step without further purification. MS (ESI) calcd. for (C$_{10}$H$_{12}$NO$_5$) [M+H]$^+$, 225.0, found, 225.9. $^1$H NMR (400 MHz, CD$_3$OD) δ 4.18-4.03 (m, 3H), 3.73 (t, J=5.7 Hz, 2H), 2.27 (t, J=5.7 Hz, 2H), 1.24 (t, J=7.0 Hz, 2H).

Step 4: 6,8-dihydro-5H-pyrano[3,4-b]pyridine-2,4-diol

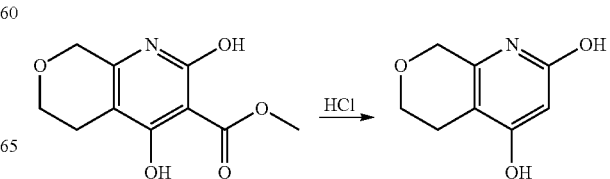

Aqueous HCl (6 M, 20 mL, 120 mmol) was added to methyl 2,4-dihydroxy-6,8-dihydro-5H-pyrano[3,4-b]pyridine-3-carboxylate (1 g, crude) and the mixture was stirred at 100° C. for 4 h. The solvent was removed under reduced pressure to give the product which was used in the next step without further purification. MS (ESI) calcd. for ($C_8H_{10}NO_3$) $[M+H]^+$, 168.0, found, 167.8.

Step 5: 2,4-dichloro-6,8-dihydro-5H-pyrano[3,4-b]pyridine

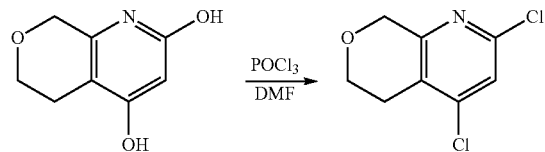

A mixture of 6,8-dihydro-5H-pyrano[3,4-b]pyridine-2,4-diol (0.9 g, crude) and DMF (5 mL, 64 mmol) in phosphoryl trichloride (4.3 mL, 48.5 mmol) was stirred at 80° C. for 12 h. The mixture was allowed to cool to room temperature and poured into ice-water and the mixture was adjusted to pH 9 with saturated aqueous $Na_2CO_3$. The mixture was extracted with EtOAc (3×50 mL). The combined organic layers were washed with brine (45 mL), dried over $Na_2SO_4$, filtered and concentrated. The residue was purified by silica gel chromatography (eluting with 100:0 to 20:1 petroleum ether/ethyl acetate) to give the product. MS (ESI) calcd. for ($C_8H_8Cl_2NO$) $[M+H]^+$, 204.0, found, 203.9. $^1$H NMR (400 MHz, $CDCl_3$) δ 7.29 (s, 1H), 5.10 (d, J=6.4 Hz, 1H), 4.86 (br. s., 1H), 3.24-3.12 (m, 2H), 2.52 (d, J=17.4 Hz, 2H), 2.11 (t, J=9.6 Hz, 2H).

Step 6: ethyl 4-chloro-6,8-dihydro-5H-pyrano[3,4-b]pyridine-2-carboxylate

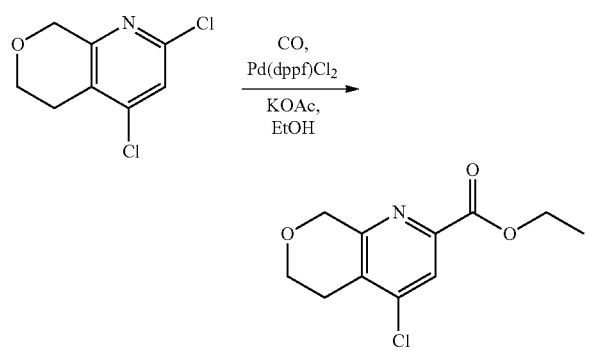

To a solution of 2,4-dichloro-6,8-dihydro-5H-pyrano[3,4-b]pyridine (100 mg, 0.49 mmol) in EtOH (20 mL) was added potassium acetate (96 mg, 0.98 mmol) and $PdCl_2$(dppf) (36 mg, 0.049 mmol) under $N_2$. The mixture was degassed and backfilled with CO (three times). The resulting mixture was stirred under 50 psi of CO at 60° C. for 1.5 h. The mixture was concentrated under reduced pressure to give the crude product, which was purified by silica gel chromatography (ISCO®; 40 g SepaFlash® Column, eluting with 0 to 20% ethyl acetate/petroleum ether at 40 mL/min) to furnish the product. MS (ESI) calcd. for ($C_{11}H_{12}ClNO_3$) $[M+H]^+$, 242.0, found, 241.9. $^1$H NMR (400 MHz, $CD_3OD$) δ 8.00 (s, 1H), 4.75 (s, 2H), 4.41 (q, J=7.2 Hz, 2H), 4.01 (t, J=5.9 Hz, 2H), 2.93 (t, J=5.7 Hz, 2H), 1.39 (t, J=7.2 Hz, 3H).

Step 7: Ethyl 4-(2,4-difluorophenyl)-6,8-dihydro-5H-pyrano[3,4-b]pyridine-2-carboxylate

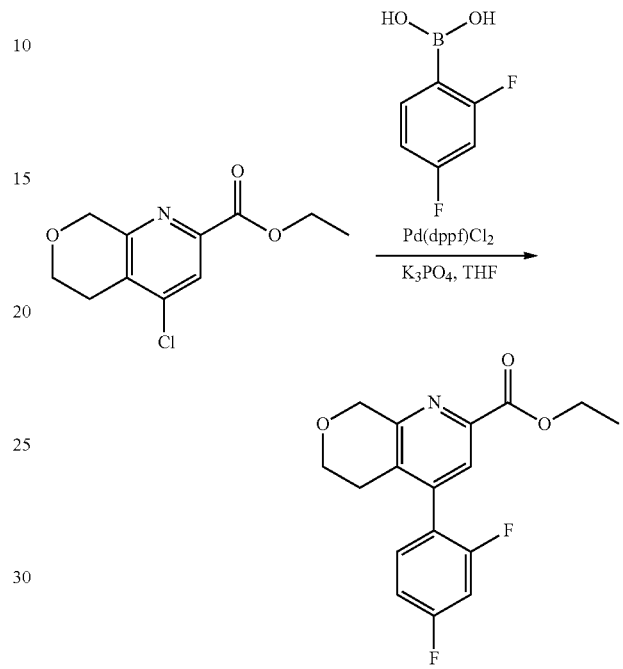

To a mixture of ethyl 4-chloro-6,8-dihydro-5H-pyrano[3,4-b]pyridine-2-carboxylate (100 mg, 0.613 mmol), (2,4-difluorophenyl)boronic acid (260 mg, 1.65 mmol) and $K_3PO_4$ (263 mg, 1.24 mmol) in THF (4.5 mL) and water (0.5 mL) was added $PdCl_2$(dppf) (51 mg, 0.082 mmol), and the mixture was degassed and backfilled with $N_2$ (three times). The mixture was heated to 80° C. for 2 h. The mixture was concentrated under reduced pressure to give the crude product, which was purified by Prep-TLC (silica gel, eluting with 1:1 ethyl acetate/petroleum ether) to give the product. MS (ESI) calcd. for ($C_{17}H_{16}F_2NO_3$) $[M+H]^+$, 320.1, found, 319.9. $^1$H NMR (400 MHz, $CD_3OD$) δ 7.85 (s, 1H), 7.46-7.34 (m, 1H), 7.13 (q, J=7.7 Hz, 2H), 4.41 (q, J=7.0 Hz, 2H), 4.03-3.85 (m, 2H), 2.80-2.66 (m, 2H), 1.39 (t, J=7.2 Hz, 3H).

Step 8: 4-(2,4-difluorophenyl)-6,8-dihydro-5H-pyrano[3,4-b]pyridine-2-carboxamide

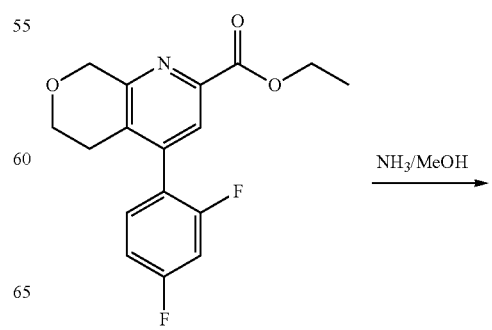

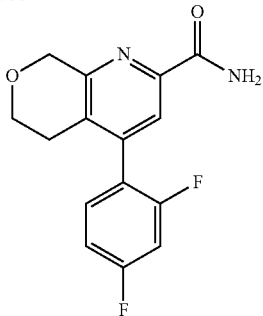

A mixture of ethyl 4-(2,4-difluorophenyl)-6,8-dihydro-5H-pyrano[3,4-b]pyridine-2-carboxylate (80 mg, 0.25 mmol) in NH$_3$ in MeOH (15 mL, 150 mmol) was stirred at 25° C. for 12 h. The mixture was concentrated under reduced pressure and purified by Prep-HPLC (Column: Agela ASB 150×25 mm, 5 um; Mobile phase: 30% to 60% water (containing 0.1% TFA)-ACN; Flow rate: 25 mL/min) to give the title compound. MS (ESI) calcd. for (C$_{15}$H$_{14}$F$_2$N$_2$O$_2$) [M+H]$^+$, 291.1, found, 291.0. $^1$H NMR (400 MHz, CD$_3$OD) δ 7.82 (s, 1H), 7.44-7.32 (m, 1H), 7.18-7.05 (m, 2H), 3.93 (t, J=5.7 Hz, 2H), 2.70 (t, J=5.3 Hz, 2H).

Example 1-2A and 1-2B

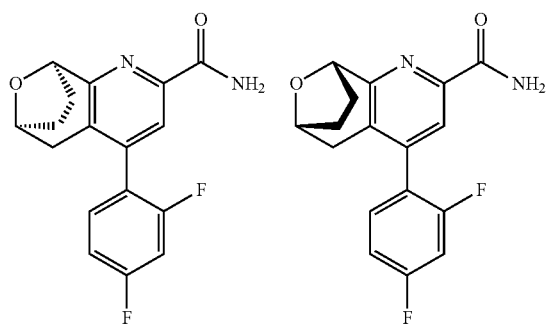

(6S,9R)-4-(2,4-difluorophenyl)-6,7,89-tetrahydro-5H-6,9-epoxycyclohepta[b]pyridine-2-carboxamide and (6R,9S)-4-(2,4-difluorophenyl)-6,7,8,9-tetrahydro-5H-6,9-epoxycyclohepta[b]pyridine-2-carboxamide Step 1: methyl 5-(3-methoxy-3-oxopropyl)furan-2-carboxylate

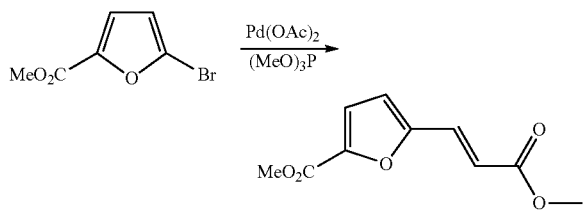

A mixture of methyl 5-bromofuran-2-carboxylate (10 g, 64 mmol), methyl acrylate (16.5 g, 192 mmol), (MeO)$_3$P (0.4 g, 0.32 mmol), Et$_3$N (17 mL, 128 mmol) and Pd(OAc)$_2$ (0.36 g, 0.16 mmol) in DMF (120 mL) was degassed and backfilled with N$_2$ (three times). The mixture was heated to 110° C. for 3 h. The cooled mixture was filtered off and the filtrate was concentrated under reduced pressure. The residue was purified by silica gel chromatography (eluting with 5:1 petroleum ether/ethyl acetate) to give the product. $^1$H NMR (400 MHz, CDCl$_3$) δ 7.45 (d, J=15.9 Hz, 1H), 7.20 (d, J=3.5 Hz, 1H), 6.68 (d, J=3.5 Hz, 1H), 6.57 (d, J=15.9 Hz, 1H), 3.92 (s, 3H), 3.81 (s, 3H).

Step 2: methyl 5-(3-methoxy-3-oxopropyl)tetrahydrofuran-2-carboxylate

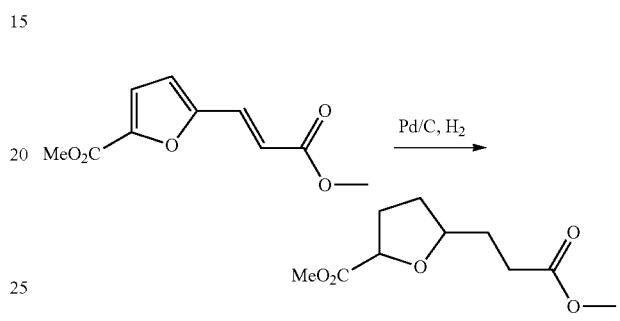

To a solution of methyl 5-(3-methoxy-3-oxopropyl)furan-2-carboxylate (4.7 g, 22 mmol) in ethyl acetate (100 mL) was added Pd/C (1 g) (10% wt) under N$_2$ atmosphere. The mixture was degassed and backfilled with H$_2$ (three times). The resulting mixture was stirred under 40 psi of H$_2$ at 50° C. for 15 h. The mixture was filtered and the filtrate was concentrated under reduced pressure to give the product which was used in subsequent steps without further purification. $^1$H NMR (400 MHz, CDCl$_3$) δ 4.42 (dd, J=5.0, 8.5 Hz, 1H), 4.07-3.95 (m, 1H), 3.74-3.67 (m, 3H), 3.64 (s, 3H), 2.57-2.36 (m, 2H), 2.20 (qd, J=8.4, 12.6 Hz, 1H), 2.11-1.81 (m, 5H), 1.58 (qd, J=8.2, 11.9 Hz, 1H).

Step 3: methyl 2-oxo-8-oxabicyclo[3.2.1]octane-3-carboxylate

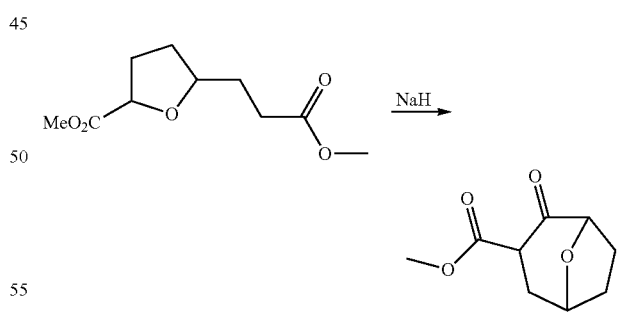

To a mixture of methyl 5-(3-methoxy-3-oxopropyl)tetrahydrofuran-2-carboxylate (4.6 g, 21 mmol) in THF (60 mL) was added NaH (840 mg, 60% in oil) slowly under N$_2$ and the mixture was heated at reflux for 6 h. The reaction was quenched with NH$_4$Cl (50 mL) and extracted with ethyl acetate (3×50 mL). The combined organic layers were washed with brine (60 mL), dried over Na$_2$SO$_4$, filtered and concentrated under reduced pressure. The residue was purified by silica gel chromatography (eluting with 5:1 petroleum ether/ethyl acetate) to give the product. $^1$H NMR (400

MHz, CDCl₃) δ 4.65-4.48 (m, 1H), 4.41-4.22 (m, 1H), 3.75-3.64 (m, 1H), 2.69 (dd, J=4.9, 15.7 Hz, 1H), 2.40-2.29 (m, 1H), 2.18-2.01 (m, 3H), 1.94-1.72 (m, 2H).

Step 4: methyl 2-amino-8-oxabicyclo[3.2.1]oct-2-ene-3-carboxylate

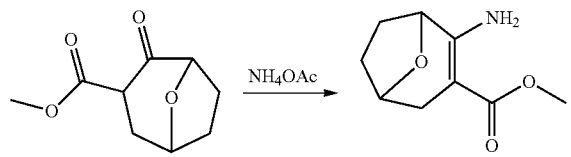

A mixture of methyl 2-oxo-8-oxabicyclo[3.2.1]octane-3-carboxylate (200 mg, 1.08 mmol) and NH₄OAc (770 mg, 10 mmol) in MeOH was stirred in a sealed tube at 90° C. for 15 h. The mixture was concentrated under reduced pressure. The residue was dissolved in water (10 mL) and extracted with ethyl acetate (5×15 mL). The combined organic layers were washed with brine (30 mL), dried over Na₂SO₄, filtered and concentrated under reduced pressure. The residue was purified by silica gel chromatography (eluting with 5:1 petroleum ether/ethyl acetate) to give the product. ¹H NMR (400 MHz, CDCl₃) δ 4.52 (t, J=5.0 Hz, 1H), 4.38 (br. s., 1H), 3.52 (s, 3H), 2.56 (d, J=5.3 Hz, 1H), 2.00-1.82 (m, 5H), 1.58 (t, J=8.2 Hz, 1H).

Step 5: Methyl 2-(3-ethoxy-3-oxopropanamido)-8-oxabicyclo[3.2.1]oct-2-ene-3-carboxylate

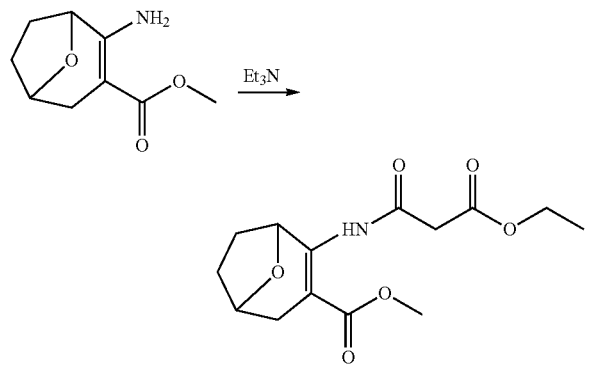

Methyl 2-amino-8-oxabicyclo[3.2.1]oct-2-ene-3-carboxylate (490 mg, 2.67 mmol) and Et₃N (0.7 mL, 5.3 mmol) were dissolved in DCM (20 mL), ethyl-3-chloro-3-oxopropanoate (481 mg, 3.1 mmol) was added and the resulting solution was stirred for 2 h at 20° C. The mixture was quenched with water (15 mL) and extracted with ethyl acetate (3×20 mL). The combined organic layers were washed with brine (20 mL), dried over Na₂SO₄, filtered and concentrated. The residue was purified by silica gel chromatography (eluting with 4:1 petroleum ether/ethyl acetate) to give the product. MS (ESI) calcd. for (C₁₄H₂₀NO₆) [M+H]⁺, 298.1, found, 298.1.

Step 6: methyl 2,4-dihydroxy-6,7,8,9-tetrahydro-5H-6,9-epoxycyclohepta[b]pyridine-3-carboxylate

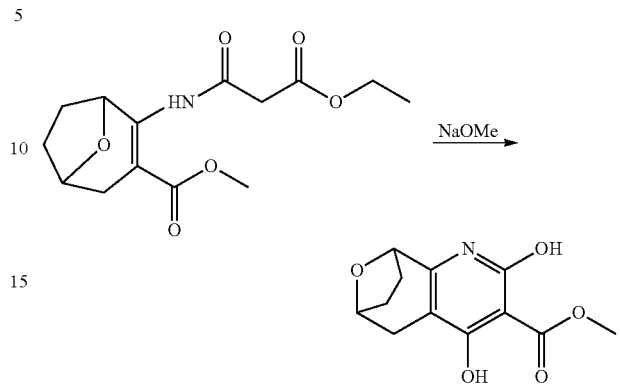

Methyl 2-(3-ethoxy-3-oxopropanamido)-8-oxabicyclo [3.2.1]oct-2-ene-3-carboxylate (4.8 g, 16 mmol) was dissolved in MeOH (80 mL), sodium methanolate (368 mg, 16.1 mmol) was added and the resulting solution was stirred for 1.5 h at 80° C. The cooled mixture was filtered and concentrated under reduced pressure to afford the product which was used in the next step without further purification. MS (ESI) calcd. for (C₁₂H₁₄NO₅) [M+H]⁺, 252.1, found, 252.0.

Step 7: 6,7,8,9-tetrahydro-5H-6,9-epoxycyclohepta[b]pyridine-2,4-diol

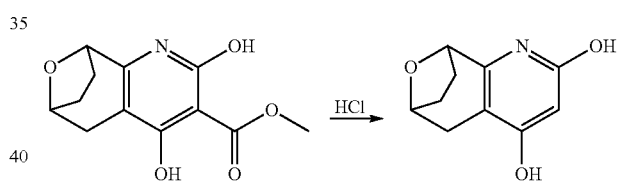

Aqueous HCl (20 mL, 120 mmol, 6 M) was added to methyl 2,4-dihydroxy-6,7,8,9-tetrahydro-5H-6,9-epoxycyclohepta[b]pyridine-3-carboxylate (1.2 g, 4.8 mmol) and the mixture was stirred at 100° C. for 20 h. The mixture was extracted with 3:1 DCM/i-PrOH (4×100 mL). The combined organic layers were dried over anhydrous Na₂SO₄ and concentrated under reduced pressure to give the product which was used in the next step without further purification. MS (ESI) calcd. for (C₁₀H₁₁NO₃) [M+H]⁺, 194.1, found, 193.9.

Step 8: 2,4-dichloro-6,7,8,9-tetrahydro-5H-6,9-epoxycyclohepta[b]pyridine

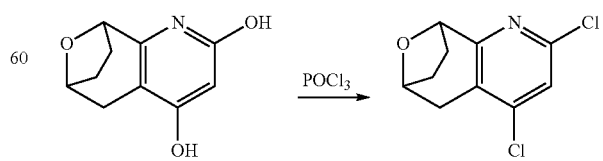

A mixture of 6,7,8,9-tetrahydro-5H-6,9-epoxycyclohepta [b]pyridine-2,4-diol (1.2 g, 6.21 mmol) and DMF (6.5 mL, 6.21 mmol) in phosphoryl trichloride (8.48 g, 55.3 mmol) was stirred at 90° C. for 15 h. DMF (0.2 mL) was added and the mixture was stirred at 90° C. for 15 h. The cooled mixture was poured into ice-water and the pH was adjusted to 7 with Sat'd. NaHCO$_3$. The mixture was extracted with ethyl acetate (3×50 mL). The combined organic layers were washed with brine (45 mL), dried over Na$_2$SO$_4$, filtered and concentrated, the residue was purified by silica gel chromatography (eluting with 4:1 petroleum ether/ethyl acetate) to give the product. MS (ESI) calcd. for (C$_{10}$H$_{10}$Cl$_2$NO) [M+H]$^+$, 230.0, found, 230.1. $^1$H NMR (400 MHz, CDCl$_3$) δ 7.29 (s, 1H), 5.10 (d, J=6.4 Hz, 1H), 4.86 (br. s., 1H), 3.24-3.12 (m, 2H), 2.52 (d, J=17.4 Hz, 2H), 2.11 (t, J=9.6 Hz, 2H).

Step 9: ethyl 4-chloro-6,7,8,9-tetrahydro-5H-6,9-epoxycyclohepta[b]pyridine-2-carboxylate

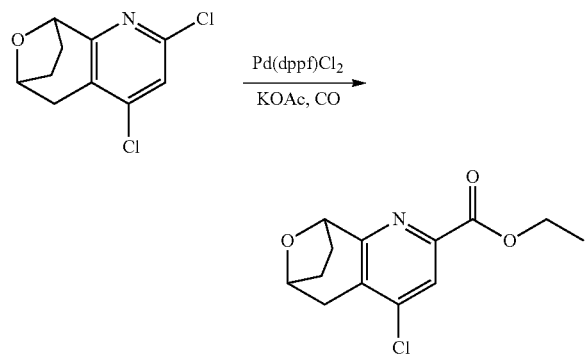

To a solution of 2,4-dichloro-6,7,8,9-tetrahydro-5H-6,9-epoxycyclohepta[b]pyridine (330 mg, 1.434 mmol) in EtOH (10 mL) was added potassium acetate (282 mg, 2.87 mmol) and PdCl$_2$(dppf) (105 mg, 0.143 mmol) under N$_2$ atmosphere. The mixture was degassed and backfilled with CO (three times). The resulting mixture was stirred under 50 psi of CO at 80° C. for 2 h. The mixture was concentrated under reduced pressure to give the crude product, which was purified by silica gel chromatography (ISCO®; 40 g SepaFlash® Column, eluting with 0 to 20% ethyl acetate/petroleum ether) to furnish the product. MS (ESI) calcd. for (C$_{13}$H$_{15}$ClNO$_3$) [M+H]$^+$, 268.1, found, 268.1.

Step 10: ethyl 4-(2,4-difluorophenyl)-6,7,8,9-tetrahydro-5H-6,9-epoxycyclohepta[b]pyridine-2-carboxylate

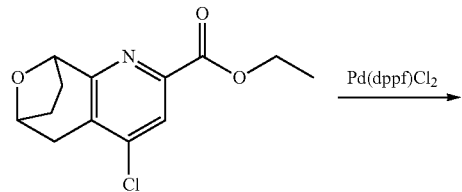

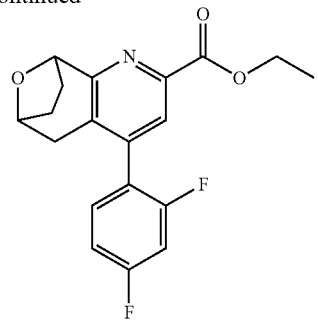

To a mixture of ethyl 4-chloro-6,7,8,9-tetrahydro-5H-6,9-epoxycyclohepta[b]pyridine-2-carboxylate (140 mg, 0.523 mmol), (2,4-difluorophenyl)boronic acid (165 mg, 1.046 mmol) and K$_2$CO$_3$ (145 mg, 1.046 mmol) in 1,4-dioxane (5 mL) and water (0.5 mL) was added PdCl$_2$(dppf) (38.3 mg, 0.052 mmol). The mixture was degassed and backfilled with N$_2$ (three times) then heated to 100° C. for 2 h. The mixture was concentrated under reduced pressure to give the crude product, which was purified by silica gel chromatography (ISCO®; 40 g SepaFlash® Column, eluting with of 0 to 30% ethyl acetate/petroleum ether) to give the product. MS (ESI) calcd. for (C$_{19}$H$_{18}$F$_2$NO$_3$) [M+H]$^+$, 346.1, found, 346.0. $^1$H NMR (400 MHz, CDCl$_3$) δ 7.86 (s, 1H), 7.21 (d, J=6.26 Hz, 1H), 6.91-7.06 (m, 2H), 5.37 (d, J=6.26 Hz, 1H), 4.73-4.80 (m, 1H), 4.49 (d, J=7.04 Hz, 2H), 3.12-3.22 (m, 1H), 2.20-2.36 (m, 4H), 1.57-1.76 (m, 2H), 1.43 (t, J=7.04 Hz, 3H).

Step 11: ethyl (6S,9R)-4-(2,4-difluorophenyl)-6,7,8,9-tetrahydro-5H-6,9-epoxycyclohepta[b]pyridine-2-carboxylate and ethyl (6R,9S)-4-(2,4-difluorophenyl)-6,7,8,9-tetrahydro-5H-6,9-epoxycyclohepta[b]pyridine-2-carboxylate

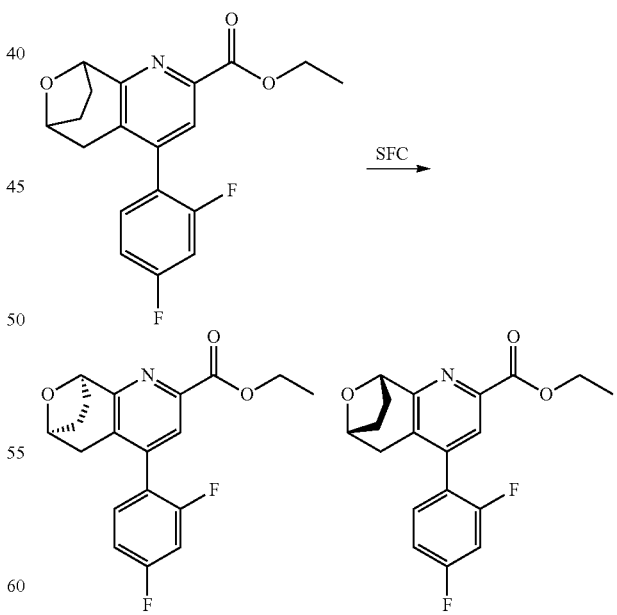

Racemic ethyl 4-(2,4-difluorophenyl)-6,7,8,9-tetrahydro-5H-6,9-epoxycyclohepta[b]pyridine-2-carboxylate (100 mg, 0.290 mmol) was resolved via chiral SFC (Column: Chiralpak AD 250×30 mm, 5 um; Mobile phase: 15% to 15% EtOH (containing 0.05% DEA) in CO$_2$; Flow rate: 60 mL/min) to give the two enantiomers.

Step 12: (6S,9R)-4-(2,4-difluorophenyl)-6,7,8,9-tetrahydro-5H-6,9-epoxycyclohepta[b]pyridine-2-carboxamide and (6R,9S)-4-(2,4-difluorophenyl)-6,7,8,9-tetrahydro-5H-6,9-epoxycyclohepta[b]pyridine-2-carboxamide

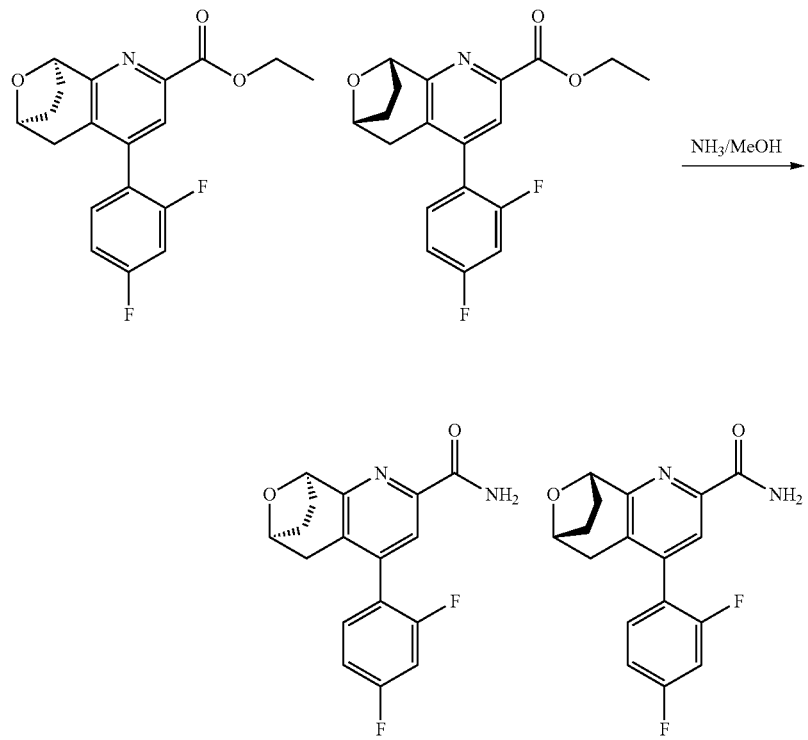

One enantiomer of ethyl 4-(2,4-difluorophenyl)-6,7,8,9-tetrahydro-5H-6,9-epoxycyclohepta[b]pyridine-2-carboxylate (40 mg, 0.116 mmol) was mixed with ammonia in MeOH (15 mL, 150 mmol) and stirred at 20° C. for 17 h. The mixture was concentrated under reduced pressure to give one enantiomer of the title compound. MS (ESI) calcd. for ($C_{17}H_{15}F_2N_2O_2$) [M+H]$^+$, 317.1, found, 317.0. $^1$H NMR (400 MHz, CD$_3$OD) δ 7.82 (s, 1H), 7.31-7.41 (m, 1H), 7.07-7.18 (m, 2H), 5.17 (d, J=5.95 Hz, 1H), 4.75 (t, J=5.84 Hz, 1H), 3.11 (br. s., 1H), 2.03-2.39 (m, 5H), 1.69 (br. s., 1H).

Similar treatment of the other enantiomer of ethyl 4-(2,4-difluorophenyl)-6,7,8,9-tetrahydro-5H-6,9-epoxycyclohepta[b]pyridine-2-carboxylate afforded the other enantiomer of the title compound. MS (ESI) calcd. for ($C_{17}H_{15}F_2N_2O_2$) [M+H]$^+$, 317.1, found, 317.0. $^1$H NMR (400 MHz, CD$_3$OD) δ 7.81 (s, 1H), 7.36 (d, J=6.39 Hz, 1H), 7.07-7.18 (m, 2H), 5.17 (d, J=5.95 Hz, 1H), 4.74 (br. s., 1H), 3.12 (dd, J=17.42, 5.29 Hz, 1H), 2.03-2.39 (m, 4H), 1.62-1.72 (m, 1H).

The following compounds were prepared according to the procedures described above.

| Example | Structure | Name | MS (ESI) calcd | MS (ESI) found | $^1$H NMR |
|---|---|---|---|---|---|
| 1-3A | 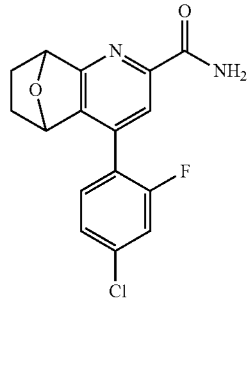 [SMILES: NC(=O)c1cc(-c2ccc(Cl)cc2F)c2c(n1)C1CCC2O1] | (6S,9R)- or (6R,9S)-4-(4-chloro-2-fluorophenyl)-6,7,8,9-tetrahydro-5H-6,9-epoxycyclohepta[b]pyridine-2-carboxamide | 333.07 | 333.0 | (400 MHz, CD$_3$OD)δ 7.85 (s, 1H), 7.33-7.45 (m, 3H), 5.21 (d, J = 5.87 Hz, 1H), 4.78 (t, J = 5.48 Hz, 1H), 3.15 (dd, J = 17.61, 5.09 Hz, 1H), 2.37 (d, J = 17.22 Hz, 1H), 2.17-2.31 (m, 2H), 2.08-2.16 (m, 1H), 1.66-1.78 (m, 1H). |

-continued

| Example | Structure | Name | MS (ESI) calcd | MS (ESI) found | ¹H NMR |
|---|---|---|---|---|---|
| 1-3B | 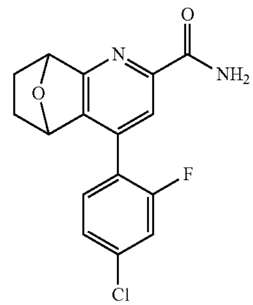 [SMILES: NC(=O)c1cc(-c2ccc(Cl)cc2F)c2c(n1)C1CCC2O1] | (6R,9S)- or (6S,9R)-4-(4-chloro-2-fluorophenyl)-6,7,8,9-tetrahydro-5H-6,9-epoxycyclohepta[b]pyridine-2-carboxamide | 333.07 | 333.0 | (400 MHz, CD$_3$OD) δ 7.45 (s, 1H), 6.92-7.04 (m, 3H), 4.80 (d, J = 5.87 Hz, 1H), 4.38 (t, J = 5.67 Hz, 1H), 2.75 (dd, J = 17.41, 5.28 Hz, 1H), 1.96 (d, J = 17.61 Hz, 1H), 1.79-1.91 (m, 2H), 1.68-1.75 (m, 1H), 1.25-1.37 (m, 1H). |
| 1-4A | 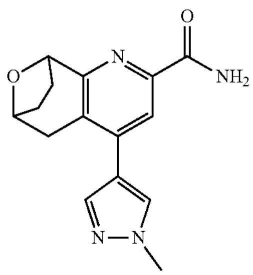 [SMILES: Cn1cc(-c2cc(C(N)=O)nc3c2CC2CCC3O2)cn1] | (6R,9S)- or (6S,9R)-4-(1-methyl-1H-pyrazol-4-yl)-6,7,8,9-tetrahydro-5H-6,9-epoxycyclohepta[b]pyridine-2-carboxamide | 285.1 | 285.1 | (400 MHz, CDCl$_3$) δ 8.10 (s, 1H), 7.89 (br. s., 1H), 7.82 (s, 1H), 7.72 (s, 1H), 5.88 (br. s., 1H), 5.14 (d, J = 5.73 Hz, 1H), 4.78-4.96 (m, 1H), 3.99 (s, 3H), 3.41 (dd, J = 5.18, 16.87 Hz, 1H), 2.59 (d, J = 16.76 Hz, 1H), 2.17-2.37 (m, 2H), 1.99-2.13 (m, 1H), 1.55-1.76 (m, 1H). |
| 1-4B | 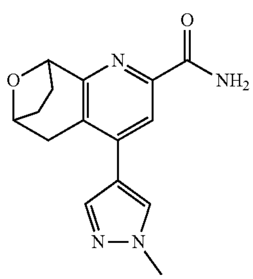 [SMILES: Cn1cc(-c2cc(C(N)=O)nc3c2CC2CCC3O2)cn1] | (6S,9R)- or (6R,9S)-4-(1-methyl-1H-pyrazol-4-yl)-6,7,8,9-tetrahydro-5H-6,9-epoxycyclohepta[b]pyridine-2-carboxamide | 285.1 | 285.1 | (400 MHz, CDCl$_3$) δ 8.10 (s, 1H), 7.97 (br. s., 1H), 7.83 (s, 1H), 7.73 (s, 1H), 6.29 (br. s., 1H), 5.15 (d, J = 5.51 Hz, 1H), 4.73-4.99 (m, 1H), 4.00 (s, 3H), 3.41 (dd, J = 5.18, 16.87 Hz, 1H), 2.60 (d, J = 16.98 Hz, 1H), 2.17-2.36 (m, 2H), 1.98-2.14 (m, 1H), 1.53-1.76 (m, 1H). |
| 1-5A | 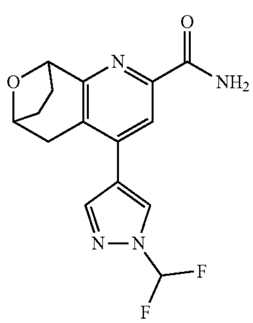 [SMILES: NC(=O)c1cc(-c2cnn(C(F)F)c2)c2c(n1)C1CCC(C2)O1] | (6R,9S)- or (6S,9R)-4-(1-(difluoromethyl)-1H-pyrazol-4-yl)-6,7,8,9-tetrahydro-5H-6,9-epoxycyclohepta[b]pyridine-2-carboxamide | 321.1 | 321.1 | (400 MHz, CDCl$_3$) δ 8.12 (s, 2H), 8.04 (br. s., 1H), 7.98 (s, 1H), 7.42 (s, 0.24H), 7.25-7.27 (m, 0.52H), 7.12 (s, 0.24H), 6.74 (br. s., 1H), 5.19 (d, J = 5.73 Hz, 1H), 4.76-5.02 (m, 1H), 3.44 (dd, J = 5.29, 16.98 Hz, 1H), 2.60 (d, J = 16.98 Hz, 1H), 2.19-2.43 (m, 2H), 1.95-2.15 (m, 1H), 1.54-1.78 (m, 1H). |
| 1-5B | 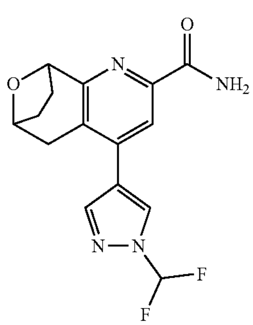 [SMILES: NC(=O)c1cc(-c2cnn(C(F)F)c2)c2c(n1)C1CCC(C2)O1] | (6S,9R)- or (6R,9S)-4-(1-(difluoromethyl)-1H-pyrazol-4-yl)-6,7,8,9-tetrahydro-5H-6,9-epoxycyclohepta[b]pyridine-2-carboxamide | 321.1 | 321.1 | (400 MHz, CDCl$_3$) δ 8.12 (d, J = 3.09 Hz, 2H), 7.98 (s, 2H), 7.42 (s, 0.24H), 7.25-7.27 (m, 0.54H), 7.12 (s, 0.24H), 6.36 (br. s., 1H), 5.18 (d, J = 5.95 Hz, 1H), 4.78-4.98 (m, 1H), 3.44 (dd, J = 5.29, 16.98 Hz, 1H), 2.60 (d, J = 16.98 Hz, 1H), 2.19-2.43 (m, 2H), 1.98-2.15 (m, 1H), 1.60-1.79 (m, 1H). |

Example 1-6A and 1-6B

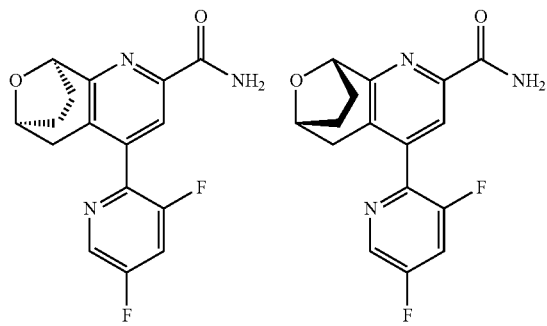

(6S,9R)-4-(3,5-difluoropyridin-2-yl)-6,7,8,9-tetrahydro-5H-6,9-epoxycyclohepta[b]pyridine-2-carboxamide and (6R,9S)-4-(3,5-difluoropyridin-2-yl)-6,7,8,9-tetrahydro-5H-6,9-epoxycyclohepta[b]pyridine-2-carboxamide

Step 1: (2-(ethoxycarbonyl)-6,7,8,9-tetrahydro-5H-6,9-epoxycyclohepta[b]pyridin-4-yl)boronic acid

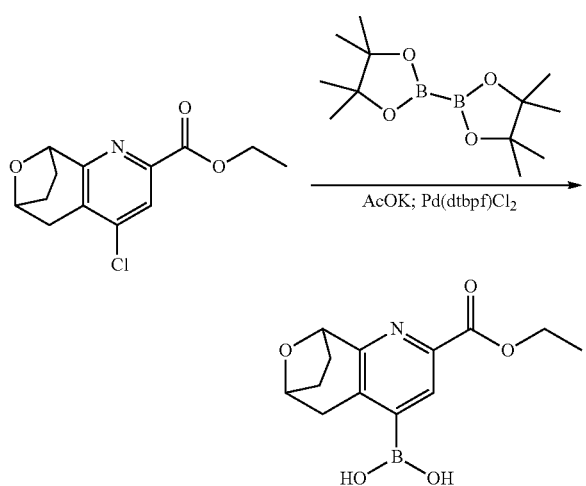

A mixture of ethyl 4-chloro-6,7,8,9-tetrahydro-5H-6,9-epoxycyclohepta[b]pyridine-2-carboxylate (Example 1-2 Step 9) (200 mg, 0.75 mmol), 4,4,4',4',5,5,5',5'-octamethyl-2,2'-bi(1,3,2-dioxaborolane) (1900 mg, 7.5 mmol), Pd(dtbpf)Cl₂ (48.7 mg, 0.08 mmol) and AcOK (220 mg, 2.2 mmol) in 1,4-dioxane (5 mL) was stirred at 100° C. under N₂ for 2 h. The mixture was concentrated under reduced pressure. The residue was purified by Prep-HPLC (Column: Waters Xbridge Prep OBD C18 100×19 mm, 5 um; Mobile phase: 28% to 58% water (containing 0.05% ammonia hydroxide v/v)-ACN; Flow rate: 25 mL/min) to give the product. MS (ESI) calcd. for (C₁₃H₁₇BNO₅) [M+H]⁺, 278.1, found, 277.9.

Step 2: Ethyl 4-(3,5-difluoropyridin-2-yl)-6,7,8,9-tetrahydro-5H-6,9-epoxycyclohepta[b]pyridine-2-carboxylate

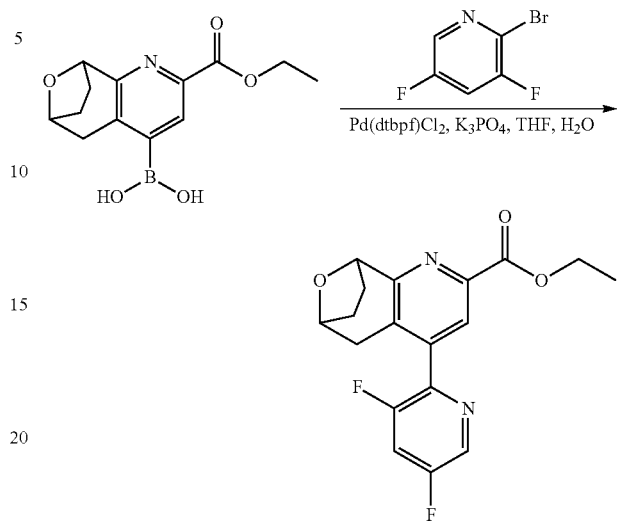

A mixture of (2-(ethoxycarbonyl)-6,7,8,9-tetrahydro-5H-6,9-epoxycyclohepta[b]pyridin-4-yl)boronic acid (100 mg, 0.361 mmol), 2-bromo-3,5-difluoropyridine (140 mg, 0.722 mmol), Pd(dtbpf)Cl₂ (23.5 mg, 0.04 mmol) and K₃PO₄ (230 mg, 1.08 mmol) in THF (5 mL) and H₂O (1 mL) was stirred at 80° C. under N₂ for 2 h. The mixture was concentrated under reduced pressure, and purified by Prep-HPLC (Column: Phenomenex Synergi C18 150×30 mm, 4 um; Mobile phase: 41% to 61% water (containing 0.1% TFA)-ACN; Flow rate: 25 mL/min) to give the product. MS (ESI) calcd. for (C₁₈H₁₇F₂N₂O₃) [M+H]⁺, 347.1, found, 346.9.

Step 3: ethyl (6R,9S)-4-(3,5-difluoropyridin-2-yl)-6,7,8,9-tetrahydro-5H-6,9-epoxycyclohepta[b]pyridine-2-carboxylate and ethyl (6S,9R)-4-(3,5-difluoropyridin-2-yl)-6,7,8,9-tetrahydro-5H-6,9-epoxycyclohepta[b]pyridine-2-carboxylate

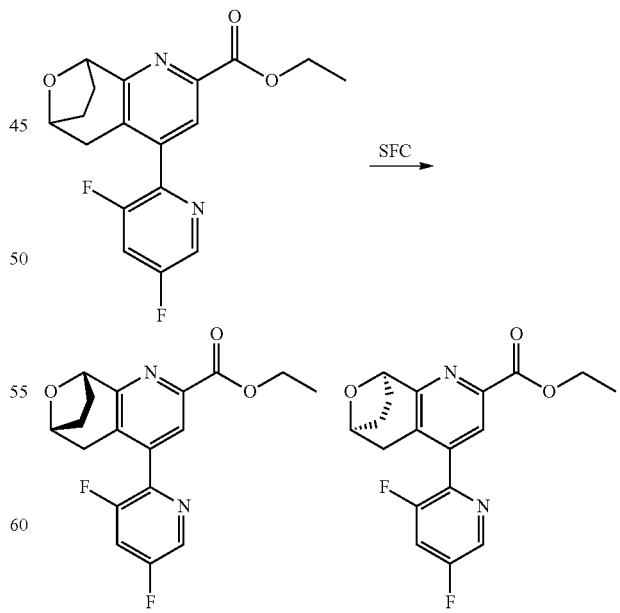

Racemic ethyl 4-(3,5-difluoropyridin-2-yl)-6,7,8,9-tetrahydro-5H-6,9-epoxycyclohepta[b]pyridine-2-carboxylate (30 mg, 0.087 mmol) was resolved by chiral SFC (Column:

Chiralpak AD 250×30 mm, 10 um; Mobile phase: 45% EtOH (containing 0.05% DEA) in $CO_2$; Flow rate: 80 mL/min) to give the two enantiomers.

Step 4: (6R,9S)-4-(3,5-difluoropyridin-2-yl)-6,7,8,9-tetrahydro-5H-6,9-epoxycyclohepta[b]pyridine-2-carboxamide and (6S,9R)-4-(3,5-difluoropyridin-2-yl)-6,7,8,9-tetrahydro-5H-6,9-epoxycyclohepta[b]pyridine-2-carboxamide

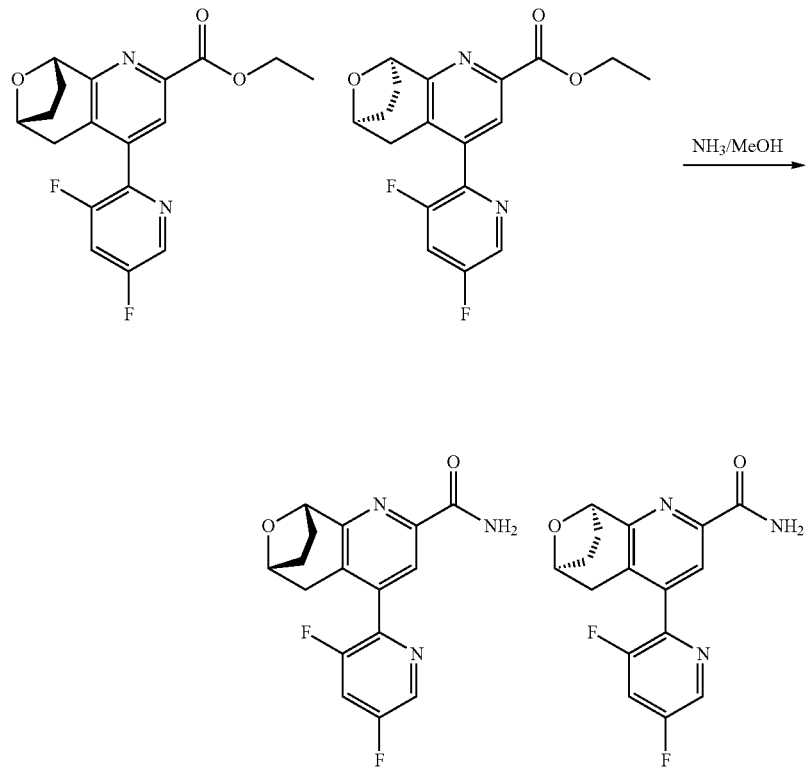

A solution of one enantiomer of ethyl 4-(3,5-difluoropyridin-2-yl)-6,7,8,9-tetrahydro-5H-6,9-epoxycyclohepta[b]pyridine-2-carboxylate (12 mg, 0.035 mmol) in ammonia (10M in MeOH) (20 mL) was stirred at 26° C. for 12 h. The mixture was concentrated under reduced pressure and purified by Prep-HPLC (Column: Phenomenex Synergi C18 150×30 mm, 4 um; Mobile phase: 25% to 45% water (containing 0.1% TFA)-ACN; Flow rate: 25 mL/min) to give one enantiomer of the title compound. MS (ESI) calcd. for ($C_{16}H_{14}F_2N_3O_2$) $[M+H]^+$, 318.1, found, 317.9. $^1$H NMR (400 MHz, $CD_3OD$) δ 8.53 (s, 1H), 7.96 (s, 1H), 7.79 (t, J=8.38 Hz, 1H), 5.19 (d, J=5.95 Hz, 1H), 4.68-4.79 (m, 1H), 3.25 (dd, J=5.40, 17.75 Hz, 1H), 2.48 (d, J=17.86 Hz, 1H), 2.07-2.32 (m, 4H), 1.71 (br. s., 1H).

Similar treatment of the other enantiomer of ethyl 4-(3,5-difluoropyridin-2-yl)-6,7,8,9-tetrahydro-5H-6,9-epoxycyclohepta[b]pyridine-2-carboxylate afforded the other enantiomer of the title compound. MS (ESI) calcd. for ($C_{16}H_{14}F_2N_3O_2$) $[M+H]^+$, 318.1, found, 317.9. $^1$H NMR (400 MHz, $CD_3OD$) δ 8.53 (s, 1H), 7.97 (s, 1H), 7.79 (t, J=8.16 Hz, 1H), 5.19 (d, J=5.51 Hz, 1H), 4.65-4.80 (m, 1H), 3.20-3.27 (m, 1H), 2.48 (d, J=17.42 Hz, 1H), 2.16-2.31 (m, 2H), 2.05-2.16 (m, 1H), 1.71 (br. s., 1H).

Example 1-7A and 1-7B

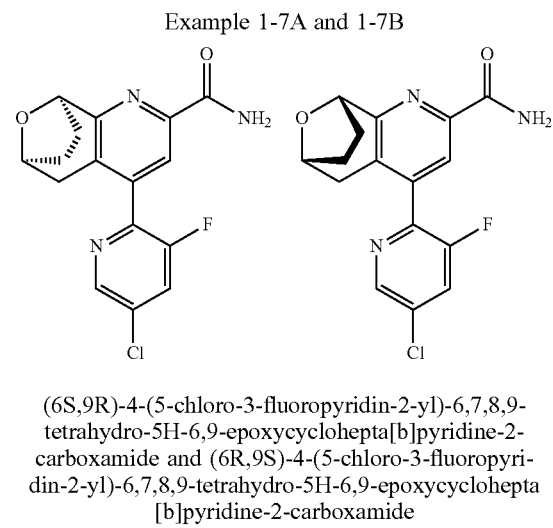

(6S,9R)-4-(5-chloro-3-fluoropyridin-2-yl)-6,7,8,9-tetrahydro-5H-6,9-epoxycyclohepta[b]pyridine-2-carboxamide and (6R,9S)-4-(5-chloro-3-fluoropyridin-2-yl)-6,7,8,9-tetrahydro-5H-6,9-epoxycyclohepta[b]pyridine-2-carboxamide The title compounds were prepared according to the same procedure as Example 1-6A and 1-6B, substituting 2-bromo-5-chloro-3-fluoropyridine for 2-bromo-3,5-difluoropyridine.

Enantiomer 1: MS (ESI) calcd. for ($C_{16}H_{13}ClFN_3O_2$) [M+H]$^+$, 334.07, found, 333.8. $^1$H NMR (400 MHz, $CD_3OD$) δ 8.56 (s, 1H), 7.94-8.00 (m, 2H), 5.18 (d, J=5.87 Hz, 1H), 4.73 (t, J=5.67 Hz, 1H), 3.20-3.26 (m, 1H), 2.48 (d, J=17.61 Hz, 1H), 2.17-2.27 (m, 2H), 2.08 (t, J=9.78 Hz, 1H), 1.63-1.75 (m, 1H).

Enantiomer 2: MS (ESI) calcd. for ($C_{16}H_{13}ClFN_3O_2$) [M+H]$^+$, 334.07, found, 333.8. $^1$H NMR (400 MHz, $CD_3OD$) δ 8.56 (s, 1H), 7.93-8.00 (m, 2H), 5.17 (d, J=6.26 Hz, 1H), 4.73 (t, J=5.87 Hz, 1H), 3.24 (dd, J=17.80, 5.28 Hz, 1H), 2.47 (d, J=18.00 Hz, 1H), 2.12-2.30 (m, 2H), 2.04-2.12 (m, 1H), 1.63-1.75 (m, 1H).

Compounds of Formula I (where, in Scheme 2, $R^2$, $R^{2A}$, $R^3$, $R^{3A}$, ring B, n, and each $R^1$ are as described in Formula I, and wherein $R^{2x}$, $R^{2y}$ $R^{3x}$, $R^{3y}$ correspond to $R^2$, $R^{2A}$, $R^3$, $R^{3A}$, or can be converted by methods known to those skilled in the art to $R^2$, $R^{2A}$ $R^3$, $R^{3A}$, respectively) may be prepared according to Scheme 2 by a Wittig reaction with aldehyde 2-1 followed by reduction (and/or addition as appropriate) and cyclization of 2-3 to form bicycle 2-4. Alternatively, 2-3 can be formed via an alkylation of the aldehyde 2-1 followed by radical deoxygenation and subsequent reduction (and/or addition as appropriate). Bicycle 2-4 is sequentially carbonylated and treated with ammonia to furnish 2-6. Reactions on the carbon chain of 2-2 and 2-3 and/or on the $R^{2x}$, $R^{2y}$ $R^{3x}$, $R^{3y}$ group of 2-2, 2-2a, 2-3 or 2-4 can be used to make further changes to the bicyclic core or substituents thereof.

Scheme 2

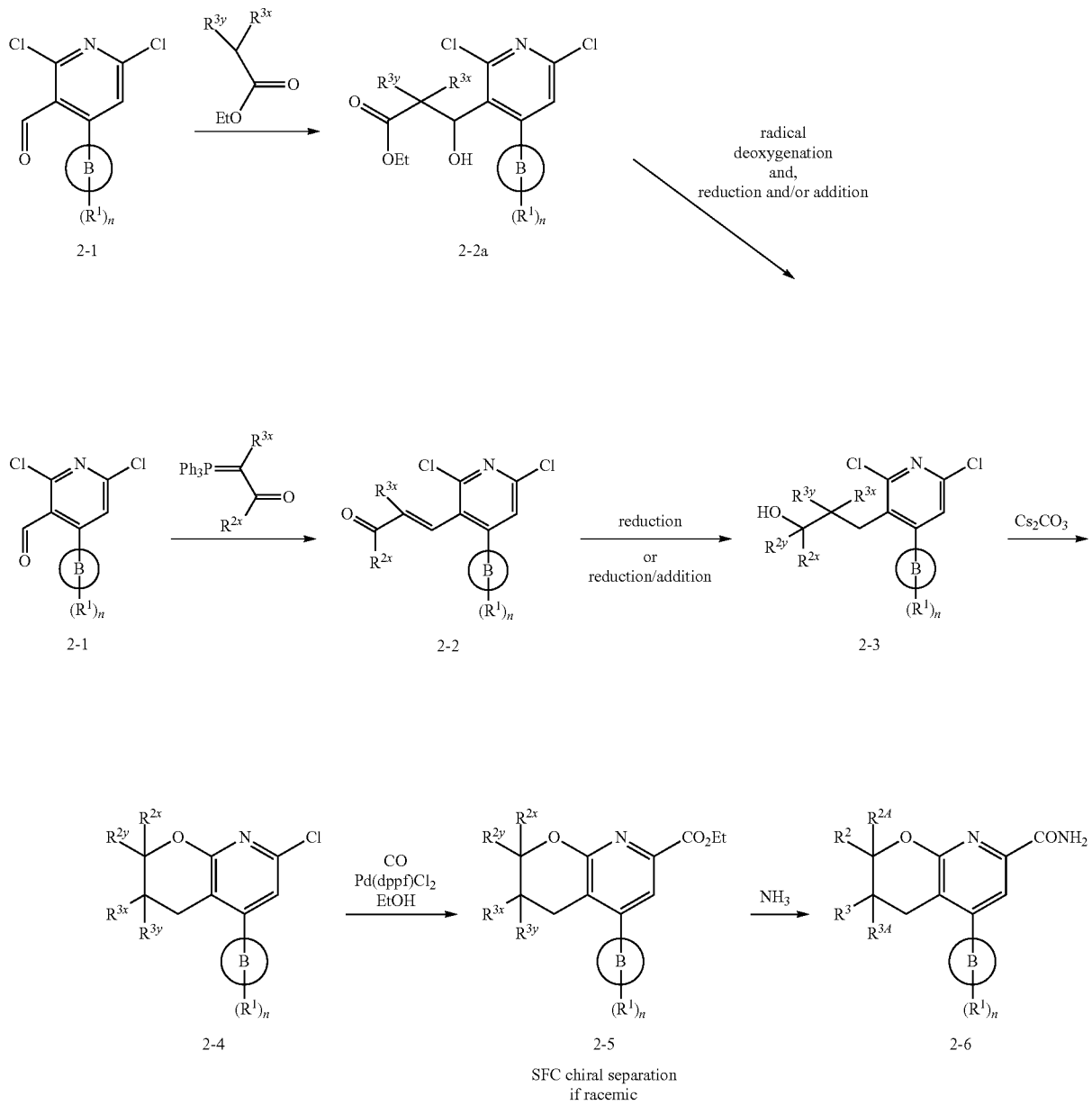

Example 2-1A and 2-1B

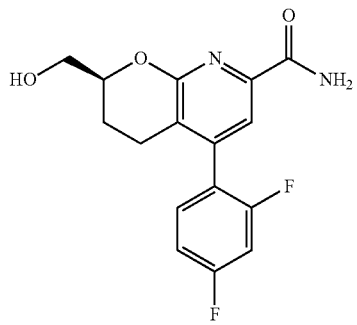

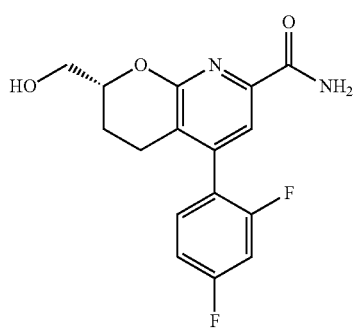

(S)-5-(2,4-difluorophenyl)-2-(hydroxmethyl)-3,4-dihydro-2H-pyrano[2,3-b]pyridine-7-carboxamide and (R)-5-(2,4-difluorophenyl)-2-(hydroxymethyl)-3,4-dihydro-2H-pyrano[2,3-b]pyridine-7-carboxamide Step 1: ethyl (E)-4-(2,6-dichloro-4-(2,4-difluorophenyl)pyridin-3-yl)-2-oxobut-3-enoate (Intermediate 2-2)

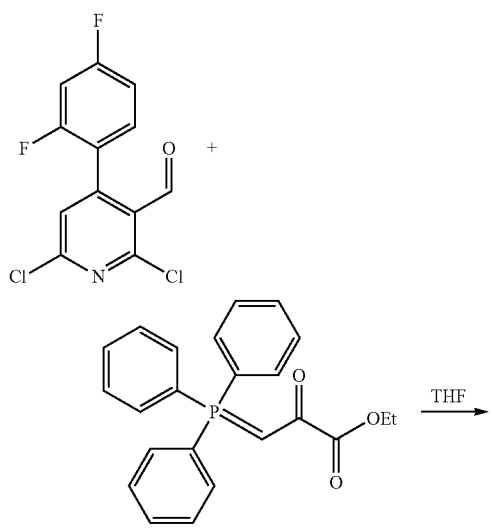

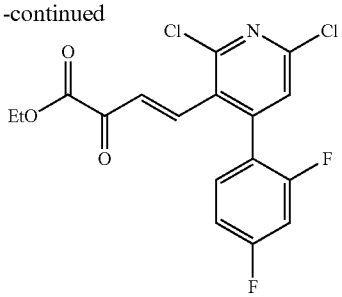

To a stirred solution of 2,6-dichloro-4-(2,4-difluorophenyl)nicotinaldehyde (Intermediate 2-1, 500 mg, 1.7 mmol) in THF (30 mL) was added ethyl 2-oxo-3-(triphenylphosphoranylidene)propanoate (653 mg, 1.7 mmol) at 15° C., then the solution was stirred at 80° C. for 24 h. The reaction was concentrated under reduced pressure and the residue was purified by silica gel chromatography (ISCO®; 24 g SepaFlash® Column, eluting with 0 to 5% ethyl acetate/petroleum ether) to afford the product. MS (ESI) calcd for ($C_{17}H_{12}Cl_2F_2NO_3$) [M+H]$^+$, 386.0, found, 385.9. $^1$H NMR (400 MHz, CDCl$_3$) δ 7.72 (d, J=16.4 Hz, 1H), 7.25-7.19 (m, 2H), 7.02 (t, J=7.2 Hz, 1H), 6.96-6.87 (m, 1H), 6.82 (d, J=16.4 Hz, 1H), 4.34-4.25 (m, 2H), 1.33 (t, J=7.2 Hz, 3H)

Step 2: ethyl 4-(2,6-dichloro-4-(2,4-difluorophenyl)pyridin-3-yl)-2-hydroxybutanoate (Intermediate 2-3)

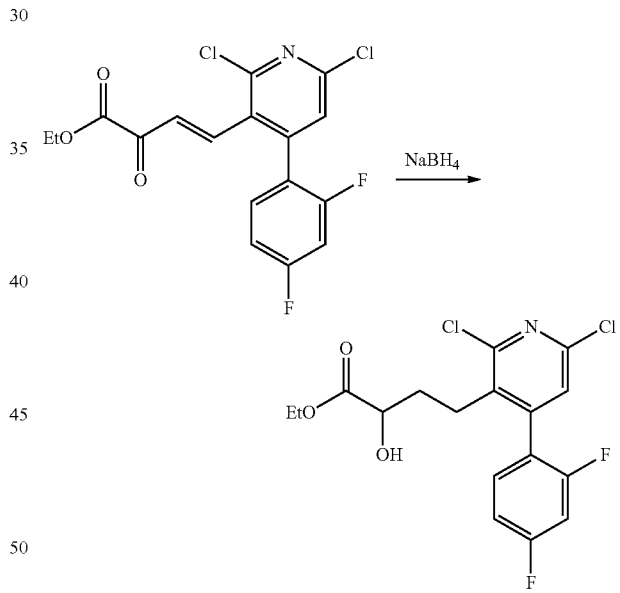

To a solution of (E)-ethyl 4-(2,6-dichloro-4-(2,4-difluorophenyl)pyridin-3-yl)-2-oxobut-3-enoate obtained from Step 1 (1.1 g, 2.85 mmol) in ethanol (20 mL) was added NaBH$_4$ (0.11 g, 2.85 mmol) at 20° C. and the mixture was stirred at 20° C. for 25 min. The reaction was quenched with water (250 mL) and extracted with ethyl acetate (2×200 mL), the combined organic layers were dried over Na$_2$SO$_4$, filtered and concentrated under reduced pressure. The residue was purified by silica gel chromatography (ISCO®; 24 g SepaFlash® Column, eluting with 5-15% ethyl acetate/petroleum ether) to afford the product. MS (ESI) calcd for ($C_{17}H_{16}Cl_2F_2NO_3$) [M+H]$^+$, 390.0, found, 389.9. $^1$H NMR (400 MHz, CDCl$_3$) δ 7.21-7.13 (m, 1H), 7.11 (s, 1H), 7.04-6.88 (m, 2H), 4.28-3.98 (m, 3H), 2.79-2.54 (m, 2H), 1.99-1.69 (m, 2H), 1.24 (t, J=7.2 Hz, 3H)

Step 3: ethyl 7-chloro-5-(2,4-difluorophenyl)-3,4-dihydro-2H-pyrano[2,3-b]pyridine-2-carboxylate

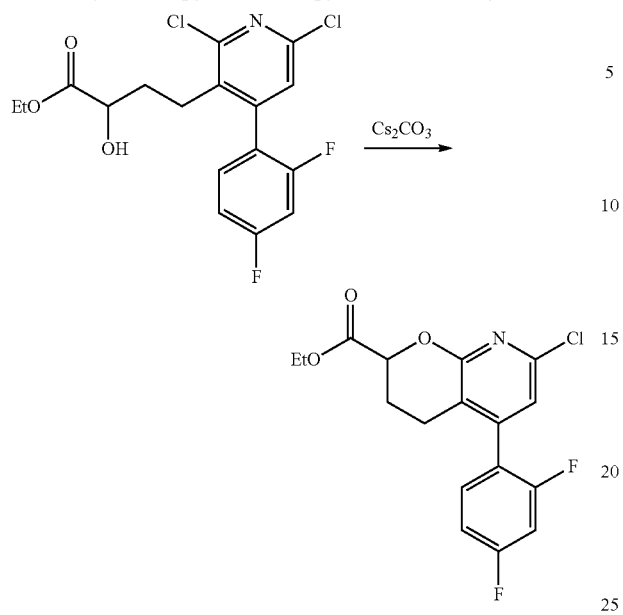

A mixture of ethyl 4-(2,6-dichloro-4-(2,4-difluorophenyl)pyridin-3-yl)-2-hydroxybutanoate (Intermediate 2-3, 450 mg, 1.2 mmol) and Cs$_2$CO$_3$ (751 mg, 2.3 mmol) in acetonitrile (20 mL) was stirred at 90° C. for 2.5 h. The mixture was diluted in water (100 mL) and extracted with ethyl acetate (2×100 mL), the combined organic layers were dried over Na$_2$SO$_4$, filtered and the filtrate was concentrated under reduced pressure and purified by silica gel chromatography (ISCO®; 12 g SepaFlash® Column, eluting with 0 to 20% ethyl acetate/petroleum ether at 30 mL/min) to afford the product. $^1$H NMR (400 MHz, CDCl$_3$) δ 7.23-7.14 (m, 1H), 7.02-6.87 (m, 2H), 6.86 (s, 1H), 4.96 (t, J=4.9 Hz, 1H), 4.25 (qq, J=7.2, 10.8 Hz, 2H), 2.50 (br. s., 2H), 2.25-2.10 (m, 2H), 1.33-1.17 (m, 3H.)

Step 4: (7-chloro-5-(2,4-difluorophenyl)-3,4-dihydro-2H-pyrano[2,3-b]pyridin-2-yl)methanol

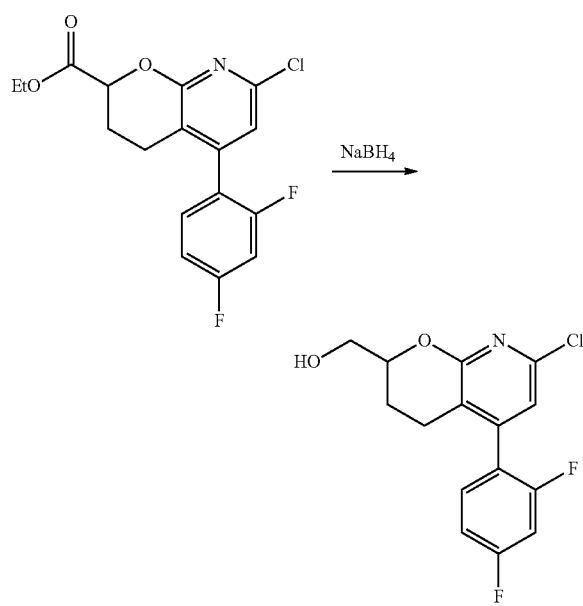

A stirred solution of ethyl 7-chloro-5-(2,4-difluorophenyl)-3,4-dihydro-2H-pyrano[2,3-b]pyridine-2-carboxylate (300 mg, 0.85 mmol) in ethanol (6 mL) was added NaBH$_4$ (32 mg, 0.85 mmol) at 20° C., and the mixture was stirred at 20° C. for 1.5 h. NaBH$_4$ (32 mg, 0.85 mmol) was added, and the mixture was stirred at 20° C. for 2 h. Acetone (1 mL) was added to quench the reaction, then the mixture was dissolved in water (60 mL) and extracted with ethyl acetate (2×60 mL), the combined organics were dried over Na$_2$SO$_4$, filtered and concentrated under reduced pressure. The residue was purified by silica gel chromatography (ISCO®; 4 g SepaFlash® Column, eluting with 30 to 70% ethyl acetate/petroleum ether) to afford the product. MS (ESI) calcd for (C$_{15}$H$_{13}$ClF$_2$NO$_2$) [M+H]$^+$, 312.0, found, 311.9. $^1$H NMR (400 MHz, CDCl$_3$) δ 7.25-7.17 (m, 1H), 7.03-6.90 (m, 2H), 6.86 (s, 1H), 4.46-4.29 (m, 1H), 4.01-3.85 (m, 1H), 3.85-3.69 (m, 1H), 2.68 (d, J=11.7 Hz, 1H), 2.54-2.43 (m, 1H), 2.16 (t, J=6.8 Hz, 1H), 2.00-1.91 (m, 1H), 1.89-1.75 (m, 1H)

Step 5: ethyl 5-(2,4-difluorophenyl)-2-(hydroxymethyl)-3,4-dihydro-2H-pyrano[2,3-b]pyridine-7-carboxylate (Intermediate 2-4)

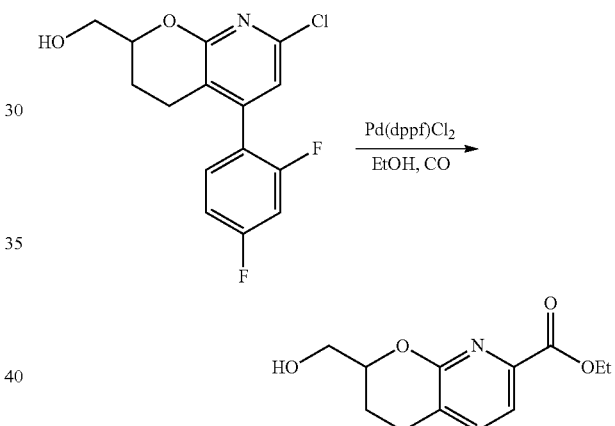

To a stirred solution of (7-chloro-5-(2,4-difluorophenyl)-3,4-dihydro-2H-pyrano[2,3-b]pyridin-2-yl)methanol (160 mg, 0.51 mmol) in ethanol (20 mL) was added PdCl$_2$(dppf) (38 mg, 0.05 mmol) and potassium acetate (101 mg, 1.0 mmol) at 80° C. under N$_2$ atmosphere. The mixture was degassed and backfilled with CO (three times). The resulting mixture was stirred under 50 psi of CO at 80° C. for 20 h. The mixture was concentrated under reduced pressure, the residue was purified by silica gel chromatography (ISCO®; 4 g SepaFlash® Column, eluting with 30 to 80% ethyl acetate/petroleum ether) to afford the product. MS (ESI) calcd for (C$_{18}$H$_{18}$F$_2$NO$_4$) [M+H]$^+$, 350.1, found, 350.1. $^1$H NMR (400 MHz, CDCl$_3$) δ 7.66 (s, 1H), 7.25-7.20 (m, 1H), 7.10-6.89 (m, 2H), 4.53-4.32 (m, 3H), 4.00-3.90 (m, 1H), 3.86-3.74 (m, 1H), 2.60 (d, J=17.2 Hz, 1H), 2.25 (t, J=6.6 Hz, 1H), 2.02-1.80 (m, 2H), 1.41 (t, J=7.2 Hz, 3H)

Step 6: ethyl (S)-5-(2,4-difluorophenyl)-2-(hydroxymethyl)-3,4-dihydro-2H-pyrano[2,3-b]pyridine-7-carboxylate and ethyl (R)-5-(2,4-difluorophenyl)-2-(hydroxymethyl)-3,4-dihydro-2H-pyrano[2,3-b]pyridine-7-carboxylate

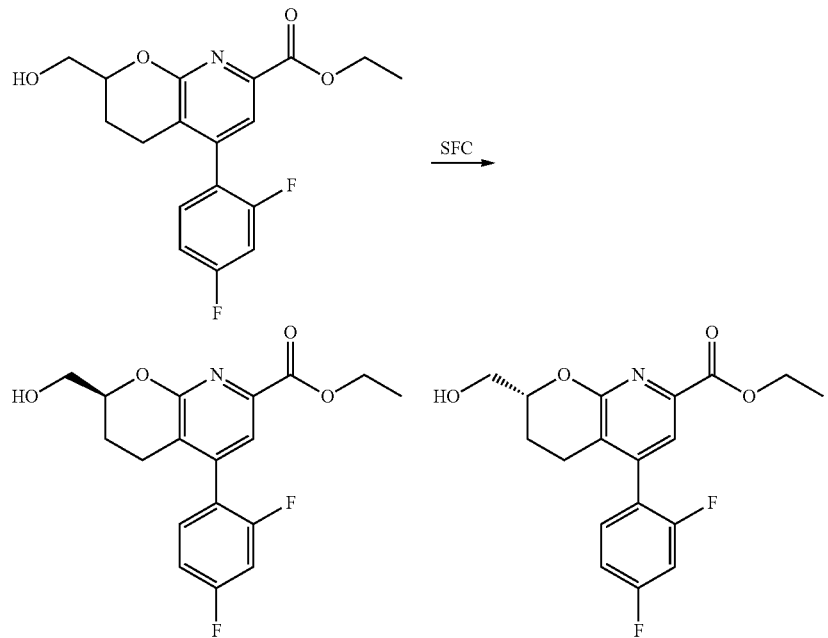

Racemic ethyl 5-(2,4-difluorophenyl)-2-(hydroxymethyl)-3,4-dihydro-2H-pyrano[2,3-b]-pyridine-7-carboxylate (60 mg, 0.17 mmol) was separated by chiral SFC (Column: Chiralpak Whelk 250×30 mm, 10 um; Mobile phase: 40% to 40% MeOH (containing 0.05% DEA) in $CO_2$; Flow rate: 60 mL/min) to afford the two enantiomers.

Step 7: (S)-5-(2,4-difluorophenyl)-2-(hydroxymethyl)-3,4-dihydro-2H-pyrano[2,3-b]pyridine-7-carboxamide and (R)-5-(2,4-difluorophenyl)-2-(hydroxymethyl)-3,4-dihydro-2H-pyrano[2,3-b]pyridine-7-carboxamide

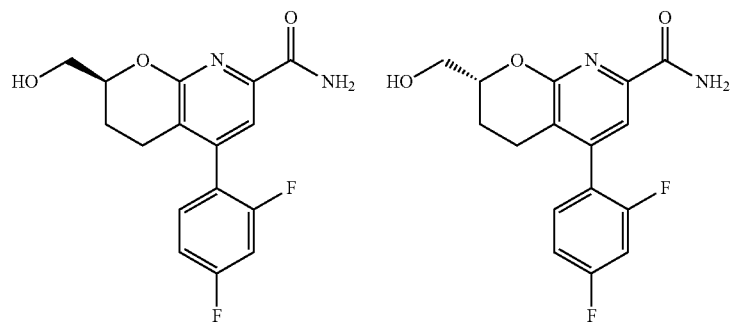

A solution of one enantiomer of ethyl (S)-5-(2,4-difluorophenyl)-2-(hydroxymethyl)-3,4-dihydro-2H-pyrano[2,3-b]pyridine-7-carboxylate (25 mg, 0.07 mmol) in ammonia (10M in MeOH) (10 mL) and stirred at 26° C. for 12 h. The mixture was concentrated under reduced pressure and the residue was purified by prep-TLC (silica gel, eluting with 4:1 ethyl acetate/petroleum ether) to afford one enantiomer of the title compound. MS (ESI) calcd. for (C₁₆H₁₅F₂N₂O₃) [M+H]⁺, [321.1], found, [321.0]. ¹H NMR (400 MHz, CDCl₃) δ 7.55 (s, 1H), 7.40-7.35 (m, 1H), 7.14-7.08 (m, 2H), 4.59-4.32 (m, 1H), 3.79-3.77 (m, 2H), 2.83-2.75 (m, 1H), 2.59-2.55 (m, 1H), 2.06-2.02 (m, 1H), 1.75-1.73 (m, 1H).

Similar treatment of the other enantiomer of ethyl 5-(2,4-difluorophenyl)-2-(hydroxymethyl)-3,4-dihydro-2H-pyrano[2,3-b]pyridine-7-carboxylate afforded the other enantiomer of the title compound. MS (ESI) calcd. for (C₁₆H₁₅F₂N₂O₃) [M+H]⁺, [321.1], found, [321.0]. ¹H NMR (400 MHz, CDCl₃) δ 7.56 (s, 1H), 7.42-7.38 (m, 1H), 7.15-7.12 (m, 2H), 4.36-4.34 (m, 1H), 3.8 (s, 2H), 2.84-2.76 (m, 1H), 2.60-2.56 (m, 1H), 2.07-2.03 (m, 1H), 1.80-1.75 (m, 1H).

Example 2-2A, 2-2B, 2-2C and 2-2D

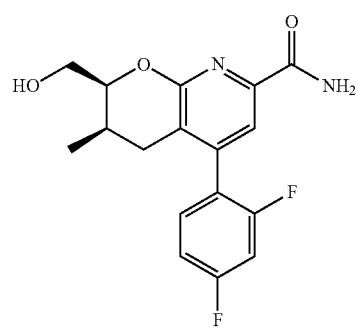

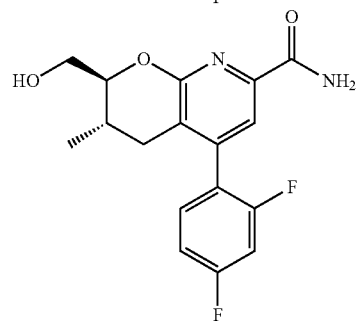

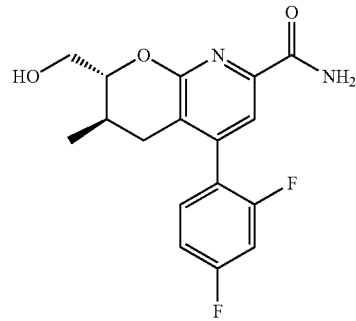

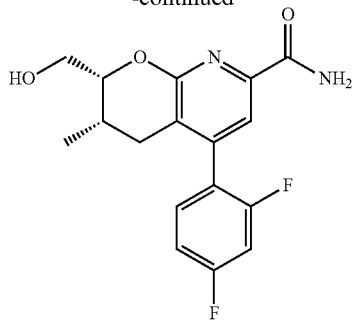

(2S,3R)-5-(2,4-difluorophenyl)-2-(hydroxymethyl)-3-methyl-3,4-dihydro-2H-pyrano[2,3-b]pyridine-7-carboxamide, (2S,3S)-5-(2,4-difluorophenyl)-2-(hydroxymethyl)-3-methyl-3,4-dihydro-2H-pyrano[2,3-b]pyridine-7-carboxamide, (2R,3R)-5-(2,4-difluorophenyl)-2-(hydroxymethyl)-3-methyl-3,4-dihydro-2H-pyrano[2,3-b]pyridine-7-carboxamide, (2R,3S)-5-(2,4-difluorophenyl)-2-(hydroxmethyl)-3-methyl-3,4-dihydro-2H-pyrano[2,3-b]pyridine-7-carboxamide Step 1: ethyl 4-(2,6-dichloro-4-(2,4-difluorophenyl)pyridin-3-yl)-2-oxobutanoate

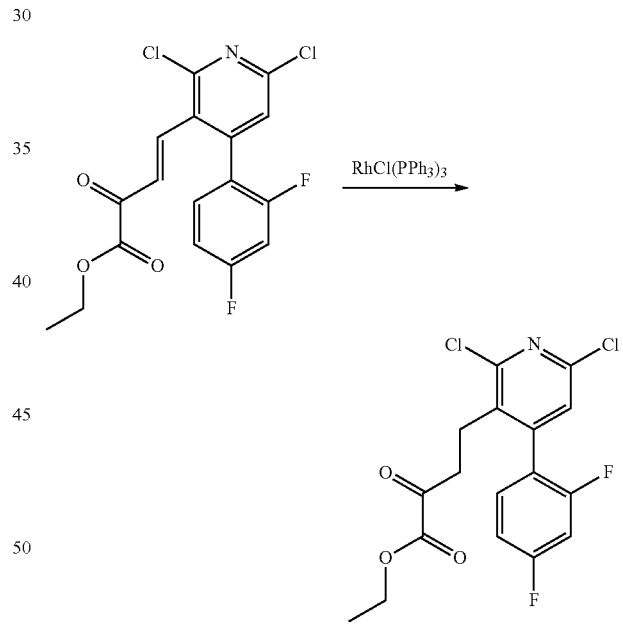

A solution of (E)-ethyl 4-(2,6-dichloro-4-(2,4-difluorophenyl)pyridin-3-yl)-2-oxobut-3-enoate (Intermediate 2-2, 1.6 g, 4.14 mmol) and tris(triphenylphosphine)rhodium(I) chloride (0.77 g, 0.83 mmol) in THF (20 mL) and t-BuOH (20.00 mL) was stirred at 35° C. under 50 psi H₂ for 1.5 h. The solution was concentrated in vacuo, the residue was purified by silica gel chromatography (ISCO®; 24 g Sepa-Flash® Column, eluting with [0-5]% ethyl acetate/petroleum ether at 35 mL/min) to afford the product. MS (ESI) calcd. for (C₁₇H₁₄Cl₂F₂NO₃) [M+H]⁺, 389.1, found, 387.7. ¹H NMR (400 MHz, CDCl₃) δ 7.05-7.22 (m, 2H), 6.84-6.99 (m, 2H), 4.22 (q, J=7.04 Hz, 2H), 2.94-3.05 (m, 2H), 2.83 (d, J=7.43 Hz, 2H), 1.24-1.33 (m, 3H).

Step 2: ethyl 3-((2,6-dichloro-4-(2,4-difluorophenyl)pyridin-3-yl)methyl)-2-oxobut-3-enoate

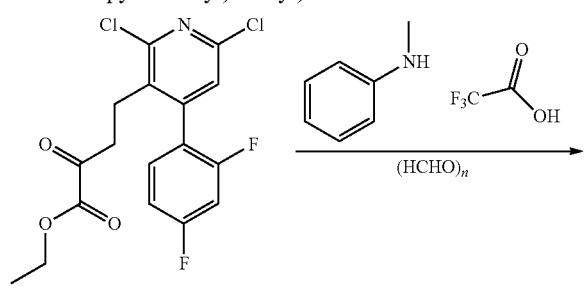

To a solution of ethyl 4-(2,6-dichloro-4-(2,4-difluorophenyl)pyridin-3-yl)-2-oxobutanoate (3 g, 7.73 mmol) and N-methylanilinium trifluoroacetate (6.84 g, 31 mmol) in THF (70 mL) was added paraformaldehyde (234 mg, 7.7 mmol), then the mixture was stirred at 70° C. under $N_2$ for 14 h. The reaction was concentrated under reduced pressure. The residue was purified by silica gel chromatography (eluting with 50:1 to 10:1 petroleum ether:ethyl acetate) to give the product. MS (ESI) calcd. for ($C_{18}H_{14}Cl_2F_2NO_3$) [M+H]$^+$, 400.2, found: 399.9. $^1$H NMR (400 MHz, CDCl$_3$) δ 7.21 (s, 1H), 7.09-7.17 (m, 1H), 6.88-7.00 (m, 2H), 6.21 (s, 1H), 5.73 (s, 1H), 4.34 (q, J=7.06 Hz, 2H), 3.62 (br. s., 2H), 1.36 (t, J=7.06 Hz, 3H).

Step 3: ethyl 4-(2,6-dichloro-4-(2,4-difluorophenyl)pyridin-3-yl)-3-methyl-2-oxobutanoate

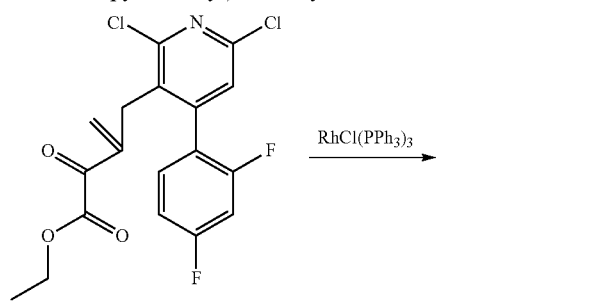

A solution of ethyl 3-((2,6-dichloro-4-(2,4-difluorophenyl)pyridin-3-yl)methyl)-2-oxobut-3-enoate (750 mg, 1.87 mmol) and tris(triphenylphosphine)rhodium(I) chloride (347 mg, 0.38 mmol) in THF (15 mL) and t-BuOH (15.00 mL) was stirred at 40° C. under 50 psi $H_2$ for 2 h. The solution was concentrated in vacuo, the residue was purified by silica gel chromatography (ISCO®; 4 g SepaFlash® Column, eluting with 0% to 5% ethyl acetate/petroleum ether) to afford the product. MS (ESI) calcd. for ($C_{18}H_{16}Cl_2F_2NO_3$) [M+H]$^+$, 402.1, found, 401.9. $^1$H NMR (400 MHz, CDCl$_3$) δ 7.10-7.17 (m, 1H), 7.07 (s, 1H), 6.86-6.98 (m, 2H), 4.13-4.20 (m, 2H), 2.37-3.20 (m, 3H), 1.13-1.32 (m, 6H)

Step 4: ethyl 4-(2,6-dichloro-4-(2,4-difluorophenyl)pyridin-3-yl)-2-hydroxy-3-methylbutanoate

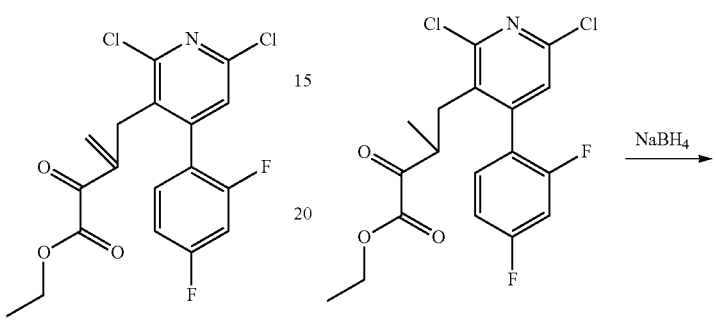

To a solution of ethyl 4-(2,6-dichloro-4-(2,4-difluorophenyl)pyridin-3-yl)-3-methyl-2-oxobutanoate (470 mg, 1.169 mmol) in EtOH (15 mL) was added NaBH$_4$ (30 mg, 0.79 mmol) at 0° C. under $N_2$. The reaction mixture was stirred for 0.5 h. Then the mixture was poured into 15 mL saturated aqueous NH$_4$Cl. The aqueous layer was extracted with EtOAc (30 mL×3). The combined organic layers were washed with brine (sat. 10 mL), dried over anhydrous Na$_2$SO$_4$, filtered and concentrated. The crude compound was purified by silica gel chromatography (ISCO®; 4 g SepaFlash® Column, eluting with 0% to 10% ethyl acetate/petroleum ether) to afford the product. MS (ESI) calcd. for ($C_{18}H_{18}Cl_2F_2NO_3$) [M+H]$^+$, 404.0, found, 403.9. $^1$H NMR (400 MHz, CDCl$_3$) δ 7.03-7.17 (m, 2H), 6.83-6.98 (m, 2H), 4.01-4.22 (m, 3H), 2.41-2.87 (m, 3H), 1.11-1.27 (m, 6H).

Step 5: ethyl 7-chloro-5-(2,4-difluorophenyl)-3-methyl-3,4-dihydro-2H-pyrano[2,3-b]pyridine-2-carboxylate

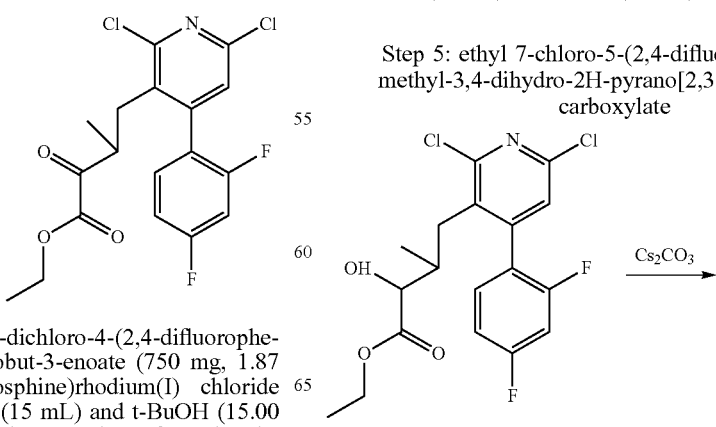

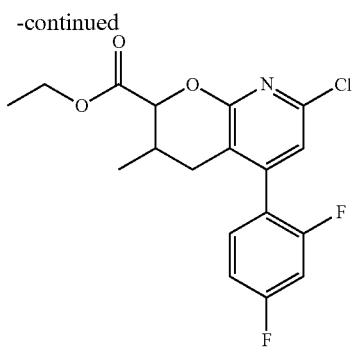

To a solution of ethyl 4-(2,6-dichloro-4-(2,4-difluorophenyl)pyridin-3-yl)-2-hydroxy-3-methylbutanoate (410 mg, 1.01 mmol) in acetonitrile (30 mL) was added Cs$_2$CO$_3$ (661 mg, 2.03 mmol), the reaction mixture was stirred at 85° C. for 2 h under N$_2$. The mixture was filtered and the filtrate was evaporated. The crude mixture was purified by silica gel chromatography (eluting with 20:1 to 5:1 petroleum ether: ethyl acetate) to give the product. MS (ESI) calcd for (C$_{18}$H$_{17}$ClF$_2$NO$_3$) [M+H]$^+$, 368.0, found, 368.0. $^1$H NMR (400 MHz, CDCl$_3$) δ 7.11-7.23 (m, 1H), 6.83-7.02 (m, 3H), 4.59-4.86 (m, 1H), 4.13-4.32 (m, 2H), 2.11-2.67 (m, 3H), 1.23-1.27 (m, 3H), 0.96-1.09 (m, 3H).

Step 6: (7-chloro-5-(2,4-difluorophenyl)-3-methyl-3,4-dihydro-2H-pyrano[2,3-b]pyridin-2-yl)methanol

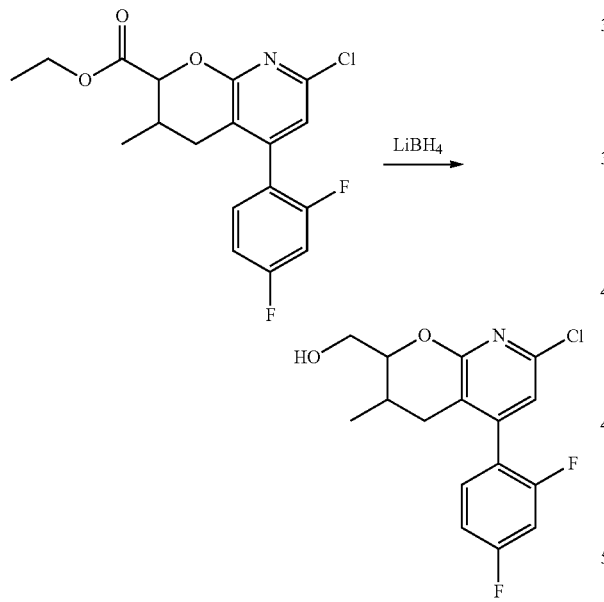

To a solution of ethyl 7-chloro-5-(2,4-difluorophenyl)-3-methyl-3,4-dihydro-2H-pyrano[2,3-b]pyridine-2-carboxylate (310 mg, 0.84 mmol) in THF (15 mL) was added LiBH$_4$ (73.4 mg, 3.37 mmol) and the mixture was stirred at 20° C. under N$_2$ for 1 h. The mixture was poured into 15 mL saturated aqueous NH$_4$Cl. The aqueous layer was extracted with EtOAc (30 mL×3). The combined organic layers were washed with brine (sat. 10 mL), dried over anhydrous Na$_2$SO$_4$, filtered and the filtrate was evaporated. The crude mixture was purified by silica gel chromatography (ISCO®; 4 g SepaFlash® Column, eluting with 0% to 40% ethyl acetate/petroleum ether) to afford the product. MS (ESI) calcd. for (C$_{16}$H$_{15}$ClF$_2$NO$_2$) [M+H]$^+$, 326.1, found, 325.9. $^1$H NMR (400 MHz, CDCl$_3$) δ 7.15-7.23 (m, 1H), 6.88-7.02 (m, 2H), 6.83 (d, J=3.52 Hz, 1H), 3.86-4.04 (m, 2H), 3.66-3.85 (m, 1H), 2.16-2.48 (m, 3H), 0.86-1.05 (m, 3H).

Step 7: ethyl 5-(2,4-difluorophenyl)-2-(hydroxymethyl)-3-methyl-3,4-dihydro-2H-pyrano[2,3-b]pyridine-7-carboxylate

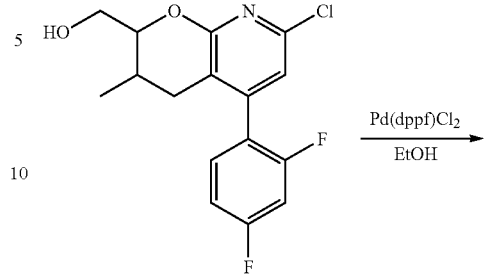

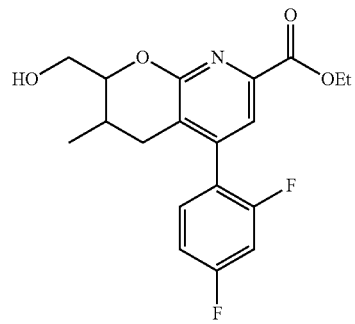

To a solution of (7-chloro-5-(2,4-difluorophenyl)-3-methyl-3,4-dihydro-2H-pyrano[2,3-b]pyridin-2-yl)methanol (210 mg, 0.65 mmol), potassium acetate (190 mg, 1.93 mmol) in dry EtOH (50 mL) was added Pd(dppf)Cl$_2$ (70.8 mg, 0.10 mmol) under an atmosphere of CO. The reaction mixture was stirred at 70° C. under 50 psi CO for 14 h. The solution was concentrated in vacuo, the residue was purified by silica gel chromatography (ISCO®; 4 g SepaFlash® Column, eluting with 0% to 70% ethyl acetate/petroleum ether) to afford the product. MS (ESI) calcd. for (C$_{19}$H$_{20}$F$_2$NO$_4$) [M+H]$^+$, 364.1, found, 364.3. $^1$H NMR (400 MHz, CDCl$_3$) δ 7.66 (d, J=2.65 Hz, 1H), 7.19-7.25 (m, 1H), 6.87-7.06 (m, 2H), 4.45 (q, J=7.06 Hz, 2H), 3.92-4.15 (m, 2H), 3.69-3.88 (m, 1H), 2.20-2.63 (m, 2H), 2.05-2.14 (m, 1H), 1.41 (t, J=7.06 Hz, 3H), 0.88-1.09 (m, 3H).

Step 8: ethyl (2S,3R)-5-(2,4-difluorophenyl)-2-(hydroxymethyl)-3-methyl-3,4-dihydro-2H-pyrano[2,3-b]pyridine-7-carboxylate, ethyl (2S,3S)-5-(2,4-difluorophenyl)-2-(hydroxymethyl)-3-methyl-3,4-dihydro-2H-pyrano[2,3-b]pyridine-7-carboxylate, ethyl (2R,3R)-5-(2,4-difluorophenyl)-2-(hydroxymethyl)-3-methyl-3,4-dihydro-2H-pyrano[2,3-b]pyridine-7-carboxylate and ethyl (2R,3S)-5-(2,4-difluorophenyl)-2-(hydroxmethyl)-3-methyl-3,4-dihydro-2H-pyrano[2,3-b]pyridine-7-carboxylate (Intermediates 2-5A, 2-5B, 2-5C, 2-5D)

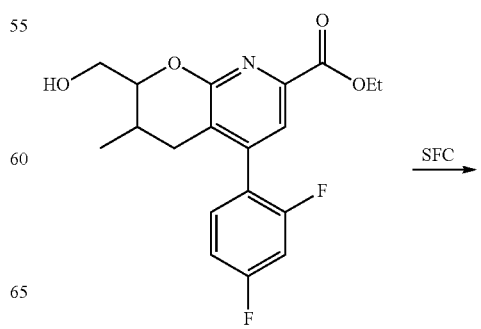

-continued

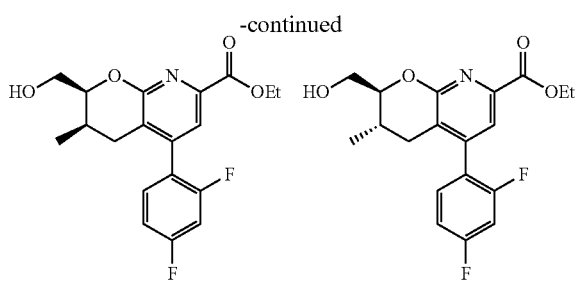

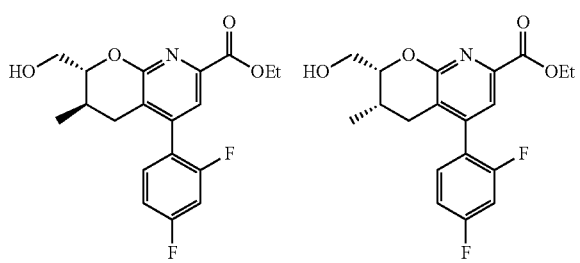

Diastereomeric ethyl 5-(2,4-difluorophenyl)-2-(hydroxymethyl)-3-methyl-3,4-dihydro-2H-pyrano[2,3-b]pyridine-7-carboxylate (30 mg, 0.083 mmol) was resolved by chiral SFC (Column: Chiralpak Whelk-01 250×30 mm, 10 um; Mobile phase: 40% to 40% MeOH (containing 0.05% DEA) in CO₂; Flow rate: 60 mL/min) to give the four isomers of the title compounds.

Step 9: (2S,3R)-5-(2,4-difluorophenyl)-2-(hydroxymethyl)-3-methyl-3,4-dihydro-2H-pyrano[2,3-b]pyridine-7-carboxamide, (2S,3S)-5-(2,4-difluorophenyl)-2-(hydroxymethyl)-3-methyl-3,4-dihydro-2H-pyrano[2,3-b]pyridine-7-carboxamide, (2R,3R)-5-(2,4-difluorophenyl)-2-(hydroxymethyl)-3-methyl-3,4-dihydro-2H-pyrano[2,3-b]pyridine-7-carboxamide, (2R,3S)-5-(2,4-difluoropheny)-2-(hydroxmethyl)-3-methyl-3,4-dihydro-2H-pyrano[2,3-b]pyridine-7-carboxamide

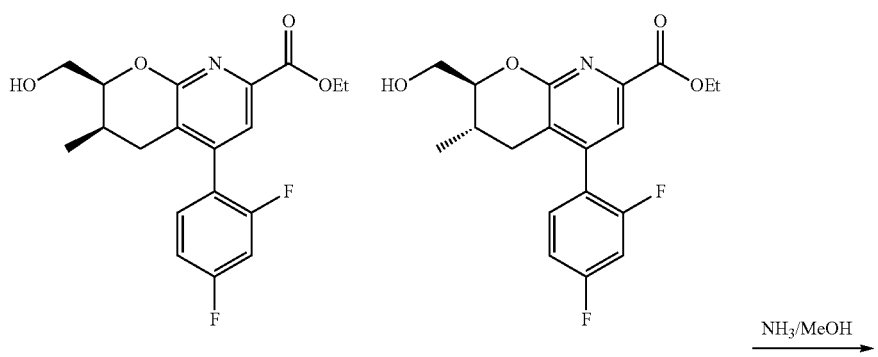

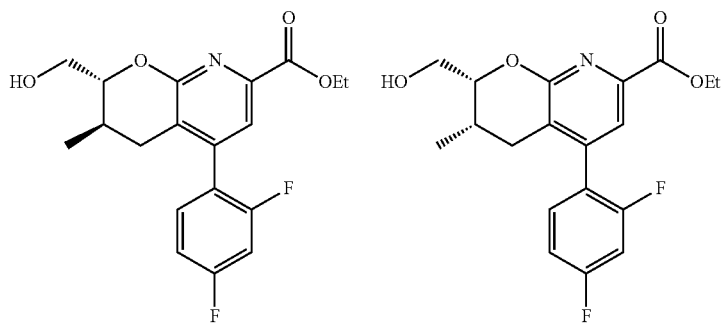

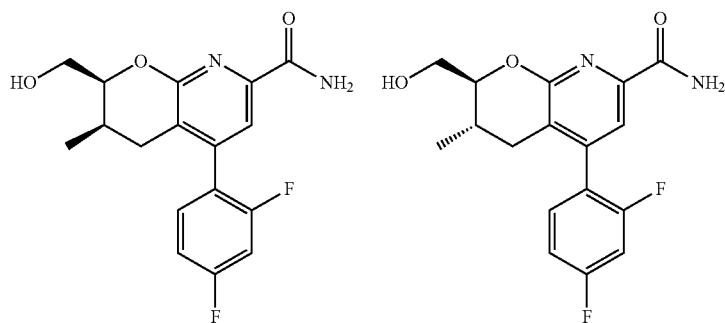

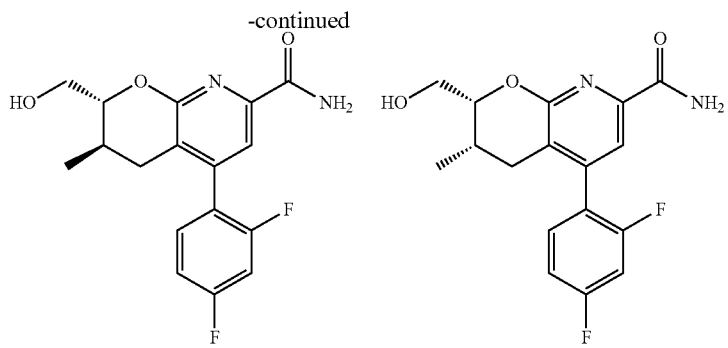

A solution of one resolved isomer of ethyl 5-(2,4-difluorophenyl)-2-(hydroxymethyl)-3-methyl-3,4-dihydro-2H-pyrano[2,3-b]pyridine-7-carboxylate (8 mg, 0.028 mmol) in ammonia (10 M in MeOH) (10 mL) was stirred at room temperature for 10 h. The mixture was concentrated and the residue was purified by Prep-HPLC (Column: Phenomenex Synergi C18 150×30 mm, 4 um; Mobile phase: 42% to 62% water (containing 0.1% TFA)-ACN; Flow rate: 25 mL/min) to give one isomer of the title compound. MS (ESI) calcd. for ($C_{17}H_{17}F_2N_2O_3$) [M+H]$^+$, 335.0, found, 334.9. $^1$H NMR (400 MHz, CD$_3$OD) δ 7.57 (s, 1H), 7.29-7.45 (m, 1H), 7.02-7.19 (m, 2H), 4.00-4.09 (m, 1H), 3.90-3.99 (m, 1H), 3.77-3.89 (m, 1H), 2.53-2.67 (m, 1H), 2.40-2.52 (m, 1H), 2.05 (d, J=16.32 Hz, 1H), 1.05 (d, J=6.39 Hz, 3H).

Similar treatment of the other isomers of ethyl 5-(2,4-difluorophenyl)-2-(hydroxymethyl)-3-methyl-3,4-dihydro-2H-pyrano[2,3-b]pyridine-7-carboxylate afforded the other isomers of the title compound.

Isomer 2: MS (ESI) calcd. for ($C_{17}H_{17}F_2N_2O_3$) [M+H]$^+$, 335.0, found, 334.9. $^1$H NMR (400 MHz, CD$_3$OD) δ 7.65-7.82 (m, 2H), 7.18-7.24 (m, 1H), 6.86-7.08 (m, 2H), 5.98-6.18 (m, 1H), 4.47 (br. s., 1H), 3.92-4.05 (m, 1H), 3.77-3.88 (m, 1H), 2.76-2.94 (m, 1H), 2.19-2.42 (m, 2H), 0.94 (d, J=6.39 Hz, 3H).

Isomer 3: MS (ESI) calcd. for ($C_{17}H_{17}F_2N_2O_3$) [M+H]$^+$, 335.0, found, 334.9. $^1$H NMR (400 MHz, CD$_3$OD) δ 7.55 (s, 1H), 7.29-7.44 (m, 1H), 6.99-7.21 (m, 2H), 3.98-4.07 (m, 1H), 3.89-3.97 (m, 1H), 3.77-3.87 (m, 1H), 2.51-2.63 (m, 1H), 2.38-2.50 (m, 1H), 1.97-2.13 (m, 1H), 1.03 (d, J=6.65 Hz, 3H).

Isomer 4: MS (ESI) calcd. for ($C_{17}H_{17}F_2N_2O_3$) [M+H]$^+$, 335.0, found, 334.9. $^1$H NMR (400 MHz, CDCl$_3$) δ 7.67 (br. s., 2H), 7.13-7.18 (m, 1H), 6.78-6.99 (m, 2H), 5.82 (br. s., 1H), 4.41 (br. s., 1H), 3.86-4.08 (m, 1H), 3.75 (d, J=9.00 Hz, 1H), 2.68-2.96 (m, 1H), 2.15-2.40 (m, 2H), 0.87 (d, J=5.87 Hz, 3H).

Example 2-3A and 2-3B

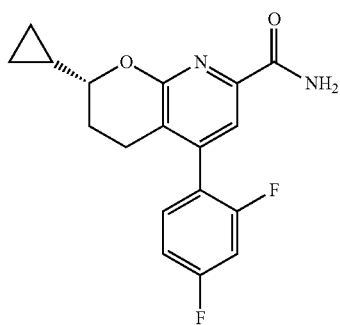

2-3A

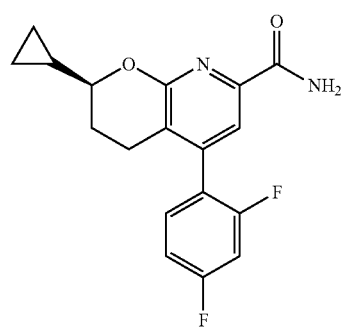

2-3B 2-3A: (R)-2-cyclopropyl-5-(2,4-difluorophenyl)-3,4-dihydro-2H-pyrano[2,3-b]pyridine-7-carboxamide
and 2-3B: (S)-2-cyclopropyl-5-(2,4-difluorophenyl)-3,4-dihydro-2H-pyrano[2,3-b]pyridine-7-carboxamide Step 1: (E)-methyl 3-(4-bromo-2,6-dichloropyridin-3-yl)acrylate

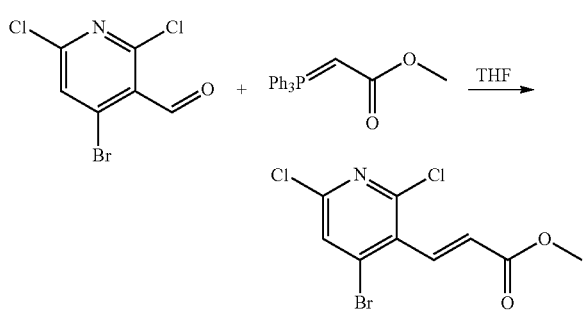

A solution of 4-bromo-2,6-dichloronicotinaldehyde (6 g, 23.8 mmol) and methyl 2-(triphenylphosphoranylidene)acetate (9.5 g, 30 mmol) in THF (150 mL) was stirred at 80° C. under N$_2$ for 2 h. The solvent was removed under reduced pressure, the residue was purified by silica gel chromatography (eluting with 20:1 petroleum ether/ethyl acetate) to give the product.

Step 2: (E)-methyl 3-(2,6-dichloro-4-(2,4-difluorophenyl)pyridin-3-yl)acrylate

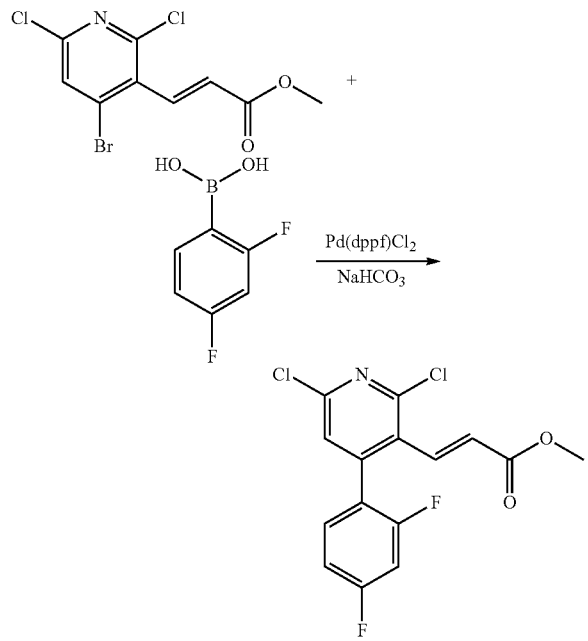

A mixture of (E)-methyl 3-(4-bromo-2,6-dichloropyridin-3-yl)acrylate (6.5 g, 21 mmol), (2,4-difluorophenyl)boronic acid (3.3 g, 21 mmol), Pd(dppf)Cl$_2$ (1.5 g, 2.1 mmol) and NaHCO$_3$ (3.5 g, 42 mmol) in 1,4-dioxane/water (50 mL/10 mL) was stirred at 100° C. under N$_2$ for 3 h. The mixture was concentrated in vacuo. The residue was purified by silica gel chromatography (20:1 petroleum ether/ethyl acetate to give the product. MS (ESI) calcd. for (C$_{15}$H$_{10}$Cl$_2$F$_2$NO$_2$) [M+H]$^+$, 344.0, found, 344.2. $^1$H NMR (400 MHz, CDCl$_3$) δ 7.55 (d, J=16 Hz, 1H), 6.96-7.20 (m, 2H), 6.86-6.92 (m, 2H), 5.90 (m, 1H), 3.71 (s, 3H).

Step 3: methyl 3-(2,6-dichloro-4-(2,4-difluorophenyl)pyridin-3-yl)propanoate (Intermediate 2-6)

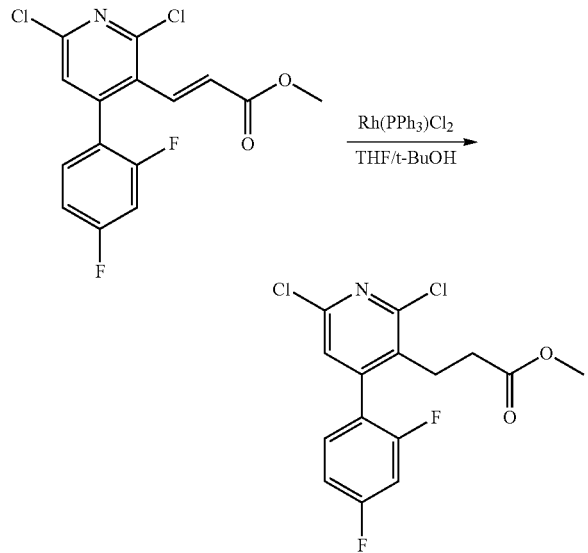

A solution of Rh(PPh$_3$)Cl$_2$ (1.35 g, 1.46 mmol) and (E)-methyl 3-(2,6-dichloro-4-(2,4-difluorophenyl)pyridin-3-yl)acrylate (2.5 g, 7.3 mmol) in THF/t-BuOH (20 mL/20 mL) was stirred at 40° C. under 50 psi H$_2$ for 12 h. MeOH was removed under reduced pressure and the crude residue was purified by silica gel chromatography (5:1 petroleum ether/ethyl acetate) to give the product. MS (ESI) calcd. for (C$_{15}$H$_{12}$Cl$_2$F$_2$NO$_2$) [M+H]$^+$, 346.0, found, 346.1. $^1$H NMR (400 MHz, CDCl$_3$) δ 7.10-7.17 (m, 2H), 6.92-7.01 (m, 2H), 3.58 (s, 3H), 2.86-2.90 (m, 2H), 2.44-2.48 (m, 2H).

Step 4: 3-(2,6-dichloro-4-(2,4-difluorophenyl)pyridin-3-yl)propan-1-ol

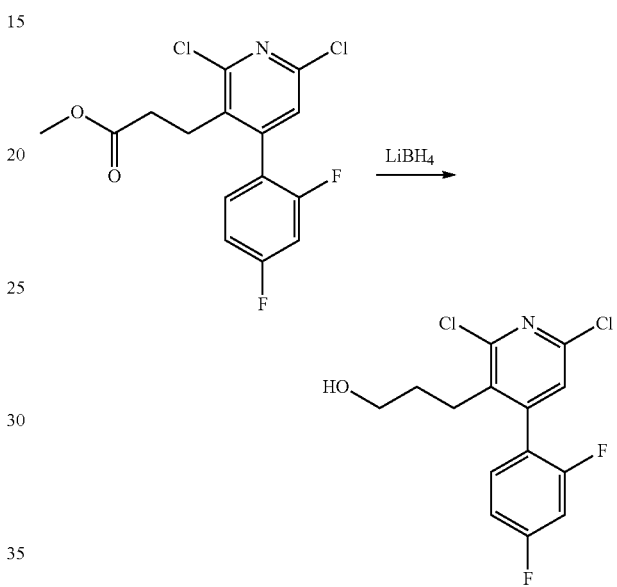

To the solution of methyl 3-(2,6-dichloro-4-(2,4-difluorophenyl)pyridin-3-yl)propanoate (850 mg, 2.5 mmol) in THF (15 mL) was added LiBH$_4$ (68.2 mg, 9.82 mmol) at 0° C. under N$_2$. The resulting mixture was stirred at 18° C. for 16 h. The reaction was poured into water (30 mL) and extracted with ethyl acetate (30 mL×3). The combined organic layers were concentrated in vacuo and the residue was purified by silica gel chromatography (ISCO®; 4 g SepaFlash® Column, eluting with 0-30% ethyl acetate/petroleum ether) to give the product. MS (ESI) calcd. for (C$_{14}$H$_{12}$Cl$_2$F$_2$NO) [M+H]$^+$, 318.0, found, 318.1. $^1$H NMR (400 MHz, CDCl$_3$) δ 7.15-7.22 (m, 1H), 7.12 (s, 1H), 6.91-7.03 (m, 2H), 3.49-3.55 (m, 2H), 2.66 (br. s., 2H), 1.68 (br. s., 2H).

Step 5: 3-(2,6-dichloro-4-(2,4-difluorophenyl)pyridin-3-yl)propanal (Intermediate 2-7)

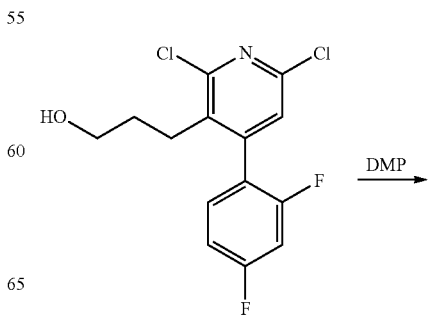

-continued

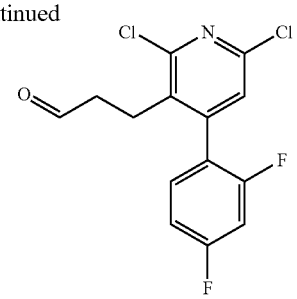

To a solution of 3-(2,6-dichloro-4-(2,4-difluorophenyl)pyridin-3-yl)propan-1-ol (525 mg, 1.65 mmol) in DCM (10 mL) was added DMP (840 mg, 1.980 mmol) at 0° C. and the reaction was stirred at 0° C. for 1 h. The mixture was concentrated in vacuo and the residue was purified by silica gel chromatography (ISCO®; 12 g SepaFlash® Column, eluting with 15% ethyl acetate/petroleum ether) to give the product. MS (ESI) calcd. for $(C_{14}H_{10}Cl_2F_2NO)$ $[M+H]^+$, 316.0, found, 315.9.

Step 6: 1-cyclopropyl-3-(2,6-dichloro-4-(2,4-difluorophenyl)pyridin-3-yl)propan-1-ol

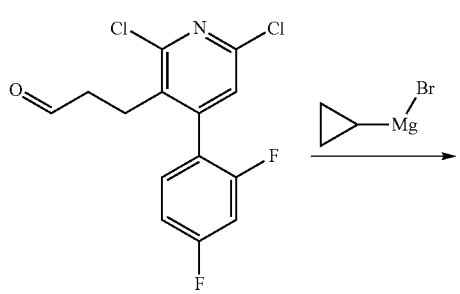

To a solution of 3-(2,6-dichloro-4-(2,4-difluorophenyl)pyridin-3-yl)propanal (350 mg, 1.1 mmol) in THF (15 mL) at 0° C. was added cyclopropylmagnesium bromide (4.4 mL, 2.2 mmol). The mixture was stirred at 0° C. for 1 h. The reaction was poured into saturated aqueous NH$_4$Cl solution (30 mL). The mixture was extracted with ethyl acetate (20 mL×3), the combined organic layers were washed with brine (50 mL), dried over Na$_2$SO$_4$, filtered and concentrated in vacuo. The residue was purified by silica gel chromatography (ISCO®; 12 g SepaFlash® Column, eluting with 15% ethyl acetate/petroleum ether) to give the product. MS (ESI) calcd. for $(C_{17}H_{16}Cl_2F_2NO)$ $[M+H]^+$, 358.1, found, 357.9. $^1$H NMR (400 MHz, CDCl$_3$) δ 7.07-7.15 (m, 1H), 7.04 (s, 1H), 6.83-6.95 (m, 2H), 3.40 (s, 2H), 2.60-2.69 (m, 2H), 1.52 (br. s., 1H), 0.66 (dd, J=4.41, 8.16 Hz, 1H), 0.35 (d, J=7.94 Hz, 2H), 0.07-0.15 (m, 1H), −0.02-0.06 (m, 1H).

Step 7: 7-chloro-2-cyclopropyl-5-(2,4-difluorophenyl)-3,4-dihydro-2H-pyrano[2,3-b]pyridine

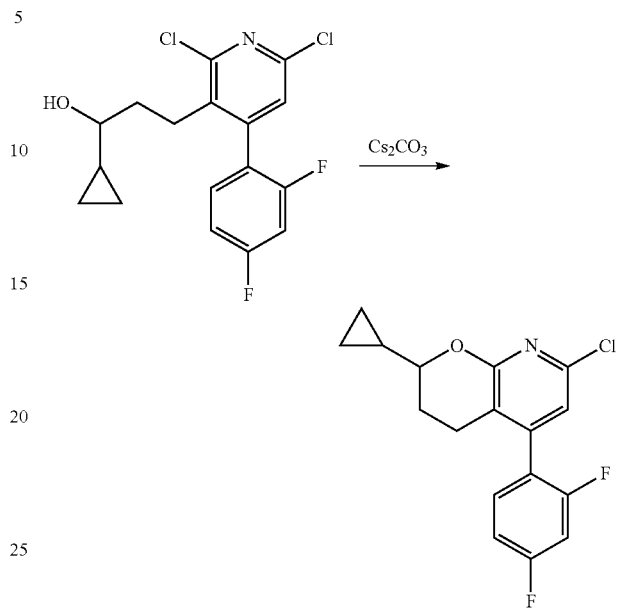

A mixture of 1-cyclopropyl-3-(2,6-dichloro-4-(2,4-difluorophenyl)pyridin-3-yl) propan-1-ol (250 mg, 0.698 mmol) and Cs$_2$CO$_3$ (568 mg, 1.745 mmol) in MeCN (10 mL) was stirred at 90° C. for 16 h. The mixture was concentrated in vacuo and the residue was purified by silica gel chromatography (ISCO®; 12 g SepaFlash® Column, eluting with 15% ethyl acetate/petroleum ether) to give the product. MS (ESI) calcd. for $(C_{17}H_{15}ClF_2NO)$ $[M+H]^+$, 322.0, found, 321.9.

Step 5: Ethyl 2-cyclopropyl-5-(2,4-difluorophenyl)-3,4-dihydro-2H-pyrano[2,3-b]pyridine-7-carboxylate

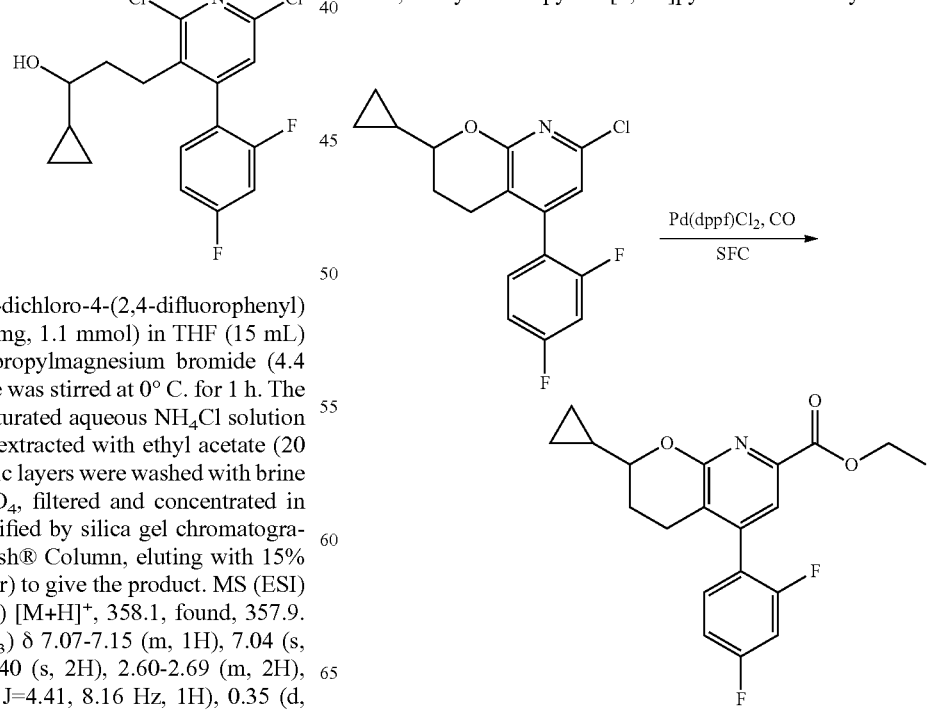

A mixture of 7-chloro-2-cyclopropyl-5-(2,4-difluorophenyl)-3,4-dihydro-2H-pyrano[2,3-b]pyridine (180 mg, 0.56 mmol), potassium acetate (110 mg, 1.1 mmol) and PdCl$_2$(dppf) (82 mg, 0.11 mmol) in EtOH (15 mL) was stirred at 80° C. under 50 Psi of CO for 5 h. The mixture was concentrated in vacuo and the residue was purified by silica gel chromatography (ISCO®; 4 g SepaFlash® Column, eluting with 20% ethyl acetate/petroleum ether) to give the product. MS (ESI) calcd. for (C$_{20}$H$_{19}$F$_2$NO$_3$Na) [M+Na]$^+$, 382.1, found, 382.0.

Step 8: ethyl (S)-2-cyclopropyl-5-(2,4-difluorophenyl)-3,4-dihydro-2H-pyrano[2,3-b]pyridine-7-carboxylate and ethyl (R)-2-cyclopropyl-5-(2,4-difluorophenyl)-3,4-dihydro-2H-pyrano[2,3-b]pyridine-7-carboxylate

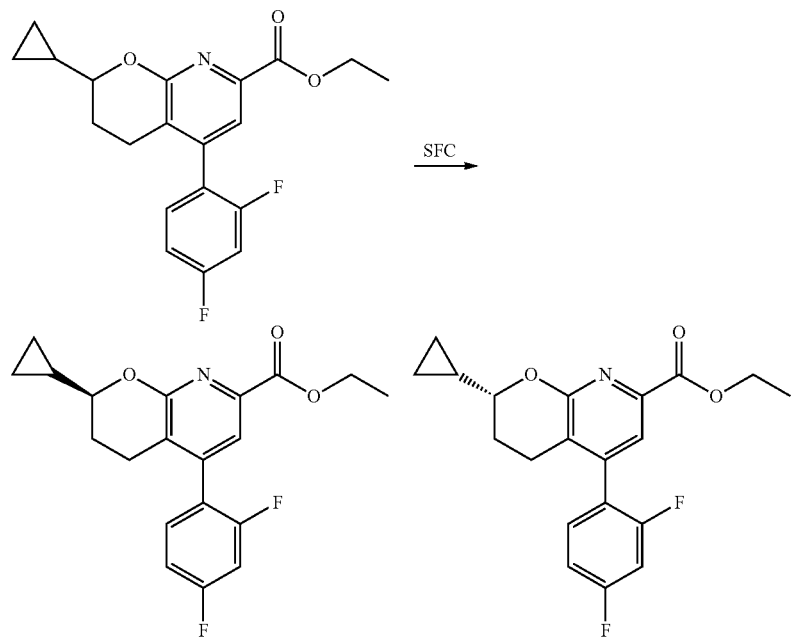

Racemic ethyl 2-cyclopropyl-5-(2,4-difluorophenyl)-3,4-dihydro-2H-pyrano[2,3-b]pyridine-7-carboxylate (160 mg, 0.45 mmol) was resolved by chiral SFC (Column: Chiralpak AD 250×30 mm, 5 um; Mobile phase: 40% to 40% EtOH (containing 0.05% DEA) in CO$_2$; Flow rate: 65 mL/min) to give the two enantiomers.

Step 9: (S)-2-cyclopropyl-5-(2,4-difluorophenyl)-3,4-dihydro-2H-pyrano[2,3-b]pyridine-7-carboxamide and (R)-2-cyclopropyl-5-(2,4-difluorophenyl)-3,4-dihydro-2H-pyrano[2,3-b]pyridine-7-carboxamide

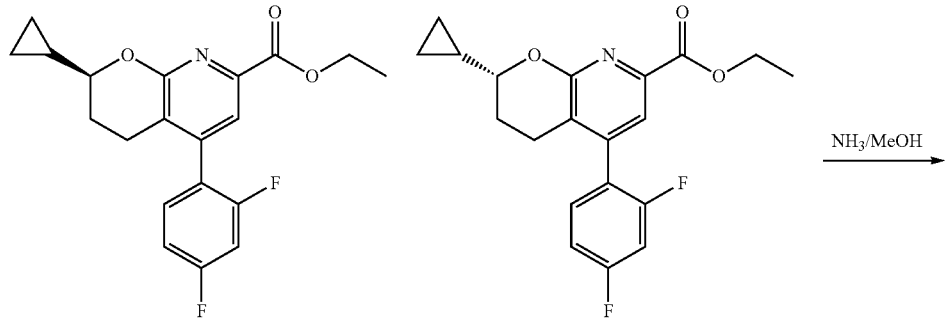

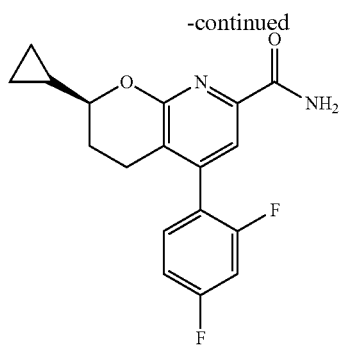
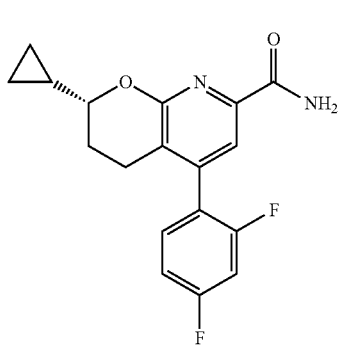

A solution of one enantiomer of ethyl 2-cyclopropyl-5-(2,4-difluorophenyl)-3,4-dihydro-2H-pyrano[2,3-b]pyridine-7-carboxylate (70 mg, 0.20 mmol) in ammonia (10 M in MeOH) (15 mL) was stirred at 19° C. for 5 h. The reaction was concentrated in vacuo and the residue was purified by Prep-HPLC (Column: Phenomenex Synergi C18 150×30 mm, 4 um; Mobile phase: 50% to 70% water (containing 0.1% TFA)-ACN; Flow rate: 25 mL/min) to give one enantiomer of the title compound. MS (ESI) calcd. for ($C_{18}H_{17}F_2N_2O_2$) [M+H]$^+$, 331.1, found, 331.0. $^1$H NMR (400 MHz, CD$_3$OD) δ 7.18 (s, 1H), 6.96-7.06 (m, 1H), 6.69-6.80 (m, 2H), 3.28 (t, J=8.27 Hz, 1H), 2.31-2.43 (m, 1H), 2.17-2.28 (m, 1H), 1.79 (d, J=13.67 Hz, 1H), 1.38-1.51 (m, 1H), 0.72-0.84 (m, 1H), 0.13-0.34 (m, 3H), −0.01-0.08 (m, 1H).

Similar treatment of the other enantiomer of ethyl 2-cyclopropyl-5-(2,4-difluorophenyl)-3,4-dihydro-2H-pyrano[2,3-b]pyridine-7-carboxylate afforded the other enantiomer of the title compound. $^1$H NMR (400 MHz, CD$_3$OD) δ 7.19 (s, 1H), 6.96-7.05 (m, 1H), 6.70-6.79 (m, 2H), 3.28 (t, J=8.38 Hz, 1H), 2.31-2.44 (m, 1H), 2.15-2.28 (m, 1H), 1.79 (d, J=13.89 Hz, 1H), 1.37-1.51 (m, 1H), 0.72-0.83 (m, 1H), 0.13-0.34 (m, 3H), −0.02-0.07 (m, 1H).

Example 2-4A and 2-4B

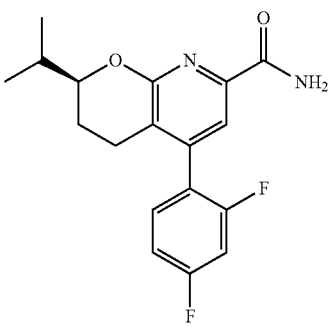

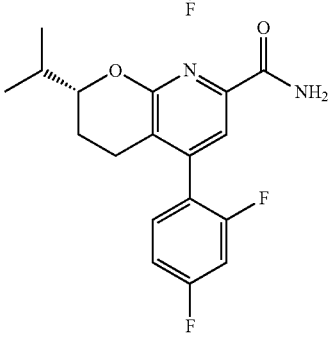

(S)-5-(2,4-difluorophenyl)-2-isopropyl-3,4-dihydro-2H-pyrano[2,3-b]pyridine-7-carboxamide and (R)-5-(2,4-difluorophenyl)-2-isopropyl-3,4-dihydro-2H-pyrano[2,3-b]pyridine-7-carboxamide Step 1: (E)-ethyl 3-(2,6-dichloro-4-(2,4-difluorophenyl)pyridin-3-yl)acrylate

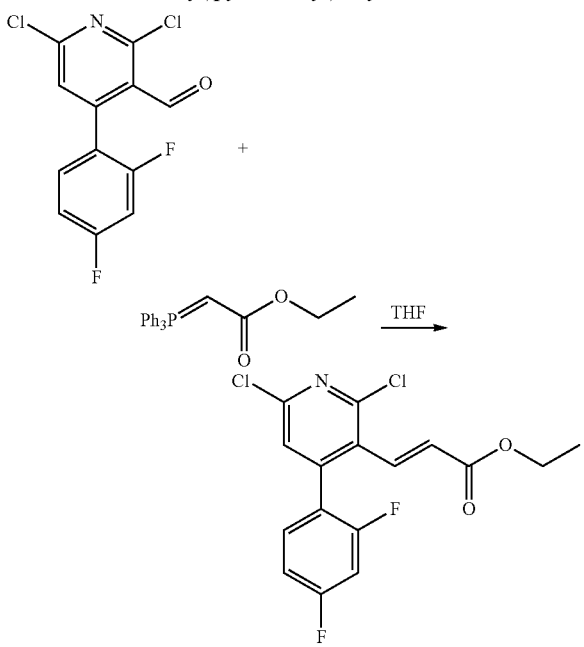

A solution of 2,6-dichloro-4-(2,4-difluorophenyl)nicotinaldehyde (6 g, 21 mmol) and ethyl 2-(triphenylphosphoranylidene)acetate (8.7 g, 25 mmol) in THF (100 mL) was stirred at 70° C. for 12 h. The solvent was removed under reduced pressure. The residue was purified by silica gel chromatography (10:1 petroleum ether/ethyl acetate) to give the product. MS (ESI) calcd. for ($C_{16}H_{12}Cl_2F_2NO_2$) [M+H]$^+$, 358.0, found, 358.2.

Step 2: ethyl 3-(2,6-dichloro-4-(2,4-difluorophenyl)pyridin-3-yl)propanoate

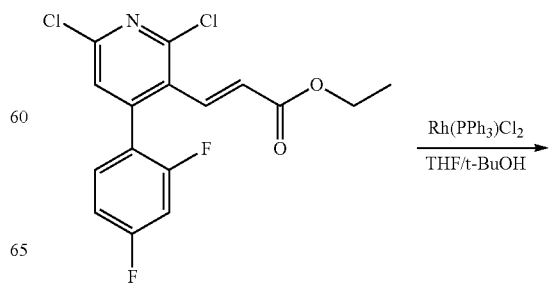

-continued

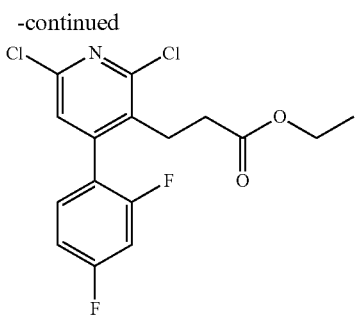

A solution of Rh(PPh₃)Cl₂ (5.8 g, 6.3 mmol) and (E)-ethyl 3-(2,6-dichloro-4-(2,4-difluorophenyl)pyridin-3-yl)acrylate (7.5 g, 21.0 mmol) in THF/t-BuOH (50 mL/50 mL) was stirred at 50° C. under 40 psi H₂ for 12 h. MeOH was removed under reduced pressure and the residue was purified by silica gel chromatography (10:1 petroleum ether/ethyl acetate) to give the product. MS (ESI) calcd. for ($C_{16}H_{14}Cl_2F_2NO_2$) [M+H]⁺, 360.0, found, 360.2. ¹H NMR (400 MHz, CD₃OD) δ 7.32-7.38 (m, 2H), 7.18-7.10 (m, 2H), 4.01 (t, J=6.4 Hz, 2H), 2.89 (m, 2H), 2.43 (t, J=8.4 Hz, 2H), 1.14 (t, J=7.6 Hz, 3H).

Step 3: 3-(2,6-dichloro-4-(2,4-difluoropheny)pyridin-3-yl)propanoic acid

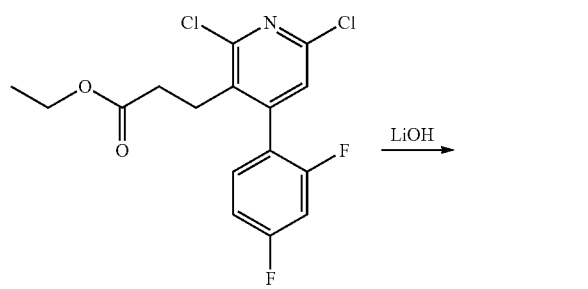

Ethyl 3-(2,6-dichloro-4-(2,4-difluorophenyl)pyridin-3-yl) propanoate (0.6 g, 1.7 mmol) was dissolved in (40 mL) (THF:H₂O=3:1). The mixture was stirred at 25° C. Then LiOH (0.21 g, 5.1 mmol) was added to the solution. The mixture was stirred at 25° C. for 4 h. The mixture was concentrated under reduce pressure and adjusted to pH 5 with citric acid monohydrate. The mixture was extracted with ethyl acetate (20 mL×3) and dried over anhydrous Na₂SO₄. The combined organic layers were concentrated to afford the product which was used in the next step without further purification. MS (ESI) calcd for ($C_{14}H_{10}Cl_2F_2NO_2$) [M+H]⁺, 332.0, found, 331.9.

Step 4: 3-(2,6-dichloro-4-(2,4-difluorophenyl)pyridin-3-yl)-N-methoxy-N-methylpropanamide

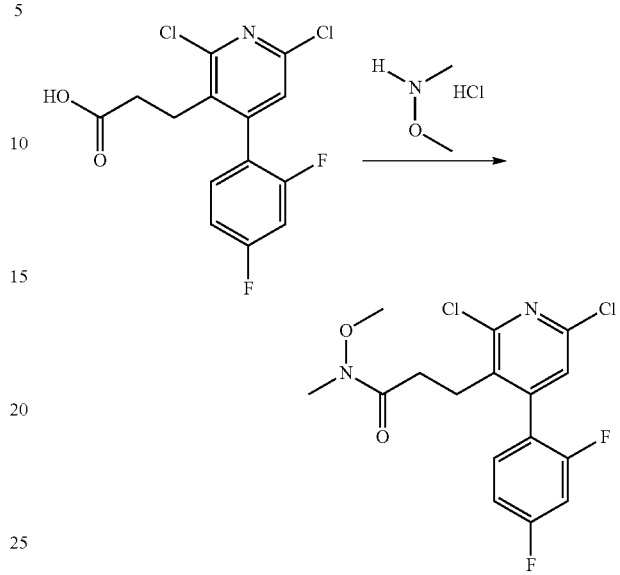

To a solution of 3-(2,6-dichloro-4-(2,4-difluorophenyl) pyridin-3-yl)propanoic acid (0.5 g, 1.5 mmol) in THF (15 mL) was added HATU (0.76 g, 2 mmol) followed by TEA (0.45 g, 4.5 mmol). The mixture was stirred at 25° C. for 10 min. Then N,O-dimethylhydroxylamine hydrochloride (0.2 g, 2.0 mmol) was added to the mixture. The reaction was stirred at 25° C. for 1 h. The mixture was concentrated under reduce pressure and the residue was purified by silica gel chromatography (ISCO®; 4 g SepaFlash® Column, eluting with 0% to 20% ethyl acetate/petroleum ether) to give the product. MS (ESI) calcd for ($C_{16}H_{15}Cl_2F_2N_2O_2$) [M+H]⁺, 375.0, found, 374.9.

Step 5: 1-(2,6-dichloro-4-(2,4-difluorophenyl)pyridin-3-yl)-4-methylpentan-3-one

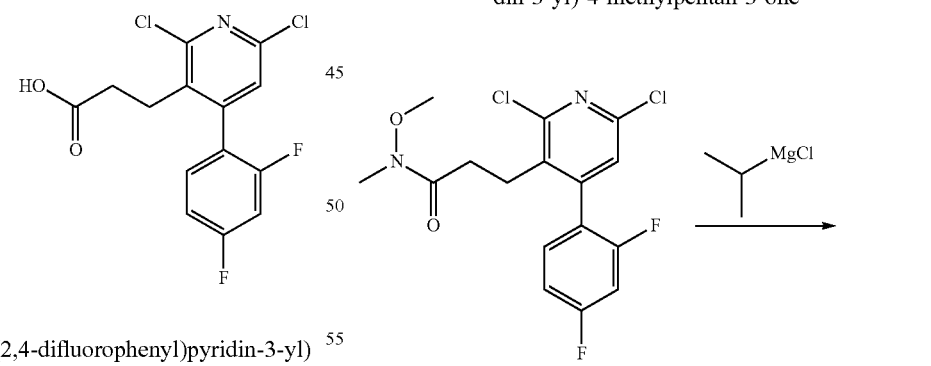

To a solution of 3-(2,6-dichloro-4-(2,4-difluorophenyl)pyridin-3-yl)-N-methoxy-N-methylpropanamide (0.5 g, 1.3 mmol) in THF (20 mL) at 0° C. under $N_2$ was added isopropylmagnesium chloride (1.3 mL) dropwise. The mixture was stirred at 25° C. for 6 h. The mixture was concentrated under reduced pressure and poured into water (50 mL) and extracted with ethyl acetate (30 mL×3). The combined organic phases were washed with HCl (1 M, 2×20 mL) and brine (20 mL), dried over $Na_2SO_4$ and concentrated under reduced pressure. The residue was purified by silica gel chromatography (eluting with ethyl acetate/petroleum ether) to afford the product. MS (ESI) calcd for ($C_{17}H_{16}Cl_2F_2NO$) [M+H]$^+$, 358.0, found, 357.9.

Step 6: 1-(2,6-dichloro-4-(2,4-difluorophenyl)pyridin-3-yl)-4-methylpentan-3-ol

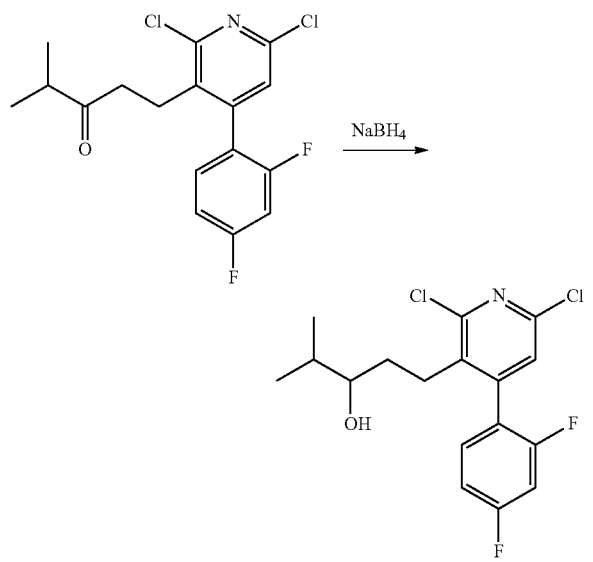

To a solution of 1-(2,6-dichloro-4-(2,4-difluorophenyl)pyridin-3-yl)-4-methylpentan-3-one (0.14 g, 0.39 mmol) in $CH_3OH$ (10 mL) at 0° C. under $N_2$ was added $NaBH_4$ (0.015 g, 0.4 mmol). The mixture was stirred at 0° C. for 0.5 h. The mixture was poured into water (10 mL) and extracted with ethyl acetate (20 mL×3). The combined organic layers were concentrated under reduce pressure. The residue was purified by Prep-TLC (silica gel, eluting with 1:10 ethyl acetate/petroleum ether) to afford the product. MS (ESI) calcd for ($C_{17}H_{18}Cl_2F_2NO$) [M+H]$^+$, 360.1, found, 359.9.

Step 7: 7-chloro-5-(2,4-dimethylphenyl)-2-isopropyl-3,4-dihydro-2H-pyrano[2,3-b]pyridine

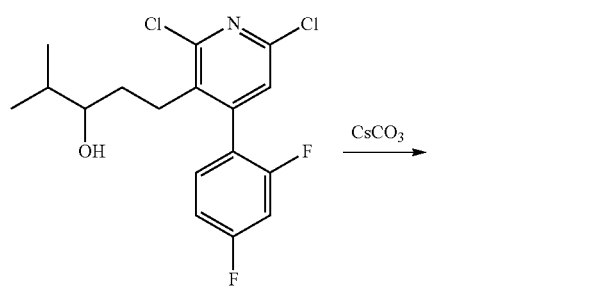

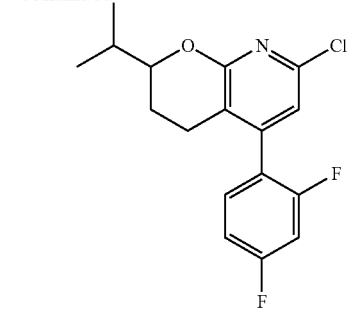

To a solution of 1-(2,6-dichloro-4-(2,4-difluorophenyl)pyridin-3-yl)-4-methylpentan-3-ol in $CH_3CN$ (20 mL) was added $Cs_2CO_3$ (0.2 g, 0.6 mmol) and the mixture was stirred at 90° C. for 10 h. The solution was poured into $H_2O$ (20 mL) and extracted with ethyl acetate (20 mL×3). The combined organic layers were concentrated under reduce pressure and purified by Prep-TLC (silica gel, eluting with 1:10 ethyl acetate/petroleum ether) to afford the product. $^1$H NMR (400 MHz, CDCl$_3$) δ 7.18-7.07 (m, 1H), 6.96-6.80 (m, 2H), 6.72 (s, 1H), 3.98-3.85 (m, 1H), 2.64-2.46 (m, 1H), 2.42-2.30 (m, 1H), 2.00-1.81 (m, 2H), 1.66-1.47 (m, 1H), 1.05-0.90 (m, 6H)

Step 8: ethyl 5-(2,4-difluorophenyl)-2-isopropyl-3,4-dihydro-2H-pyrano[2,3-b]pyridine-7-carboxylate

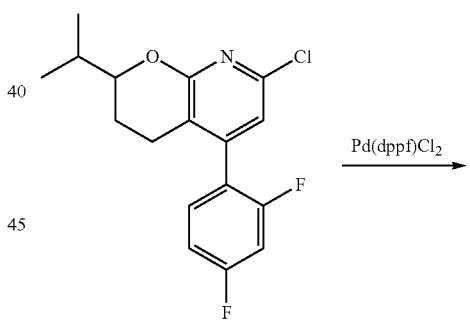

To a solution of 7-chloro-5-(2,4-dimethylphenyl)-2-isopropyl-3,4-dihydro-2H-pyrano[2,3-b]pyridine (0.1 g, 0.29 mmol) in EtOH (15 mL) was added Pd(dppf)Cl$_2$ (0.021 g, 0.029 mmol) and KOAc (0.058 g, 0.58 mmol). The mixture was stirred at 60° C. under an atmosphere of CO for 10 h. The reaction mixture was concentrated under reduced pressure and the residue was purified by Prep-TLC (silica gel, eluting with 1:4 ethyl acetate/petroleum ether) to afford the product. MS (ESI) calcd for ($C_{20}H_{22}F_2NO_3$) [M+H]$^+$, 362.0, found, 361.9. $^1$H NMR (400 MHz, CDCl$_3$) δ 7.56 (s, 1H), 7.27-7.13 (m, 1H), 7.03-6.82 (m, 2H), 4.40 (q, J=7.3 Hz, 2H), 3.98 (dd, J=5.7, 9.2 Hz, 1H), 2.79-2.44 (m, 2H), 2.11-1.82 (m, 3H), 1.72-1.54 (m, 1H), 1.37 (t, J=7.0 Hz, 3H), 1.11-0.93 (m, 6H).

Step 9: ethyl (S)-5-(2,4-difluorophenyl)-2-isopropyl-3,4-dihydro-2H-pyrano[2,3-b]pyridine-7-carboxylate and ethyl (R)-5-(2,4-difluorophenyl)-2-isopropyl-3,4-dihydro-2H-pyrano[2,3-b]pyridine-7-carboxylate

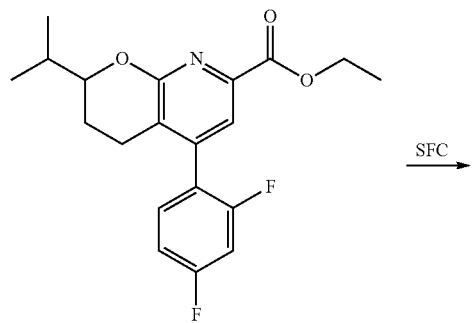

SFC →

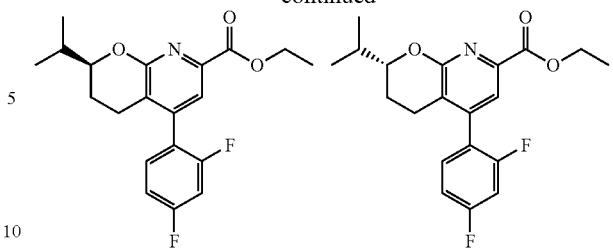

Racemic ethyl 5-(2,4-difluorophenyl)-2-isopropyl-3,4-dihydro-2H-pyrano[2,3-b]pyridine-7-carboxylate (90 mg, 0.25 mmol) was resolved by chiral SFC (Column: Chiralpak AD 250×30 mm, 5 um; Mobile phase: 40% to 40% EtOH (containing 0.05% DEA) in CO$_2$; Flow rate: 65 mL/min) to give the two enantiomers.

Step 10

(S)-5-(2,4-difluorophenyl)-2-isopropyl-3,4-dihydro-2H-pyrano[2,3-b]pyridine-7-carboxamide and ethyl (R)-5-(2,4-difluorophenyl)-2-isopropyl-3,4-dihydro-2H-pyrano[2,3-b]pyridine-7-carboxylate

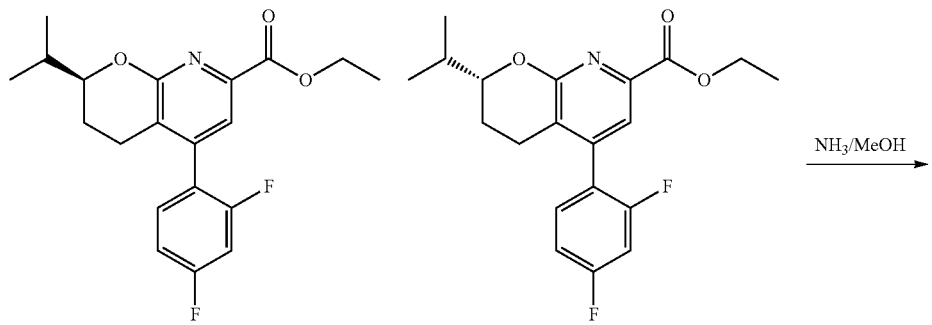

NH$_3$/MeOH →

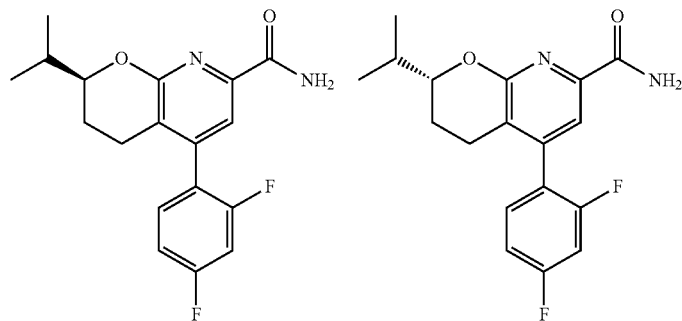

A solution of one enantiomer of ethyl 5-(2,4-difluorophenyl)-2-isopropyl-3,4-dihydro-2H-pyrano[2,3-b]pyridine-7-carboxylate (40 mg, 0.11 mmol) in ammonia (10 M in MeOH) (20 mL) was stirred at 20° C. for 16 h. The mixture was concentrated under reduced pressure. The residue was purified by Prep-TLC to give one enantiomer of the title compound. MS (ESI) calcd. for ($C_{18}H_{19}F_2N_2O_2$) [M+H]$^+$, 333.1, found, 332.9. $^1$H NMR (400 MHz, CD$_3$OD) δ 7.46 (br. s., 1H), 7.35-7.24 (m, 1H), 7.09-6.97 (m, 2H), 3.96 (dd, J=5.6, 9.2 Hz, 1H), 2.76-2.60 (m, 1H), 2.54-2.39 (m, 1H), 2.00-1.82 (m, 2H), 1.67-1.47 (m, 1H), 0.99 (dd, J=6.8, 16.8 Hz, 6H)

Similar treatment of the other enantiomer of ethyl 5-(2,4-difluorophenyl)-2-isopropyl-3,4-dihydro-2H-pyrano[2,3-b]pyridine-7-carboxylate afforded the other enantiomer of the title compound. MS (ESI) calcd. for ($C_{18}H_{19}F_2N_2O_2$) [M+H]$^+$, 333.1, found, 332.9. $^1$H NMR (400 MHz, CD$_3$OD) δ 7.56 (br. s., 1H), 7.43-7.34 (m, 1H), 7.18-7.06 (m, 2H), 4.05 (dd, J=5.4, 9.4 Hz, 1H), 2.87-2.68 (m, 1H), 2.64-2.49 (m, 1H), 2.13-1.91 (m, 2H), 1.77-1.59 (m, 1H), 1.09 (dd, J=6.7, 16.6 Hz, 6H).

Example 2-5

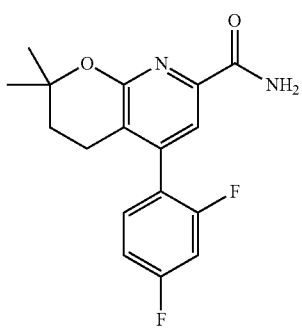 [SMILES: CC1(C)CCc2c(-c3ccc(F)cc3F)cc(C(N)=O)nc2O1]

5-(2,4-difluorophenyl)-2,2-dimethyl-3,4-dihydro-2H-pyrano[2,3-b]pyridine-7-carboxamide Step 1: 4-(2,6-dichloro-4-(2,4-difluorophenyl)pyridin-3-yl)-2-methylbutan-2-ol

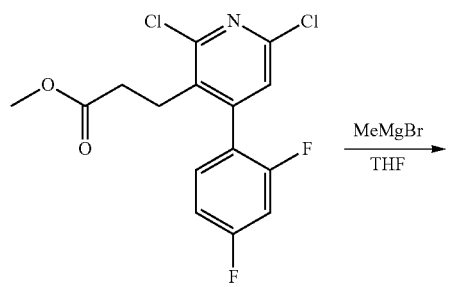

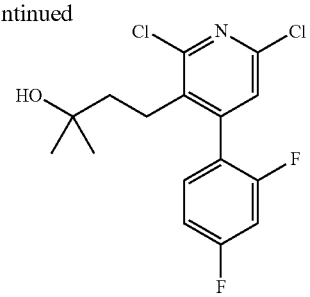

Methylmagnesium bromide (0.64 mL, 1.9 mmol) was added dropwise to a solution of methyl 3-(2,6-dichloro-4-(2,4-difluorophenyl)pyridin-3-yl)propanoate (Intermediate 2-6, 110 mg, 0.32 mmol) in THF (3 mL) at 0° C. under an atmosphere of N$_2$. The resulting mixture was stirred at 0° C. for 1 h. The mixture was quenched with saturated aqueous NH$_4$Cl (20 mL). Then the mixture was extracted with ethyl acetate (10 mL×3). The mixture was concentrated in vacuo and the residue was purified by Prep-TLC (silica gel, eluting with 1:3 ethyl acetate/petroleum ether) to give the product. MS (ESI) calcd. for ($C_{16}H_{16}Cl_2F_2NO$) [M+H]$^+$, 346.0, found, 345.9. $^1$H NMR (400 MHz, CDCl$_3$) δ 7.22-7.14 (m, 1H), 7.11 (s, 1H), 7.04-6.91 (m, 2H), 2.64 (br. s., 2H), 1.53 (d, J=3.9 Hz, 2H), 1.09 (s, 6H).

Step 2: 7-chloro-5-(2,4-difluorophenyl)-2,2-dimethyl-3,4-dihydro-2H-pyrano[2,3-b]pyridine

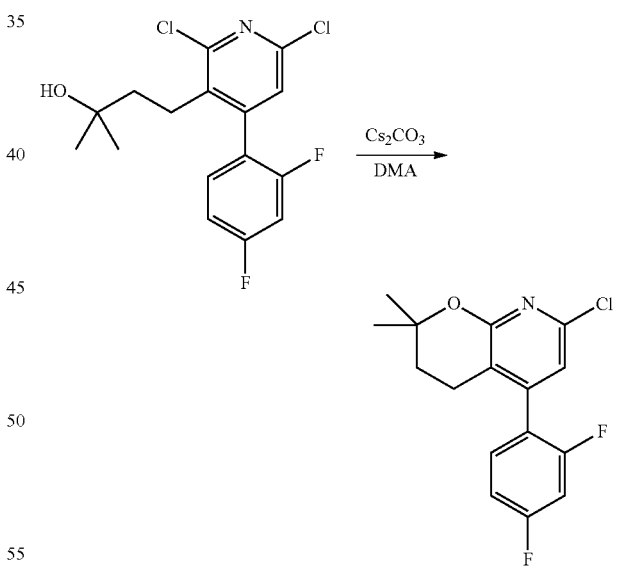

A mixture of 4-(2,6-dichloro-4-(2,4-difluorophenyl)pyridin-3-yl)-2-methylbutan-2-ol (65 mg, 0.19 mmol) and Cs$_2$CO$_3$ (120 mg, 0.38 mmol) in DMA (5 mL) was stirred at 120° C. for 19 h. The reaction mixture was washed with water (10 mL) and extracted with ethyl acetate (5 mL×3). The combined organic layers were concentrated in vacuo to give crude product, which was purified by Prep-TLC (silica gel, eluting with 1:3 ethyl acetate/petroleum ether) to give the product. MS (ESI) calcd. for ($C_{16}H_{15}ClF_2NO$) [M+H]$^+$, 310.1, found, 310.1.

Step 3: ethyl 5-(2,4-difluorophenyl)-2,2-dimethyl-3,4-dihydro-2H-pyrano[2,3-b]pyridine-7-carboxylate

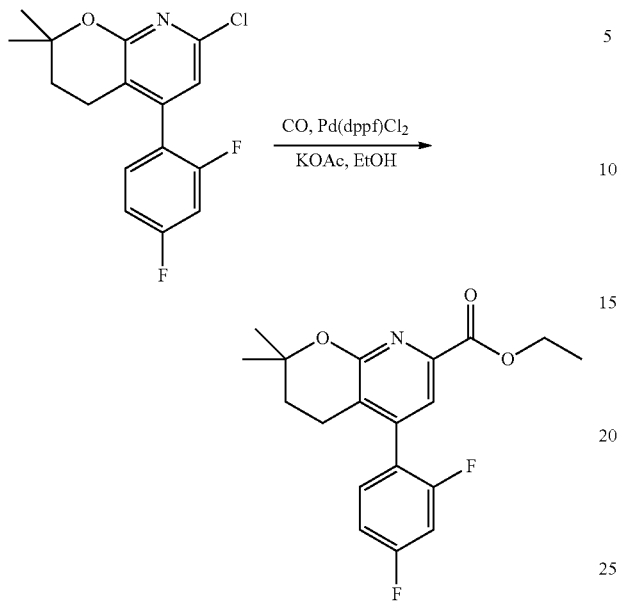

To a solution of 7-chloro-5-(2,4-difluorophenyl)-2,2-dimethyl-3,4-dihydro-2H-pyrano[2,3-b]pyridine (25 mg, 0.08 mmol) and potassium acetate (15.8 mg, 0.16 mmol) in EtOH (10 mL) was added PdCl$_2$(dppf) (11.8 mg, 0.016 mmol) under N$_2$ atmosphere. The mixture was degassed and backfilled with CO (three times). The resulting mixture was stirred under 50 psi of CO at 80° C. for 30 h. The catalyst was filtered off and filtrate was concentrated under reduced pressure and purified by Prep-TLC (silica gel, eluting with 1:5 ethyl acetate/petroleum ether) to give the product. MS (ESI) calcd. for (C$_{19}$H$_{20}$F$_2$NO$_3$) [M+H]$^+$, 348.1, found, 348.5.

Step 4: 5-(2,4-difluorophenyl)-2,2-dimethyl-3,4-dihydro-2H-pyrano[2,3-b]pyridine-7-carboxamide

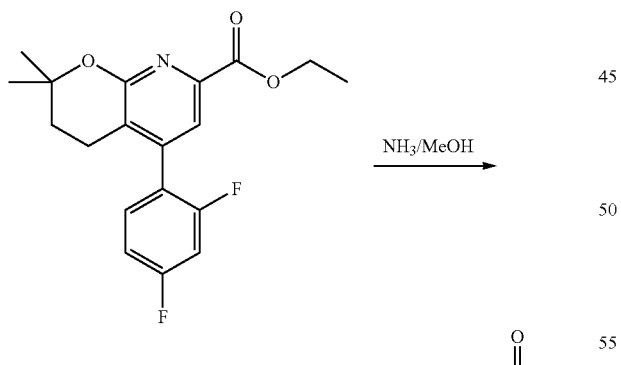

A solution of 5-(2,4-difluorophenyl)-2,2-dimethyl-3,4-dihydro-2H-pyrano[2,3-b]pyridine-7-carboxylate (15 mg, 0.05 mmol) in NH$_3$/MeOH (20 mL) was stirred at 25° C. for 24 h. The mixture was concentrated under reduced pressure and purified by Prep-TLC (silica gel, ethyl acetate) to give the title compound. MS (ESI) calcd. for (C$_{17}$H$_{17}$F$_2$N$_2$O$_2$) [M+H]$^+$, 319.1, found, 318.9. $^1$H NMR (400 MHz, CD$_3$OD) δ 7.55 (s, 1H), 7.45-7.35 (m, 1H), 7.19-7.07 (m, 1H), 2.66 (t, J=6.5 Hz, 2H), 1.84 (t, J=6.7 Hz, 2H), 1.43 (s, 6H).

Example 2-6A and 2-6B

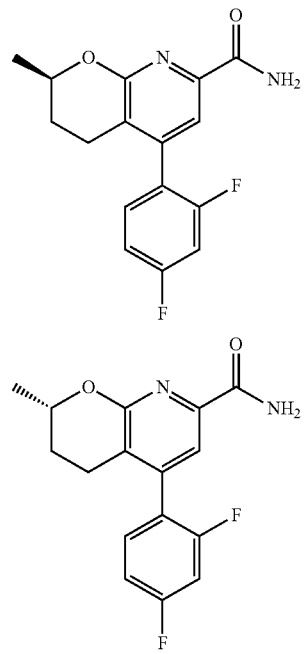

(R)-5-(2,4-difluorophenyl)-2-methyl-3,4-dihydro-2H-pyrano[2,3-b]pyridine-7-carboxamide and (S)-5-(2,4-difluorophenyl)-2-methyl-3,4-dihydro-2H-pyrano[2,3-b]pyridine-7-carboxamide Step 1: 4-(2,6-dichloro-4-(2,4-difluorophenyl)pyridin-3-yl)butan-2-ol

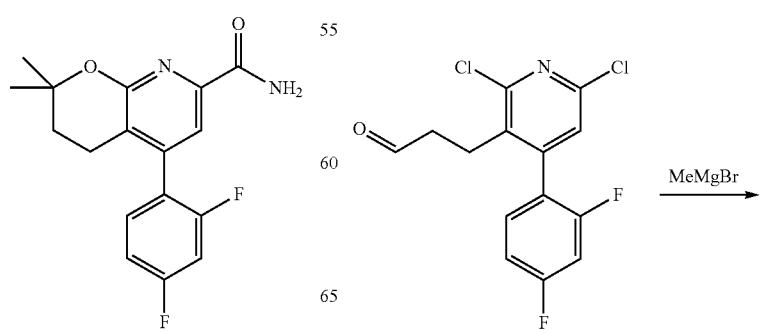

-continued

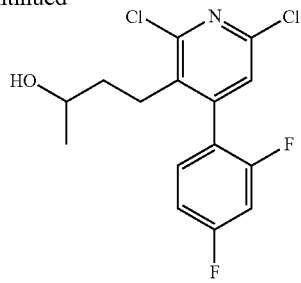

Methylmagnesium bromide (1.7 mL, 5.1 mmol) was added to the solution of 3-(2,6-dichloro-4-(2,4-difluorophenyl)pyridin-3-yl)propanal (Intermediate 2-7, 270 mg, 0.85 mmol) in THF (10 mL) at 0° C. under $N_2$. The resulting mixture was stirred at 0° C. for 1.5 h. The mixture was quenched with saturated aqueous $NH_4Cl$ (50 mL) and extracted with ethyl acetate (50 mL×3). The combined organic layers were concentrated in vacuo and purified by silica gel chromatography (ISCO®; 4 g SepaFlash® Column, eluting with 0-30% ethyl acetate/petroleum ether) to give the product. MS (ESI) calcd. for ($C_{15}H_{14}Cl_2F_2NO$) [M+H]$^+$, 332.0, found, 331.9.

Step 2: 7-chloro-5-(2,4-difluorophenyl)-2-methyl-3,4-dihydro-2H-pyrano[2,3-b]pyridine

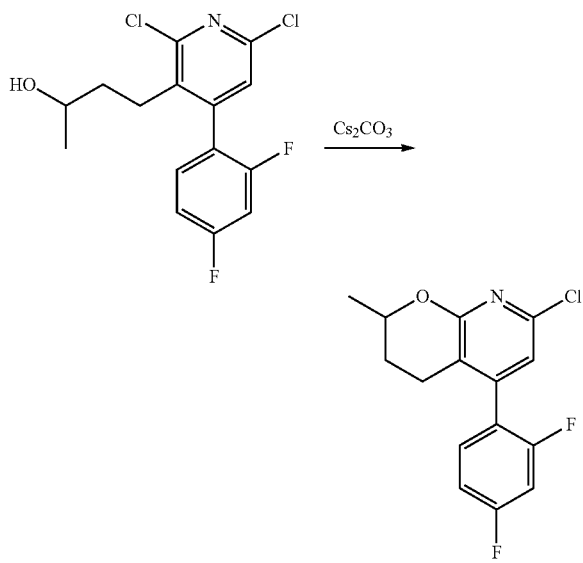

A mixture of 4-(2,6-dichloro-4-(2,4-difluorophenyl)pyridin-3-yl)butan-2-ol (200 mg, 0.60 mmol) and $Cs_2CO_3$ (392 mg, 1.20 mmol) in MeCN (10 mL) was stirred at 90° C. for 22 h. The reaction mixture was poured into water (50 mL) and extracted with ethyl acetate (30 mL×3). The combined organic layers were concentrated in vacuo and purified by Prep-TLC (silica gel, eluting with 1:3 ethyl acetate/petroleum ether) to give the product. MS (ESI) calcd. for ($C_{15}H_{13}ClF_2NO$) [M+H]$^+$, 296.1, found, 296.1.

Step 3: ethyl (R)-5-(2,4-difluorophenyl)-2-methyl-3,4-dihydro-2H-pyrano[2,3-b]pyridine-7-carboxylate and ethyl (S)-5-(2,4-difluorophenyl)-2-methyl-3,4-dihydro-2H-pyrano[2,3-b]pyridine-7-carboxylate

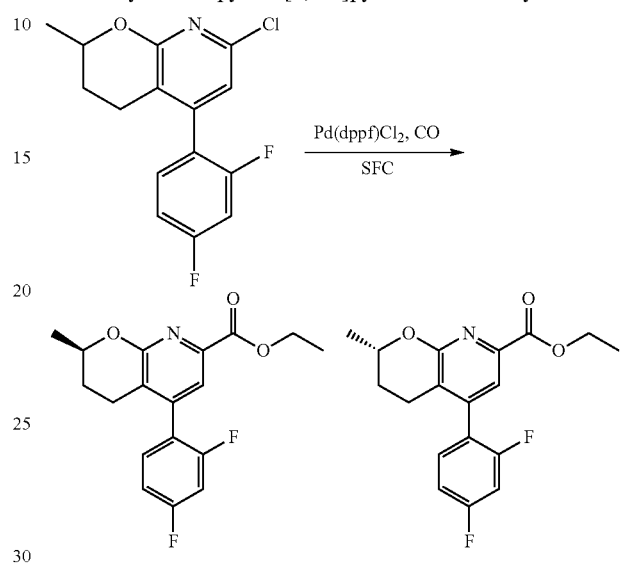

To a solution of 7-chloro-5-(2,4-difluorophenyl)-2-methyl-3,4-dihydro-2H-pyrano[2,3-b]pyridine (120 mg, 0.41 mmol) in EtOH (10 mL) was added potassium acetate (80 mg, 0.81 mmol) and $PdCl_2$(dppf) (30 mg, 0.04 mmol) under $N_2$ atmosphere. The mixture was degassed and backfilled with CO (three times). The resulting mixture was stirred under 50 psi CO at 70° C. for 7 h. The mixture was concentrated under reduced pressure to give the crude product, which was purified by prep-TLC (silica gel, eluting with 5:1 petroleum ether:ethyl acetate) to afford the racemic product. MS (ESI) calcd. for ($C_{18}H_{18}F_2NO_3$) [M+H]$^+$, 334.1, found, 334.1.

Racemic ethyl 5-(2,4-difluorophenyl)-2-methyl-3,4-dihydro-2H-pyrano[2,3-b]pyridine-7-carboxylate was resolved by chiral SFC (Column: Chiralpak Whelk-O1 250× 30 mm, 10 um; Mobile phase: 40% to 40% MeOH (containing 0.05% DEA) in $CO_2$; Flow rate: 50 mL/min) to give the two enantiomers.

Step 4: (R)-5-(2,4-difluorophenyl)-2-methyl-3,4-dihydro-2H-pyrano[2,3-b]pyridine-7-carboxamide and (S)-5-(2,4-difluorophenyl)-2-methyl-3,4-dihydro-2H-pyrano[2,3-b]pyridine-7-carboxamide

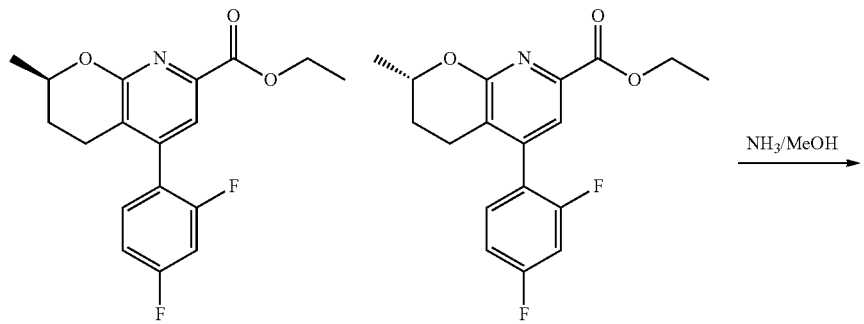

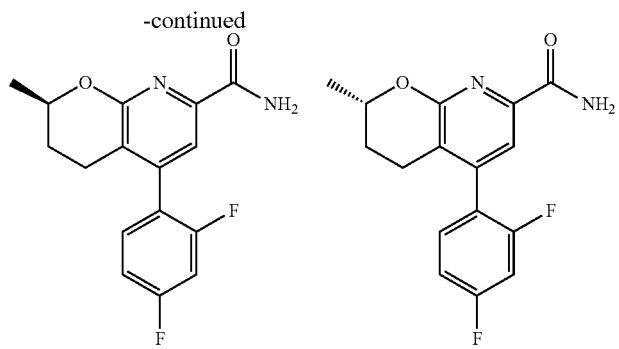

A solution of one enantiomer of ethyl 5-(2,4-difluorophenyl)-2-methyl-3,4-dihydro-2H-pyrano[2,3-b]pyridine-7-carboxylate (35 mg, 0.11 mmol) in ammonia (10 M in MeOH) (20 mL) was stirred at 15° C. for 15 h. The mixture was concentrated in vacuo and purified by Prep-HPLC (Column: Phenomenex Synergi C18 150×30 mm, 4 um; Mobile phase: 43% to 63% water (containing 0.1% TFA)-ACN; Flow rate: 25 mL/min) to give one enantiomer of the title compound. MS (ESI) calcd. for $(C_{16}H_{15}F_2N_2O_2)$ $[M+H]^+$, 305.1, found, 305.0. $^1$H NMR (400 MHz, CDCl$_3$) δ 7.79-7.66 (m, 2H), 7.27-7.20 (m, 1H), 7.03-6.88 (m, 2H), 5.81 (br. s., 1H), 4.50-4.38 (m, 1H), 2.75 (br. s., 1H), 2.56 (d, J=16.5 Hz, 1H), 2.07-1.97 (m, 1H), 1.76-1.59 (m, 1H), 1.52 (d, J=6.2 Hz, 3H).

Similar treatment of the other enantiomer of ethyl 5-(2,4-difluorophenyl)-2-methyl-3,4-dihydro-2H-pyrano[2,3-b]pyridine-7-carboxylate afforded the other enantiomer of the title compound. MS (ESI) calcd. for $(C_{16}H_{15}F_2N_2O_2)$ $[M+H]^+$, 305.1, found, 305.0. $^1$H NMR (400 MHz, CDCl$_3$) δ 7.72 (s, 2H), 7.26-7.20 (m, 1H), 7.03-6.88 (m, 2H), 5.66 (br. s., 1H), 4.50-4.39 (m, 1H), 2.73 (br. s., 1H), 2.62-2.50 (m, 1H), 2.07-1.97 (m, 1H), 1.76-1.62 (m, 1H), 1.52 (d, J=6.2 Hz, 3H).

Example 2-7

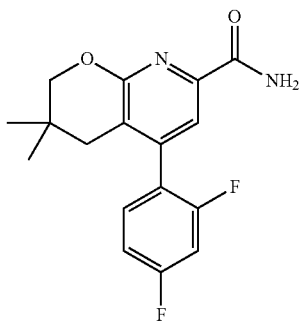 [SMILES: CC1(C)COc2nc(C(N)=O)cc(-c3ccc(F)cc3F)c2C1]

5-(2,4-difluorophenyl)-3,3-dimethyl-3,4-dihydro-2H-pyrano[2,3-b]pyridine-7-carboxamide Step 1: methyl 3-(2,6-dichloro-4-(2,4-difluorophenyl)pyridin-3-yl)-3-hydroxy-2,2-dimethylpropanoate

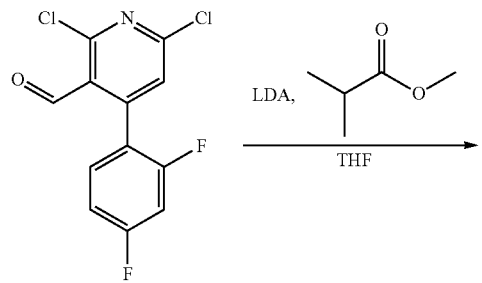

To a solution of methyl isobutyrate (1.7 g, 17 mmol) in THF (20 mL) under N$_2$ at −60° C. was added LDA (8.35 mL, 16.7 mmol). The reaction was stirred at −60° C. for 0.5 h. 2,6-dichloro-4-(2,4-difluorophenyl)nicotinaldehyde (Intermediate 2-1, 4 g, 14 mmol) was added to slowly over 30 min. The reaction was stirred at −60° C. for 1 h. The mixture was quenched with saturated aqueous NH$_4$Cl (20 mL) and extracted with EtOAc (50 mL). The combined organic extracts were concentrated under reduced pressure and purified by silica gel chromatography (ISCO®; 40 g SepaFlash® Column, eluting with 10%-20% ethyl acetate/petroleum ether) to give the product. MS (ESI) calcd. for $(C_{17}H_{16}Cl_2F_2NO_3)$ $[M+H]^+$, 390.0, found, 389.9. $^1$H NMR (400 MHz, CD$_3$OD) δ 7.51-7.32 (m, 1H), 7.26 (s, 1H), 7.15-6.96 (m, 2H), 3.60 (s, 3H), 1.02-0.91 (m, 6H).

Step 2: 1-(2,6-dichloro-4-(2,4-difluorophenyl)pyridin-3-yl)-3-methoxy-2,2-dimethyl-3-oxopropyl ethyl oxalate

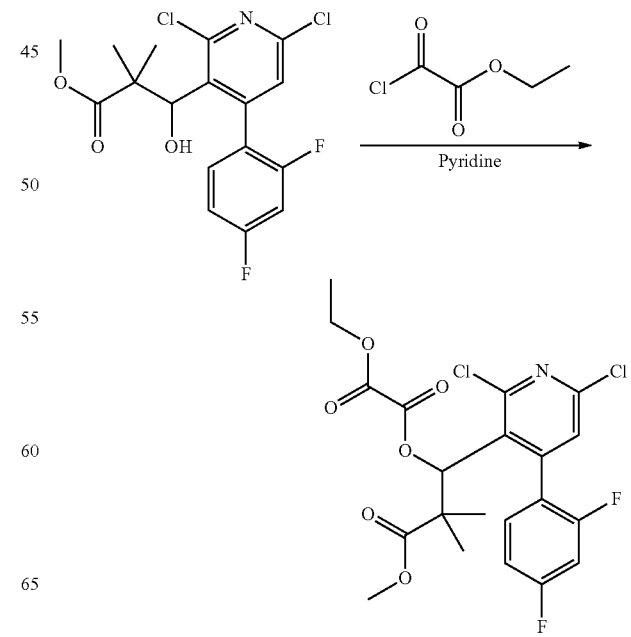

A mixture of 3-(2,6-dichloro-4-(2,4-difluorophenyl)pyridin-3-yl)-3-hydroxy-2,2-dimethylpropanoate (1.2 g, 3.1 mmol), ethyl 2-chloro-2-oxoacetate (830 mg, 6.1 mmol) and pyridine (478 mg, 6.1 mmol) in DCM (20 mL) was stirred at 25° C. for 12 h. The mixture was quenched with water (20 mL), extracted with EtOAc (50 mL) and concentrated under reduced pressure to give the product which was used in subsequent steps without further purification.

Step 3: methyl 3-(2,6-dichloro-4-(2,4-difluorophenyl)pyridin-3-yl)-2,2-dimethylpropanoate

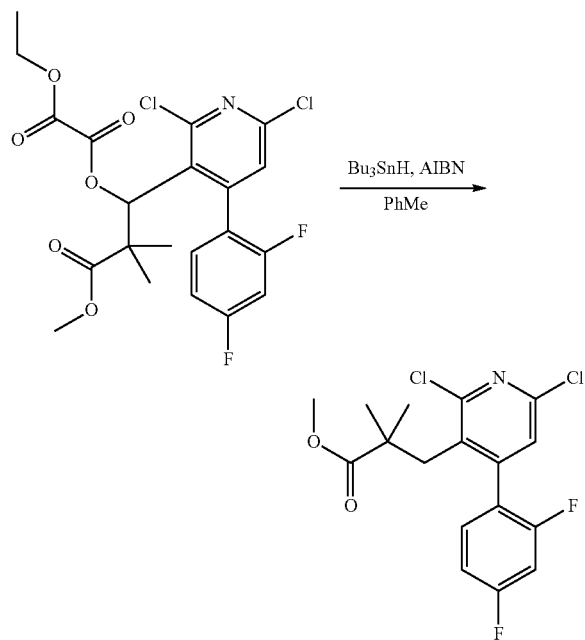

To a mixture of 1-(2,6-dichloro-4-(2,4-difluorophenyl)pyridin-3-yl)-3-methoxy-2,2-dimethyl-3-oxopropyl ethyl oxalate (750 mg, 1.5 mmol), and Bu₃SnH (890 mg, 3.1 mmol) in toluene (20 mL) was added AIBN (75 mg, 0.46 mmol) under N₂ atmosphere. The reaction was stirred at 80° C. for 1 h. The solvent was removed under reduced pressure the residue was purified by Prep-TLC (silica gel, eluting with 5:1 ethyl acetate/petroleum ether) to give the product. MS (ESI) calcd. for (C₁₇H₁₆Cl₂F₂NO₂) [M+H]⁺, 374.0, found, 374.0. ¹H NMR (400 MHz, CDCl₃) δ 7.19-7.12 (m, 1H), 7.06 (s, 1H), 6.99-6.83 (m, 2H), 3.48 (s, 3H), 3.27-3.12 (m, 1H), 3.05-2.89 (m, 1H), 0.88 (d, J=10.6 Hz, 6H).

Step 4: 3-(2,6-dichloro-4-(2,4-difluoropheny)pyridin-3-yl)-2,2-dimethylpropan-1-ol

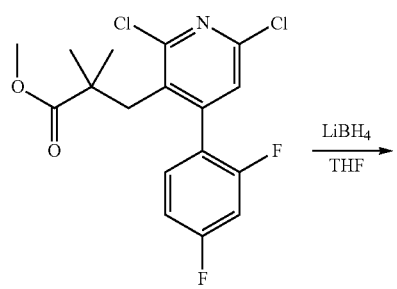

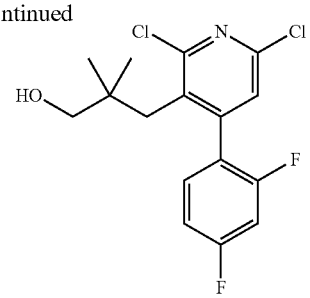

To a solution of methyl 3-(2,6-dichloro-4-(2,4-difluorophenyl)pyridin-3-yl)-2,2-dimethylpropanoate (130 mg, 0.34 mmol) in THF (4 mL) was added LiBH₄ (14.5 mg, 0.66 mmol) under N₂ atmosphere. The reaction was stirred at 60° C. for 4 h then quenched with saturated aqueous NH₄Cl (5 mL) and extracted with EtOAc (10 mL×3). The combined organic layers were dried over Na₂SO₄, filtered and concentrated to give a residue which was purified by silica gel chromatography (eluting with 10:1 ethyl acetate/petroleum ether) to give the product. MS (ESI) calcd. for (C₁₆H₁₆Cl₂F₂NO) [M+H]⁺, 346.0, found, 345.9. ¹H NMR (400 MHz, CDCl₃) δ 7.19-7.13 (m, 1H), 7.07 (s, 1H), 6.99-6.83 (m, 2H), 3.09 (br. s., 2H), 2.99-2.85 (m, 1H), 2.73 (br. s., 1H), 0.61 (br. s., 6H).

Step 5: 7-chloro-5-(2,4-difluoropheny)-3,3-dimethyl-3,4-dihydro-2H-pyrano[2,3-b]pyridine

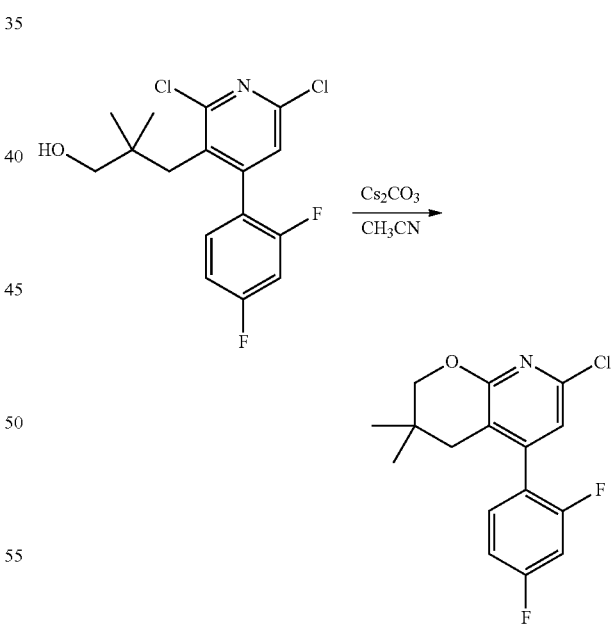

A mixture of 3-(2,6-dichloro-4-(2,4-difluorophenyl)pyridin-3-yl)-2,2-dimethylpropan-1-ol (100 mg, 0.29 mmol) and Cs₂CO₃ (190 mg, 0.58 mmol) in CH₃CN (20 mL) was stirred at 70° C. for 12 h. The solvent was removed under reduced pressure and the residue was purified by silica gel chromatography (eluting with 10:1 ethyl acetate/petroleum ether) to give the product. MS (ESI) calcd.

($C_{16}H_{15}ClF_2NO$) [M+H]+, 310.0, found, 310.1. 1H NMR (400 MHz, CDCl3) δ 7.22-7.13 (m, 1H), 7.01-6.88 (m, 2H), 6.80 (s, 1H), 3.95 (s, 2H), 2.26 (br. s., 2H), 0.96 (s, 6H).

Step 6: ethyl 5-(2,4-difluorophenyl)-3,3-dimethyl-3,4-dihydro-2H-pyrano[2,3-b]pyridine-7-carboxylate

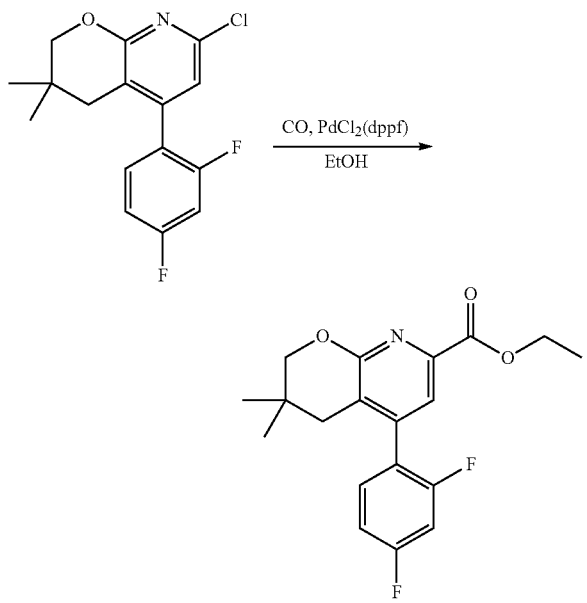

To a solution of 7-chloro-5-(2,4-difluorophenyl)-3,3-dimethyl-3,4-dihydro-2H-pyrano[2,3-b]pyridine (60 mg, 0.19 mmol) in EtOH (10 mL) was added potassium acetate (98 mg, 0.58 mmol) and PdCl2(dppf) (28 mg, 0.04 mmol) under N2 atmosphere. The mixture was degassed and backfilled with CO (three times). The resulting mixture was stirred under 50 psi CO at 70° C. for 8 h. The mixture was concentrated under reduced pressure and the residue was purified by Prep-TLC (silica gel, eluting with 5:1 ethyl acetate/petroleum ether) to give the product. MS (ESI) calcd. for ($C_{19}H_{20}F_2NO_3$) [M+H]+, 348.1, found, 348.0. 1H NMR (400 MHz, CDCl3) δ 7.63 (s, 1H), 7.25-7.18 (m, 1H), 7.05-6.90 (m, 2H), 4.43 (q, J=7.1 Hz, 2H), 4.00 (s, 2H), 1.41 (t, J=7.1 Hz, 3H), 0.99 (s, 6H).

Step 7: 5-(2,4-difluorophenyl)-3,3-dimethyl-3,4-dihydro-2H-pyrano[2,3-b]pyridine-7-carboxamide

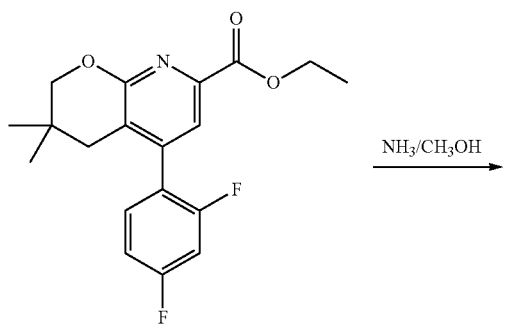

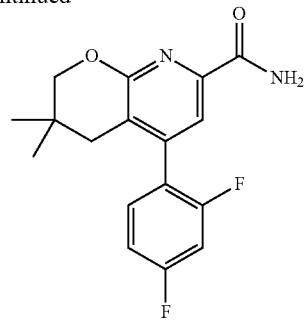

A mixture of ethyl 5-(2,4-difluorophenyl)-3,3-dimethyl-3,4-dihydro-2H-pyrano[2,3-b]pyridine-7-carboxylate (50 mg, 0.14 mmol) and ammonia in MeOH (15 mL, 150 mmol) was stirred at 25° C. for 12 h. The mixture was concentrated under reduced pressure to give the title compound. MS (ESI) calcd. for ($C_{17}H_{17}F_2N_2O_2$) [M+H]+, 319.1, found, 319.1. 1H NMR (400 MHz, CD3OD) δ 7.57 (s, 1H), 7.42-7.32 (m, 1H), 7.19-7.08 (m, 2H), 4.04 (s, 2H), 2.43 (s, 2H), 1.93 (s, 2H), 0.99 (s, 6H).

Example 2-8A and 2-8B (S)-2-((difluoromethoxy)methyl)-5-(2,4-difluorophenyl)-2-methyl-3,4-dihydro-2H-pyrano[2,3-b]pyridine-7-carboxamide Step 1: ethyl 4-(2,6-dichloro-4-(2,4-difluorophenyl)pyridin-3-yl)-2-oxobutanoate

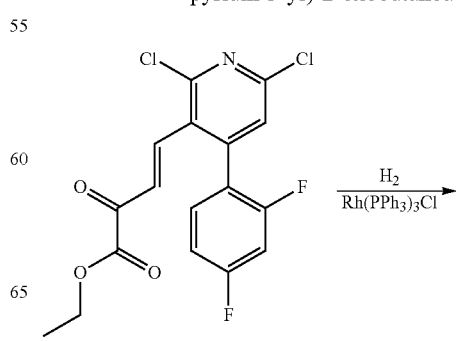

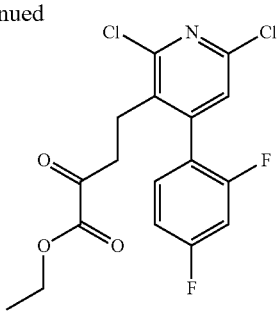

To a stirred solution of ethyl (E)-4-(2,6-dichloro-4-(2,4-difluorophenyl)pyridin-3-yl)-2-oxobut-3-enoate (Intermediate 2-2, 2.1 g, 5.44 mmol) in THF (20 mL) and t-BuOH (20 mL) was added tris(triphenylphosphine)rhodium(I) chloride (1.0 g, 1.1 mmol) at 25° C., the solution was stirred at 40° C. under 50 psi H$_2$ for 19 h. The mixture was concentrated under reduced pressure, the residue was purified by silica gel chromatography (ISCO®; 40 g SepaFlash® Column, eluting with 0% to 3% ethyl acetate/petroleum ether) to afford the product. MS (ESI) calcd for (C17H14Cl2F2NO3) [M+H]$^+$, 388.0, found, 388.0. $^1$H NMR (400 MHz, CDCl$_3$) δ 7.23-7.16 (m, 1H), 7.14 (s, 1H), 7.06-6.91 (m, 2H), 4.34-4.22 (m, 2H), 3.16-2.98 (m, 2H), 2.90 (d, J=6.8 Hz, 2H), 1.34 (t, J=7.1 Hz, 3H)

Step 2: ethyl 4-(2,6-dichloro-4-(2,4-difluorophenyl)pyridin-3-yl)-2-hydroxy-2-methylbutanoate

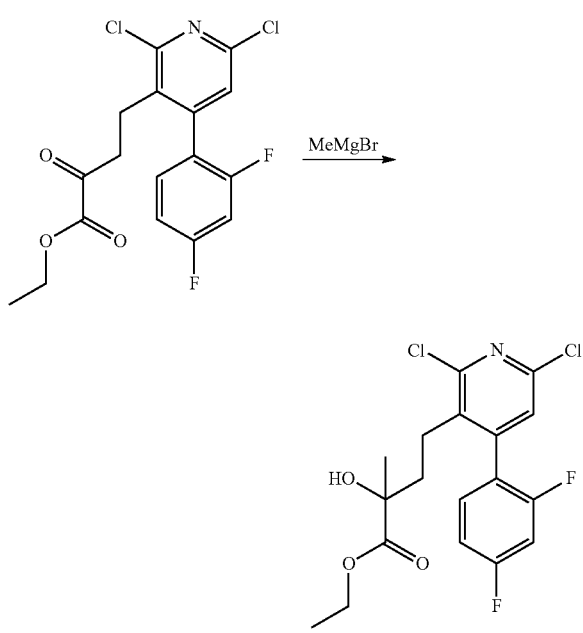 [SMILES: "MeMgBr" ; CCOC(=O)C(=O)CCc1c(-c2ccc(F)cc2F)cc(Cl)nc1Cl ; CCOC(=O)C(C)(O)CCc1c(-c2ccc(F)cc2F)cc(Cl)nc1Cl]

MeMgBr (0.54 mL, 1.73 mmol) was added dropwise slowly to a solution of ethyl 4-(2,6-dichloro-4-(2,4-difluorophenyl)pyridin-3-yl)-2-oxobutanoate (670 mg, 1.73 mmol) in THF (18 mL) at 0° C. under N$_2$ atmosphere. The mixture was stirred at 25° C. for 1 h. Saturated aqueous NH$_4$Cl (30 mL) was added and the aqueous phase was extracted with ethyl acetate (30 mL×2).

The combined organic layers were dried over Na$_2$SO$_4$, filtered and concentrated under reduced pressure. The residue was purified by silica gel chromatography (ISCO®; 12 g SepaFlash® Column, eluting with 0% to 10% ethyl acetate/petroleum ether) to afford the product. MS (ESI) calcd for (C$_{18}$H$_{17}$Cl$_2$F$_2$NO$_3$) [M+H]$^+$, 406.2, found 405.9. $^1$H NMR (400 MHz, CDCl$_3$) δ 7.27-7.18 (m, 1H), 7.16 (s, 1H), 7.09-6.95 (m, 2H), 4.28-4.18 (m, 1H), 4.18-4.07 (m, 1H), 3.09 (s, 1H), 2.79 (dt, J=3.8, 12.9 Hz, 1H), 2.48 (dt, J=4.8, 12.9 Hz, 1H), 1.95 (dt, J=4.5, 12.8 Hz, 1H), 1.81-1.68 (m, 1H), 1.35 (s, 3H), 1.33-1.26 (m, 3H).

Step 3: ethyl 7-chloro-5-(2,4-difluorophenyl)-2-methyl-3,4-dihydro-2H-pyrano[2,3-b]pyridine-2-carboxylate

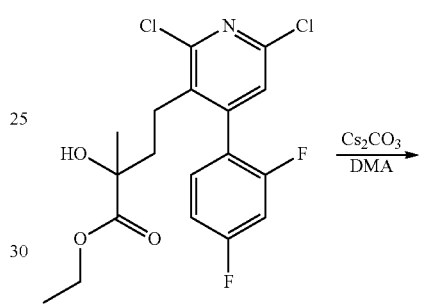

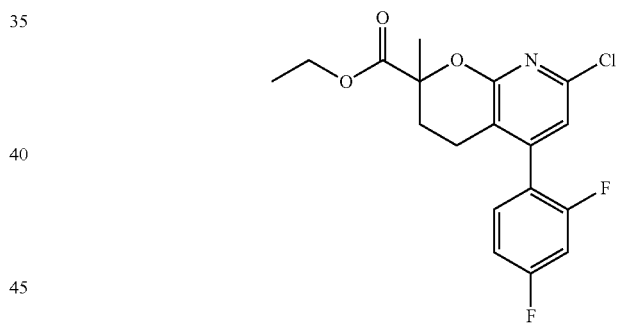

To a solution of ethyl 4-(2,6-dichloro-4-(2,4-difluorophenyl)pyridin-3-yl)-2-hydroxy-2-methylbutanoate (270 mg, 0.66 mmol) in DMA (5 mL), Cs$_2$CO$_3$ (429 mg, 1.32 mmol) was added. The mixture was degassed and backfilled with N$_2$ three times. The mixture was stirred at 100° C. for 100 min. The solution was poured into water (25 mL) and extracted with ethyl acetate (25 mL×2). The combined organic layers were washed with water (20 mL), dried over with anhydrous Na$_2$SO$_4$, filtered and concentrated under reduced pressure. The residue was purified by silica gel chromatography (ISCO®; 12 g SepaFlash® Column, eluting with 0% to 10% ethyl acetate/petroleum ether) to give the product. MS (ESI) calcd for (C$_{18}$H$_{16}$ClF$_2$NO$_3$) [M+H]$^+$, 368.0, found 367.9. $^1$H NMR (400 MHz, CDCl$_3$) δ 7.17-7.07 (m, 1H), 6.95-6.81 (m, 2H), 6.78 (s, 1H), 4.25-4.07 (m, 2H), 2.95-2.83 (m, 1H), 2.46-2.25 (m, 3H), 1.64 (s, 3H), 1.14 (t, J=7.3 Hz, 3H).

Step 4: (7-chloro-5-(2,4-difluorophenyl)-2-methyl-3,
4-dihydro-2H-pyrano[2,3-b]pyridin-2-yl)methanol

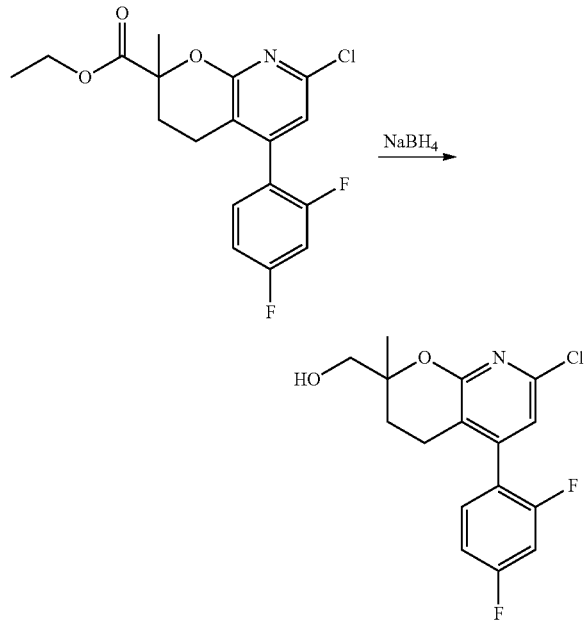

To a solution of ethyl 7-chloro-5-(2,4-difluorophenyl)-2-methyl-3,4-dihydro-2H-pyrano[2,3-b]pyridine-2-carboxylate (166 mg, 0.45 mmol) in EtOH (5 mL) was added NaBH$_4$ (34.8 mg, 0.9 mmol). The mixture was stirred at 0° C. for 1.5 h under N$_2$. Acetone (1 mL) was added to the mixture, the solvent was removed under reduced pressure. The residue was purified by silica gel chromatography (ISCO®; 12 g SepaFlash® Column, eluting with 10% to 30% ethyl acetate/petroleum ether) to give the product. MS (ESI) calcd for (C$_{16}$H$_{14}$ClF$_2$NO$_2$) [M+H]$^+$, 326.0, found 325.9. $^1$H NMR (400 MHz, CDCl$_3$) δ 7.25-7.19 (m, 1H), 7.04-6.90 (m, 2H), 6.85 (s, 1H), 3.81-3.71 (m, 1H), 3.67-3.57 (m, 1H), 2.56-2.43 (m, 1H), 2.08-1.94 (m, 1H), 1.76-1.65 (m, 1H), 1.36 (s, 3H), 1.29-1.21 (m, 1H).

Step 5: ethyl 5-(2,4-difluorophenyl)-2-(hydroxymethyl)-2-methyl-3,4-dihydro-2H-pyrano[2,3-b]pyridine-7-carboxylate

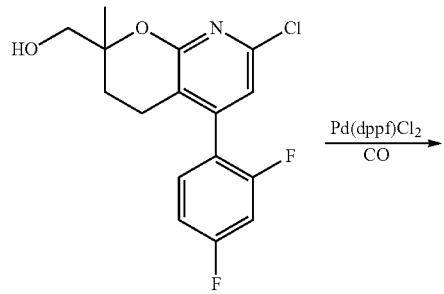

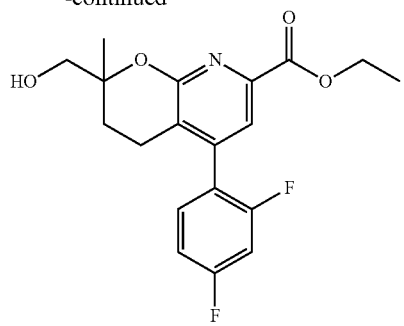

To a mixture of (7-chloro-5-(2,4-difluorophenyl)-2-methyl-3,4-dihydro-2H-pyrano[2,3-b]pyridin-2-yl) methanol (106 mg, 0.326 mmol) and Pd(dppf)Cl$_2$ (24 mg, 0.03 mmol) in EtOH (30 mL) under argon was added KOAc (63.9 mg, 0.652 mmol). The mixture was degassed and backfilled with argon three times. The resulting mixture was stirred under 50 Psi of CO at 70° C. for 24 h. The mixture was filtered and the filtrate was concentrated under reduced pressure. The residue was purified by silica gel chromatography (ISCO®; 12 g SepaFlash® Column, eluting with 10% to 60% ethyl acetate/petroleum ether) to give the product. MS (ESI) calcd for (C$_{19}$H$_{19}$F$_2$NO$_4$) [M+H]$^+$, 364.1, found 364.0.

Step 6: ethyl 2-((difluoromethoxy)methyl)-5-(2,4-difluorophenyl)-2-methyl-3,4-dihydro-2H-pyrano[2,3-b]pyridine-7-carboxylate

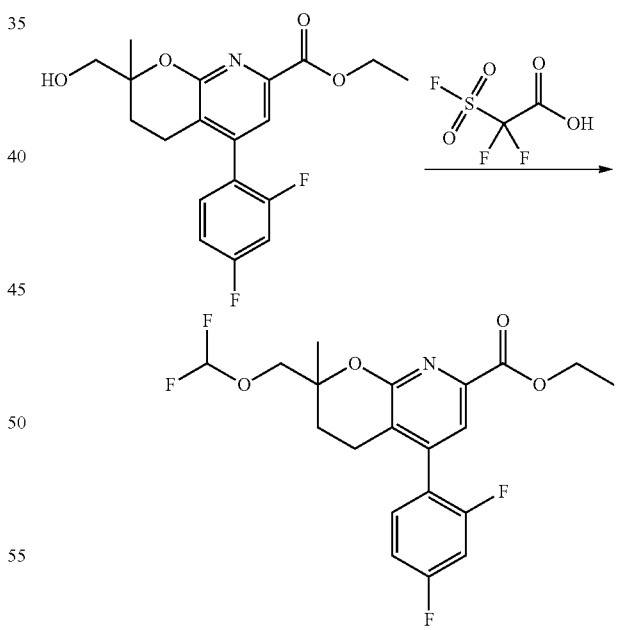

To a stirred solution of ethyl 5-(2,4-difluorophenyl)-2-(hydroxymethyl)-2-methyl-3,4-dihydro-2H-pyrano[2,3-b]pyridine-7-carboxylate (70 mg, 0.193 mmol) in acetonitrile (7 mL) at 25° C. under N$_2$ was added cuprous iodide (7.34 mg, 0.04 mmol) and 2,2-difluoro-2-(fluorosulfonyl)acetic acid (68.6 mg, 0.39 mmol). The solution was stirred at 50° C. for 30 min. A further portion of 2,2-difluoro-2-(fluorosulfonyl)acetic acid (137 mg, 0.771 mmol) was added at 50° C. and the solution was stirred at 50° C. for 40 min. The solution was poured into saturated aqueous NaHCO₃ (40 mL) and extracted with ethyl acetate (40 mL×2), the combined organic layers were dried over Na₂SO₄, filtered and concentrated under reduced pressure. The residue was purified by prep-TLC (silica gel, eluting with 2:1 petroleum ether:ethyl acetate) to give the product. MS (ESI) calcd for (C₂₀H₂₀F₄NO₄) [M+H]⁺, 414.1, found, 414.0.

Step 7: ethyl (S)-2-((difluoromethoxy)methyl)-5-(2,4-difluorophenyl)-2-methyl-3,4-dihydro-2H-pyrano[2,3-b]pyridine-7-carboxylate and ethyl (R)-2-((difluoromethoxy)methyl)-5-(2,4-difluorophenyl)-2-methyl-3,4-dihydro-2H-pyrano[2,3-b]pyridine-7-carboxylate

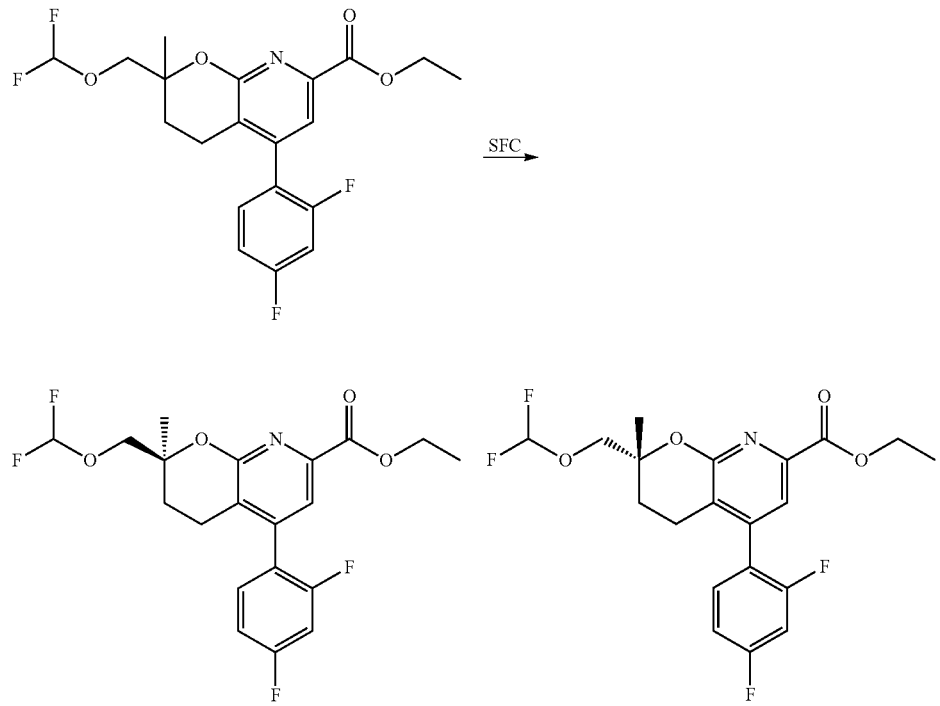

Racemic ethyl 2-((difluoromethoxy)methyl)-5-(2,4-difluorophenyl)-2-methyl-3,4-dihydro-2H-pyrano[2,3-b]pyridine-7-carboxylate (22.8 mg, 0.055 mmol) was resolved by chiral SFC (Column: Chiralpak AY 250×30 mm, 10 um; Mobile phase: 10% to 10% EtOH (containing 0.05% DEA) in CO₂; Flow rate: 60 mL/min) to afford the two enantiomers.

Step 8: (S)-2-((difluoromethoxy)methyl)-5-(2,4-difluorophenyl)-2-methyl-3,4-dihydro-2H-pyrano[2,3-b]pyridine-7-carboxamide and (R)-2-((difluoromethoxy)methyl)-5-(2,4-difluorophenyl)-2-methyl-3,4-dihydro-2H-pyrano[2,3-b]pyridine-7-carboxamide

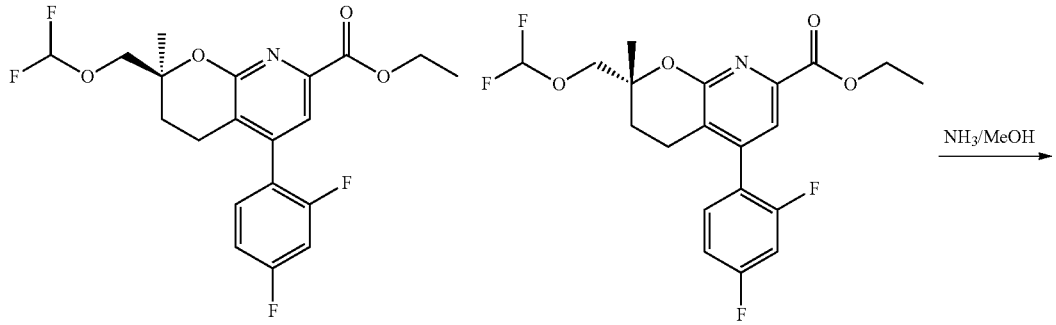

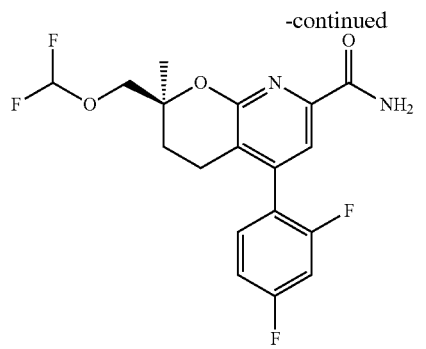

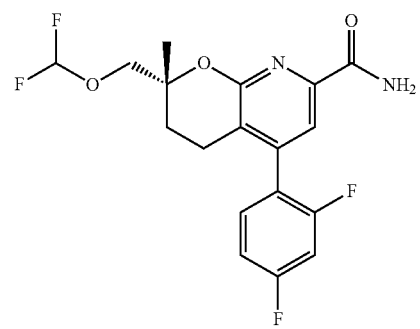

A solution of one enantiomer of ethyl 2-((difluoromethoxy)methyl)-5-(2,4-difluorophenyl)-2-methyl-3,4-dihydro-2H-pyrano[2,3-b]pyridine-7-carboxylate (10 mg, 0.024 mmol) in ammonia (10 M in MeOH) (20 mL) was stirred at 25° C. for 18 h. The mixture was concentrated under reduced pressure and the residue was purified by Prep-HPLC (Column: Phenomenex Synergi C18 150×30 mm, 4 um; Mobile phase: 50% to 70% water (containing 0.1% TFA)-ACN; Flow rate: 25 mL/min) to afford one enantiomer of the title compound. MS (ESI) calcd for ($C_{18}H_{17}F_4N_2O_3$) [M+H]$^+$, 385.1, found, 385.0. $^1$H NMR (400 MHz, CDCl$_3$) δ 7.90 (br. s., 1H), 7.74 (s, 1H), 7.30-7.26 (m, 1H), 7.07-6.87 (m, 2H), 6.66 (br. s., 1H), 6.53-6.07 (m, 1H), 4.08-3.87 (m, 2H), 2.10-1.96 (m, 1H), 1.91-1.73 (m, 1H), 1.48 (s, 3H).

Similar treatment of the other enantiomer of ethyl 2-((difluoromethoxy)methyl)-5-(2,4-difluorophenyl)-2-methyl-3,4-dihydro-2H-pyrano[2,3-b]pyridine-7-carboxylate afforded the other enantiomer of the title compound. MS (ESI) calcd for ($C_{18}H_{17}F_4N_2O_3$) [M+H]$^+$, 385.1, found, 385.0. $^1$H NMR (400 MHz, CDCl$_3$) δ 7.92 (br. s., 1H), 7.74 (s, 1H), 7.29 (br. s., 1H), 7.07-6.90 (m, 2H), 6.78 (br. s., 1H), 6.59-6.02 (m, 1H), 4.08-3.86 (m, 2H), 2.10-1.96 (m, 1H), 1.90-1.75 (m, 1H), 1.48 (s, 3H).

Example 2-9A, 2-9B, 2-9C and 2-9D

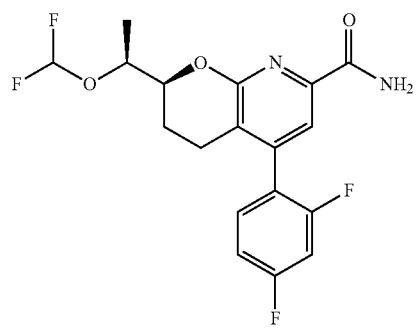

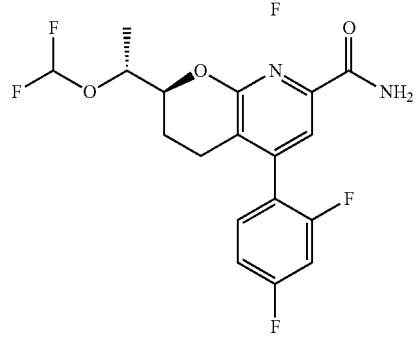

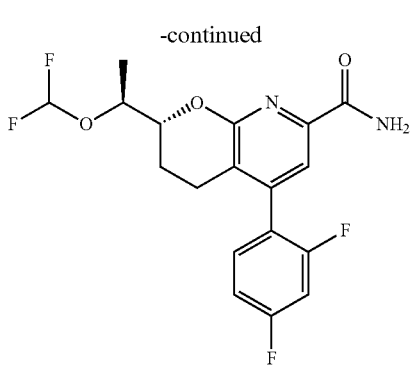

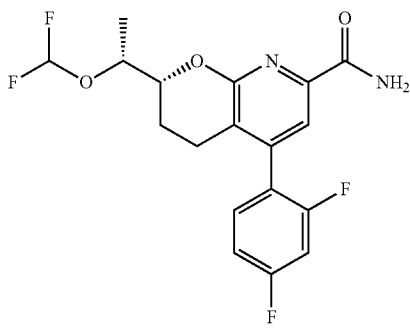

(S)-2-((S)-1-(difluoromethoxy)ethyl)-5-(2,4-difluoropheny)-3,4-dihydro-2H-pyrano[2,3-b]pyridine-7-carboxamide, (S)-2-((R)-1-(difluoromethoxy)ethyl)-5-(2,4-difluorophenyl)-3,4-dihydro-2H-pyrano[2,3-b]pyridine-7-carboxamide, (R)-2-((S)-1-(difluoromethoxy)ethyl)-5-(2,4-difluorophenyl)-3,4-dihydro-2H-pyrano[2,3-b]pyridine-7-carboxamide and (R)-2-((R)-1-(difluoromethoxy)ethyl)-5-(2,4-difluorophenyl)-3,4-dihydro-2H-pyrano[2,3-b]pyridine-7-carboxamide Step 1: 7-chloro-5-(2,4-difluorophenyl)-3,4-dihydro-2H-pyrano[2,3-b]pyridine-2-carboxylic acid (Intermediate 3-2)

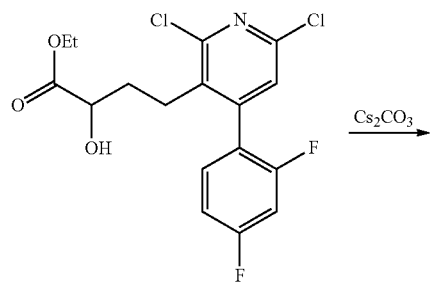

To a solution of ethyl 4-(2,6-dichloro-4-(2,4-difluorophenyl)pyridin-3-yl)-2-hydroxybutanoate (Intermediate 2-3, 1.15 g, 2.9 mmol) and Cs$_2$CO$_3$ (1.9 g, 5.8 mmol) in CH$_3$CN (15 mL). The mixture was stirred at 90° C. for 6 h. The mixture was poured into water (60 mL) and extracted with EtOAc (20 mL). The aqueous phase was adjusted to pH-4 with citric acid and extracted with EtOAc (40 mL×3). The combined organic extracts were concentrated under reduce pressure to afford the product which was used in next step without purification. MS (ESI) calcd for (C$_{15}$H$_{11}$ClF$_2$NO$_3$) [M+H]$^+$, 325.9 found, 325.9. $^1$H NMR (400 MHz, CDCl$_3$) δ 7.30-7.08 (m, 2H), 7.03-6.85 (m, 2H), 4.98 (dd, J=3.9, 6.7 Hz, 1H), 2.78-2.43 (m, 2H), 2.36-2.07 (m, 2H).

Step 2: 7-chloro-5-(2,4-difluorophenyl)-N-methoxy-N-methyl-3,4-dihydro-2H-pyrano[2,3-b]pyridine-2-carboxamide

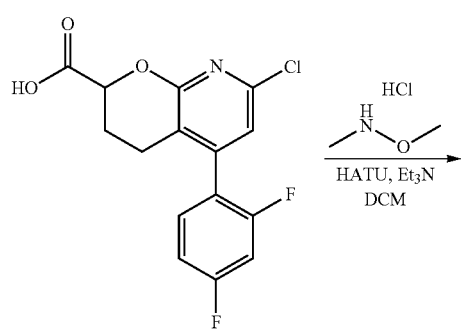

A mixture of 7-chloro-5-(2,4-difluorophenyl)-3,4-dihydro-2H-pyrano[2,3-b]pyridine-2-carboxylic acid (0.8 g, 2.5 mmol), N,O-dimethylhydroxylamine hydrochloride (264 mg, 2.7 mmol), HATU (1.02 g, 2.7 mmol) and Et$_3$N (720 mg, 7.35 mmol) in DCM (15 mL) was stirred at 25° C. for 2 h. The reaction was poured into water (20 mL) and extracted with EtOAc (50 mL×3). The combined organic layers were dried over sodium sulfate, filtered and evaporated and the residue was purified by silica gel chromatography (eluting with 1:1 petroleum ether/ethyl acetate) to give the product. MS (ESI) calcd. for (C$_{17}$H$_{16}$ClF$_2$N$_2$O$_3$) [M+H]$^+$, 369.0, found, 369.1.

Step 3: 1-(7-chloro-5-(2,4-difluorophenyl)-3,4-dihydro-2H-pyrano[2,3-b]pyridin-2-yl)ethanone

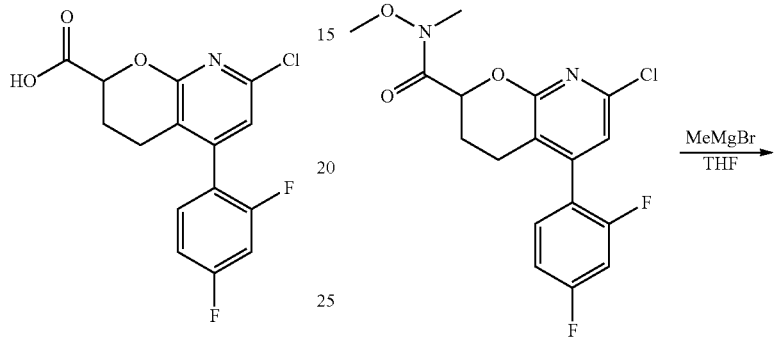

To a solution of 7-chloro-5-(2,4-difluorophenyl)-N-methoxy-N-methyl-3,4-dihydro-2H-pyrano[2,3-b]pyridine-2-carboxamide (400 mg, 1.1 mmol) in THF (10 mL) was added dropwise MeMgBr (0.4 mL, 1.2 mmol) at −65° C. under N$_2$ and the reaction was stirred for 2 h at −65° C. The reaction was quenched with saturated aqueous NH$_4$Cl (10 mL) and extracted with EtOAc (200 mL×3). The combined organic layers were dried over sodium sulfate, filtered and evaporated and purified by silica gel chromatography (eluting with 5:1 petroleum ether/ethyl acetate) to give the product. MS (ESI) calcd. for (C$_{16}$H$_{13}$ClF$_2$NO$_2$) [M+H]$^+$, 324.0, found, 324.1. $^1$H NMR (400 MHz, CDCl$_3$) δ 7.23-7.14 (m, 1H), 7.03-6.85 (m, 3H), 4.77-4.56 (m, 1H), 2.69-2.53 (m, 1H), 2.52-2.42 (m, 1H), 2.39 (s, 3H), 2.26-2.13 (m, 1H), 2.00-1.85 (m, 1H).

Step 4: 1-(7-chloro-5-(2,4-difluorophenyl)-3,4-dihydro-2H-pyrano[2,3-b]pyridin-2-yl)ethanol

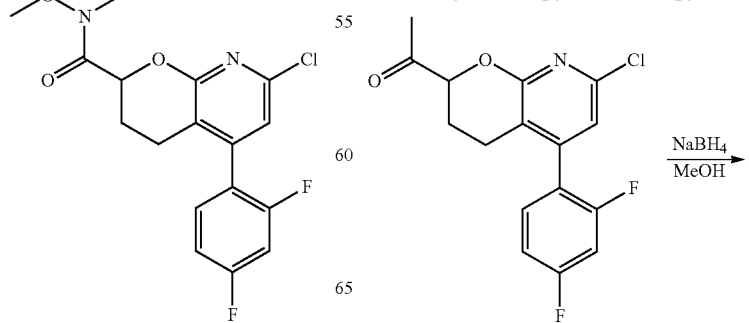

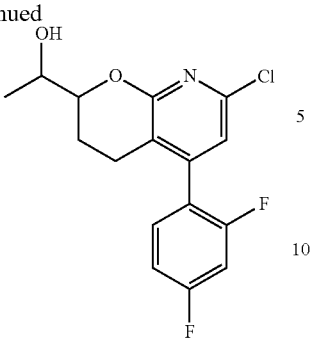
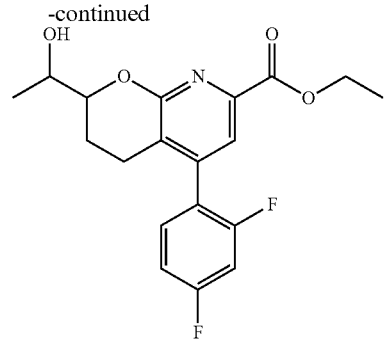

A mixture of 1-(7-chloro-5-(2,4-difluorophenyl)-3,4-dihydro-2H-pyrano[2,3-b]pyridin-2-yl)ethanone (130 mg, 0.40 mmol) and NaBH$_4$ (16 mg, 0.40 mmol) in MeOH (5 mL) was stirred at 0° C. for 0.5 h. The reaction was poured into water (20 mL) and extracted with EtOAc (50 mL×3). The combined organic layers were dried over sodium sulfate, filtered and evaporated and the residue was purified by silica gel chromatography (eluting with 5:1 petroleum ether/ethyl acetate) to give the product. MS (ESI) calcd. for (C$_{16}$H$_{15}$ClF$_2$NO$_2$) [M+H]$^+$, 326.0, found, 325.8. $^1$H NMR (400 MHz, CDCl$_3$) δ 7.25-7.16 (m, 1H), 7.04-6.90 (m, 2H), 6.85 (d, J=3.3 Hz, 1H), 4.25-4.01 (m, 2H), 2.56-2.42 (m, 1H), 2.04 (s, 1H), 2.03-1.91 (m, 1H), 1.35-1.29 (m, 3H).

Step 5: ethyl 5-(2,4-difluorophenyl)-2-(1-hydroxyethyl)-3, 4-dihydro-2H-pyrano[2,3-b]pyridine-7-carboxylate

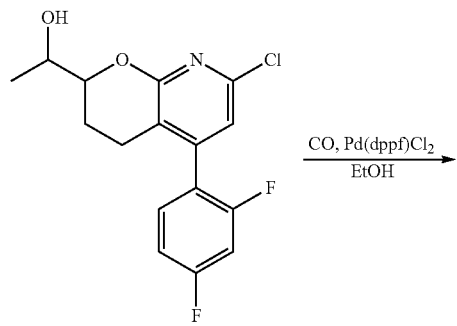

To a solution of 1-(7-chloro-5-(2,4-difluorophenyl)-3,4-dihydro-2H-pyrano[2,3-b]pyridin-2-yl)ethanol (130 mg, 0.4 mmol) in EtOH (20 mL) was added potassium acetate (117 mg, 1.2 mmol) and PdCl$_2$(dppf) (29 mg, 0.05 mmol) under N$_2$ atmosphere. The mixture was degassed and backfilled with CO (three times). The resulting mixture was stirred under 50 psi CO at 70° C. for 12 h. The mixture was concentrated under reduced pressure to give the crude product, which was purified by silica gel chromatography (ISCO®; 4 g SepaFlash® Column, eluting with 0% to 20% ethyl acetate/petroleum ether) to afford the product. MS (ESI) calcd. for (C$_{19}$H$_{20}$F$_2$NO$_4$) [M+H]$^+$, 364.1, found, 364.1. $^1$H NMR (400 MHz, CD$_3$OD) δ 7.58 (s, 1H), 7.46-7.35 (m, 1H), 7.23-7.03 (m, 2H), 4.44-4.34 (m, 2H), 4.20-4.05 (m, 1H), 4.02-3.87 (m, 1H), 2.79 (dtd, J=6.0, 11.9, 17.5 Hz, 1H), 2.66-2.53 (m, 1H), 2.22-2.02 (m, 1H), 1.83-1.68 (m, 1H), 1.42-1.29 (m, 6H).

Step 6: ethyl (S)-2-((S)-1-(difluoromethoxy)ethyl)-5-(2,4-difluorophenyl)-3,4-dihydro-2H-pyrano[2,3-b]pyridine-7-carboxylate, ethyl (S)-2-((R)-1-(difluoromethoxy)ethyl)-5-(2,4-difluorophenyl)-3,4-dihydro-2H-pyrano[2,3-b]pyridine-7-carboxylate, ethyl (R)-2-((S)-1-(difluoromethoxy)ethyl)-5-(2,4-difluorophenyl)-3,4-dihydro-2H-pyrano[2,3-b]pyridine-7-carboxylate and ethyl (R)-2-((R)-1-(difluoromethoxy)ethyl)-5-(2A-difluorophenyl)-3-dihydro-2H-pyrano[2,3-b]pyridine-7-carboxylate

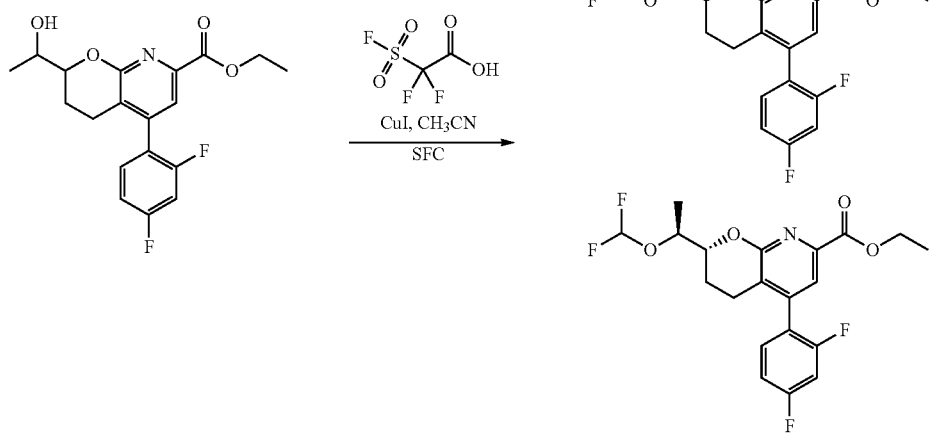

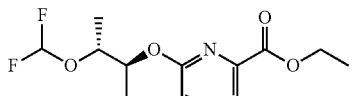
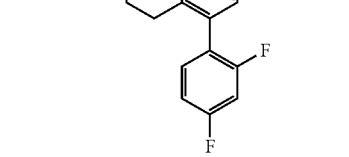

To a solution of ethyl 5-(2,4-difluorophenyl)-2-(1-hydroxyethyl)-3,4-dihydro-2H-pyrano[2,3-b]pyridine-7-carboxylate (85 mg, 0.23 mmol) and CuI (17 mg, 0.09 mmol) in CH$_3$CN (3 mL) was added dropwise 2,2-difluoro-2-(fluorosulfonyl)acetic acid (200 mg, 1.13 mmol) at 45° C. under N$_2$ and the reaction was stirred for 2 h at 50° C. The reaction was quenched with saturated aqueous NaHCO$_3$ (5 mL) and extracted with EtOAc (20 mL×3). The combined organic layers were dried over sodium sulfate, filtered and evaporated to give crude product, which was purified by silica gel chromatography (eluting with 5:1 petroleum ether/ethyl acetate) to give two diastereomers of the product. MS (ESI) calcd. for (C$_{20}$H$_{20}$F$_4$NO$_4$) [M+H]$^+$, 414.1, found, 414.0. and MS (ESI) calcd. for (C$_{20}$H$_{20}$F$_4$NO$_4$) [M+H]$^+$, 414.1, found, 414.0.

Each diastereomeric mixture of enantiomers was resolved by chiral SFC (Column: Chiralpak Whelk-01 250×30 mm, 10 um; Mobile phase: 45% to 45% EtOH (containing 0.05% DEA) in CO$_2$; Flow rate: 60 mL/min) to afford the four isomers of the product.

Isomer 1: MS (ESI) calcd. for (C$_{20}$H$_{20}$F$_4$NO$_4$) [M+H]$^+$, 414.1, found, 414.1.
Isomer 2: MS (ESI) calcd. for (C$_{20}$H$_{20}$F$_4$NO$_4$) [M+H]$^+$, 414.1, found, 414.1.
Isomer 3: MS (ESI) calcd. for (C$_{20}$H$_{19}$F$_4$NO$_4$) [M+H]$^+$, 414.1, found, 414.1.
Isomer 4: MS (ESI) calcd. for (C$_{20}$H$_{19}$F$_4$NO$_4$) [M+H]$^+$, 414.1, found, 414.1.

Step 7: (S)-2-((S)-1-(difluoromethoxy)ethyl)-5-(2,4-difluorophenyl)-3,4-dihydro-2H-pyrano 2,3-bpyridine-7-carboxamide, (S)-2-((R)-1-(difluoromethoxy)ethyl)-5-(2,4-difluorophenyl)-3,4-dihydro-2H-pyrano[2,3-b]pyridine-7-carboxamide, (R)-2-((S)-1-(difluoromethoxy)ethyl)-5-(2,4-difluorophenyl)-3,4-dihydro-2H-pyrano[2,3-b]pyridine-7-carboxamide and (R)-2-((R)-1-(difluoromethoxy)ethyl)-5-(2,4-difluorophenyl)-3,4-dihydro-2H-pyrano[2,3-b]pyridine-7-carboxamide

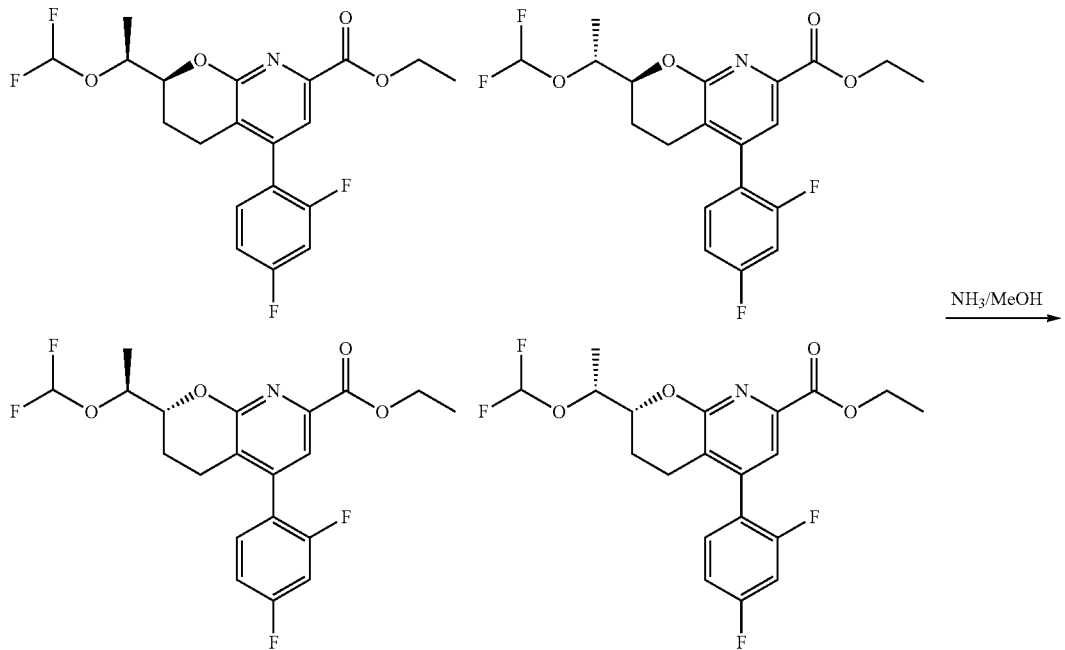

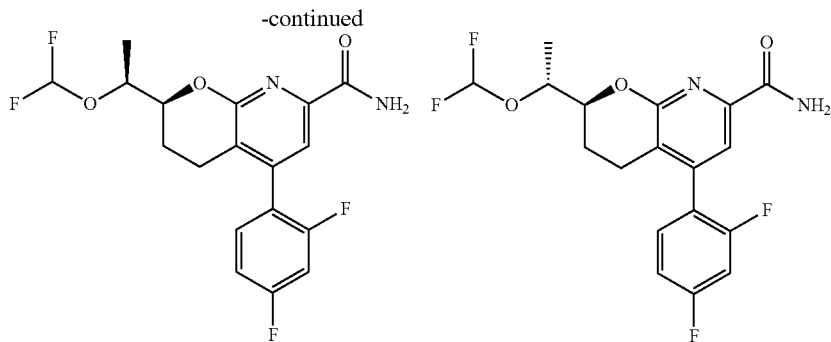

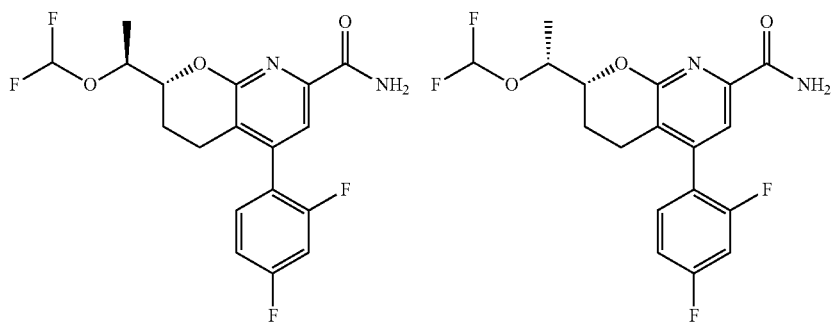

A solution of one isomer of ethyl 2-(1-(difluoromethoxy)ethyl)-5-(2,4-difluorophenyl)-3,4-dihydro-2H-pyrano[2,3-b]pyridine-7-carboxylate (10 mg, 0.023 mmol) other in ammonia (10 M in MeOH) (15 mL) was stirred at 25° C. for 12 h. The mixture was concentrated under reduced pressure to give one isomer of the title compound. MS (ESI) calcd. for ($C_{18}H_{17}F_4N_2O_3$) [M+H]$^+$, 385.1, found, 385.1. $^1$H NMR (400 MHz, CD$_3$OD) δ 7.59 (s, 1H), 7.45-7.35 (m, 1H), 7.20-7.07 (m, 2H), 6.77-6.31 (m, 1H), 4.54-4.43 (m, 1H), 4.34 (d, J=11.0 Hz, 1H), 2.82 (ddd, J=5.7, 12.2, 17.4 Hz, 1H), 2.59 (dd, J=2.2, 17.4 Hz, 1H), 2.05 (td, J=2.6, 13.9 Hz, 1H), 1.88-1.73 (m, 1H), 1.45 (d, J=6.4 Hz, 3H).

Similar treatment of the other isomers of ethyl 2-(1-(difluoromethoxy)ethyl)-5-(2,4-difluorophenyl)-3,4-dihydro-2H-pyrano[2,3-b]pyridine-7-carboxylate afforded the other isomers of the title compound.

Isomer 2: MS (ESI) calcd. for ($C_{18}H_{17}F_4N_2O_3$) [M+H]$^+$, 385.1, found, 385.1. $^1$H NMR (400 MHz, CD$_3$OD) δ 7.58 (br. s., 1H), 7.44-7.33 (m, 1H), 7.21-7.03 (m, 2H), 6.77-6.26 (m, 1H), 4.45 (d, J=5.5 Hz, 1H), 4.39-4.26 (m, 1H), 2.90-2.72 (m, 1H), 2.67-2.49 (m, 1H), 2.04 (d, J=9.4 Hz, 1H), 1.85-1.69 (m, 1H), 1.44 (d, J=6.3 Hz, 3H).

Isomer 3: MS (ESI) calcd. for ($C_{18}H_{17}F_4N_2O_3$) [M+H]$^+$, 385.1, found, 385.1. H NMR (400 MHz, CD$_3$OD) δ 7.58 (s, 1H), 7.46-7.31 (m, 1H), 7.12 (q, J=7.7 Hz, 2H), 6.75-6.26 (m, 1H), 4.53-4.42 (m, 1H), 4.31 (d, J=11.0 Hz, 1H), 2.79 (ddd, J=5.7, 12.1, 17.4 Hz, 1H), 2.67-2.51 (m, 1H), 2.14 (dd, J=2.7, 11.0 Hz, 1H), 1.84-1.65 (m, 1H), 1.50-1.37 (m, 3H).

Isomer 4: MS (ESI) calcd. for ($C_{18}H_{17}F_4N_2O_3$) [M+H]$^+$, 385.1, found, 385.1. $^1$H NMR (400 MHz, CD$_3$OD) δ 7.58 (s, 1H), 7.45-7.32 (m, 1H), 7.23-7.02 (m, 2H), 6.81-6.23 (m, 1H), 4.58-4.41 (m, 1H), 4.30 (d, J=10.6 Hz, 1H), 2.79 (ddd, J=5.5, 12.0, 17.3 Hz, 1H), 2.66-2.52 (m, 1H), 2.21-2.07 (m, 1H), 1.84-1.66 (m, 1H), 1.48-1.34 (m, 3H).

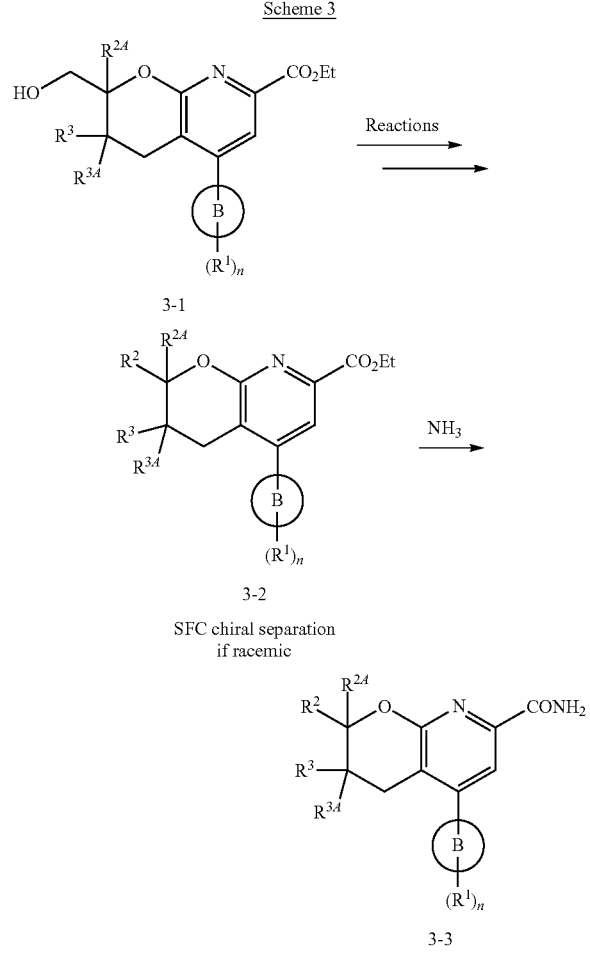

Scheme 3

Compounds of Formula I (where, in Scheme 3, $R^{2A}$, and $R^{3A}$ are each hydrogen and $R^2$, $R^3$, ring B, n, and each $R^1$ are as described in formula I or the alternative embodiments described herein) may be prepared according to Scheme 3 by various reactions on alcohol 3-1 (e.g. alkylation, fluorination, oxidation followed by fluorination, etc.) followed by treatment with ammonia.

Example 3-1A and 3-1B

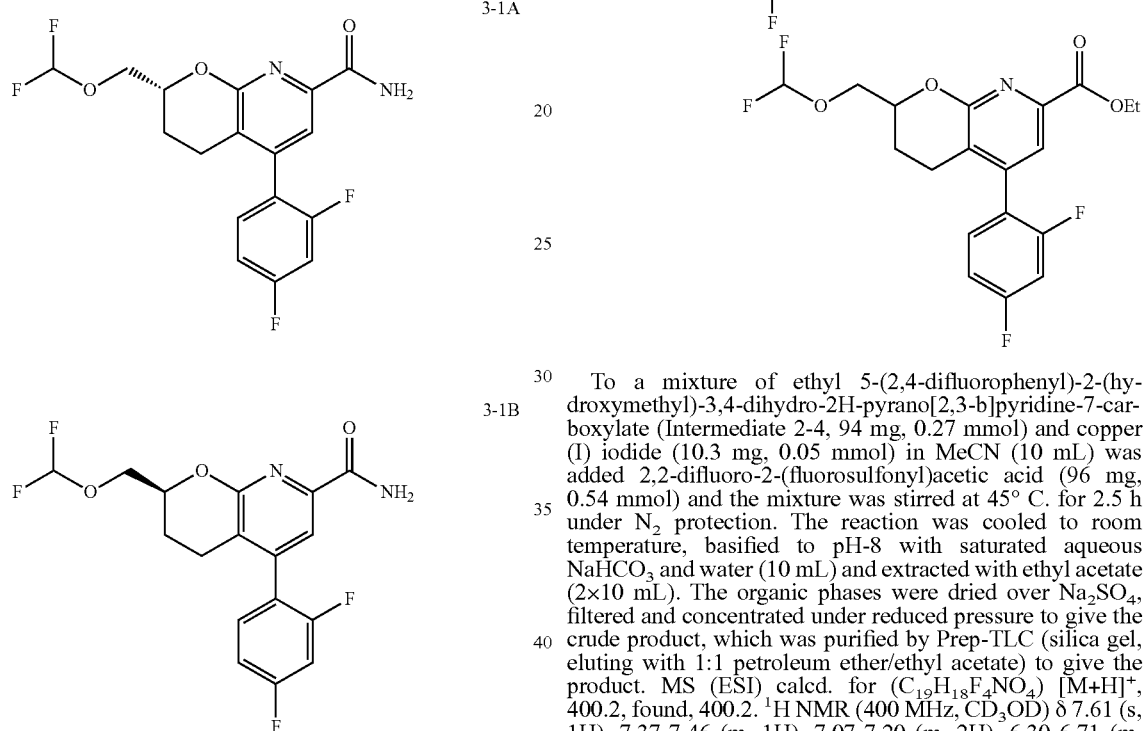

3-1A: (R)-2-((difluoromethoxy)methyl)-5-(2,4-difluorophenyl)-3,4-dihydro-2H-pyrano[2,3-b]pyridine-7-carboxamide and 3-1B: (S)-2-((difluoromethoxy)methyl)-5-(2,4-difluorophenyl)-3,4-dihydro-2H-pyrano[2,3-b]pyridine-7-carboxamide Step 1: ethyl 2-((difluoromethoxy)methyl)-5-(2,4-difluorophenyl)-3,4-dihydro-2H-pyrano[2,3-b]pyridine-7-carboxylate

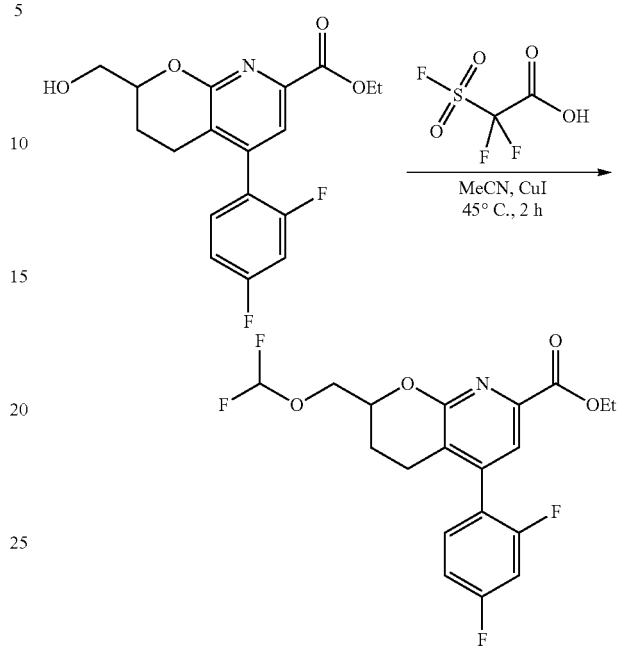

To a mixture of ethyl 5-(2,4-difluorophenyl)-2-(hydroxymethyl)-3,4-dihydro-2H-pyrano[2,3-b]pyridine-7-carboxylate (Intermediate 2-4, 94 mg, 0.27 mmol) and copper (I) iodide (10.3 mg, 0.05 mmol) in MeCN (10 mL) was added 2,2-difluoro-2-(fluorosulfonyl)acetic acid (96 mg, 0.54 mmol) and the mixture was stirred at 45° C. for 2.5 h under $N_2$ protection. The reaction was cooled to room temperature, basified to pH-8 with saturated aqueous $NaHCO_3$ and water (10 mL) and extracted with ethyl acetate (2×10 mL). The organic phases were dried over $Na_2SO_4$, filtered and concentrated under reduced pressure to give the crude product, which was purified by Prep-TLC (silica gel, eluting with 1:1 petroleum ether/ethyl acetate) to give the product. MS (ESI) calcd. for $(C_{19}H_{18}F_4NO_4)$ $[M+H]^+$, 400.2, found, 400.2. $^1$H NMR (400 MHz, $CD_3OD$) δ 7.61 (s, 1H), 7.37-7.46 (m, 1H), 7.07-7.20 (m, 2H), 6.30-6.71 (m, 1H), 4.51-4.61 (m, 1H), 4.39 (q, J=7.1 Hz, 2H), 4.08-4.20 (m, 2H), 2.85 (ddd, J=5.8, 11.9, 17.4 Hz, 1H), 2.57-2.67 (m, 1H), 2.10 (td, J=2.8, 13.8 Hz, 1H), 1.75-1.88 (m, 1H), 1.38 (t, J=7.2 Hz, 3H).

Step 2: ethyl (S)-2-((difluoromethoxy)methyl)-5-(2,4-difluorophenyl)-3,4-dihydro-2H-pyrano[2,3-b]pyridine-7-carboxylate and ethyl (R)-2-((difluoromethoxy)methyl)-5-(2,4-difluorophenyl)-3,4-dihydro-2H-pyrano[2,3-b]pyridine-7-carboxylate

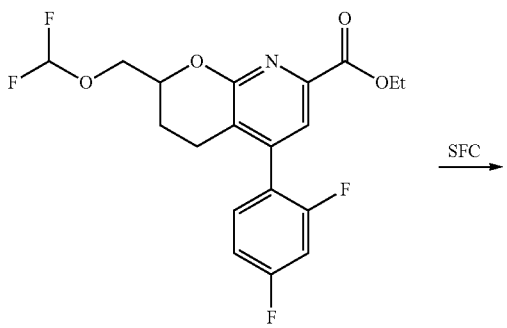

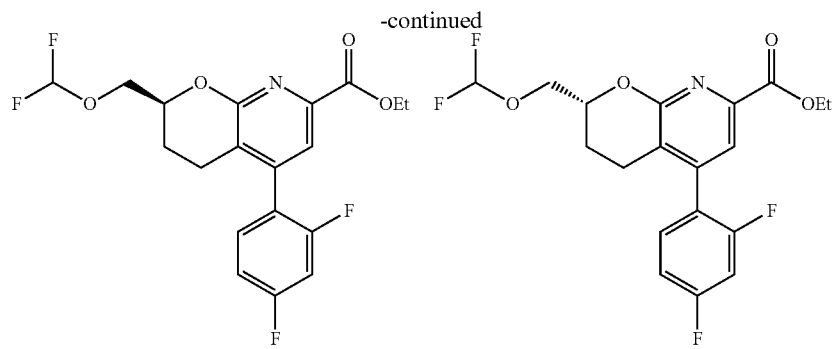

Racemic ethyl 2-((difluoromethoxy)methyl)-5-(2,4-difluorophenyl)-3,4-dihydro-2H-pyrano[2,3-b]pyridine-7-carboxylate (40 mg, 0.100 mmol) was resolved by chiral SFC (Column: Chiralpak AD 250×30 mm, 5 um; Mobile phase: 30% to 30% IPA (containing 0.05% DEA) in $CO_2$; Flow rate: 70 mL/min) to give the two enantiomers.

Step 3: (S)-2-((difluoromethoxy)methyl)-5-(2,4-difluorophenyl)-3,4-dihydro-2H-pyrano[2,3-b]pyridine-7-carboxamide and (R)-2-((difluoromethoxy)methyl)-5-(2,4-difluorophenyl)-3,4-dihydro-2H-pyrano[2,3-b]pyridine-7-carboxamide

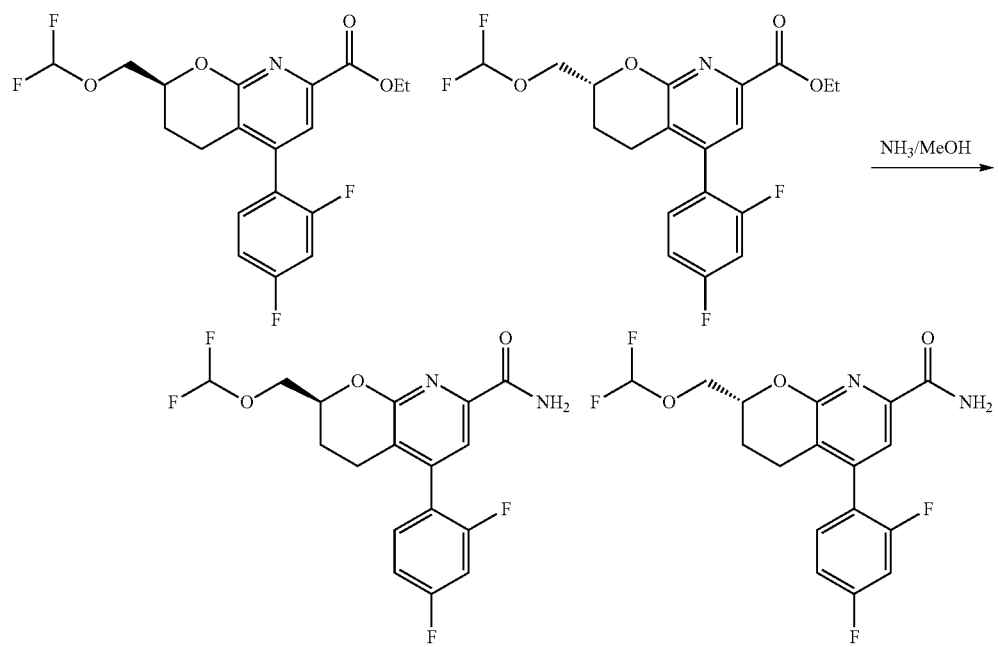

A solution of one enantiomer of ethyl 2-((difluoromethoxy)methyl)-5-(2,4-difluorophenyl)-3,4-dihydro-2H-pyrano[2,3-b]pyridine-7-carboxylate (20 mg, 0.05 mmol) in ammonia (10 M in MeOH) (40 mL) was stirred at 20° C. for 16 h. The mixture was concentrated under reduced pressure. The residue was purified by Prep-HPLC (Column: Phenomenex Gemini C18 250×21.2 mm, 5 um; Mobile phase: 30% to 60% water (containing 10 mM $NH_4HCO_3$)-ACN; Flow rate: 25 mL/min) to give one enantiomer of the title compound. MS (ESI) calcd. for ($C_{17}H_{15}F_4N_2O_3$) [M+H]$^+$, 371.1, found, 371.0. $^1$H NMR (400 MHz, $CD_3OD$) δ 7.58 (s, 1H), 7.34-7.42 (m, 1H), 7.07-7.16 (m, 2H), 6.25-6.70 (m, 1H), 4.49-4.56 (m, 1H), 4.06-4.17 (m, 2H), 2.82 (dd, J=5.67, 11.93, 17.22 Hz, 1H), 2.58 (d, J=16.04 Hz, 1H), 2.03-2.11 (m, 1H), 1.72-1.85 (m, 1H)

Similar treatment of the other enantiomer of ethyl 2-((difluoromethoxy)methyl)-5-(2,4-difluorophenyl)-3,4-dihydro-2H-pyrano[2,3-b]pyridine-7-carboxylate afforded the other enantiomer of the title compound. MS (ESI) calcd. for ($C_{17}H_{15}F_4N_2O_3$) [M+H]$^+$, 371.1, found, 371.0. $^1$H NMR (400 MHz, $CD_3OD$) δ 7.58 (s, 1H), 7.33-7.42 (m, 1H), 7.07-7.17 (m, 2H), 6.27-6.71 (m, 1H), 4.49-4.56 (m, 1H), 4.06-4.16 (m, 2H), 2.82 (dd, J=5.48, 11.84, 17.12 Hz, 1H), 2.58 (d, J=16.43 Hz, 1H), 2.03-2.12 (m, 1H), 1.72-1.85 (m, 1H).

The following compounds were prepared according to the procedures described for Example 3-1A and 3-1B.

| Example | Structure | Name | MS (ESI) calcd | MS (ESI) found | ¹H NMR |
|---|---|---|---|---|---|
| 3-2A | 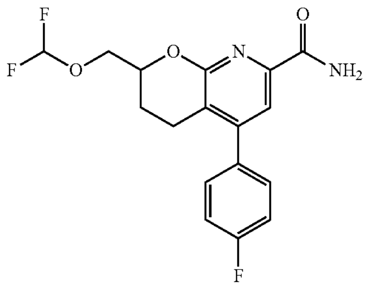 [SMILES: NC(=O)c1cc(-c2ccc(F)cc2)c2c(n1)OC(COC(F)F)CC2] | (S)- or (R)-2-((difluoromethoxy)methyl)-5-(4-fluorophenyl)-3,4-dihydro-2H-pyrano[2,3-b]pyridine-7-carboxamide | 353.1 | 352.9 | (400 MHz, CD$_3$OD) 7.61 (br. s., 1H), 7.35-7.50 (m, 2H), 7.11-7.30 (m, 2H), 6.23-6.74 (m, 1H), 4.55 (br. s., 1H), 4.01-4.18 (m, 2H), 2.88-3.06 (m, 1H), 2.70 (d, J = 16.54 Hz, 1H), 2.02-2.15 (m, 1H), 1.64-1.84 (m, 1H). |
| 3-2B | 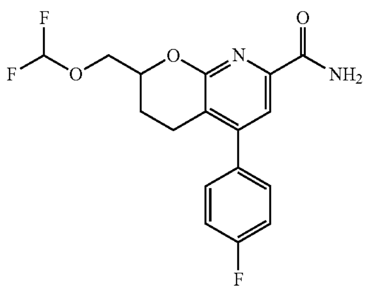 [SMILES: NC(=O)c1cc(-c2ccc(F)cc2)c2c(n1)OC(COC(F)F)CC2] | (R)- or (S)-2-((difluoromethoxy)methyl)-5-(4-fluorophenyl)-3,4-dihydro-2H-pyrano[2,3-b]pyridine-7-carboxamide | 353.1 | 352.9 | (400 MHz, CD$_3$OD) 7.61 (br. s., 1H), 7.44 (br. s., 2H), 7.23 (t, J = 7.61 Hz, 2H), 6.22-6.74 (m, 1H), 4.55 (br. s., 1H), 4.13 (br. s., 2H), 2.97 (d, J = 13.45 Hz, 1H), 2.70 (d, J = 16.54 Hz, 1H), 1.99-2.16 (m, 1H), 1.77 (br. s., 1H) |
| 3-3A | 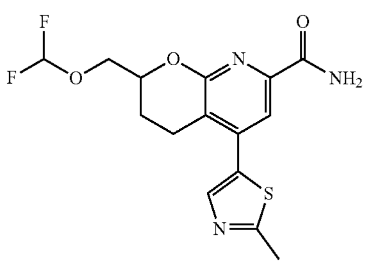 [SMILES: Cc1ncc(-c2cc(C(N)=O)nc3c2CCC(COC(F)F)O3)s1] | (S)- or (R)-2-((difluoromethoxy)methyl)-5-(2-methylthiazol-5-yl)-3,4-dihydro-2H-pyrano[2,3-b]pyridine-7-carboxamide | 356.1 | 355.9 | (400 MHz, CD$_3$OD) 7.89 (br. s., 1H), 7.76 (br. s, 1H), 6.24-6.73 (m, 1H), 4.53 (br. s., 1H), 4.14 (br. s., 2H), 2.76 (br. s., 3H), 2.17 (br. s., 1H), 1.29 (br. s., 1H) |
| 3-3B | 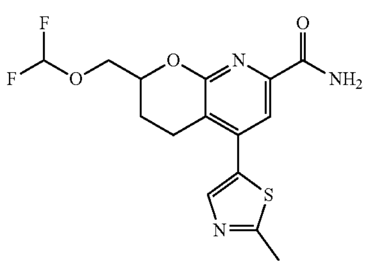 [SMILES: Cc1ncc(-c2cc(C(N)=O)nc3c2CCC(COC(F)F)O3)s1] | (R)- or (S)-2-((difluoromethoxy)methyl)-5-(2-methylthiazol-5-yl)-3,4-dihydro-2H-pyrano[2,3-b]pyridine-7-carboxamide | 356.1 | 355.9 | (400 MHz, CD$_3$OD) 7.89 (s, 1H), 7.76 (s, 1H), 6.25-6.73 (m, 1H), 4.55 (br. s., 1H), 4.14 (d, J = 7.28 Hz, 2H), 2.90-3.15 (m, 2H), 2.77 (s, 3H), 2.18 (d, J = 8.38 Hz, 1H), 1.74-1.91 (m, 1H) |

| Example | Structure | Name | MS (ESI) calcd | MS (ESI) found | ¹H NMR |
|---|---|---|---|---|---|
| 3-4A | 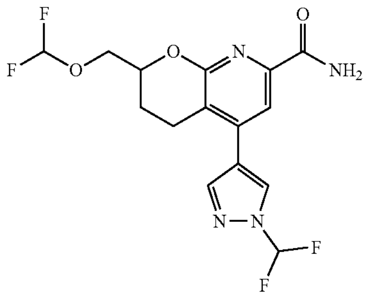 [SMILES: NC(=O)c1cc(-c2cnn(C(F)F)c2)c2c(n1)OC(COC(F)F)CC2] | (S)- or (R)-2-((difluoromethoxy)methyl)-5-(1-(difluoromethyl)-1H-pyrazol-4-yl)-3,4-dihydro-2H-pyrano[2,3-b]pyridine-7-carboxamide | 374.1 | 375.0 | (400 MHz, CD$_3$OD) 8.49 (s, 1H), 8.10 (s, 1H), 7.82 (s, 1H), 7.39-7.76 (m, 1H), 6.28-6.72 (m, 1H), 4.48-4.62 (m, 1H), 4.08-4.22 (m, 2H), 2.90-3.18 (m, 2H), 2.19 (dd, J = 3.09, 11.03 Hz, 1H), 1.74-1.95 (m, 1H). |
| 3-4B | 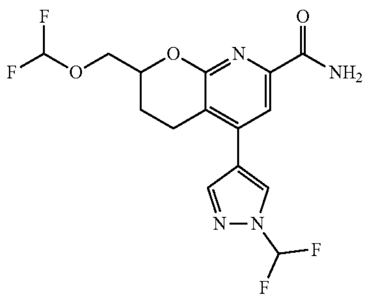 [SMILES: NC(=O)c1cc(-c2cnn(C(F)F)c2)c2c(n1)OC(COC(F)F)CC2] | (R)- or (S)-2-((difluoromethoxy)methyl)-5-(1-(difluoromethyl)-1H-pyrazol-4-yl)-3,4-dihydro-2H-pyrano[2,3-b]pyridine-7-carboxamide | 374.1 | 375.0 | (400 MHz, CD$_3$OD) 8.49 (s, 1H), 8.09 (s, 1H), 7.82 (s, 1H), 7.39-7.75 (m, 1H), 6.29-6.72 (m, 1H), 4.48-4.60 (m, 1H), 4.06-4.22 (m, 2H), 2.87-3.18 (m, 2H), 2.12-2.29 (m, 1H), 1.77-1.92 (m, 1H). |

Example 3-5A and 3-5B (S)-5-(2,4-difluorophenyl)-2-(methoxymethyl)-3,4-dihydro-2H-pyrano[2,3-b]pyridine-7-carboxamide and (R)-5-(2,4-difluorophenyl)-2-(methoxymethyl)-3,4-dihydro-2H-pyrano[2,3-b]pyridine-7-carboxamide Step 1: ethyl 5-(2,4-difluorophenyl)-2-(methoxymethyl)-3,4-dihydro-2H-pyrano[2,3-b]pyridine-7-carboxylate

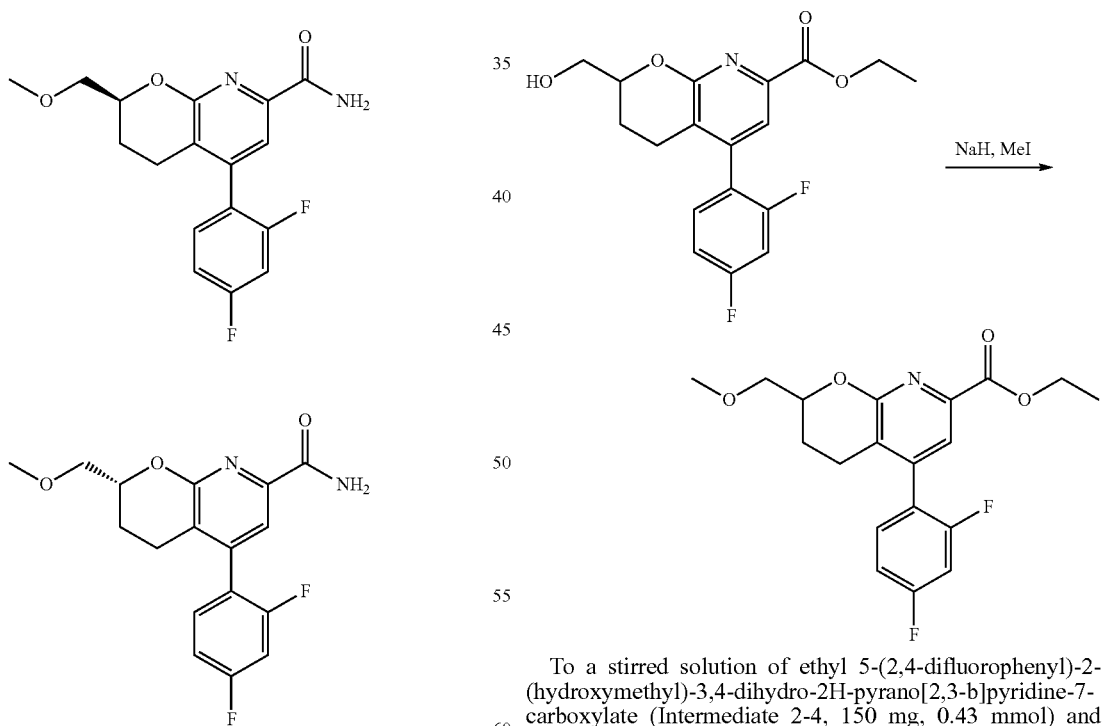

To a stirred solution of ethyl 5-(2,4-difluorophenyl)-2-(hydroxymethyl)-3,4-dihydro-2H-pyrano[2,3-b]pyridine-7-carboxylate (Intermediate 2-4, 150 mg, 0.43 mmol) and iodomethane (67.0 mg, 0.47 mmol) in dry DMF (4 mL) was added sodium hydride (18.89 mg, 0.472 mmol) at 0° C. under N$_2$ atmosphere. The resulting mixture was stirred at 0° C. for 30 min. The solution was concentrated under reduced pressure, the residue was purified by prep-TLC (silica gel, eluting with 2:1 ethyl acetate/petroleum ether) to afford the product. MS (ESI) calcd. for (C$_{19}$H$_{20}$F$_2$NO$_4$) [M+H]$^+$, 364.1, found, 364.0.

Step 2: ethyl (S)-5-(2,4-difluorophenyl)-2-(methoxymethyl)-3,4-dihydro-2H-pyrano[2,3-b]pyridine-7-carboxylate and ethyl (R)-5-(2,4-difluorophenyl)-2-(methoxymethyl)-3,4-dihydro-2H-pyrano[2,3-b]pyridine-7-carboxylate

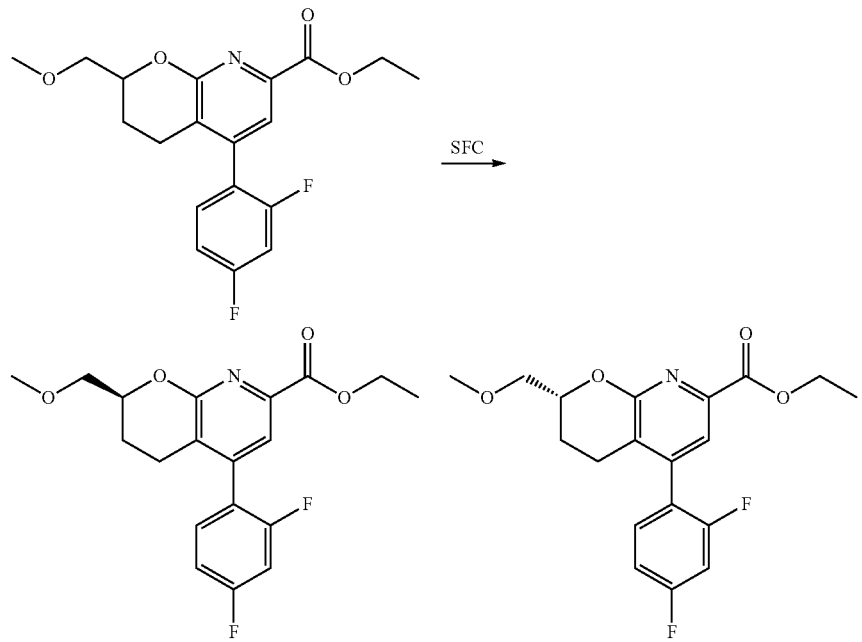

Racemic ethyl 5-(2,4-difluorophenyl)-2-(methoxymethyl)-3,4-dihydro-2H-pyrano[2,3-b]pyridine-7-carboxylate (93 mg, 0.256 mmol) was separated by SFC (Column: Chiralpak OJ 250×30 mm, 5 um; Mobile phase: 45% to 45% MeOH (containing 0.05% DEA) in $CO_2$; Flow rate: 60 mL/min) to afford the two enantiomers.

Step 3: (S)-5-(2,4-difluorophenyl)-2-(methoxymethyl)-3,4-dihydro-2H-pyrano[2,3-b]pyridine-7-carboxamide and (R)-5-(2,4-difluorophenyl)-2-(methoxymethyl)-3,4-dihydro-2H-pyrano[2,3-b]pyridine-7-carboxamide

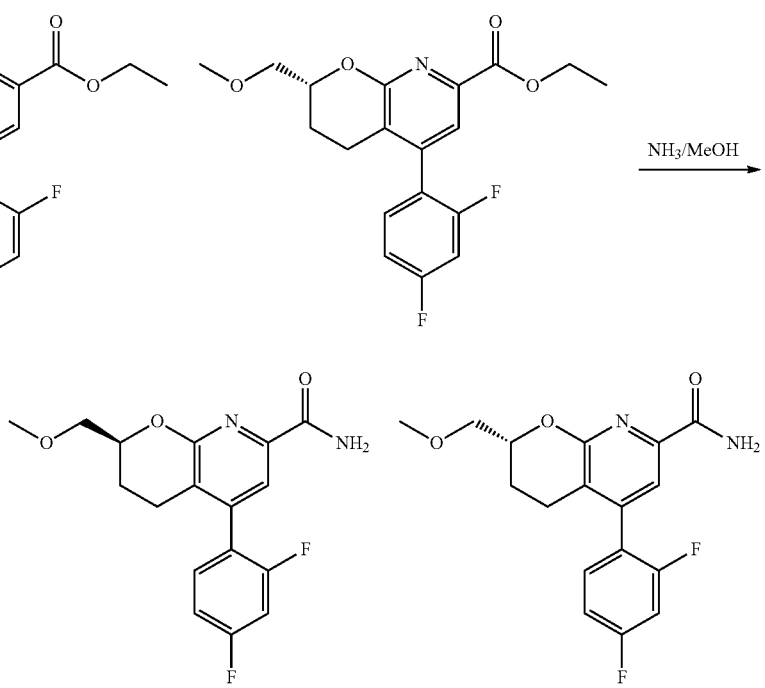

A solution of one enantiomer of ethyl 5-(2,4-difluorophenyl)-2-(methoxymethyl)-3,4-dihydro-2H-pyrano[2,3-b]pyridine-7-carboxylate (41 mg, 0.11 mmol) in ammonia (10 M in MeOH) (15 mL) was stirred at 26° C. for 12 h. The mixture was concentrated under reduced pressure and the residue was purified by prep-TLC (silica gel, eluting with 2:1 ethyl acetate/petroleum ether) to afford one enantiomer of the title compound. MS (ESI) calcd. for ($C_{17}H_{17}F_2N_2O_3$) [M+H]$^+$, [335.1], found, [335.0]. $^1$H NMR (400 MHz, CDCl$_3$) δ 7.71 (s, 2H), 7.26-7.22 (m, 1H), 6.99-6.89 (m, 2H), 5.50 (s, 1H), 4.46-4.44 (m, 1H), 3.73-3.62 (m, 2H), 3.44 (s, 3H), 2.74-2.56 (m, 2H), 2.15-2.02 (m, 1H), 1.85-1.79 (m, 1H).

Similar treatment of the other enantiomer of ethyl 5-(2,4-difluorophenyl)-2-(methoxymethyl)-3,4-dihydro-2H-pyrano[2,3-b]pyridine-7-carboxylate afforded the other enantiomer of the title compound. MS (ESI) calcd. for ($C_{17}H_{17}F_2N_2O_3$) [M+H]$^+$, [335.1], found, [335.0]. $^1$H NMR (400 MHz, CDCl$_3$) δ 7.66 (s, 2H), 7.21-7.15 (m, 1H), 6.94-6.84 (m, 2H), 5.50 (s, 1H), 4.41-4.39 (m, 1H), 3.68-3.57 (m, 2H), 3.39 (s, 3H), 2.70-2.50 (m, 2H), 2.10-1.97 (m, 1H), 1.80-1.74 (m, 1H).

Example 3-6A and 3-6B

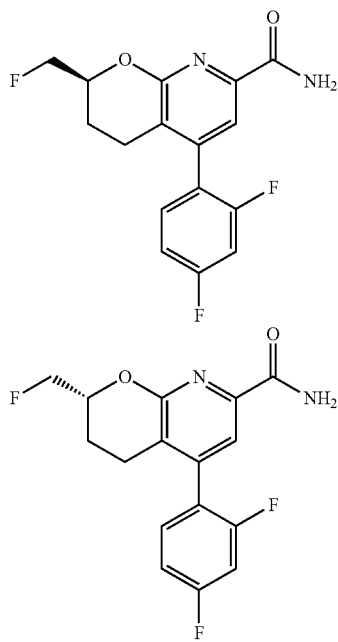

(S)-5-(2,4-difluorophenyl)-2-(fluoromethyl)-3,4-dihydro-2H-pyrano[2,3-b]pyridine-7-carboxamide and (R)-5-(2,4-difluorophenyl)-2-(fluoromethyl)-3,4-dihydro-2H-pyrano[2,3-b]pyridine-7-carboxamide Step 1: ethyl 5-(2,4-difluorophenyl)-2-(fluoromethyl)-3,4-dihydro-2H-pyrano[2,3-b]pyridine-7-carboxylate

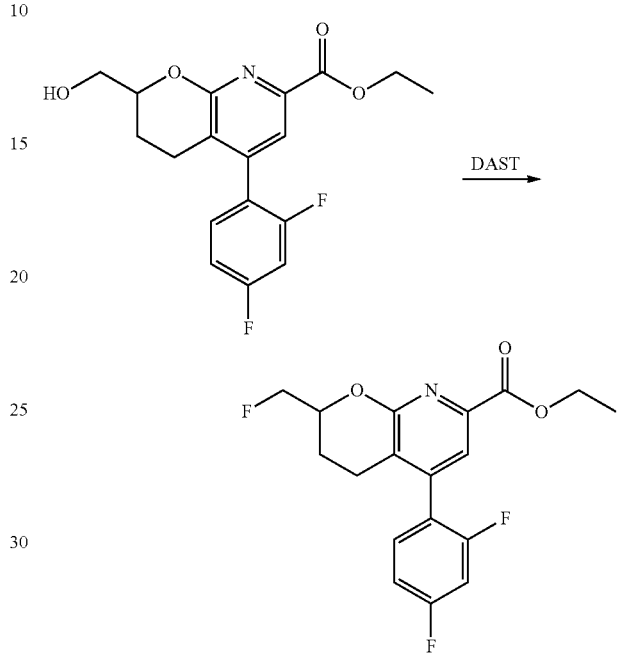

To a solution of ethyl 5-(2,4-difluorophenyl)-2-(hydroxymethyl)-3,4-dihydro-2H-pyrano[2,3-b]pyridine-7-carboxylate (Intermediate 2-4, 300 mg, 0.86 mmol) in DCM (15 mL) at −40° C. was added DAST (0.34 ml, 2.6 mmol) in DCM (3 mL). The reaction mixture was stirred at 0° C. for 100 min under N$_2$. The mixture was quenched with saturated aqueous NaHCO$_3$ (30 mL) and extracted with DCM (2×20 mL). The combined organics were dried with Na$_2$SO$_4$, filtered and concentrated under reduced pressure. The residue was purified by silica gel chromatography (eluting with 20:1 to 1:3 petroleum ether/ethyl acetate) to afford the product. MS (ESI) calcd for ($C_{18}H_{17}F_3NO_3$) [M+H]$^+$, 352.1, found, 352.1.

Step 2: ethyl (S)-5-(2,4-difluorophenyl)-2-(fluoromethyl)-3,4-dihydro-2H-pyrano[2,3-b]pyridine-7-carboxylate and ethyl (R)-5-(2,4-difluorophenyl)-2-(fluoromethyl)-3,4-dihydro-2H-pyrano[2,3-b]pyridine-7-carboxylate

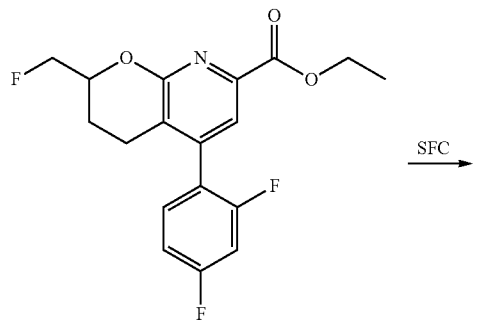

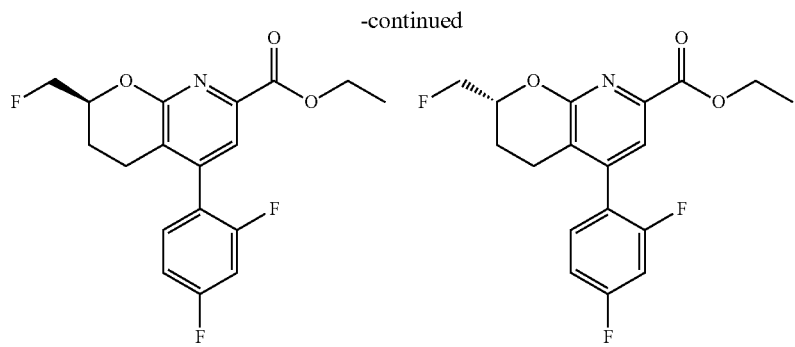

Racemic ethyl 5-(2,4-difluorophenyl)-2-(fluoromethyl)-3,4-dihydro-2H-pyrano[2,3-b]pyridine-7-carboxylate (990 mg, 2.82 mmol) was resolved by chiral SFC (Column: Chiralpak Whelk-01 250×30 mm, 10 um; Mobile phase: 50% to 50% EtOH (containing 0.05% DEA) in $CO_2$; Flow rate: 60 mL/min) to give the two enantiomers.

Step 3: (S)-5-(2,4-difluoropheny)-2-(fluoromethyl)-3,4-dihydro-2H-pyrano[2,3-b]pyridine-7-carboxamide and (R)-5-(2,4-difluorophenyl)-2-(fluoromethyl)-3,4-dihydro-2H-pyrano[2,3-b]pyridine-7-carboxamide

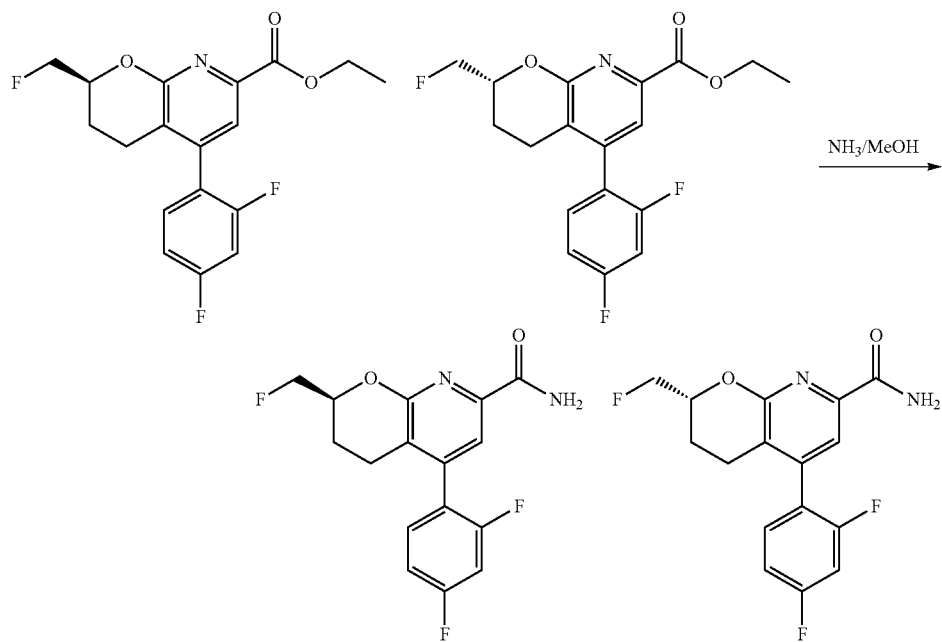

A solution of one enantiomer of ethyl 5-(2,4-difluorophenyl)-2-(fluoromethyl)-3,4-dihydro-2H-pyrano[2,3-b]pyridine-7-carboxylate (485 mg, 1.38 mmol) in ammonia (10 M in MeOH) (50 mL) was stirred at 23° C. for 4 h. The mixture was concentrated in vacuo to furnish. The solid was washed with $CH_3CN$ (2 mL). The mixture was filtered and the solid residue was dried under reduced pressure to afford one enantiomer of the title compound. MS (ESI) calcd. for $(C_{16}H_{14}F_3N_2O_2)$ $[M+H]^+$, 323.0, found, 323.1. $^1H$ NMR (400 MHz, $CD_3OD$) δ 7.59 (s, 1H), 7.43-7.37 (m, 1H), 7.16-7.10 (m, 2H), 4.87-4.54 (m, 3H), 2.87-2.80 (m, 1H), 2.63-2.58 (m, 1H), 2.09-2.06 (m, 1H), 1.84-1.79 (m, 1H).

Similar treatment of the other enantiomer of ethyl 5-(2,4-difluorophenyl)-2-(fluoromethyl)-3,4-dihydro-2H-pyrano[2,3-b]pyridine-7-carboxylate furnished the other enantiomer of the title compound. MS (ESI) calcd. for $(C_{16}H_{14}F_3N_2O_2)$ $[M+H]^+$, 323.0, found, 323.1. $^1H$ NMR (400 MHz, $CD_3OD$) δ 7.59 (s, 1H), 7.43-7.37 (m, 1H), 7.16-7.10 (m, 2H), 4.87-4.54 (m, 3H), 2.86-2.81 (m, 1H), 2.63-2.59 (m, 1H), 2.09-2.04 (m, 1H), 1.82-1.79 (m, 1H).

Example 3-7A and 3-7B

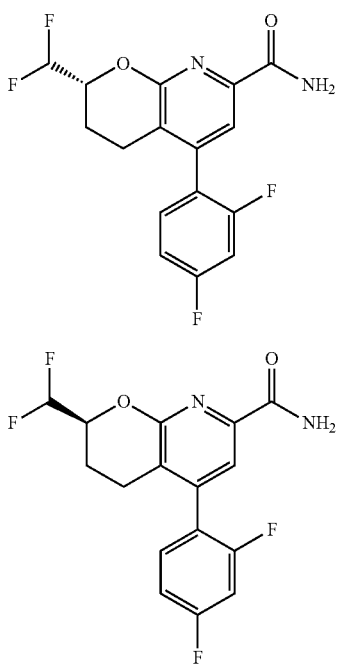

3-7A: (R)-2-(difluoromethyl)-5-(2,4-difluorophenyl)-3,4-dihydro-2H-pyrano[2,3-b]pyridine-7-carboxamide and 3-7B: (S)-2-(difluoromethyl)-5-(2,4-difluorophenyl)-3,4-dihydro-2H-pyrano[2,3-b]pyridine-7-carboxamide Step 1: ethyl 5-(2,4-difluorophenyl)-2-formyl-3,4-dihydro-2H-pyrano[2,3-b]pyridine-7-carboxylate (Intermediate 3-1)

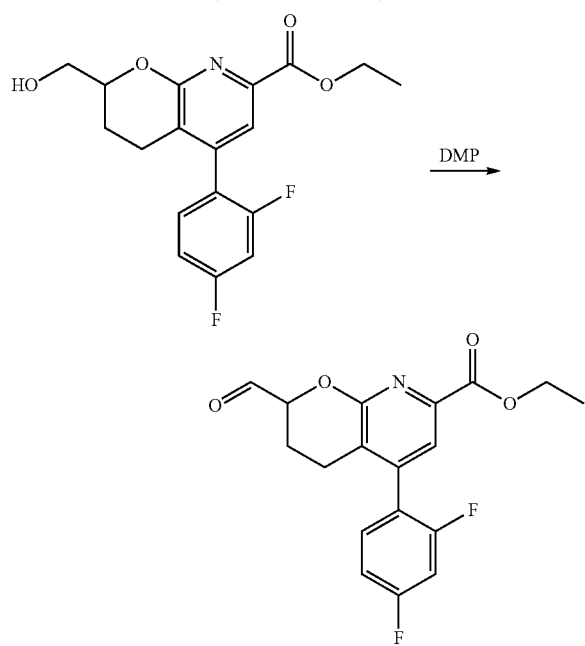

A stirred solution of racemic ethyl 5-(2,4-difluorophenyl)-2-(hydroxymethyl)-3,4-dihydro-2H-pyrano[2,3-b]pyridine-7-carboxylate (Intermediate 2-4, 300 mg, 0.86 mmol) in DCM (20 mL) was added DMP (474 mg, 1.1 mmol) at 0° C. under N$_2$ atmosphere. The resulting mixture was stirred at 0° C. for 1 h. Saturated aqueous NaHCO$_3$ (50 mL) was added. The organic layer was separated, dried over anhydrous NaSO$_4$, filtered and concentrated under reduced pressure to afford the product which was used in the next step without further purification. MS (ESI) calcd. for (C$_{18}$H$_{18}$F$_2$NO$_5$) [M+H+H$_2$O]$^+$, 366.1, found, 366.1.

Step 2: ethyl 2-(difluoromethyl)-5-(2,4-difluorophenyl)-3,4-dihydro-2H-pyrano[2,3-b]pyridine-7-carboxylate

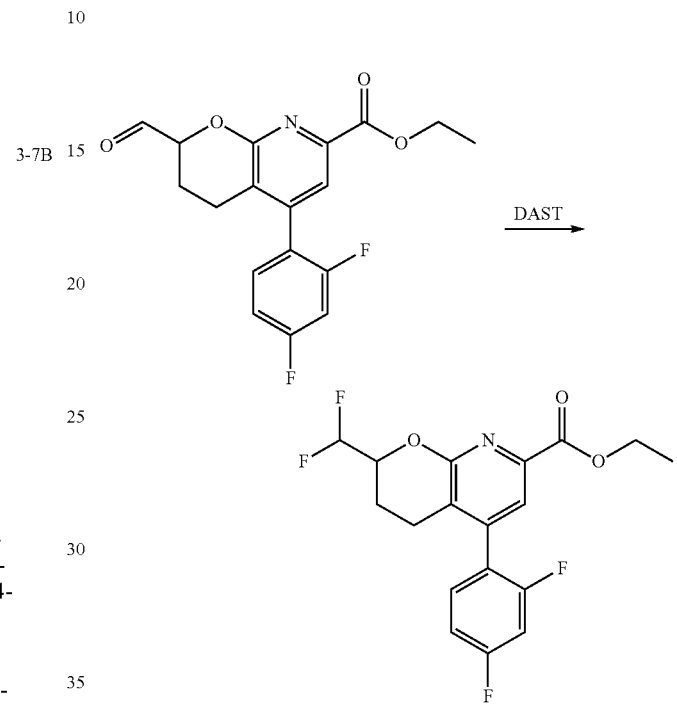

To a solution of ethyl 5-(2,4-difluorophenyl)-2-formyl-3,4-dihydro-2H-pyrano[2,3-b]pyridine-7-carboxylate (380 mg, 1.1 mmol) in DCM (20 mL) and EtOH (0.01 mL) was added DAST (0.289 ml, 2.2 mmol) at 0° C. After addition, the mixture was stirred at 24° C. for 2 h. To the reaction mixture was slowly added saturated aqueous sodium bicarbonate (20 mL). The organic layer was separated, dried over sodium sulfate, and concentrated under reduced pressure. The residue was purified by prep-TLC (silica gel, eluting with 1:2 ethyl acetate/petroleum ether) to give the product. MS (ESI) calcd. for (C$_{18}$H$_{16}$F$_4$NO$_3$) [M+H]$^+$, 370.2, found, 370.0.

Step 3: 2-(difluoromethyl)-5-(2,4-difluorophenyl)-3,4-dihydro-2H-pyrano[2,3-b]pyridine-7-carboxamide

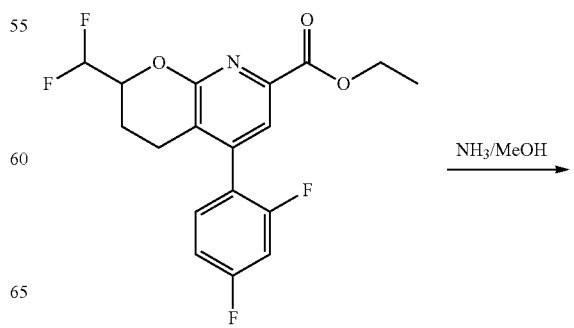

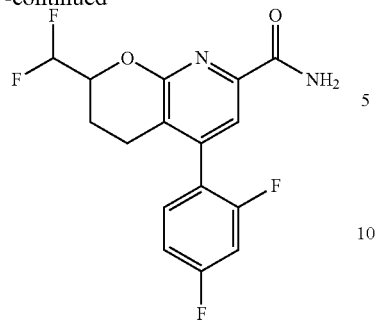

A solution of ethyl 2-(difluoromethyl)-5-(2,4-difluorophenyl)-3,4-dihydro-2H-pyrano[2,3-b]-pyridine-7-carboxylate (81 mg, 0.22 mmol) in ammonia (10 M in MeOH) (15 mL) was stirred at 25° C. for 3 h. The mixture was concentrated under reduced pressure to give the product. MS (ESI) calcd. for ($C_{16}H_{13}F_4N_2O_2$) [M+H]$^+$, [341.1], found, [341.0].

Step 4: (R)-2-(difluoromethyl)-5-(2,4-difluorophenyl)-3,4-dihydro-2H-pyrano[2,3-b]pyridine-7-carboxamide and (S)-2-(difluoromethyl)-5-(2,4-difluorophenyl)-3,4-dihydro-2H-pyrano[2,3-b]pyridine-7-carboxamide

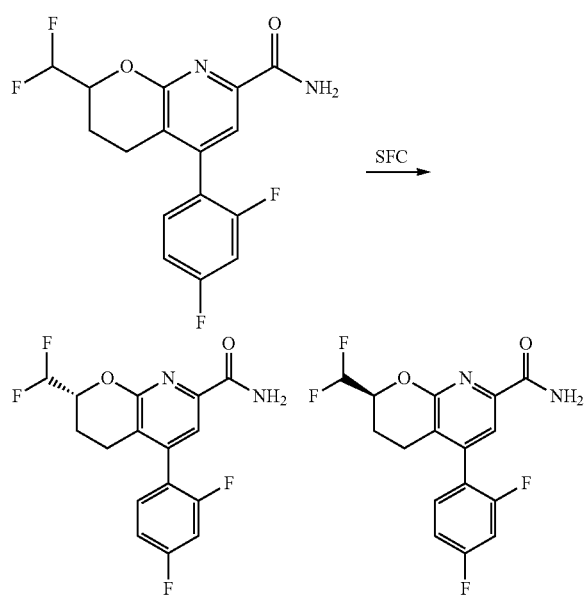

Racemic ethyl 2-(difluoromethyl)-5-(2,4-difluorophenyl)-3,4-dihydro-2H-pyrano[2,3-b]pyridine-7-carboxamide (64 mg, 0.19 mmol) was separated by SFC (Column: Chiralpak AD 250×30 mm, 5 um; Mobile phase: 20% to 20% MeOH (containing 0.05% DEA) in CO$_2$; Flow rate: 60 mL/min) to afford the two enantiomers:

One enantiomer: MS (ESI) calcd. for ($C_{16}H_{13}F_4N_2O_2$) [M+H]$^+$, 341.1, found, 341.0. $^1$H NMR (400 MHz, CD$_3$OD) δ 7.63 (s, 1H), 7.43-7.38 (m, 1H), 7.17-7.11 (m, 2H), 6.22-5.94 (m, 1H), 4.87-4.54 (m, 1H), 3.30-2.81 (m, 1H), 2.67-2.63 (m, 1H), 2.19-2.16 (m, 1H), 1.90-1.84 (m, 1H).

Other enantiomer: MS (ESI) calcd. for ($C_{16}H_{13}F_4N_2O_2$) [M+H]$^+$, 341.1, found, 341.0. $^1$H NMR (400 MHz, CD$_3$OD) δ 7.63 (s, 1H), 7.43-7.38 (m, 1H), 7.17-7.11 (m, 2H), 6.22-5.94 (m, 1H), 4.62-4.54 (m, 1H), 3.30-2.81 (m, 1H), 2.67-2.63 (m, 1H), 2.19-2.16 (m, 1H), 1.90-1.84 (m, 1H).

Example 3-8A and 3-8B

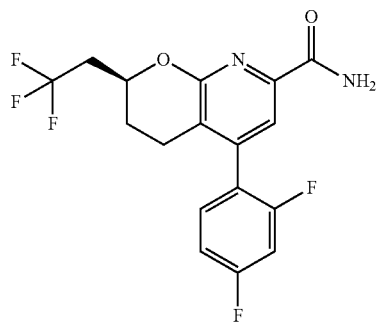

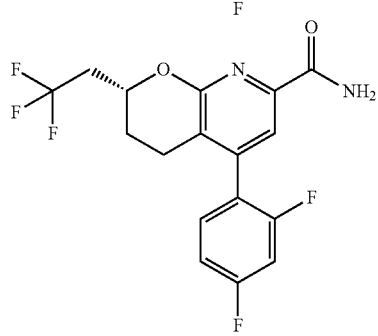

(S)-5-(2,4-difluorophenyl)-2-(2,2,2-trifluoroethyl)-3,4-dihydro-2H-pyrano[2,3-b]pyridine-7-carboxamide and (R)-5-(2,4-difluorophenyl)-2-(2,2,2-trifluoroethyl)-3,4-dihydro-2H-pyrano[2,3-b]pyridine-7-carboxamide Step 1: ethyl 5-(2,4-difluorophenyl)-2-(2,2,2-trifluoro-1-hydroxyethyl)-3,4-dihydro-2H-pyrano[2,3-b]pyridine-7-carboxylate and 5-(2,4-difluorophenyl)-2-(2,2,2-trifluoro-1-((trimethylsilyl)oxy)ethyl)-3,4-dihydro-2H-pyrano[2,3-b]pyridine-7-carboxylate

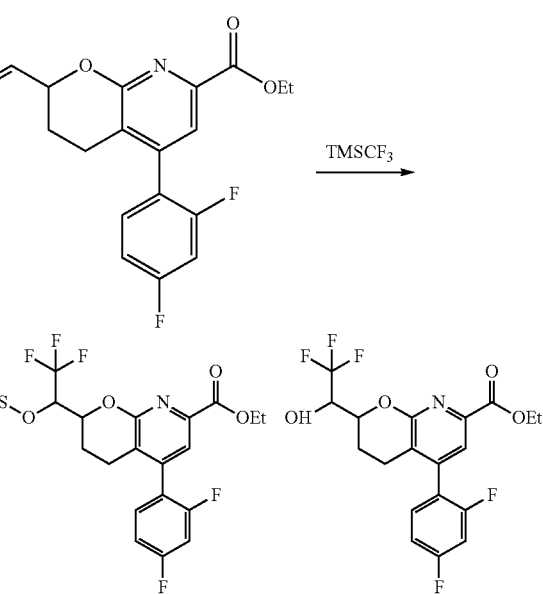

To a solution of ethyl 5-(2,4-difluorophenyl)-2-formyl-3,4-dihydro-2H-pyrano[2,3-b]pyridine-7-carboxylate (Intermediate 3-1, 700 mg, 2.0 mmol), cesium fluoride (918 mg, 6.1 mmol) in THF (15 mL) was added trimethyl(trifluoromethyl)silane (860 mg, 6.1 mmol) at 0° C. under N₂. The reaction mixture was stirred at 0° C. for 2 h under N₂. The mixture was quenched with H₂O (15 mL), and extracted with EtOAc (3×25 mL). The combined organic layers were dried over anhydrous Na₂SO₄, filtered and the filtrate was concentrated under reduced pressure. Silica gel chromatography eluting with 20:1 to 2:1 petroleum ether:ethyl acetate afforded the products. MS (ESI) calcd. for (C₂₂H₂₅F₅NO₄Si) [M+H]⁺, 490.5, found, 490.4. ¹H NMR (400 MHz, CDCl₃) δ 7.48 (s, 1H), 6.97-7.07 (m, 1H), 6.72-6.88 (m, 2H), 4.21-4.38 (m, 3H), 2.59 (br. s., 1H), 2.47 (br. s., 1H), 1.83-2.04 (m, 1H), 1.62-1.83 (m, 1H), 1.23 (t, J=7.04 Hz, 3H), 0.01 (d, J=11.35 Hz, 9H).

Step 2: ethyl 5-(2,4-difluorophenyl)-2-(2,2,2-trifluoro-1-hydroxyethyl)-3,4-dihydro-2H-pyrano[2,3-b]pyridine-7-carboxylate

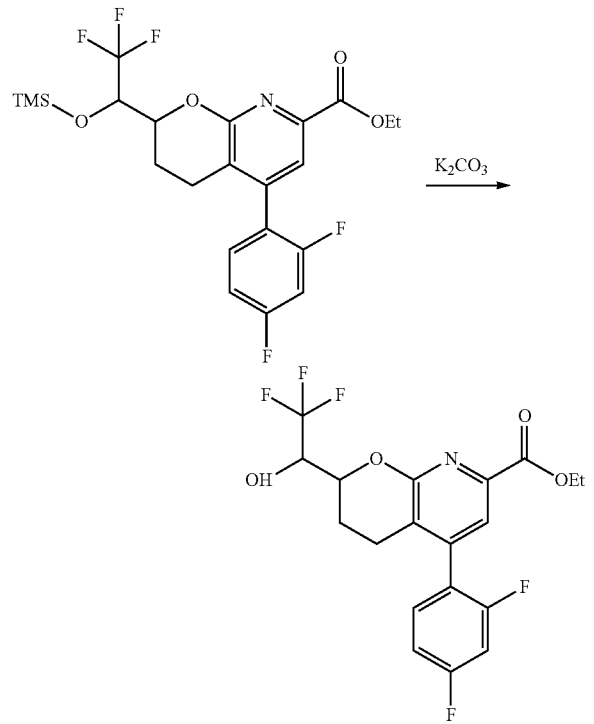

To a solution of ethyl 5-(2,4-difluorophenyl)-2-(2,2,2-trifluoro-1-((trimethylsilyl)oxy)ethyl)-3,4-dihydro-2H-pyrano[2,3-b]pyridine-7-carboxylate (300 mg, 0.61 mmol) in ethanol (15 mL) was added K₂CO₃ (102 mg, 0.74 mmol) at 18° C. The mixture was stirred at 18° C. for 40 min. The mixture was filtered and the filtrate was concentrated in vacuo and the residue was purified by prep-TLC (silica gel, eluting with 2:1 petroleum ether:ethyl acetate) to give the product. MS (ESI) calcd. for (C₁₉H₁₇F₅NO₄) [M+H]⁺, 418.0, found, 417.9. ¹H NMR (400 MHz, CDCl₃) δ 7.68 (d, J=10.17 Hz, 1H), 7.22 (br. s., 1H), 6.86-7.06 (m, 2H), 4.53-4.66 (m, 1H), 4.43 (quin, J=7.24 Hz, 2H), 4.11 (q, J=7.30 Hz, 1H), 2.81 (br. s., 1H), 2.58-2.69 (m, 1H), 2.04-2.19 (m, 2H), 1.40 (q, J=7.43 Hz, 3H).

Step 3: 5-(2,4-difluorophenyl)-2-(2,2,2-trifluoro-1-(((methylthio)carbonothioyl)oxy)ethyl)-3,4-dihydro-2H-pyrano[2,3-b]pyridine-7-carboxylic acid

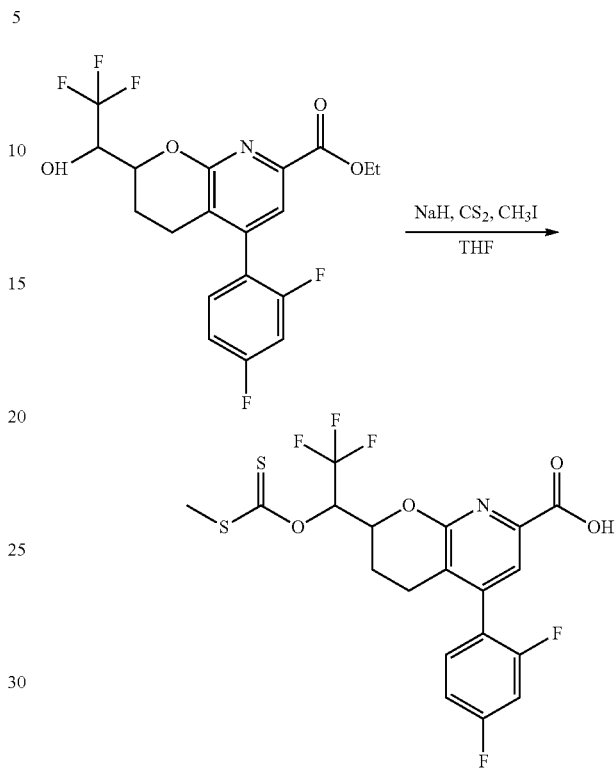

To a solution of ethyl 5-(2,4-difluorophenyl)-2-(2,2,2-trifluoro-1-hydroxyethyl)-3,4-dihydro-2H-pyrano[2,3-b]pyridine-7-carboxylate (280 mg, 0.67 mmol) in THF (2 mL) was added NaH (40.3 mg, 1.0 mmol) at 0° C. under N₂. After stirring for 30 min, carbon disulfide (0.10 mL, 1.68 mmol) and iodomethane (0.31 mL, 5.00 mmol) were added and the mixture was stirred at 0° C. under N₂ for 1 h. The reaction was diluted with 15 mL water and 5 drops HCl (concentrated, 12M), extracted with EtOAc (3×15 mL), the combined organics were dried over Na₂SO₄, filtered and concentrated in vacuo to give the product, which was used in next step without further purification. MS (ESI) calcd. for (C₁₉H₁₅F₅NO₄S₂) [M+H]⁺, 480.1, found, 480.2.

Step 4: ethyl 5-(2,4-difluorophenyl)-2-(2,2,2-trifluoro-1-(((methylthio)carbonothioyl)oxy)ethyl)-3,4-dihydro-2H-pyrano[2,3-b]pyridine-7-carboxylate

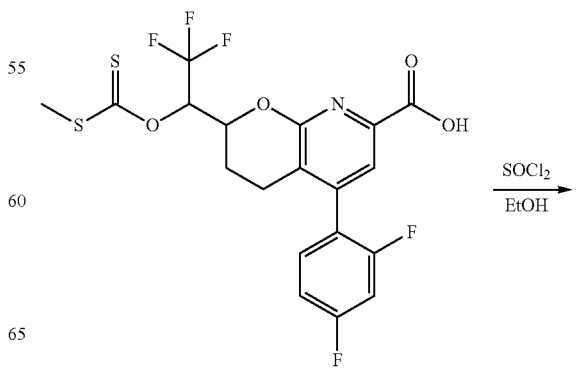

131

-continued

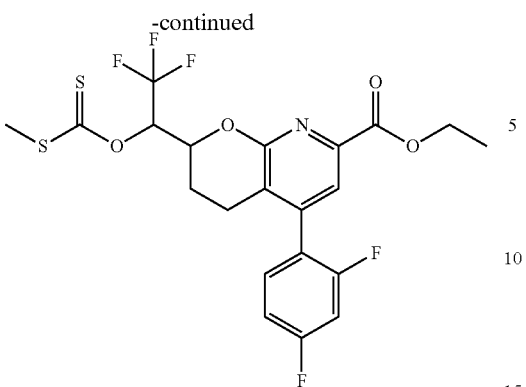

To a solution of 5-(2,4-difluorophenyl)-2-(2,2,2-trifluoro-1-(((methylthio)carbonothioyl)oxy)ethyl)-3,4-dihydro-2H-pyrano[2,3-b]pyridine-7-carboxylic acid (430 mg, 0.90 mmol) in dry EtOH (10 mL) was added sulfurous dichloride (320 mg, 2.69 mmol) under $N_2$. The mixture was stirred at 85° C. under $N_2$ for 2.5 h. The mixture was quenched with $H_2O$ (15 mL), then the mixture was adjusted to pH=8 with solid $NaHCO_3$. The mixture was extracted with EtOAc (3×20 mL). The combined organic layers were dried over anhydrous $Na_2SO_4$, filtered and concentrated under reduced pressure. Silica gel chromatography eluting with 10:1 to 5:1 petroleum ether:ethyl acetate afforded the product. MS (ESI) calcd for $(C_{21}H_{19}F_5NO_4S_2)$ [M+H]$^+$, 508.4, found, 508.3. $^1$H NMR (400 MHz, CDCl$_3$) δ 7.65 (d, J=2.74 Hz, 1H), 7.17-7.23 (m, 1H), 6.87-7.04 (m, 2H), 4.68-4.82 (m, 1H), 4.42 (dq, J=2.35, 7.04 Hz, 2H), 2.70-2.89 (m, 1H), 2.66 (br. s., 1H), 2.60 (s, 3H), 2.07-2.25 (m, 1H), 1.80-2.00 (m, 1H), 1.39 (dt, J=1.96, 7.04 Hz, 3H).

Step 5: ethyl 5-(2,4-difluorophenyl)-2-(2,2,2-trifluoroethyl)-3,4-dihydro-2H-pyrano[2,3-b]pyridine-7-carboxylate

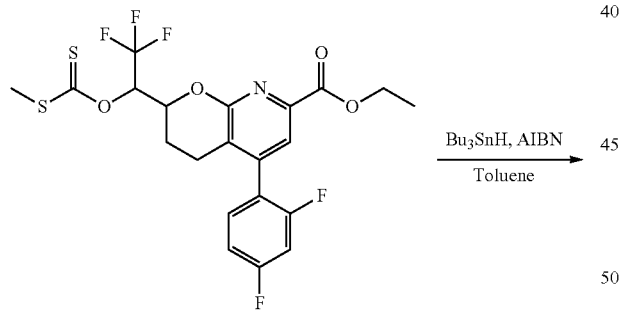

132

-continued

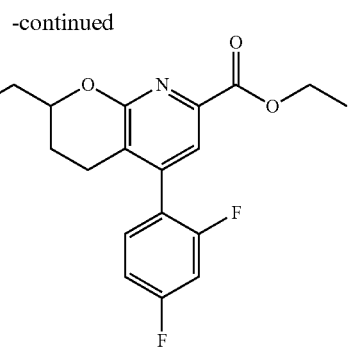

To a solution of ethyl 5-(2,4-difluorophenyl)-2-(2,2,2-trifluoro-1-(((methylthio)carbonothioyl)oxy)ethyl)-3,4-dihydro-2H-pyrano[2,3-b]pyridine-7-carboxylate (230 mg, 0.45 mmol) and tributylstannane (1.18 g, 4.05 mmol) in Toluene (10 mL) was added azobisisobutyronitrile (20 mg, 0.12 mmol) under $N_2$. The reaction mixture was heated to 100° C. and stirred under $N_2$ for 1 h. The reaction was diluted with 20 mL water, extracted with EtOAc (20 mL×3), the combined organic layers were dried over $Na_2SO_4$, filtered and concentrated under reduced pressure to give the crude product. The residue was purified by silica gel chromatography (eluting with 10:1 to 5:1 petroleum ether:ethyl acetate) to give the product. MS (ESI) calcd for $(C_{19}H_{17}F_5NO_3)$ [M+H]$^+$, 402.1, found, 402.1. $^1$H NMR (400 MHz, CDCl$_3$) δ 7.65 (s, 1H), 7.18-7.24 (m, 1H), 6.87-7.04 (m, 2H), 4.58 (td, J=5.23, 10.27 Hz, 1H), 4.42 (q, J=7.04 Hz, 2H), 2.71-2.94 (m, 2H), 2.42-2.65 (m, 2H), 2.12-2.24 (m, 1H), 1.69-1.86 (m, 1H), 1.39 (t, J=7.04 Hz, 3H).

Step 6: ethyl (S)-5-(2,4-difluorophenyl)-2-(2,2,2-trifluoroethyl)-3,4-dihydro-2H-pyrano[2,3-b]pyridine-7-carboxylate and ethyl (R)-5-(2,4-difluorophenyl)-2-(2,2,2-trifluoroethyl)-3,4-dihydro-2H-pyrano[2,3-b]pyridine-7-carboxylate

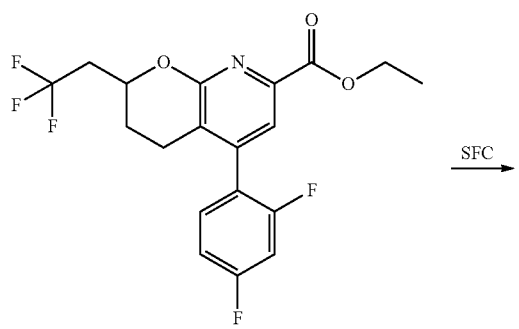

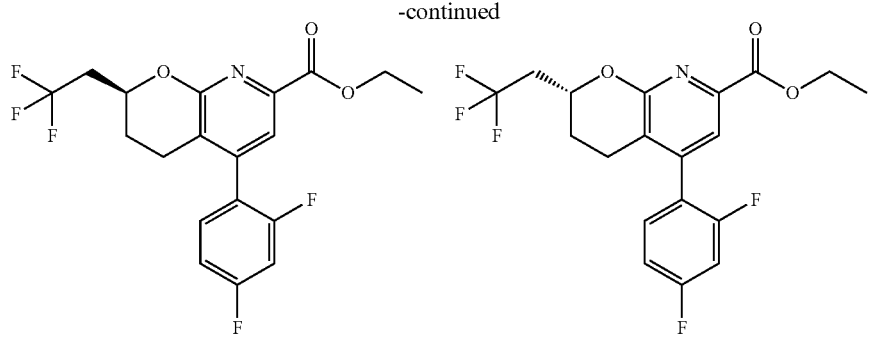

Racemic ethyl 5-(2,4-difluorophenyl)-2-(2,2,2-trifluoroethyl)-3,4-dihydro-2H-pyrano[2,3-b]pyridine-7-carboxylate (120 mg, 0.3 mmol) was resolved via chiral SFC (Column: Chiralpak IC 250×30 mm, 10 um; Mobile phase: 30% to 30% IPA (containing 0.05% DEA in $CO_2$; Flow rate: 6 mL/min) to give the two enantiomers which were used in next step without further purification.

Step 7: (S)-5-(2,4-difluorophenyl)-2-(2,2,2-trifluoroethyl)-3,4-dihydro-2H-pyrano[2,3-b]pyridine-7-carboxamide and (R)-5-(2,4-difluorophenyl)-2-(2,2,2-trifluoroethyl)-3,4-dihydro-2H-pyrano[2,3-b]pyridine-7-carboxamide

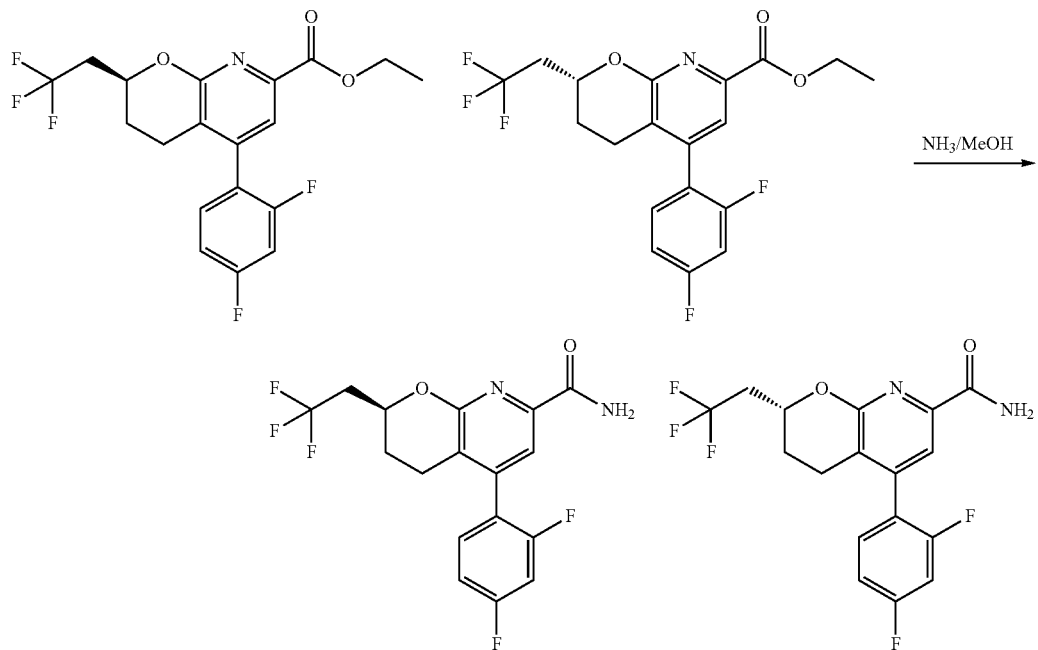

A solution of one enantiomer of ethyl 5-(2,4-difluorophenyl)-2-(2,2,2-trifluoroethyl)-3,4-dihydro-2H-pyrano[2,3-b]pyridine-7-carboxylate (45 mg, 0.11 mmol) in ammonia (10 M in MeOH) (20 mL) was stirred at 10° C. for 20 h. The mixture was concentrated and purified by Prep-HPLC (Column: Phenomenex Synergi C18 150×30 mm, 4 um; Mobile phase: 43% to 63% water (containing 0.05% HCl)-ACN; Flow rate: 25 mL/min) to give one enantiomer of the title compound. MS (ESI) calcd. for $(C_{17}H_{14}F_5N_2O_2)$ $[M+H]^+$, 373.1, found, 372.9. $^1H$ NMR (400 MHz, $CD_3OD$) δ 7.59 (br. s., 1H), 7.38 (d, J=6.26 Hz, 1H), 7.01-7.18 (m, 2H), 4.65 (br. s., 1H), 2.49-2.89 (m, 4H), 2.05-2.24 (m, 1H), 1.79 (br. s., 1H).

Similar treatment of the other enantiomer of ethyl 5-(2,4-difluorophenyl)-2-(2,2,2-trifluoroethyl)-3,4-dihydro-2H-pyrano[2,3-b]pyridine-7-carboxylate afforded the other enantiomer of the title compound. MS (ESI) calcd. for $(C_{17}H_{14}F_5N_2O_2)$ $[M+H]^+$, 373.1, found, 372.9. $^1H$ NMR (400 MHz, $CD_3OD$) δ 7.60 (s, 1H), 7.35-7.45 (m, 1H), 7.08-7.18 (m, 2H), 4.67 (br. s., 1H), 2.54-2.90 (m, 4H), 2.09-2.20 (m, 1H), 1.73-1.88 (m, 1H)

Example 3-9A, 3-9B, 3-9C and 3-9D

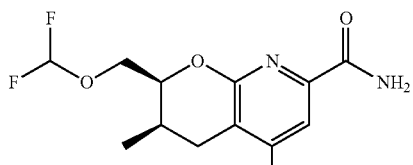

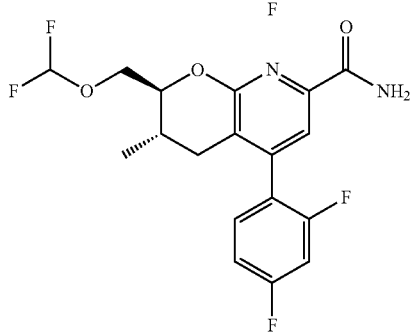

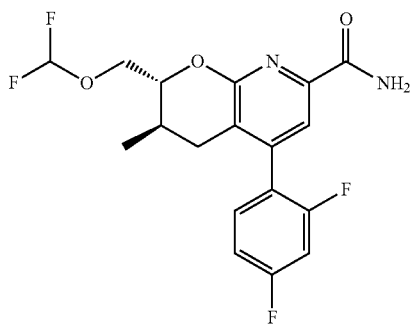

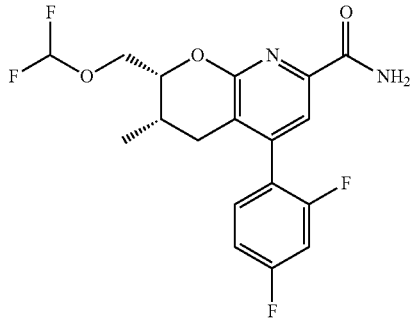

(2S,3R)-2-((difluoromethoxy)methyl)-5-(2,4-difluorophenyl)-3-methyl-3,4-dihydro-2H-pyrano[2,3-b]pyridine-7-carboxamide, (2S,3S)-2-((difluoromethoxy)methyl)-5-(2,4-difluorophenyl)-3-methyl-3,4-dihydro-2H-pyrano[2,3-b]pyridine-7-carboxamide, (2R,3R)-2-((difluoromethoxy)methyl)-5-(2,4-difluoropheny)-3-methyl-3,4-dihydro-2H-pyrano[2,3-b]pyridine-7-carboxamide and (2R,3S)-2-((difluoromethoxy)methyl)-5-(2,4-difluorophenyl)-3-methyl-3,4-dihydro-2H-pyrano[2,3-b]pyridine-7-carboxamide Step 1: ethyl (2S,3R)-, (2S,3S)-, (2R,3R) or (2R,3S)-2-((difluoromethoxy)methyl)-5-(2,4-difluorophenyl)-3-methyl-3,4-dihydro-2H-pyrano[2,3-b]pyridine-7-carboxylate

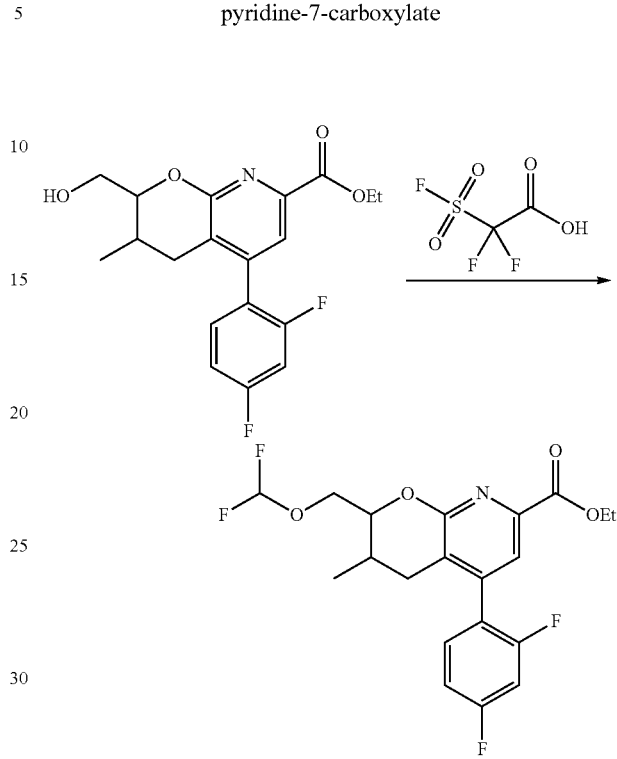

To a solution of one isomer of ethyl 5-(2,4-difluorophenyl)-2-(hydroxymethyl)-3-methyl-3,4-dihydro-2H-pyrano[2,3-b]pyridine-7-carboxylate (Intermediate 2-5A, 2-5B, 2-5C or 2-5D) 140 mg, 0.39 mmol) in acetonitrile (8 mL) was added copper(I) iodide (14.7 mg, 0.077 mmol) and the mixture was heated to 45° C. under $N_2$. 2,2-difluoro-2-(fluorosulfonyl)acetic acid (0.2 mL, 1.9 mmol) was added dropwise, the mixture was stirred at 45° C. for 2 h. The mixture was cooled in an ice bath and saturated aqueous $NaHCO_3$ (15 mL) was added. The aqueous layer was extracted with EtOAc (25 mL×3). The combined organic layers were washed with brine (sat. 20 mL), dried over $Na_2SO_4$, filtered and concentrated under reduced pressure to give the crude product. The residue was purified by Prep-TLC (silica gel, eluting with 2:1 petroleum ether:ethyl acetate) to give one isomer of the product. MS (ESI) calcd. for ($C_{20}H_{20}F_4NO_4$) [M+H]$^+$, 414.1, found, 414.3. $^1$H NMR (400 MHz, CDCl$_3$) δ 7.59 (d, J=6.26 Hz, 1H), 7.13-7.19 (m, 1H), 6.85-7.01 (m, 2H), 5.99-6.48 (m, 1H), 4.37 (q, J=7.04 Hz, 2H), 3.93-4.26 (m, 3H), 2.01-2.61 (m, 3H), 1.24-1.41 (m, 3H), 0.77-1.06 (m, 3H).

Similar treatment of the other isomers of ethyl 5-(2,4-difluorophenyl)-2-(hydroxymethyl)-3-methyl-3,4-dihydro-2H-pyrano[2,3-b]pyridine-7-carboxylate afforded the other isomers of the product.

Step 2: (2S,3R)-, (2S,3S)-, (2R,3R) or (2R,3S)-2-((difluoromethoxy)methyl)-5-(2,4-difluorophenyl)-3-methyl-3,4-dihydro-2H-pyrano[2,3-b]pyridine-7-carboxamide

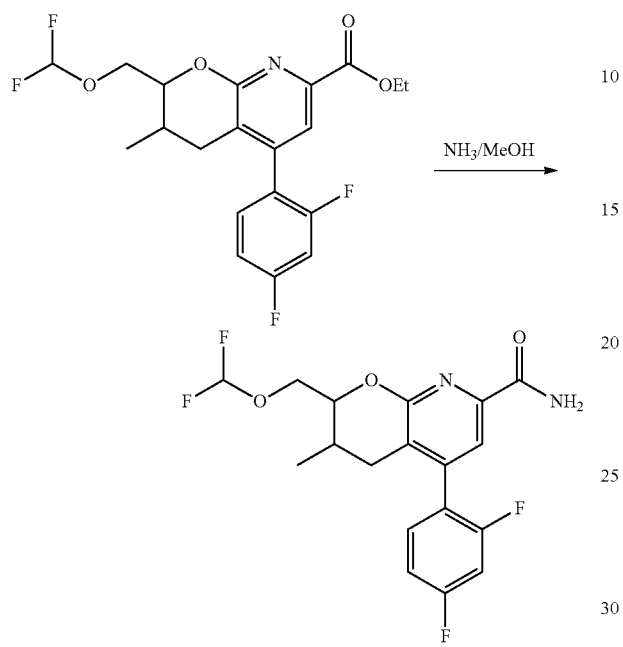

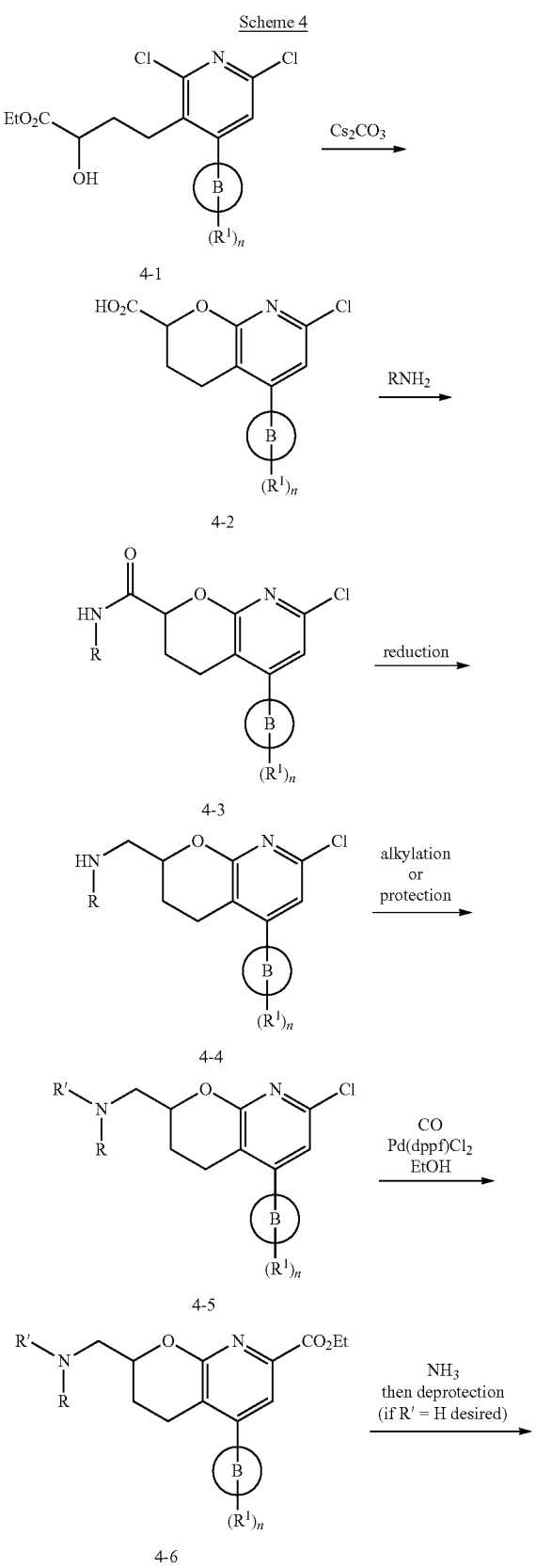

Scheme 4

A solution of one isomer of ethyl 2-((difluoromethoxy)methyl)-5-(2,4-difluorophenyl)-3-methyl-3,4-dihydro-2H-pyrano[2,3-b]pyridine-7-carboxylate (13 mg, 0.03 mmol) in ammonia (10 M in MeOH) (10 mL) was stirred at room temperature for 10 h. The mixture was concentrated and the residue was purified by Prep-HPLC (Column: Phenomenex Synergi C18 150×30 mm, 4 um; Mobile phase: 40% to 60% water (containing 0.1% TFA)-ACN; Flow rate: 25 mL/min) to give one isomer of the title compound. MS (ESI) calcd. for ($C_{18}H_{17}F_4N_2O_3$) [M+H]$^+$, 385.1, found, 385.0. $^1$H NMR (400 MHz, CD$_3$OD) δ 7.59 (s, 1H), 7.28-7.45 (m, 1H), 6.99-7.21 (m, 2H), 6.23-6.71 (m, 1H), 4.58 (br. s., 1H), 4.01-4.19 (m, 2H), 2.88-3.03 (m, 1H), 2.23-2.44 (m, 2H), 0.90 (d, J=6.26 Hz, 3H).

Similar treatment of the other isomers of ethyl 2-((difluoromethoxy)methyl)-5-(2,4-difluorophenyl)-3-methyl-3,4-dihydro-2H-pyrano[2,3-b]pyridine-7-carboxylate afforded the other isomers of the title compound.

Isomer 2: MS (ESI) calcd. for ($C_{18}H_{17}F_4N_2O_3$) [M+H]$^+$, 385.1, found, 385.0. $^1$H NMR (400 MHz, CD$_3$OD) δ 7.59 (br. s., 1H), 7.29-7.44 (m, 1H), 7.04-7.19 (m, 2H), 6.24-6.73 (m, 1H), 4.59 (br. s., 1H), 4.10 (br. s., 2H), 2.97 (br. s., 1H), 2.32 (br. s., 2H), 0.90 (d, J=5.87 Hz, 3H).

Isomer 3: MS (ESI) calcd. for ($C_{18}H_{17}F_4N_2O_3$) [M+H]$^+$, 385.1, found, 385.0. $^1$H NMR (400 MHz, CD$_3$OD) δ 7.57 (br. s., 1H), 7.38 (d, J=5.09 Hz, 1H), 7.12 (d, J=7.43 Hz, 2H), 6.22-6.71 (m, 1H), 4.07-4.32 (m, 3H), 2.40-2.69 (m, 2H), 2.06 (br. s., 1H), 1.04 (d, J=4.30 Hz, 3H).

Isomer 4: MS (ESI) calcd. for ($C_{18}H_{17}F_4N_2O_3$) [M+H]$^+$, 385.1, found, 385.0. $^1$H NMR (400 MHz, CD$_3$OD) δ 7.58 (s, 1H), 7.29-7.46 (m, 1H), 7.04-7.20 (m, 2H), 6.25-6.68 (m, 1H), 4.10-4.31 (m, 3H), 2.41-2.69 (m, 2H), 2.07 (br. s., 1H), 1.05 (d, J=6.65 Hz, 3H).

SFC chiral separation at either stage if racemic

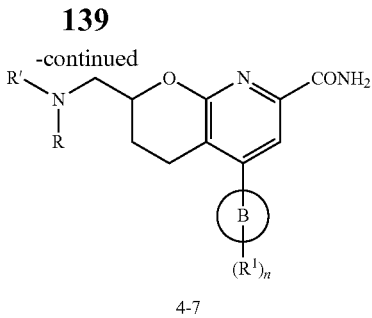

4-7

Compounds of Formula I (where, in Scheme 4, R is —$(C_{1-4})$haloalkyl, R' is H or methyl, ring B, n, and each $R^1$ are as described in Formula I or the alternative embodiments described herein) may be prepared according to Scheme 4 via cyclization of 4-1 to generate the acid 4-2. This is followed by amide formation and reduction to the amine. Subsequent alkylation (or protection for secondary amines) followed by carbonylation and treatment with ammonia affords the tertiary amines (a final deprotection furnished secondary amines).

Example 4-1A and 4-1B

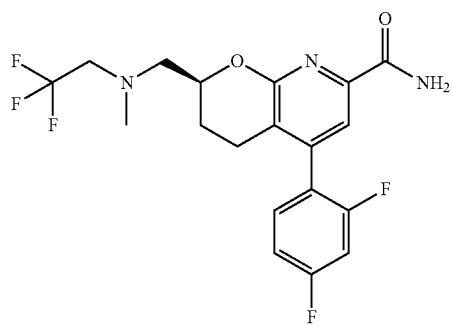

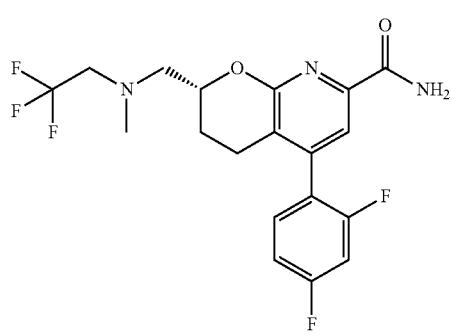

(S)-5-(2,4-difluorophenyl)-2-((methyl(2,2,2-trifluoroethyl)amino)methyl)-3,4-dihydro-2H-pyrano[2,3-b]pyridine-7-carboxamide and (R)-5-(2,4-difluorophenyl)-2-((methyl(2,2,2-trifluoroethyl)amino)methyl)-3,4-dihydro-2H-pyrano[2,3-b]pyridine-7-carboxamide Step 1: 7-chloro-5-(2,4-difluorophenyl)-N-(2,2,2-trifluoroethyl)-3,4-dihydro-2H-pyrano[2,3-b]pyridine-2-carboxamide

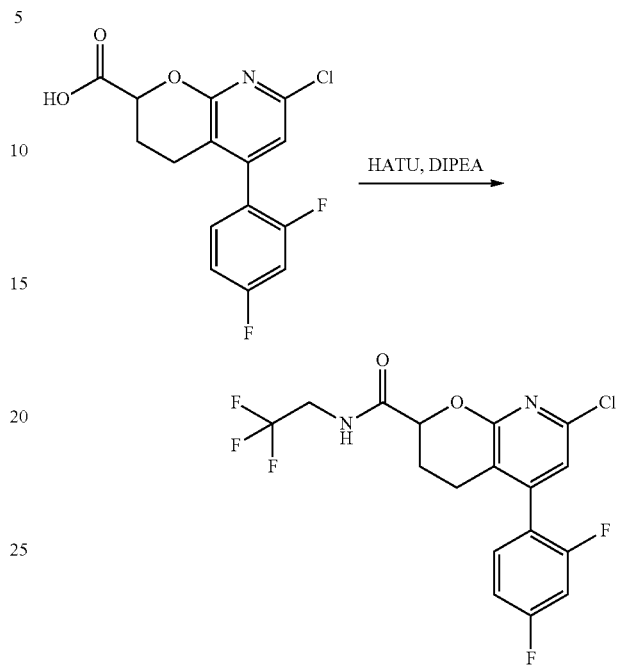

To a solution of 7-chloro-5-(2,4-difluorophenyl)-3,4-dihydro-2H-pyrano[2,3-b]pyridine-2-carboxylic acid (Intermediate 3-2, 0.8 g, 2.5 mmol) and HATU (1.2 g, 3.7 mmol) in DMF (10 mL). The mixture was stirred at 25° C. for 10 min under $N_2$. Then DIPEA (0.68 g, 4.9 mmol) was added followed by slow addition of 2,2,2-trifluoroethanamine (0.37 g, 3.7 mmol). The mixture was stirred at 25° C. for 2 h. The mixture was poured into $H_2O$ (100 mL) and extracted with EtOAc (30 mL×3). The combined organic layers were purified by silica gel chromatography [ISCO®: 4 g Sepa-Flash column eluting with 0% to 20% ethyl acetate/petroleum ether] to give the product. MS (ESI) calcd for ($C_{17}H_{13}CF_5N_2O_2$) $[M+H]^+$, 407.0 found, 407.0.

Step 2: N-((7-chloro-5-(2,4-difluorophenyl)-3,4-dihydro-2H-pyrano[2,3-b]pyridin-2-yl)methyl)-2,2,2-trifluoroethanamine

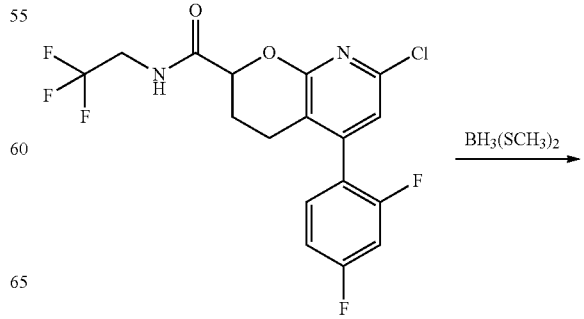

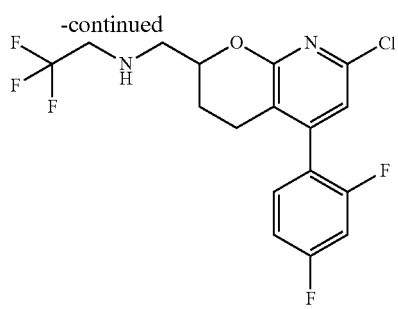

To a solution of 7-chloro-5-(2,4-difluorophenyl)-N-(2,2,2-trifluoroethyl)-3,4-dihydro-2H-pyrano[2,3-b]pyridine-2-carboxamide (0.45 g, 1.1 mmol) and BH$_3$.S(CH$_3$)$_2$ (44 mmol) in THF (10 mL). The mixture was stirred at 0° C. for 10 min then at 45° C. for another 2 h. The mixture was quenched with CH$_3$OH (40 mL) and concentrated under reduce pressure. The residue was purified by silica gel chromatography [ISCO®: 4 g SepaFlash column eluting with 0% to 20% ethyl acetate/petroleum ether] to give the product. MS (ESI) calcd for (C$_{17}$H$_{15}$ClF$_5$N$_2$O) [M+H]$^+$, 392.9 found, 392.9.

Step 3: N-((7-chloro-5-(2,4-difluorophenyl)-3,4-dihydro-2H-pyrano[2,3-b]pyridin-2-yl)methyl)-2,2,2-trifluoro-N-methylethanamine

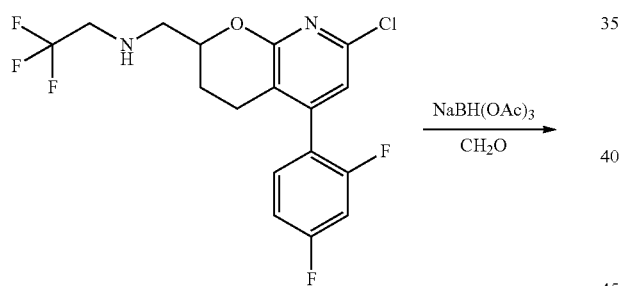

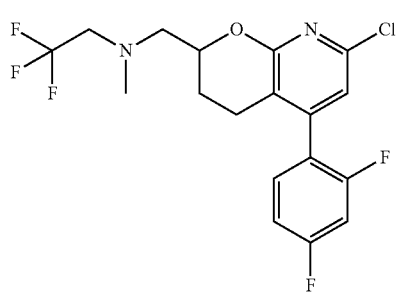

A solution of N-((7-chloro-5-(2,4-difluorophenyl)-3,4-dihydro-2H-pyrano[2,3-b]pyridin-2-yl)methyl)-2,2,2-trifluoroethanamine (0.1 g, 0.26 mmol) and CH$_2$O (0.016 g, 0.51 mmol) in DCE (10 mL) was stirred at 25° C. NaBH(OAc)$_3$ (0.11 g, 0.51 mmol) was added to the solution followed by a drop of AcOH. The mixture was stirred at 25° C. for 8 h. The mixture was poured into H$_2$O (20 mL), the pH was adjusted to ~9 with the addition of NaHCO$_3$, and the mixture was extracted with EtOAc (20 mL×3). The combined organic extracts were dried over anhydrous Na$_2$SO$_4$, filtered and concentrated. the residue was purified by silica gel chromatography [ISCO®: 4 g SepaFlash column eluting with 0% to 20% ethyl acetate/petroleum ether] to give the product. MS (ESI) calcd for (C$_{16}$H$_{19}$ClF$_5$N$_2$O) [M+H]$^+$, 407.0 found, 407.0.

Step 4: ethyl 5-(2,4-difluorophenyl)-2-((methyl(2,2,2-trifluoroethyl)amino)methyl)-3,4-dihydro-2H-pyrano[2,3-b]pyridine-7-carboxylate

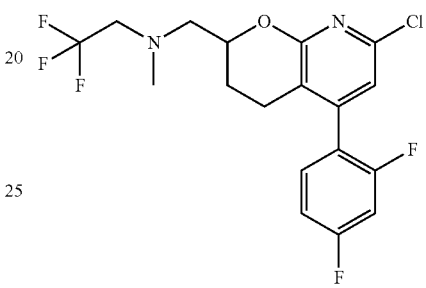

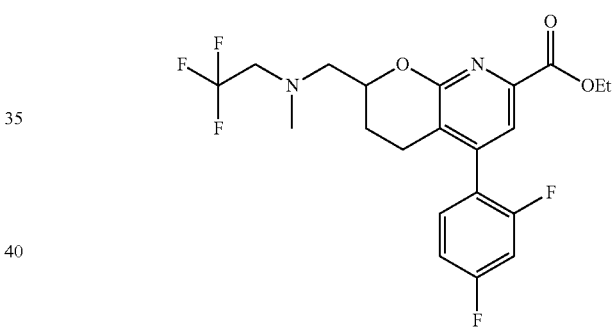

To a stirred solution of N-((7-chloro-5-(2,4-difluorophenyl)-3,4-dihydro-2H-pyrano[2,3-b]pyridin-2-yl)methyl)-2,2,2-trifluoro-N-methylethanamine (0.13 g, 0.32 mmol) in EtOH (20 mL) was added Pd(dppf)Cl$_2$ (0.023 g, 0.032 mmol) and KOAc (0.064 g, 0.64 mmol). The mixture was heated to 60° C. and stirred for 18 h under 50 psi CO. The mixture was concentrated under reduce pressure and the resulting solution was diluted with water (20 mL) and extracted with ethyl acetate (20 mL×3). The combined organic layers were dried over anhydrous Na$_2$SO$_4$, filtered and concentrated. The residue was purified by Prep-TLC (silica gel, eluting with 4:1 petroleum ether/ethyl acetate) to afford the product. MS (ESI) calcd for (C$_{21}$H$_{22}$F$_5$N$_2$O$_3$) [M+H]$^+$, 445.1, found, 445.0. $^1$H NMR (400 MHz, CDCl$_3$) δ 7.56 (s, 1H), 7.24-7.11 (m, 1H), 6.99-6.79 (m, 2H), 4.36 (q, J=7.0 Hz, 2H), 4.28 (td, J=4.9, 9.8 Hz, 1H), 3.10 (q, J=9.0 Hz, 2H), 3.04-2.91 (m, 1H), 2.78 (dd, J=6.7, 13.3 Hz, 1H), 2.49 (s, 3H), 2.16-2.02 (m, 1H), 1.74-1.56 (m, 1H), 1.33 (t, J=7.2 Hz, 3H)

Step 5: ethyl (S)-5-(2,4-difluorophenyl)-2-((methyl(2,2,2-trifluoroethyl)amino)methyl)-3,4-dihydro-2H-pyrano[2,3-b]pyridine-7-carboxylate and ethyl (R)-5-(2,4-difluorophenyl)-2-((methyl(2,2,2-trifluoroethyl)amino)methyl)-3,4-dihydro-2H-pyrano[2,3-b]pyridine-7-carboxylate

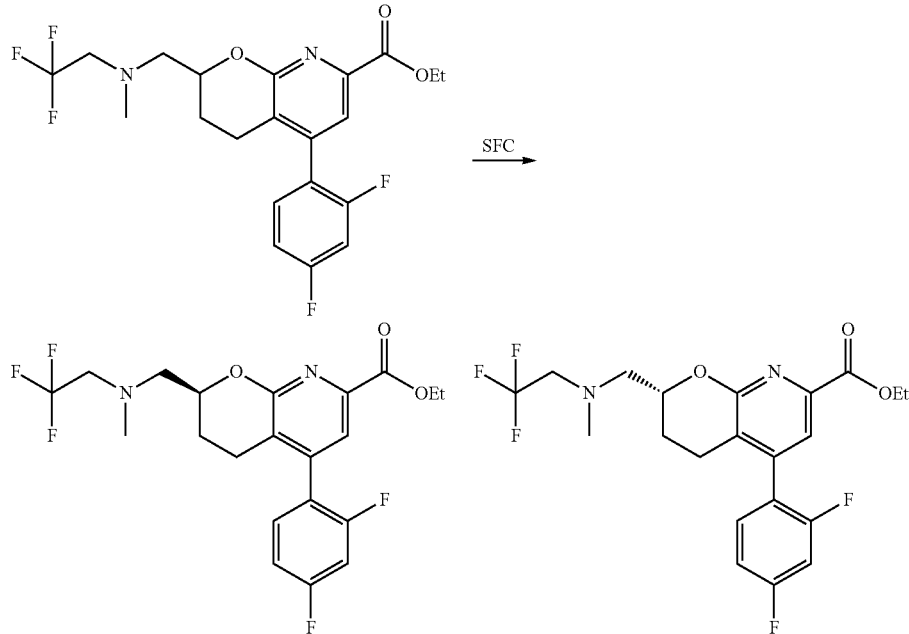

Racemic ethyl-5-(2,4-difluorophenyl)-2-((methyl(2,2,2-trifluoroethyl)amino)methyl)-3,4-dihydro-2H-pyrano[2,3-b]pyridine-7-carboxylate (100 mg, 0.28 mmol) was resolved by chiral SFC (Column: Chiralpak AD 250×30 mm, 5 um; Mobile phase: 20% to 20% IPA (containing 0.05% DEA) in $CO_2$; Flow rate: 60 mL/min) to afford the two enantiomers. MS (ESI) calcd for ($C_{21}H_{22}F_5N_2O_3$) [M+H]$^+$, 445.1, found, 445.0. MS (ESI) calcd for ($C_{21}H_{22}F_5N_2O_3$) [M+H]$^+$, 445.1, found, 445.0.

Step 6

(S)-5-(2,4-difluorophenyl)-2-((methyl(2,2,2-trifluoroethyl)amino)methyl)-3,4-dihydro-2H-pyrano[2,3-b]pyridine-7-carboxamide and (R)-5-(2,4-difluorophenyl)-2-((methyl(2,2,2-trifluoroethyl)amino)methyl)-3,4-dihydro-2H-pyrano[2,3-b]pyridine-7-carboxamide

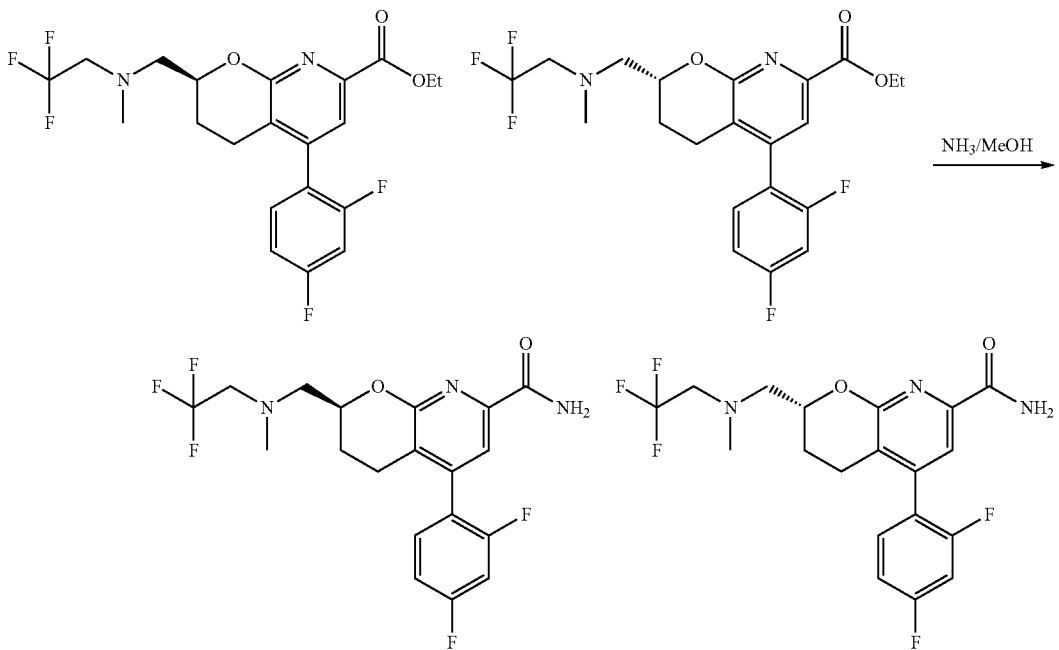

A solution of one enantiomer of ethyl 5-(2,4-difluorophenyl)-2-((methyl(2,2,2-trifluoroethyl)amino)methyl)-3,4-dihydro-2H-pyrano[2,3-b]pyridine-7-carboxylate (40 mg, 0.09 mmol) in ammonia (10 M in MeOH) (40 mL) was stirred at 20° C. for 16 h. The mixture was concentrated under reduced pressure. The residue was purified by Prep-TLC to afford one enantiomer of the title compound. MS (ESI) calcd for ($C_{19}H_{19}F_5N_3O_2$) [M+H]$^+$, 416.1, found, 416.3.

Similar treatment of the other enantiomer of ethyl 5-(2,4-difluorophenyl)-2-((methyl(2,2,2-trifluoroethyl)amino)methyl)-3,4-dihydro-2H-pyrano[2,3-b]pyridine-7-carboxylate afforded the other enantiomer of the title compound. MS (ESI) calcd for ($C_{19}H_{19}F_5N_3O_2$) [M+H]$^+$, 416.1, found, 416.3.

Example 4-2A and 4-2B

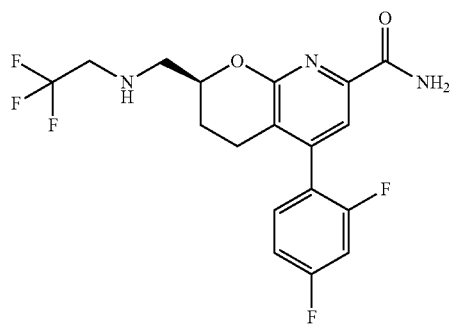

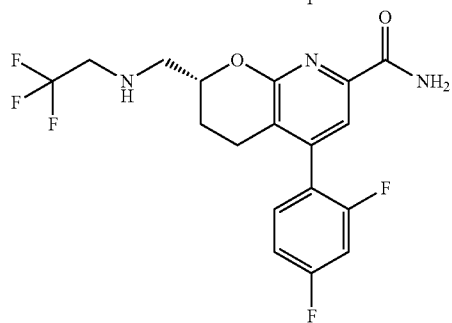

(S)-5-(2,4-difluoropheny)-2-(((2,2,2-trifluoroethyl)amino)methyl)-3,4-dihydro-2H-pyrano[2,3-b]pyridine-7-carboxamide and (R)-5-(2,4-difluorophenyl)-2-(((2,2,2-trifluoroethyl)amino)methyl)-3,4-dihydro-2H-pyrano[2,3-b]pyridine-7-carboxamide Step 1: tert-butyl ((7-chloro-5-(2,4-difluorophenyl)-3,4-dihydro-2H-pyrano[2,3-b]pyridin-2-yl)methyl)(2,2,2-trifluoroethyl)carbamate

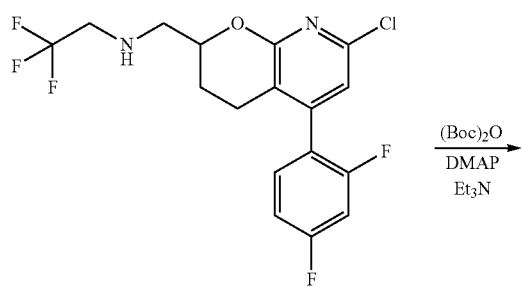

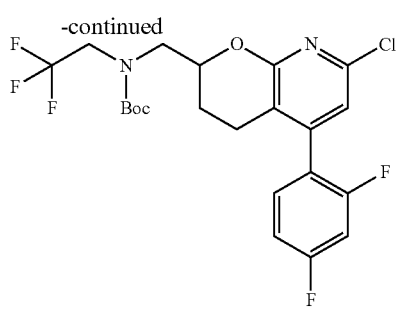

To a stirred solution of N-((7-chloro-5-(2,4-difluorophenyl)-3,4-dihydro-2H-pyrano[2,3-b]pyridin-2-yl)methyl)-2,2,2-trifluoroethanamine (150 mg, 0.38 mmol) in DCM (10 mL) was added di-tert-butyl dicarbonate (194 mg, 3.3 mmol), Et$_3$N (820 mg, 3.8 mmol) and N,N-dimethylpyridin-4-amine (4.7 mg, 0.04 mmol). Then the mixture was stirred at 25° C. for 16 h. The solution was concentrated under reduced pressure. The residue was purified by silica gel chromatography (eluting with 1:0 to 20:1 petroleum ether/ethyl acetate) to afford the product. MS (ESI) calcd. for ($C_{22}H_{23}ClF_5N_2O_3$) [M+H]$^+$, 493.12, found, 493.

Step 2: ethyl 2-(((tert-butoxycarbonyl)(2,2,2-trifluoroethyl)amino)methyl)-5-(2,4-difluorophenyl)-3,4-dihydro-2H-pyrano[2,3-b]pyridine-7-carboxylate

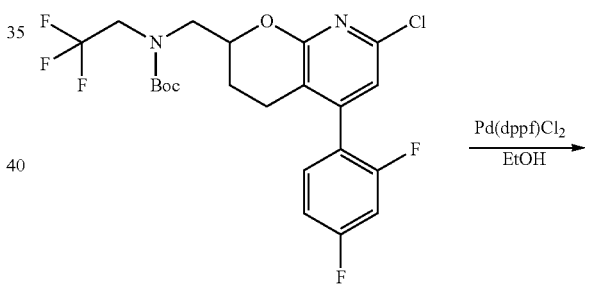

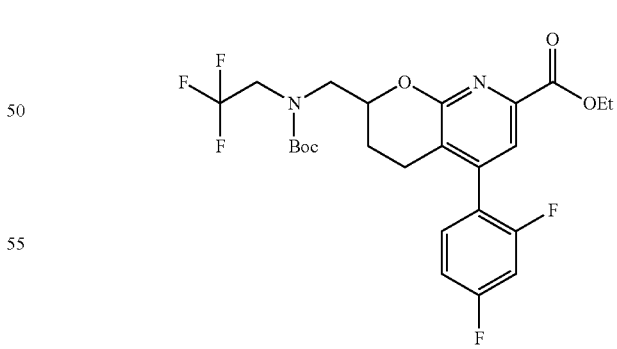

To a stirred solution of N-((7-chloro-5-(2,4-difluorophenyl)-3,4-dihydro-2H-pyrano[2,3-b]pyridin-2-yl)methyl)-2,2,2-trifluoroethanamine (71 mg, 0.14 mmol) in EtOH (15 mL) was added Pd(dppf)Cl$_2$ (10.6 mg, 0.014 mmol) and KOAc (28 mg, 0.29 mmol). Then the solution was heated to 60° C. and stirred for 18 h under 50 psi CO. The solution was concentrated under reduced pressure. The resulting solution was diluted with water (20 mL) and extracted with EtOAc (20 mL×3). The combined organic layers were dried over Na$_2$SO$_4$, filtered and concentrated under reduced pressure. The residue was purified by Prep-TLC (silica gel, eluting with 3:1 petroleum ether:ethyl acetate) to afford the product. MS (ESI) calcd. for (C$_{25}$H$_{28}$F$_5$N$_2$O$_5$) [M+H]$^+$, 531.18, found, 531.3.

Step 3: tert-butyl ((7-carbamoyl-5-(2,4-difluorophenyl)-3,4-dihydro-2H-pyrano[2,3-b]pyridin-2-yl)methyl)(2,2,2-trifluoroethyl)carbamate

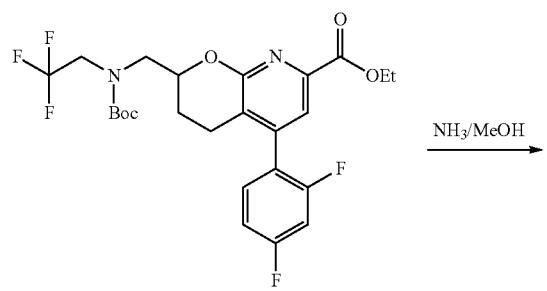

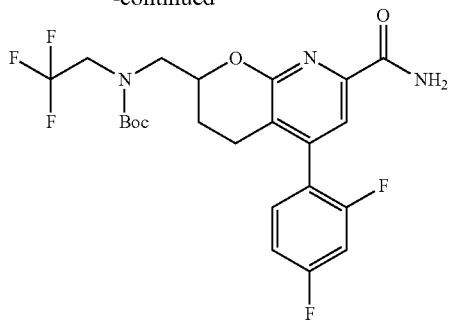

Ethyl 2-(((tert-butoxycarbonyl)(2,2,2-trifluoroethyl)amino)methyl)-5-(2,4-difluorophenyl)-3,4-dihydro-2H-pyrano[2,3-b]pyridine-7-carboxylate (53 mg, 0.1 mmol) in NH$_3$/MeOH (10 M, 15 mL) was stirred at 25° C. for 16 h. The mixture was concentrated under reduced pressure to give the product which was used in subsequent steps without further purification. MS (ESI) calcd. for (C$_{23}$H$_{25}$F$_5$N$_3$O$_4$) [M+H]$^+$, 502.17, found, 502.2.

Step 4: tert-butyl (S)-((7-carbamoyl-5-(2,4-difluorophenyl)-3,4-dihydro-2H-pyrano[2,3-b]pyridin-2-yl)methyl)(2,2,2-trifluoroethyl)carbamate and tert-butyl (R)-((7-carbamoyl-5-(2,4-difluorophenyl)-3,4-dihydro-2H-pyrano[2,3-b]pyridin-2-yl)methyl)(2,2,2-trifluoroethyl)carbamate

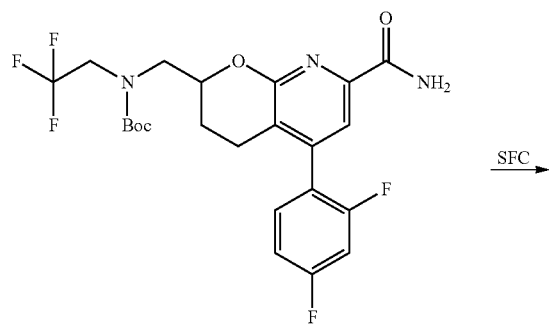

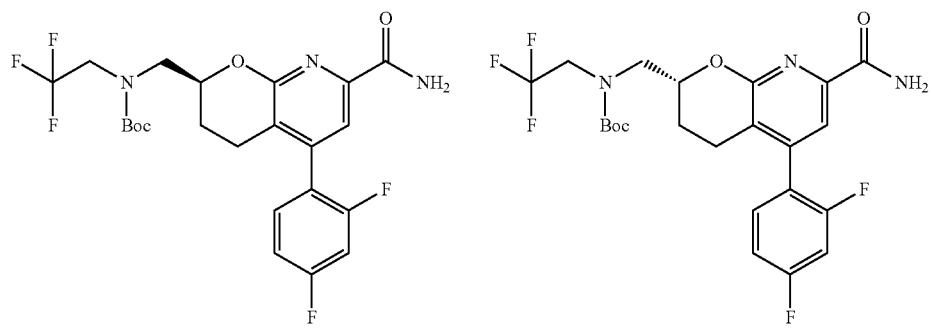

Tert-butyl((7-carbamoyl-5-(2,4-difluorophenyl)-3,4-dihydro-2H-pyrano[2,3-b]pyridin-2-yl)methyl)(2,2,2-trifluoroethyl)carbamate (40 mg, 0.08 mmol) was separated by SFC (Column: Chiralpak AS 250×30 mm, 5 um; Mobile phase: 10% to 10% MeOH (containing 0.05% DEA) in CO$_2$; Flow rate: 60 mL/min) to afford the two enantiomers.

Step 4: (S)-5-(2,4-difluorophenyl)-2-(((2,2,2-trifluoroethyl)amino)methyl)-3,4-dihydro-2H-pyrano[2,3-b]pyridine-7-carboxamide and (R)-5-(2,4-difluorophenyl)-2-(((2,2,2-trifluoroethyl)amino)methyl)-3,4-dihydro-2H-pyrano[2,3-b]pyridine-7-carboxamide

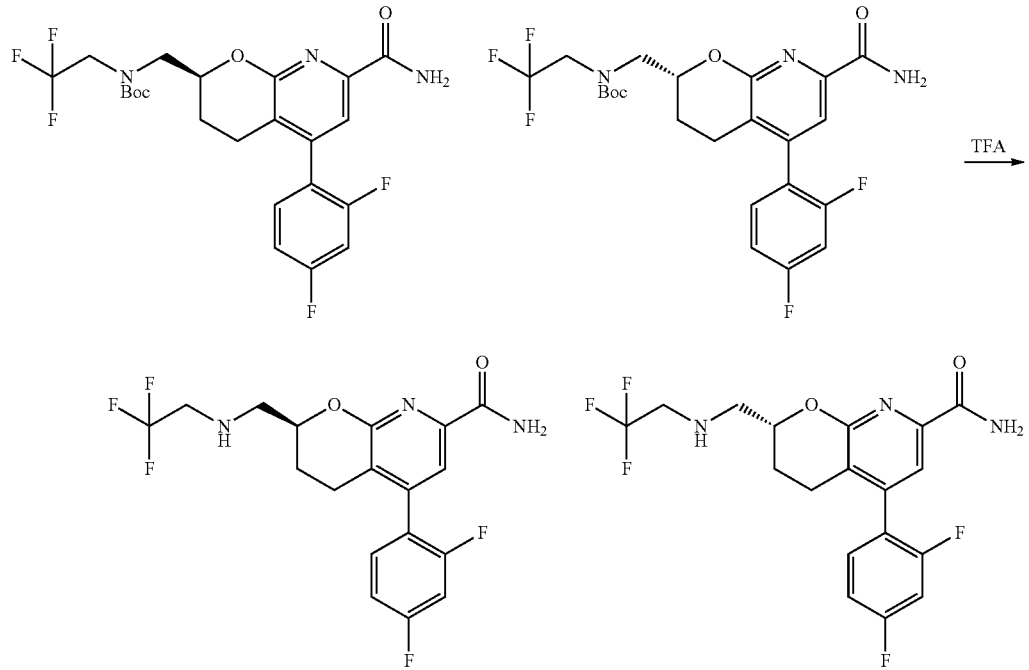

One enantiomer of tert-butyl ((7-carbamoyl-5-(2,4-difluorophenyl)-3,4-dihydro-2H-pyrano[2,3-b]pyridin-2-yl)methyl)(2,2,2-trifluoroethyl)carbamate (20 mg, 0.04 mmol) was stirred in DCM (3 mL) and TFA (0.5 mL) at 25° C. for 1 h. The reaction mixture was concentrated under reduced pressure to afford one enantiomer of the title compound. MS (ESI) calcd for ($C_{18}H_{17}F_5N_3O_2$) [M+H]$^+$, 402.1, found, 402.1.

Similar treatment of the other enantiomer of tert-butyl ((7-carbamoyl-5-(2,4-difluorophenyl)-3,4-dihydro-2H-pyrano[2,3-b]pyridin-2-yl)methyl)(2,2,2-trifluoroethyl)carbamate afforded the other enantiomer of the title compound. MS (ESI) calcd for ($C_{18}H_{17}F_5N_3O_2$) [M+H]$^+$, 402.1, found, 402.1.

Example 5A and 5B

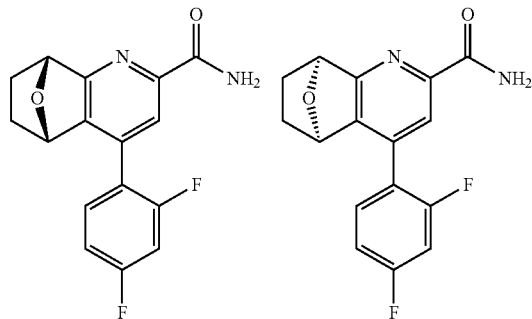

(5S,8R)-4-(2,4-difluorophenyl)-5,6,7,8-tetrahydro-5,8-epoxyquinoline-2-carboxamide and (5R,8S)-4-(2,4-difluorophenyl)-5,6,7,8-tetrahydro-5,8-epoxyquinoline-2-carboxamide Step 1: 3-(trimethylsilyl)pyridin-2-ol

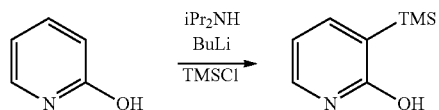 [SMILES: "TMSCl" ; Oc1ccccn1 ; C[Si](C)(C)c1cccnc1O]

To a solution of diisopropylamine (31.0 mL, 218 mmol) in THF (200 mL) was added n-butyllithium (95 mL, 238 mmol) at −78° C. After stirring for 1 h, a solution of pyridin-2-ol (9 g, 95 mmol) in THF (100 mL) was added at −78° C. The mixture was gradually warmed to 0° C. over 1 h. Chlorotrimethylsilane (13.20 mL, 104 mmol) was added to the mixture at 0° C. The resulting mixture was gradually warmed to 25° C. over 14 h. The reaction was quenched with H$_2$O (300 mL) and extracted with EtOAc (3×100 mL). The combined organic layers were washed with brine (50 mL), dried over anhydrous Na$_2$SO$_4$, filtered and concentrated. The residue was purified by silica gel chromatography (ISCO®; 40 g SepaFlash® Column, eluting with 0-30% ethyl acetate/petroleum ether) to give the product. MS (ESI) calcd. for ($C_8H_{14}$NOSi) [M+H]$^+$, 168.1, found, 168.0. $^1$H NMR (400 MHz, CDCl$_3$) δ 12.07 (br. s., 1H), 7.54 (dd, J=1.8, 6.5 Hz, 1H), 7.33 (dd, J=2.0, 6.3 Hz, 1H), 6.23 (t, J=6.5 Hz, 1H), 0.28 (s, 9H).

Step 2: 3-(trimethylsilyl)pyridin-2-yl trifluoromethanesulfonate

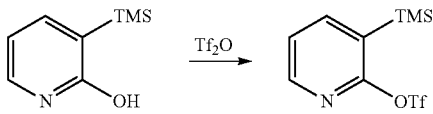 [SMILES: "Tf2O" ; C[Si](C)(C)c1cccnc1O ; C[Si](C)(C)c1cccnc1OS(=O)(=O)C(F)(F)F]

To a solution of 3-(trimethylsilyl)pyridin-2-ol (13 g, 78 mmol) in pyridine (100 mL) was added trifluoromethanesulfonic anhydride (16 mL, 95 mmol) at 0° C. under N$_2$ over 20 min. The mixture was gradually warmed to 25° C. and stirred for another 14 h. The reaction mixture was concentrated under reduced pressure and the residue was purified by silica gel chromatography (ISCO®; 120 g SepaFlash® Column, eluting with 0-10% ethyl acetate/petroleum ether) to give the product. MS (ESI) calcd. for (C$_9$H$_{13}$F$_3$NO$_3$SSi) [M+H]$^+$, 300.0, found, 300.0. $^1$H NMR (400 MHz, CDCl$_3$) δ 8.33 (dd, J=2.0, 4.7 Hz, 1H), 7.92 (dd, J=1.6, 7.0 Hz, 1H), 7.31 (dd, J=5.1, 7.0 Hz, 1H), 0.38 (s, 9H).

Step 3: 5,8-dihydro-5,8-epoxyquinoline

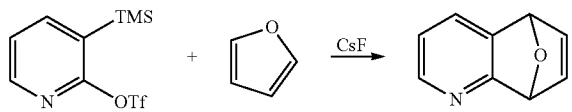

To a solution of furan (1.21 mL, 16.74 mmol) and cesium fluoride (1.015 g, 6.68 mmol) in acetonitrile (10 mL) was added 3-(trimethylsilyl)pyridin-2-yl trifluoromethanesulfonate (1 g, 3.34 mmol) in acetonitrile (10 mL) slowly at 0° C. The mixture was stirred at 28° C. for 15 h. The mixture was concentrated. Water (20 mL) was added and the mixture was extracted with ethyl acetate (3×20 mL). The combined organic layers were washed with brine (20 mL), dried over anhydrous Na$_2$SO$_4$, filtered and concentrated. The residue was purified by silica gel chromatography (ISCO®; 12 g SepaFlash® Column, eluting with 0 to 40% methyltetrabutylether/petroleum ether) to give the product. $^1$H NMR (400 MHz, CDCl$_3$) δ 8.03 (d, J=5.1 Hz, 1H), 7.42 (d, J=7.0 Hz, 1H), 7.19-7.07 (m, 2H), 6.90-6.79 (m, 1H), 5.78 (s, 1H), 5.61 (s, 1H).

Step 4: 5,6,7,8-tetrahydro-5,8-epoxyquinoline

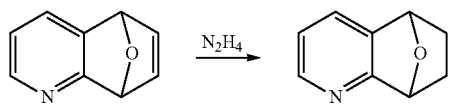

To a solution of 5,8-dihydro-5,8-epoxyquinoline (500 mg, 3.44 mmol) in EtOH (14 mL) was added hydrazine hydrate (0.683 mL, 13.78 mmol) under 10 Psi O$_2$ atmosphere. The mixture was stirred at 30° C. for 15 h. The mixture was concentrated. The residue was purified by silica gel chromatography (ISCO®; 12 g SepaFlash® Column, eluting with 0 to 30% ethyl acetate/petroleum ether) to give the product. $^1$H NMR (400 MHz, CDCl$_3$) δ 8.32-8.23 (m, 1H), 7.49 (d, J=6.8 Hz, 1H), 7.05 (dd, J=5.1, 7.4 Hz, 1H), 5.50-5.34 (m, 2H), 2.17-2.08 (m, 2H), 1.56-1.37 (m, 2H).

Step 5: 5,6,7,8-tetrahydro-5,8-epoxyquinoline 1-oxide

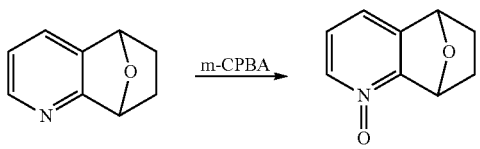

To a solution of 5,6,7,8-tetrahydro-5,8-epoxyquinoline (200 mg, 1.359 mmol) in DCM (2 mL) was added m-CPBA (630 mg, 3.10 mmol). The mixture was stirred at 25° C. for 15 h. The mixture was quenched with saturated aqueous Na$_2$SO$_3$ and extracted with DCM (3×10 mL). The combined organic layers were washed with brine (10 mL), dried over anhydrous Na$_2$SO$_4$, filtered and concentrated. The residue was purified by silica gel chromatography (ISCO®; 20 g SepaFlash® Column, eluting with 0% to 5% DCM/MeOH) to give the product. $^1$H NMR (400 MHz, CDCl$_3$) δ 7.99 (d, J=5.7 Hz, 1H), 7.18-7.04 (m, 2H), 5.85 (br. s., 1H), 5.50 (br. s., 1H), 2.19 (d, J=7.9 Hz, 2H), 1.67 (t, J=8.7 Hz, 1H), 1.51-1.40 (m, 1H).

Step 6: 4-chloro-5,6,7,8-tetrahydro-5,8-epoxyquinoline

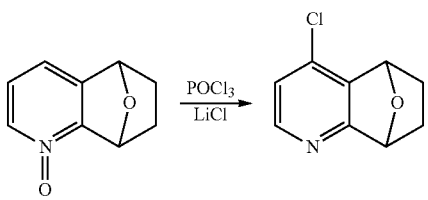

To a mixture of 5,6,7,8-tetrahydro-5,8-epoxyquinoline 1-oxide (230 mg, 1.410 mmol) and lithium chloride (72 mg, 1.698 mmol) in acetonitrile (6 mL) was added phosphoryl trichloride (1.08 g, 7.04 mmol) at 25° C. The resulting mixture was stirred at 100° C. for 2 h. After cooling to room temperature, the reaction mixture was poured into 50 g of ice and basified with solid NaHCO$_3$ to pH ~8. The mixture was extracted with EtOAC (3×20 mL). The combined organic layers were washed with brine (10 mL), dried over anhydrous Na$_2$SO$_4$, filtered and concentrated under reduced pressure. The residue was purified by Prep-TLC (silica gel, eluting with 4:1 ethyl acetate/petroleum ether) to give the product. MS (ESI) calcd. for (C$_9$H$_9$ClNO) [M+H]$^+$, 182.0, found, 181.8. $^1$H NMR (400 MHz, CDCl$_3$) δ 8.15 (d, J=5.5 Hz, 1H), 7.02 (d, J=5.5 Hz, 1H), 5.56 (d, J=3.5 Hz, 1H), 5.38 (d, J=3.9 Hz, 1H), 2.14 (dd, J=2.7, 9.8 Hz, 2H), 1.47 (d, J=9.0 Hz, 2H).

Step 7: 4-chloro-5,6,7,8-tetrahydro-5,8-epoxyquinoline 1-oxide

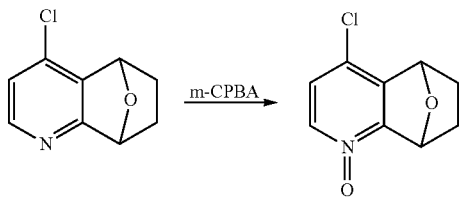

A mixture of 4-chloro-5,6,7,8-tetrahydro-5,8-epoxyquinoline (150 mg, 0.826 mmol) and mCPBA (335 mg, 1.652 mmol) in DCM (5 mL) was stirred at 40° C. for 14 h. The reaction mixture was quenched with saturated aqueous $Na_2SO_3$ (20 mL) and extracted with DCM (3×15 mL). The combined organic phases were washed with brine (10 mL), dried over anhydrous $Na_2SO_4$, filtered and concentrated under reduced pressure. The residue was purified by Prep-TLC (silica gel, eluting with 10:1 DCM/MeOH) to give the product. MS (ESI) calcd. for $(C_9H_9ClNO_2)$ $[M+H]^+$, 198.0, found, 197.8. $^1H$ NMR (400 MHz, $CDCl_3$) δ 7.88 (d, J=6.8 Hz, 1H), 7.05 (d, J=6.8 Hz, 1H), 5.83 (d, J=3.5 Hz, 1H), 5.57 (d, J=3.5 Hz, 1H), 2.28-2.14 (m, 2H), 1.66 (t, J=8.7 Hz, 1H), 1.57-1.43 (m, 1H).

Step 8: 4-chloro-5,6,7,8-tetrahydro-5,8-epoxyquinoline-2-carbonitrile

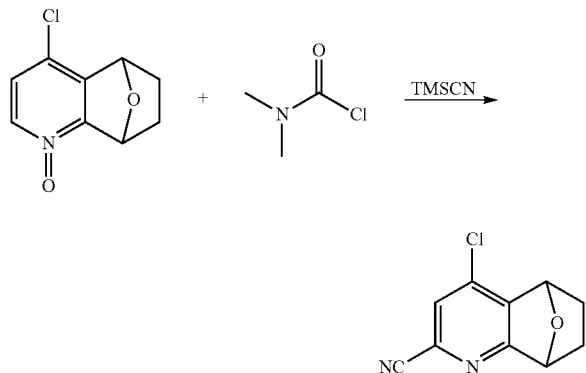

To a mixture of 4-chloro-5,6,7,8-tetrahydro-5,8-epoxyquinoline 1-oxide (44 mg, 0.223 mmol) and trimethylsilanecarbonitrile (66 mg, 0.665 mmol) in $CHCl_3$ (2 mL) was added dimethylcarbamic chloride (72 mg, 0.670 mmol) at 25° C. The resulting mixture was stirred at 60° C. for 14 h. The mixture was concentrated and purified by Prep-TLC (silica gel, eluting with 4:1 petroleum ether/ethyl acetate) to give the product. MS (ESI) calcd. for $(C_{10}H_8ClN_2O)$ $[M+H]^+$, 207.0, found, 206.8. $^1H$ NMR (400 MHz, $CDCl_3$) δ 7.42 (s, 1H), 5.55 (d, J=4.3 Hz, 1H), 5.38 (d, J=3.9 Hz, 1H), 2.16 (dd, J=3.1, 10.6 Hz, 2H), 1.53-1.36 (m, 2H).

Step 9: 4-(2,4-difluorophenyl)-5,6,7,8-tetrahydro-5,8-epoxyquinoline-2-carbonitrile

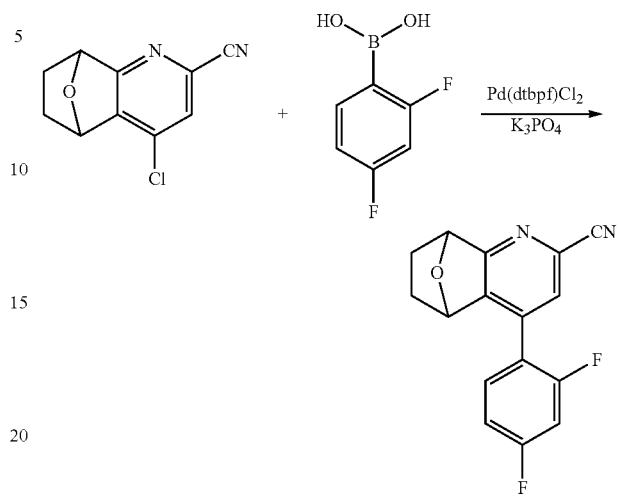

A mixture of 4-chloro-5,6,7,8-tetrahydro-5,8-epoxyquinoline-2-carbonitrile (80 mg, 0.387 mmol), (2,4-difluorophenyl)boronic acid (183 mg, 1.162 mmol), $K_3PO_4$ (250 mg, 1.178 mmol), and $PdCl_2$(dtbpf) (40 mg, 0.061 mmol) in THF (4 mL) was degassed and backfilled with $N_2$ (three times). The mixture was heated to 85° C. for 2.5 h. After cooling to room temperature, the reaction mixture was diluted with water (10 mL) and extracted with EtOAc (3×10 mL). The combined organic phases were washed with brine (5 mL), dried over anhydrous $Na_2SO_4$, filtered and concentrated under reduced pressure. The residue was purified by Prep-TLC (silica gel, eluting with 1:4 ethyl acetate/petroleum ether) to give the product. MS (ESI) calcd. for $(C_{16}H_{11}F_2N_2O)$ $[M+H]^+$, 285.1, found, 284.9. $^1H$ NMR (400 MHz, $CDCl_3$) δ 7.53 (s, 1H), 7.39-7.29 (m, 1H), 7.12-6.96 (m, 2H), 5.47-5.37 (m, 2H), 2.23 (d, J=8.2 Hz, 2H), 1.63 (d, J=11.7 Hz, 2H).

Step 10: (5S,8R)-4-(2,4-difluorophenyl)-5,6,7,8-tetrahydro-5,8-epoxyquinoline-2-carbonitrile and (5R,8S)-4-(2,4-difluorophenyl)-5,6,7,8-tetrahydro-5,8-epoxyquinoline-2-carbonitrile

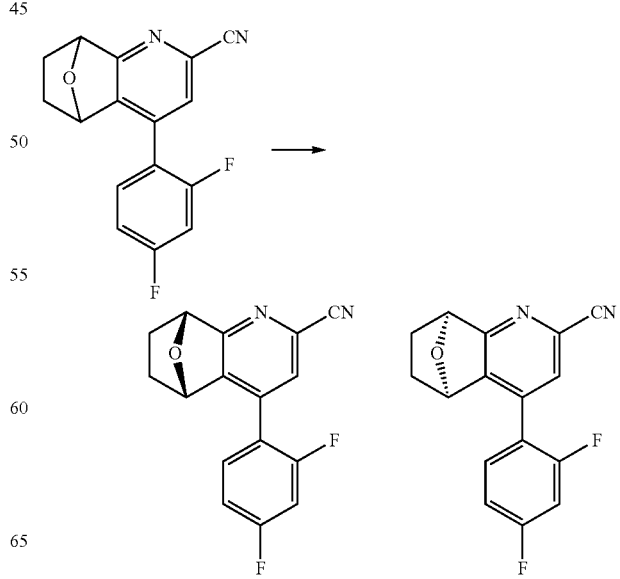

Racemic 4-(2,4-difluorophenyl)-5,6,7,8-tetrahydro-5,8-epoxyquinoline-2-carbonitrile (90 mg, 0.317 mmol) was resolved by chiral SFC (Column: Chiralpak AD 250×30 mm, 5 um; Mobile phase: 20% to 100% EtOH (containing 0.05% DEA) in $CO_2$; Flow rate: 65 mL/min) to give the two enantiomers.

Step 11: (5S,8R)-4-(2,4-difluorophenyl)-5,6,78-tetrahydro-5,8-epoxyquinoline-2-carboxamide and (5R,8S)-4-(2,4-difluorophenyl)-5,6,7,8-tetrahydro-5,8-epoxyquinoline-2-carboxamide

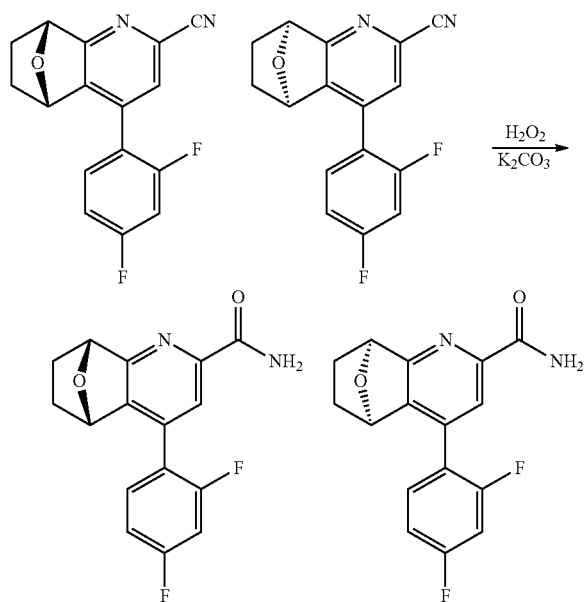

To a solution of one enantiomer of 4-(2,4-difluorophenyl)-5,6,7,8-tetrahydro-5,8-epoxyquinoline-2-carbonitrile (40 mg, 0.141 mmol) in DMSO (2 mL) was added hydrogen peroxide (65 mg, 0.573 mmol) and $K_2CO_3$ (10 mg, 0.072 mmol) at 25° C. The resulting mixture was stirred at 25° C. for 2 h. The reaction was quenched with saturated aqueous $Na_2SO_3$ (0.2 mL) and the mixture was directly purified by Prep-HPLC (Column: Waters Xbridge Prep OBD C18 150×30 mm, 5 um; Mobile phase: 24% to 54% water (containing 0.05% ammonia hydroxide v/v)-ACN; Flow rate: 25 mL/min) to give one enantiomer of the title compound. MS (ESI) calcd. for ($C_{16}H_{13}F_2N_2O_2$) $[M+H]^+$, 303.1, found, 303.1. $^1H$ NMR (400 MHz, $CDCl_3$) δ 8.08 (s, 1H), 7.79 (br. s., 1H), 7.50-7.37 (m, 1H), 7.13-6.93 (m, 2H), 5.63 (br. s., 1H), 5.42 (br. s., 2H), 2.31-2.20 (m, 2H), 1.66 (d, J=7.0 Hz, 2H).

Similar treatment of the other enantiomer of 4-(2,4-difluorophenyl)-5,6,7,8-tetrahydro-5,8-epoxyquinoline-2-carbonitrile afforded the other enantiomer of the title compound. MS (ESI) calcd. for ($C_{16}H_{13}F_2N_2O_2$) $[M+H]^+$, 303.1, found, 303.1. $^1H$ NMR (400 MHz, $CDCl_3$) δ 8.08 (s, 1H), 7.79 (br. s., 1H), 7.51-7.37 (m, 1H), 7.15-6.93 (m, 2H), 5.61 (br. s., 1H), 5.41 (d, J=3.9 Hz, 2H), 2.30-2.19 (m, 3H), 1.66 (d, J=7.0 Hz, 2H).

Biological Assays

The utility of the compounds of the invention as an inhibitor of metabotropic glutamate receptor activity, in particular mGluR2 activity, may be demonstrated by methodology known in the art and as described as follows. Inhibition constants ($IC_{50}$s; the concentration of compound required to provide 50% of maximal activity) are determined as follows. The compounds of the invention were tested in a fluorescence laser imaging plate reader based assay. This assay is a common functional assay to monitor $Ca^{2+}$ mobilization in whole cells expressing recombinant receptor coupled with a promiscuous G-protein. CHO (Chinese hamster ovary) dhfr– cells stably expressing recombinant human mGluR2 and Gα16 loaded with Fluo-4 AM (Invitrogen, Carlsbad Calif., USA) were treated with various concentrations of each of the tested compounds of the invention and the $Ca^{2+}$ response was monitored on a FLIPR384 instrument (Molecular Devices, Sunnydale Calif., USA). Maximal agonist activity was measured in the presence of 2,500 nM glutamate and the inhibition provided by a range of compound concentrations sufficient to minimally and maximally inhibit the glutamate-dependent response was monitored over time. The maximum calcium response at each concentration of compound for agonist or antagonist were plotted as dose responses and the curves were fitted with a four parameter logistic equation giving $IC_{50}$ and Hill coefficient using the iterative non-linear curve fitting software ADA (Merck & Co., Inc.). Data in the following table lists the activity of each compound to inhibit glutamate-dependent mGluR2 activity in this cellular assay.

| Example | IC50 value (nM) |
| --- | --- |
| 1-1 | 277 |
| 1-2A | 376 |
| 1-2B | 21 |
| 1-3A | 65 |
| 1-3B | 12 |
| 1-4A | >3000 |
| 1-4B | 1765 |
| 1-5A | >3000 |
| 1-5B | 326 |
| 1-6A | >3000 |
| 1-6B | 1801 |
| 1-7A | >3000 |
| 1-7B | 172 |
| 2-1A | 38 |
| 2-1B | 179 |
| 2-2A | 195 |
| 2-2B | 15 |
| 2-2C | 35 |
| 2-2D | 81 |
| 2-3A | 20 |
| 2-3B | 32 |
| 2-4A | 20 |
| 2-4B | 69 |
| 2-5 | 6 |
| 2-6A | 10 |
| 2-6B | 26 |
| 2-7 | 25 |
| 2-8A | 8 |
| 2-8B | 14 |
| 2-9A | 18 |
| 2-9B | 114 |
| 2-9C | 11 |
| 2-9D | 57 |
| 3-1A | 7 |
| 3-1B | 19 |
| 3-2A | 18 |
| 3-2B | 86 |
| 3-3A | 536 |
| 3-3B | 2519 |
| 3-4A | 274 |
| 3-4B | 1491 |
| 3-5A | 26 |
| 3-5B | 27 |
| 3-6A | 52 |
| 3-6B | 10 |
| 3-7A | 18 |

-continued

| Example | IC50 value (nM) |
|---|---|
| 3-7B | 90 |
| 3-8A | 12 |
| 3-8B | 24 |
| 3-9A | 7 |
| 3-9B | 19 |
| 3-9C | 15 |
| 3-9D | 9 |
| 4-1A | 25 |
| 4-1B | 74 |
| 4-2A | 21 |
| 4-2B | 28 |
| 5-1A | 159 |
| 5-1B | 500 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound having the structure:

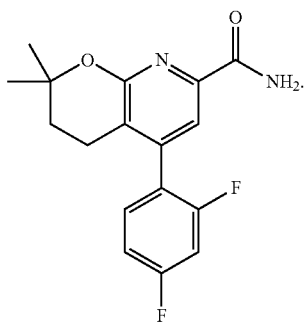 [SMILES: CC1(C)CCc2c(-c3ccc(F)cc3F)cc(C(N)=O)nc2O1]

2. A compound having the structure:

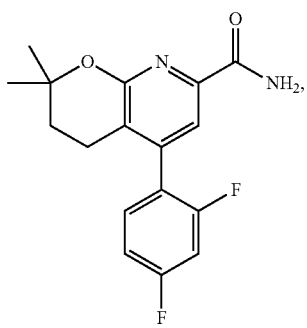 [SMILES: CC1(C)CCc2c(-c3ccc(F)cc3F)cc(C(N)=O)nc2O1]

wherein said compound is in the form of a pharmaceutically acceptable salt.

3. A compound having the structure:

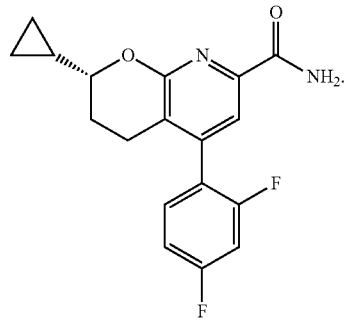 [SMILES: NC(=O)c1cc(-c2ccc(F)cc2F)c2c(n1)O[C@@H](C1CC1)CC2]

4. A compound having the structure:

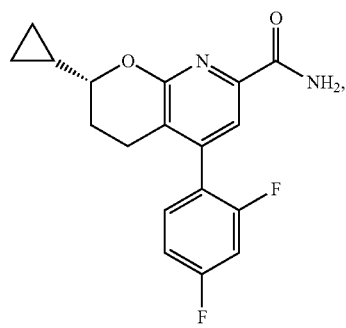 [SMILES: NC(=O)c1cc(-c2ccc(F)cc2F)c2c(n1)O[C@@H](C1CC1)CC2]

wherein said compound is in the form of a pharmaceutically acceptable salt.

5. A compound having the structure:

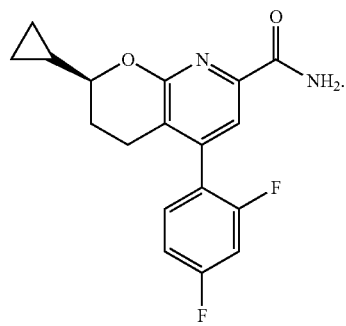 [SMILES: NC(=O)c1cc(-c2ccc(F)cc2F)c2c(n1)O[C@H](C1CC1)CC2]

6. A compound having the structure:

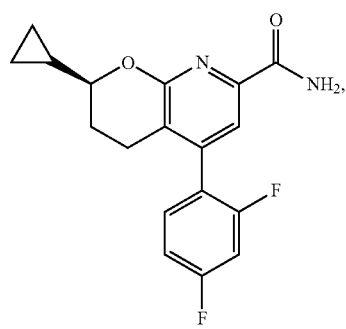 [SMILES: NC(=O)c1cc(-c2ccc(F)cc2F)c2c(n1)O[C@H](C1CC1)CC2]

wherein said compound is in the form of a pharmaceutically acceptable salt.

7. A compound having the structure:

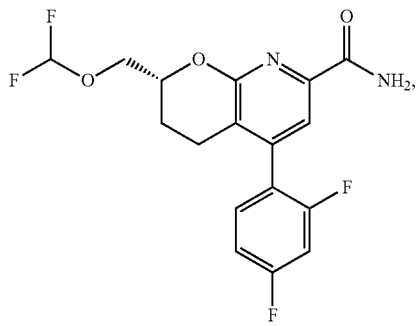 [SMILES: NC(=O)c1cc(-c2ccc(F)cc2F)c2c(n1)O[C@@H](COC(F)F)CC2]

8. A compound having the structure:

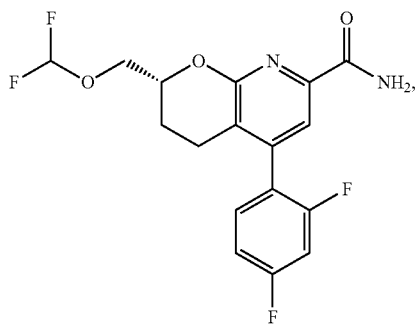 [SMILES: NC(=O)c1cc(-c2ccc(F)cc2F)c2c(n1)O[C@@H](COC(F)F)CC2]

wherein said compound is in the form of a pharmaceutically acceptable salt.

9. A compound having the structure:

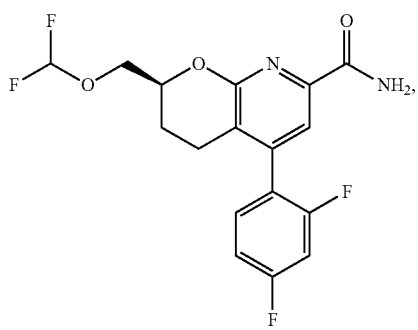

10. A compound having the structure:

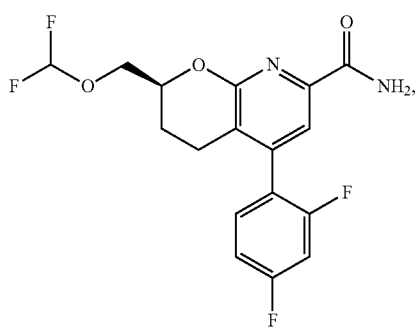 [SMILES: NC(=O)c1cc(-c2ccc(F)cc2F)c2c(n1)O[C@H](COC(F)F)CC2]

wherein said compound is in the form of a pharmaceutically acceptable salt.

11. A compound having the structure:

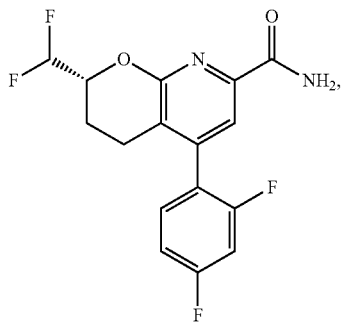 [SMILES: NC(=O)c1cc(-c2ccc(F)cc2F)c2c(n1)O[C@@H](C(F)F)CC2]

12. A compound having the structure:

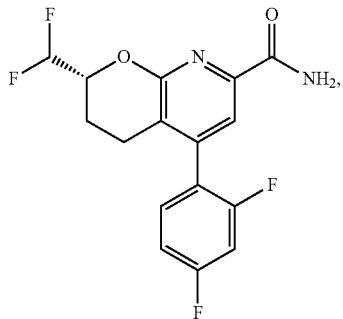 [SMILES: NC(=O)c1cc(-c2ccc(F)cc2F)c2c(n1)O[C@@H](C(F)F)CC2]

wherein said compound is in the form of a pharmaceutically acceptable salt.

13. A compound having the structure:

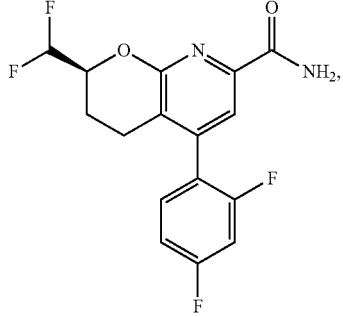 [SMILES: NC(=O)c1cc(-c2ccc(F)cc2F)c2c(n1)O[C@H](C(F)F)CC2]

14. A compound having the structure:

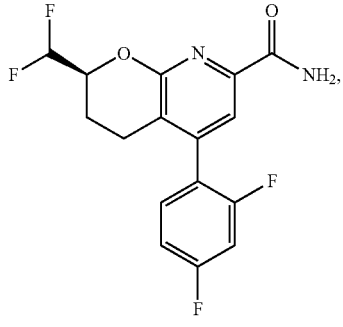 [SMILES: NC(=O)c1cc(-c2ccc(F)cc2F)c2c(n1)O[C@H](C(F)F)CC2]

wherein said compound is in the form of a pharmaceutically acceptable salt.

15. A pharmaceutical composition comprising a therapeutically effective amount of the compound of claim 1 and a pharmaceutically acceptable carrier.

16. A pharmaceutical composition comprising a pharmaceutically acceptable carrier and a therapeutically effective amount of the compound having the structure:

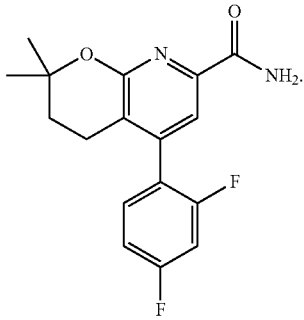 [SMILES: CC1(C)CCc2c(-c3ccc(F)cc3F)cc(C(N)=O)nc2O1]

wherein said compound is in the form of a pharmaceutically acceptable salt, according to claim 2.

17. A pharmaceutical composition comprising a therapeutically effective amount of the compound of claim 3 and a pharmaceutically acceptable carrier.

18. A pharmaceutical composition comprising a pharmaceutically acceptable carrier and a therapeutically effective amount of the compound having the structure:

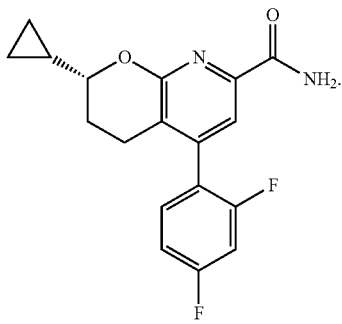 [SMILES: NC(=O)c1cc(-c2ccc(F)cc2F)c2c(n1)O[C@@H](C1CC1)CC2]

wherein said compound is in the form of a pharmaceutically acceptable salt, according to claim 4.

19. A pharmaceutical composition comprising a therapeutically effective amount of the compound of claim 5 and a pharmaceutically acceptable carrier.

20. A pharmaceutical composition comprising a pharmaceutically acceptable carrier and a therapeutically effective amount of the compound having the structure:

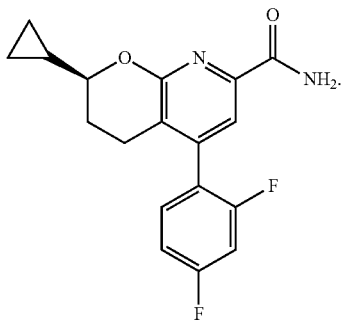 [SMILES: NC(=O)c1cc(-c2ccc(F)cc2F)c2c(n1)O[C@H](C1CC1)CC2]

wherein said compound is in the form of a pharmaceutically acceptable salt, according to claim 6.

21. A pharmaceutical composition comprising a therapeutically effective amount of the compound of claim 7 and a pharmaceutically acceptable carrier.

22. A pharmaceutical composition comprising a pharmaceutically acceptable carrier and a therapeutically effective amount of the compound having the structure:

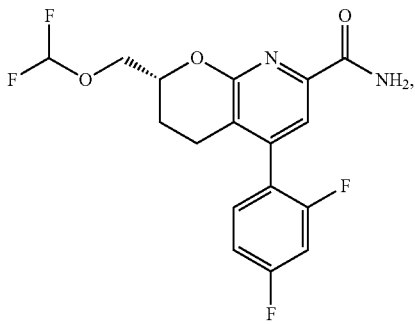 [SMILES: NC(=O)c1cc(-c2ccc(F)cc2F)c2c(n1)O[C@@H](COC(F)F)CC2]

wherein said compound is in the form of a pharmaceutically acceptable salt, according to claim 8.

23. A pharmaceutical composition comprising a therapeutically effective amount of the compound of claim 9 and a pharmaceutically acceptable carrier.

24. A pharmaceutical composition comprising a pharmaceutically acceptable carrier and a therapeutically effective amount of the compound having the structure:

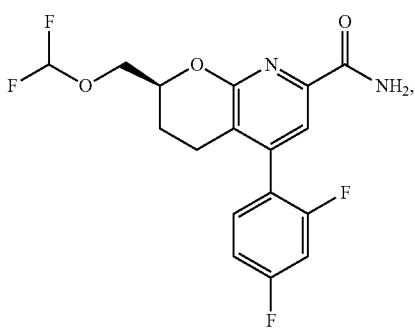 [SMILES: NC(=O)c1cc(-c2ccc(F)cc2F)c2c(n1)O[C@H](COC(F)F)CC2]

wherein said compound is in the form of a pharmaceutically acceptable salt, according to claim 10.

25. A pharmaceutical composition comprising a therapeutically effective amount of the compound of claim 11 and a pharmaceutically acceptable carrier.

26. A pharmaceutical composition comprising a pharmaceutically acceptable carrier and a therapeutically effective amount of the compound having the structure:

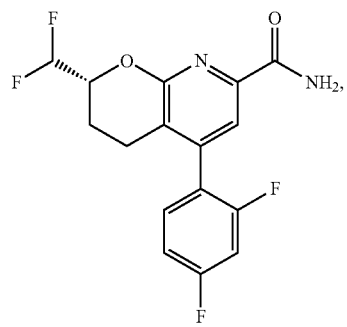 [SMILES: NC(=O)c1cc(-c2ccc(F)cc2F)c2c(n1)O[C@@H](C(F)F)CC2]

wherein said compound is in the form of a pharmaceutically acceptable salt, according to claim 12.

27. A pharmaceutical composition comprising a therapeutically effective amount of the compound of claim 13 and a pharmaceutically acceptable carrier.

28. A pharmaceutical composition comprising a pharmaceutically acceptable carrier and a therapeutically effective amount of the compound having the structure:
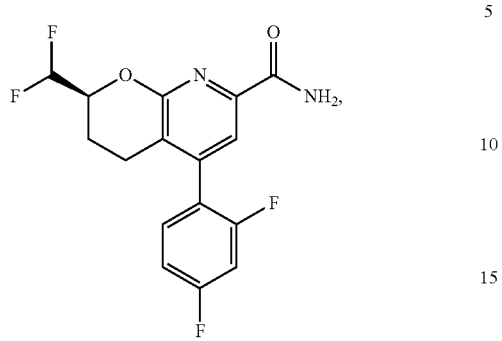
wherein said compound is in the form of a pharmaceutically acceptable salt, according to claim 14.
* * * * *